(12) United States Patent
Craig, II et al.

(10) Patent No.: US 11,851,440 B2
(45) Date of Patent: *Dec. 26, 2023

(54) MODULATORS OF EUKARYOTIC INITIATION FACTOR 2B, COMPOSITIONS AND METHODS

(71) Applicant: Denali Therapeutics Inc., South San Francisco, CA (US)

(72) Inventors: Robert A. Craig, II, South San Francisco, CA (US); Javier de Vicente Fidalgo, Foster City, CA (US); Anthony A. Estrada, Danville, CA (US); Jianwen A. Feng, San Mateo, CA (US); Brian M. Fox, Redwood City, CA (US); Christopher R. H. Hale, South San Francisco, CA (US); Katrina W. Lexa, San Francisco, CA (US); Maksim Osipov, Redwood City, CA (US); Travis Remarchuk, South San Francisco, CA (US); Zachary K. Sweeney, Redwood City, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,039

(22) Filed: Nov. 19, 2021

(65) Prior Publication Data
US 2022/0411433 A1    Dec. 29, 2022

Related U.S. Application Data

(63) Continuation of application No. 16/637,718, filed as application No. PCT/US2018/045868 on Aug. 8, 2018, now Pat. No. 11,236,100.

(Continued)

(51) Int. Cl.
| | |
|---|---|
| A61K 31/4245 | (2006.01) |
| A61K 31/4164 | (2006.01) |
| A61K 31/415 | (2006.01) |
| A61K 31/421 | (2006.01) |
| C07D 491/048 | (2006.01) |
| C07C 235/22 | (2006.01) |
| C07D 207/27 | (2006.01) |
| C07D 233/36 | (2006.01) |
| C07D 233/42 | (2006.01) |
| C07D 233/61 | (2006.01) |
| C07D 233/64 | (2006.01) |
| C07D 249/04 | (2006.01) |
| C07D 249/08 | (2006.01) |
| C07D 257/04 | (2006.01) |
| C07D 261/04 | (2006.01) |
| C07D 261/08 | (2006.01) |
| C07D 263/32 | (2006.01) |
| C07D 263/38 | (2006.01) |
| C07D 263/56 | (2006.01) |
| C07D 271/06 | (2006.01) |
| C07D 271/10 | (2006.01) |
| C07D 291/04 | (2006.01) |
| C07D 401/12 | (2006.01) |

(Continued)

(52) U.S. Cl.
CPC ........ *C07D 491/048* (2013.01); *A61K 31/415* (2013.01); *A61K 31/4164* (2013.01); *A61K 31/421* (2013.01); *A61K 31/4245* (2013.01); *C07C 235/22* (2013.01); *C07D 207/27* (2013.01); *C07D 233/36* (2013.01); *C07D 233/42* (2013.01); *C07D 233/61* (2013.01); *C07D 233/64* (2013.01); *C07D 249/04* (2013.01); *C07D 249/08* (2013.01); *C07D 257/04* (2013.01); *C07D 261/04* (2013.01); *C07D 261/08* (2013.01); *C07D 263/32* (2013.01); *C07D 263/38* (2013.01); *C07D 263/56* (2013.01); *C07D 271/06* (2013.01); *C07D 271/10* (2013.01); *C07D 291/04* (2013.01); *C07D 401/12* (2013.01); *C07D 403/04* (2013.01); *C07D 403/12* (2013.01); *C07D 413/04* (2013.01); *C07D 413/06* (2013.01); *C07D 413/12* (2013.01); *C07D 417/04* (2013.01); *C07D 471/04* (2013.01); *C07D 487/04* (2013.01)

(58) Field of Classification Search
CPC ............ A61K 31/4245; A61K 31/4164; A61K 31/415; A61K 31/421
See application file for complete search history.

(56) References Cited

U.S. PATENT DOCUMENTS

| | | | |
|---|---|---|---|
| 7,053,104 | B2 | 5/2006 | Van Wagenen et al. |
| 8,193,179 | B2 | 6/2012 | Hubschwerlen et al. |

(Continued)

FOREIGN PATENT DOCUMENTS

| | | |
|---|---|---|
| WO | WO-0023076 | 4/2000 |
| WO | WO-02080928 | 10/2002 |

(Continued)

OTHER PUBLICATIONS

Chemical Abstracts Registry No. 1135218-61-9, indexed in the Registry file on STN CAS Online Apr. 16, 2009. (Year: 2009).

(Continued)

*Primary Examiner* — Laura L Stockton
(74) *Attorney, Agent, or Firm* — SHEPPARD MULLIN RICHTER & HAMPTON LLP

(57) ABSTRACT

The present disclosure relates generally to eukaryotic initiation factor 2B modulators, or a pharmaceutically acceptable salt, stereoisomer, mixture of stereoisomers or prodrug thereof, and methods of making and using thereof.

18 Claims, No Drawings

Related U.S. Application Data

(60) Provisional application No. 62/608,504, filed on Dec. 20, 2017, provisional application No. 62/553,728, filed on Sep. 1, 2017, provisional application No. 62/543,307, filed on Aug. 9, 2017.

(51) Int. Cl.
*C07D 403/04* (2006.01)
*C07D 403/12* (2006.01)
*C07D 413/04* (2006.01)
*C07D 413/06* (2006.01)
*C07D 413/12* (2006.01)
*C07D 417/04* (2006.01)
*C07D 471/04* (2006.01)
*C07D 487/04* (2006.01)

(56) References Cited

U.S. PATENT DOCUMENTS

| | | |
|---|---|---|
| 9,408,392 B2 | 8/2016 | O'Sullivan et al. |
| 9,421,211 B2 | 8/2016 | Aktas et al. |
| 9,447,025 B2 | 9/2016 | Bunker |
| 9,693,975 B2 | 7/2017 | Bunker |
| 9,708,247 B2 | 7/2017 | Walter et al. |
| 10,343,981 B2 | 7/2019 | Walter et al. |
| 11,236,100 B2 | 2/2022 | Craig, II et al. |
| 2001/0047100 A1 | 11/2001 | Kjaersgaard et al. |
| 2003/0149089 A1 | 8/2003 | Heerding et al. |
| 2008/0221100 A1 | 9/2008 | Gless et al. |
| 2009/0131444 A1 | 5/2009 | Reck et al. |
| 2012/0264738 A1 | 10/2012 | Sugimoto et al. |
| 2013/0225644 A1 | 8/2013 | Larsen et al. |
| 2013/0324551 A1 | 12/2013 | Pulici et al. |
| 2014/0121196 A1 | 5/2014 | Sugimoto et al. |
| 2014/0275008 A1 | 9/2014 | Xu et al. |
| 2015/0259344 A1 | 9/2015 | Iwata et al. |
| 2016/0075654 A1 | 3/2016 | Bunker et al. |
| 2017/0100400 A1 | 4/2017 | Charifson et al. |
| 2017/0183355 A1 | 6/2017 | Sprott et al. |
| 2017/0342020 A1 | 11/2017 | Walter et al. |
| 2017/0369486 A1 | 12/2017 | Acharya et al. |
| 2020/0331900 A1 | 10/2020 | Craig, II et al. |
| 2021/0130308 A1 | 5/2021 | Craig, II et al. |
| 2021/0147435 A1 | 5/2021 | Craig, II et al. |
| 2021/0292311 A1 | 9/2021 | Craig, II et al. |
| 2022/0106324 A1 | 4/2022 | Sugimoto et al. |
| 2022/0177438 A1 | 6/2022 | Craig, II et al. |
| 2022/0177456 A1 | 6/2022 | Craig, II et al. |
| 2023/0114472 A1 | 4/2023 | Craig, II et al. |

FOREIGN PATENT DOCUMENTS

| | | |
|---|---|---|
| WO | WO-2004058730 | 7/2004 |
| WO | WO-2006028904 | 3/2006 |
| WO | WO-2010067332 | 6/2010 |
| WO | WO-2012088365 | 6/2012 |
| WO | WO-2012121361 | 9/2012 |
| WO | WO-2012145569 | 10/2012 |
| WO | WO-2014144952 | 9/2014 |
| WO | WO-2014149819 | 9/2014 |
| WO | WO-2015038778 | 3/2015 |
| WO | WO-2016044331 | 3/2016 |
| WO | WO-2016081679 | 5/2016 |
| WO | WO-2016138288 | 9/2016 |
| WO | WO-2016169911 | 10/2016 |
| WO | WO-2016177658 | 11/2016 |
| WO | WO-2017059965 | 4/2017 |
| WO | WO-2017193030 | 11/2017 |
| WO | WO-2017193034 | 11/2017 |
| WO | WO-2017193041 | 11/2017 |
| WO | WO-2017193063 | 11/2017 |
| WO | WO-2017212423 | 12/2017 |
| WO | WO-2017212425 | 12/2017 |
| WO | WO-2018009615 | 1/2018 |
| WO | WO-2018069863 | 4/2018 |
| WO | WO-2018107072 | 6/2018 |
| WO | WO-2018225093 | 12/2018 |
| WO | WO-2019008506 | 1/2019 |
| WO | WO-2019008507 | 1/2019 |
| WO | WO-2019032743 | 2/2019 |
| WO | WO-2019046779 | 3/2019 |
| WO | WO-2019054430 | 3/2019 |
| WO | WO-2019090069 | 5/2019 |
| WO | WO-2019090074 | 5/2019 |
| WO | WO-2019090076 | 5/2019 |
| WO | WO-2019090078 | 5/2019 |
| WO | WO-2019090081 | 5/2019 |
| WO | WO-2019090082 | 5/2019 |
| WO | WO-2019090085 | 5/2019 |
| WO | WO-2019090088 | 5/2019 |
| WO | WO-2019090090 | 5/2019 |
| WO | WO-2019118785 | 6/2019 |
| WO | WO-2019183589 | 9/2019 |
| WO | WO-2019193540 | 10/2019 |
| WO | WO-2019193541 | 10/2019 |
| WO | WO-2020012339 | 1/2020 |
| WO | WO-2020031107 | 2/2020 |
| WO | WO-2020077217 | 4/2020 |
| WO | WO-2020167994 | 8/2020 |
| WO | WO-2020168011 | 8/2020 |
| WO | WO-2020181247 | 9/2020 |
| WO | WO-2020223536 | 11/2020 |
| WO | WO-2020223538 | 11/2020 |
| WO | WO-2022133236 | 6/2022 |

OTHER PUBLICATIONS

Extended European Search Report for European Application No. 18850713.1 dated Mar. 30, 2021. 6 pages.
Extended European Search Report for European Application No. 18844666.0 dated Mar. 26, 2021. 10 pages.
Hearn et al., Structure-Activity Studies of Bis-O-Arylglycolamides: Inhibitors of the Integrated Stress Response. ChemMedChem 2016, vol. 11, pp. 870-880.
International Search Report and Written Opinion for International Application No. PCT/US2018/045868 dated Nov. 26, 2018. 9 pages.
International Search Report and Written Opinion for International Application No. PCT/US2018/049197 dated Feb. 5, 2019. 12 pages.
International Search Report and Written Opinion for International Application No. PCT/US2019/023739 dated Jul. 11, 2019. 16 pages.
International Search Report and Written Opinion for International Application No. PCT/US2020/017985 dated Apr. 23, 2020. 15 pages.
International Search Report and Written Opinion for International Application No. PCT/US2020/018007 dated Apr. 21, 2020. 11 pages.
International Search Report and Written Opinion for International Application No. PCT/US2020/021534 dated May 1, 2020. 15 pages.
Joshi et al., Small molecule modulators of eukaryotic initiation factor 2a kinases, the key regulators of protein synthesis. Biochimie 2013, vol. 95, pp. 1980-1990, XP028731042.
Kashiwagi et al., Crystal structure of eukaryotic translation initiation factor 2B. Nature 2016, vol. 531, pp. 122-125.
Kim et al., Therapeutic modulation of eIF2a phosphorylation rescues TDP-43 toxicity in amyotrophic lateral sclerosis disease models. Nature Genetics 2014, vol. 46, No. 2, pp. 152-160.
PubChem CID 13756165, 3,4-dihydro-2H-chromen-2-yl-(4-phenylpiperidin-1-yl)methanone, Feb. 8, 2007, 7 pages, retrieved from the internet: pubchem.ncbi.nlm.nih.gov/compound/13756165 on Sep. 17, 2020.
PubChem CID 65333682, 4-[2-(oxan-3-yl)-1,3-thiazol-4-yl]benzonitrile, Oct. 23, 2012, 8 pages, retrieved from the internet: pubchem.ncbi.nlm.nih.gov/compound/65333682 on Sep. 17, 2020.
PubChem CID 68023613, N-[5-Methoxy-6-(methoxymethyl)oxan-3-yl]heptanamide, Nov. 30, 2012, 12 pages, retrieved from the internet: pubchem.ncbi.nlm.nih.gov/compound/68023613 on Oct. 16, 2018.

(56) References Cited

OTHER PUBLICATIONS

PubChem CID 68310749, [(2S,5R)-5-Aminooxan-2-yl]-morpholin-4-ylmethanone, Nov. 30, 2012, 10 pages, retrieved from the internet: pubchem.ncbi.nlm.nih.gov/compound/68310749 on Sep. 17, 2020.
PubChem CID 79039022, N-[(4-hydroxyoxan-4-yl)methyl]-3-phenoxypropanamide, Oct. 19, 2014, 8 pages, retrieved from the internet: pubchem.ncbi.nlm.nih.gov/compound/79039022 on Sep. 17, 2020.
PubChem CID 828546, N-Cyclohexyl-1,2,3,4-tetrahydroisoquinoline-2-carboxamide, Jul. 9, 2005, 10 pages, retrieved from the internet: pubchem.ncbi.nlm.nih.gov/compound/828546#section=BioAssay-Results on Sep. 17, 2020.
PubChem CID 91786719, N-[(3R,4S)-4-(2-amino-2-oxoethoxy)oxan-3-yl]-4-phenoxybutanamide, Jun. 3, 2015, 9 pages, retrieved from the internet: pubchem.ncbi.nlm.nih.gov/compound/91786719 on Sep. 17, 2020.
RN 1449697-58-8, registry database compound, (2013). 1 page.
Sekine et al., Mutations in a translation initiation factor identify the target of a memory-enhancing compound. Science 2015, vol. 348, issue 6238, pp. 1027-1030.
Sidrauski et al., Pharmacological brake-release of mRNA translation enhances cognitive memory. eLife 2013;2:e00498 doi: 10.7554/eLife.00498. 22 pages.
Sidrauski et al., Pharmacological dimerization and activation of the exchange factor eIF2B antagonizes the integrated stress response. eLife 2015;4:e07314, doi: 10.7554/eLife.07314. 27 pages.
Registry (STN) [online], Oct. 3, 2012, [retrieval date: Jul. 25, 2022], CAS Registration No. 1398569-33-9. 1 page.
Registrydatabasecompounds, 2021, listing of registry database compounds. 17 pages.
Bessodes et al., Synthesis of unsaturated 4'-azido pyranosyl thymines as potential antiviral and anti-HIV agents, J. Chem. Soc. Perkin Trans. 1, 1990, pp. 3035-3039.

MODULATORS OF EUKARYOTIC INITIATION FACTOR 2B, COMPOSITIONS AND METHODS

CROSS REFERENCE TO RELATED APPLICATIONS

This application is a continuation of U.S. application Ser. No. 16/637,718, filed Feb. 7, 2020, now U.S. Pat. No. 11,236,100, which is a U.S. National Stage Application under 35 U.S.C. § 371 of International Application Number PCT/US2018/045868, filed Aug. 8, 2018, which application claims the benefit under 35 U.S.C. § 119(e) to U.S. Provisional Application No. 62/543,307, filed Aug. 9, 2017, 62/553,728, filed Sep. 1, 2017, and 62/608,504, filed Dec. 20, 2017, and all of which are hereby incorporated by reference in their entireties.

FIELD

The present disclosure relates generally to small molecule modulators of eukaryotic initiation factor 2B and their use as therapeutic agents, for example, in treating diseases such as Alzheimer's. Parkinson's, ALS and frontotemporal dementia.

BACKGROUND

Neurodegenerative diseases, such as Parkinson's disease (PD), amyotrophic lateral sclerosis (ALS), Alzheimer's disease (AD), and Frontotemporal dementia (FTD) have a negative effect on the lives of millions of people.

The multi-subunit protein complexes eukaryotic initiation factor 2B and eukaryotic initiation factor 2 are required for protein synthesis initiation and regulation in eukaryotic cells. Eukaryotic initiation factor 2B is composed of five subunits ($\alpha$, $\beta$, $\gamma$, $\delta$ and $\epsilon$), and eukaryotic initiation factor 2 is composed of three subunits ($\alpha$, $\beta$ and $\gamma$). Eukaryotic initiation factor 2B functions as a guanine nucleotide exchange factor (GEF) that catalyzes the exchange of guanosine-5'-diphosphate (GDP) with guanosine-5'-triphosphate (GTP) on eukaryotic initiation factor 2, thereby allowing the GTP bound eukaryotic initiation factor 2 to bind to the initiating methionine transfer RNA and initiate protein synthesis.

Eukaryotic initiation factor 2B is active when complexed as a ten subunit dimer. Eukaryotic initiation factor 2 is active when bound to GTP and inactive when bound to GDP. Moreover, when the $\alpha$ subunit of eukaryotic initiation factor 2 is phosphorylated on serine 51, it inhibits and regulates the guanine nucleotide exchange activity of eukaryotic initiation factor 2B. In its phosphorylated form, eukaryotic initiation factor 2 remains in an inactive GDP bound state and translation initiation is blocked.

The interaction between eukaryotic initiation factor 2B and eukaryotic initiation factor 2 plays an important role in the integrated stress response (ISR) pathway. Activation of this pathway leads in part to ATF4 (Activating Transcription Factor 4) expression and stress granule formation. Aberrant ISR activation is found in multiple neurodegenerative diseases, with a strong functional link to pathology characterized by the RNA-binding/stress-granule protein TAR DNA binding protein (TARDBP), also known as TDP43. Activation of eIF2B inhibits the ISR and ISR dependent stress granule formation and is found to be neuroprotective in multiple disease models.

Impairment of eukaryotic initiation factor 2B activity is correlated to activation of the ISR pathway that is implicated in a variety neurodegenerative diseases including Parkinson's disease, amyotrophic lateral sclerosis (ALS), Alzheimer's disease and frontotemporal dementia. Mutations in TDP43 and other RNA-binding proteins/stress-granule proteins alter stress-granule dynamics and cause ALS. Inhibition of the ISR pathway can block and promote the dissolution of stress-granules. In addition, mutations in the human eukaryotic initiation factor 2B subunits have been identified as causing leukoencephalopathy with vanishing white matter (VWM) and childhood ataxia with central nervous system hypomyelination (CACH). In VWM/CACH patients, white matter lesions severely deteriorate and neurological disorders are exacerbated after stresses, and their eukaryotic initiation factor 2B guanine nucleotide exchange activities are generally lower than normal.

DESCRIPTION

Provided herein are compounds, or a pharmaceutically acceptable salt, isotopically enriched analog, stereoisomer, mixture of stereoisomers or prodrug thereof, that are useful in treating and/or preventing neurodegenerative diseases (e.g., neurodegeneration in prion disease).

In some embodiments, provided are compounds that modulate the activity of eukaryotic initiation factor 2B. In some embodiments, the compounds modulate the regulation of eukaryotic initiation factor 2B. In some aspects the compounds modulate the inhibition of eukaryotic initiation factor 2B by phosphorylated eukaryotic initiation factor 2. In some embodiments, the compounds interfere with the interaction between eukaryotic initiation factor 2B and phosphorylated eukaryotic initiation factor 2. In some embodiments, the phosphorylated eukaryotic initiation factor 2 is phosphorylated on its alpha subunit (eukaryotic initiation factor 2 $\alpha$ phosphate).

In some embodiments, provided are compounds that act as activators of eukaryotic initiation factor 2B by increasing its GDP/GTP nucleotide exchange activity. In some embodiments, the compounds promote eukaryotic initiation factor 2B dimer formation. In other embodiments, the compounds enhances the guanine nucleotide exchange factor (GEF) activity of eukaryotic initiation factor 2B. In other embodiments, the compounds increases the guanine nucleotide exchange factor (GEF) activity of eukaryotic initiation factor 2B on its eukaryotic initiation factor 2/GDP substrate.

In some embodiments, provided are compounds that desensitizes cells to the deleterious effects of eukaryotic initiation factor 2B inhibition. In some embodiments the deleterious effects include ATF4 expression and stress granule formation.

In another embodiment, provided is a pharmaceutical composition comprising a compound as described herein, or a pharmaceutically acceptable salt, isotopically enriched analog, stereoisomer, mixture of stereoisomers or prodrug thereof, and a pharmaceutically acceptable carrier.

In another embodiment, provided is a method for treating a disease or condition mediated, at least in part, by eukaryotic initiation factor 2B, the method comprising administering an effective amount of the pharmaceutical composition comprising a compound as described herein, or a pharmaceutically acceptable salt, isotopically enriched analog, stereoisomer, mixture of stereoisomers or prodrug thereof.

In another embodiment, provided is a method for treating a disease or condition mediated, at least in part, by regulation of eukaryotic initiation factor 2B, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

In another embodiment, provided is a method for promoting or stabilizing eukaryotic initiation factor 2B dimer formation, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

In another embodiment, provided is a method for promoting eukaryotic initiation factor 2B activity, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

In another embodiment, provided is a method for desensitizing cells to eukaryotic initiation factor 2 phosphorylation, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

In another embodiment, provided is a method for inhibiting the integrated stress response pathway, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

In another embodiment, provided is a method for inhibiting stress granule formation, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

In another embodiment, provided is a method for inhibiting ATF4 expression, the method comprising administering an effective amount of the pharmaceutical composition comprising a compound as described herein, or a pharmaceutically acceptable salt, isotopically enriched analog, stereoisomer, mixture of stereoisomers or prodrug thereof, and a pharmaceutically acceptable carrier, to a subject in need thereof.

The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by eukaryotic initiation factor 2B. Moreover, the disclosure provides uses of the compounds or compositions thereof in the manufacture of a medicament for the treatment of a disease, disorder, or condition that is mediated, at least in part, by eukaryotic initiation factor 2B.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u\text{-}v}$" indicates that the following group has from u to v carbon atoms. For example, "$C_{1\text{-}6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1\text{-}20}$ alkyl), 1 to 12 carbon atoms (i.e., $C_{1\text{-}12}$ alkyl), 1 to 8 carbon atoms (i.e., $C_{1\text{-}8}$ alkyl), 1 to 6 carbon atoms (i.e., $C_{1\text{-}6}$ alkyl) or 1 to 4 carbon atoms (i.e., $C_{1\text{-}4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2\text{-}20}$ alkenyl), 2 to 8 carbon atoms (i.e., $C_{2\text{-}8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{1-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkoxyalkyl" refers to the group "alkyl-O-alkyl".

"Alkylthio" refers to the group "alkyl-S—". "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group —C(O)NR$^y$R$^z$ and an "N-amido" group which refers to the group —NR$^y$C(O)R$^y$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aminoalkyl" refers to the group "-alkyl-NR$^y$R$^z$," wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR$^y$)(NR$^z_2$), wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl or heteroaryl; each of which may be optionally substituted, as defined herein.

"Cyanoalkyl" refers to refers to an alkyl group as defined above, wherein one or more (e.g., one to three) hydrogen atoms are replaced by a cyano (—CN) group.

"Cycloalkyl" refers to a saturated or partially unsaturated cyclic alkyl group having a single ring or multiple rings including fused, bridged and spiro ring systems. The term "cycloalkyl" includes cycloalkynyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkoxy" refers to "—O-cycloalkyl."

"Cycloalkylalkyl" refers to the group "cycloalkyl-alkyl-".

"Cycloalkylalkoxy" refers to "—O-alkyl-cycloalkyl."

"Guanidino" refers to —NR$^y$C(=NR$^z$)(NR$^y$R$^z$), wherein each R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., one to five or one to three) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., one to five or one to three) hydrogen atoms are replaced by a halogen.

"Hydroxyalkyl" refers to an alkyl group as defined above, wherein one or more (e.g., one to five or one to three) hydrogen atoms are replaced by a hydroxy group.

"Heteroalkyl" refers to an alkyl group in which one or more (e.g., one to five or one to three) of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroalkylene" refers to a divalent alkyl group (i.e., alkylene) in which one or more (e.g., one to five or one to three) of the carbon atoms (and any associated hydrogen atoms) are each independently replaced with the same or different heteroatomic group. "Heteroalkylene" groups must have at least one carbon and at least one heteroatomic group within the chain. The term "heteroalkylene" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkylene groups include, e.g., —CH$_2$OCH$_2$—, —CH(CH$_3$)OCH$_2$—, —CH$_2$CH$_2$OCH$_2$—, —CH$_2$CH$_2$OCH$_2$CH$_2$OCH$_2$—, —CH$_2$SCH$_2$—, —CH(CH$_3$)SCH$_2$—, —CH$_2$CH$_2$SCH$_2$—, —CH$_2$CH$_2$SCH$_2$CH$_2$SCH$_2$—, —CH$_2$S(O)$_2$CH$_2$—, —CH(CH$_3$)S(O)$_2$CH$_2$—, —CH$_2$CH$_2$S(O)$_2$CH$_2$—, —CH$_2$CH$_2$S(O)$_2$CH$_2$CH$_2$OCH$_2$—, —CH$_2$NR$^y$CH$_2$—, —CH(CH$_3$)NR$^y$CH$_2$—, —CH$_2$CH$_2$NR$^y$CH$_2$—, —CH$_2$CH$_2$NR$^y$CH$_2$CH$_2$NR$^y$CH$_2$—, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkylene includes 1 to 10 carbon atoms, 1 to 8 carbon atoms, or 1 to 4 carbon atoms; and 1 to 3 heteroatoms, 1 to 2 heteroatoms, or 1 heteroatom. As used herein, the term "heteroalkylene" does not include groups such as amides or other functional groups having an oxo present on one or more carbon atoms.

"Heteroaryl" refers to an aromatic group having a single ring, multiple rings or multiple fused rings, with one or more ring heteroatoms independently selected from nitrogen, oxygen and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems. 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzthiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., one to three or one or two) oxo (=O) or N-oxide (—O$^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-".

"Oxime" refers to the group —$CR^y$(=NOH) wherein $R^y$ is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —$S(O)_2R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluene sulfonyl.

"Sulfinyl" refers to the group —$S(O)R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., one to five or one to three) hydrogen atoms on the designated atom or group may or may not be replaced by a moiety other than hydrogen.

In certain embodiments, $R^y$ and $R^z$ as used herein are optionally substituted. In certain embodiments, $R^y$ and $R^z$ as used herein are unsubstituted.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide or —$Si(R^y)_3$ wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., one to five or one to three) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}OR^g$, —$NR^gS(=O)_{1-2}NR^gR^h$, =$NSO_2R^g$, =$NOR^g$, —$S(=O)_{1-2}NR^gR^h$, —$SF_5$, —$SCF_3$ or —$OCF_3$. In certain embodiments, "substituted" also means any of the above groups in which one or more (e.g., one to five or one to three) hydrogen atoms are replaced with —$C(=O)R^g$, —$C(=O)OR^g$, —$C(=O)NR^gR^h$, —$CH_2SO_2R^g$, —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., one to five or one to three) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl)substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more (e.g., one to five or one to three) atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more (e.g., one to five or one to three) hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more (e.g., one to five or one to three) hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also or a pharmaceutically acceptable salt, isotopically enriched analog, deuterated analog, stereoisomer, mixture of stereoisomers, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

2. Compounds

Provided herein are compounds that are modulators of eukaryotic initiation factor 2B.

In certain embodiments, provided is a compound of Formula I:

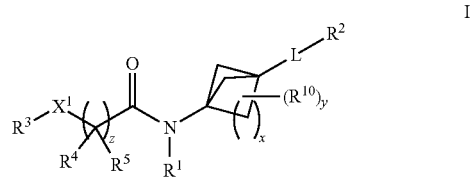

or a pharmaceutically acceptable salt, isotopically enriched analog, stereoisomer, mixture of stereoisomers or prodrug thereof, wherein:

L is a heteroalkylene optionally substituted with one to six $R^{10}$, or L is optionally substituted heterocyclyl or optionally substituted heteroaryl, provided that when L is optionally substituted heterocyclyl and bound to the bridged cycloalkyl via a nitrogen ring atom, a carbon atom on L adjacent to the point of attachment is not substituted with =O or =S;

x is 1 or 2;

z is 0 or 1, provided that when z is 0 and $X^1$ is O, then $R^3$ is not alkyl;

$X^1$ is O, $NR^9$ or a bond;

$R^1$ is hydrogen, $C_{1-12}$ alkyl, $C_{2-12}$ alkenyl, $C_{2-12}$ alkynyl, $C_{3-10}$ cycloalkyl or heterocyclyl, each of which, other than hydrogen, is optionally substituted with one or more halo, oxo, acetyl, amino, hydroxyl or $C_{1-12}$ alkyl, or $R^1$ and $R^5$ together form a heterocyclyl ring;

$R^2$ is hydrogen, $C_{1-12}$ alkyl, $C_{2-12}$ alkenyl, $C_{2-12}$ alkynyl, $C_{1-12}$ alkoxy, $C_{3-10}$ cycloalkyl, $C_{3-10}$ cycloalkoxy, heterocyclyl, aryl or heteroaryl, each of which, other than hydrogen, is optionally substituted with one or more $R^{11}$, provided that when L is a heteroalkylene, $R^2$ is $C_{3-10}$ cycloalkyl, heterocyclyl, aryl or heteroaryl, each of which is optionally substituted with one or more $R^{11}$;

$R^3$ is hydrogen, $C_{1-12}$ alkyl, $C_{2-12}$ alkenyl, $C_{2-12}$ alkynyl, $C_{3-10}$ cycloalkyl, heterocyclyl, aryl or heteroaryl, each of which, other than hydrogen, is optionally substituted with one or more $R^{11}$;

each of $R^4$ and $R^5$ is independently hydrogen, $C_{1-12}$ alkyl, $C_{2-12}$ alkenyl or $C_{2-12}$ alkynyl, each of which, other than hydrogen, is independently optionally substituted with one or more halo, oxo, acetyl, amino, or hydroxyl;

or $R^3$ and $R^4$, together with the atoms to which they are attached, join to form a $C_{3-10}$ cycloalkyl, heterocyclyl, or heteroaryl, each of which is optionally substituted with one or more $R^{11}$;

or $R^4$ and $R^5$, together with the atoms to which they are attached, join to form a $C_{3-10}$ cycloalkyl or heterocyclyl, each of which is optionally substituted with one or more $R^{11}$;

each of $R^6$, $R^7$ and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)$R^{20}$, —C(O)O$R^{20}$, —C(O)N$R^{20}R^{21}$, —S(O)$_{1-2}R^{20}$ or —S(O)$_{1-2}$ $NR^{20}$, wherein each alkyl, alkenyl, alkynyl, cycloalkyl, heterocyclyl, aryl and heteroaryl of $R^6$, $R^7$ and $R^8$ is independently optionally substituted with one or more $R^{12}$; or two of $R^6$, $R^7$ and $R^8$ are taken together with the atoms to which they are attached to form heterocyclyl independently optionally substituted by one or more halo, oxo, or $C_{1-12}$ alkyl independently optionally substituted by one or more oxo, halo, hydroxyl or amino;

$R^9$ is hydrogen, $C_{1-12}$ alkyl, $C_{2-12}$ alkenyl, $C_{2-12}$ alkynyl, $C_{3-10}$ cycloalkyl or heterocyclyl, each of which, other than hydrogen, is optionally substituted with one or more halo, oxo, acetyl, amino, hydroxyl or $C_{1-12}$ alkyl;

each $R^{10}$ is independently halo, $C_{1-12}$ alkyl, or $C_{1-12}$ haloalkyl;

y is 1, 2, 3, 4, 5, 6, 7, or 8;

each $R^{11}$ is independently halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$ or —$NR^6C(O)OR^7$, wherein each alkyl, alkenyl, alkynyl, cycloalkyl, heterocyclyl, aryl and heteroaryl of $R^{11}$ is independently optionally substituted with one or more $R^{12}$;

each $R^{12}$ is independently halo, cyano, nitro, oxo, —$OR^{30}$, —$SR^{30}$, —$SF_5$, —$NR^{30}R^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{30}$, —$C(O)OR^{30}$, —$OC(O)OR^{30}$, —$OC(O)R^{30}$, —$C(O)NR^{30}R^{31}$, —$OC(O)NR^{30}R^{31}$, —$NR^{30}C(O)NR^{30}R^{31}$, —$S(O)_{1-2}R^{30}$, —$S(O)_{1-2}NR$, —$NR^{30}S(O)_{1-2}R^{31}$, —$NR^{30}S(O)_{1-2}NR^{30}R^{31}$, —$NR^{30}C(O)R^{31}$ or —$NR^{30}C(=O)OR^{31}$, wherein each alkyl, alkenyl, alkynyl, cycloalkyl, heterocyclyl, aryl and heteroaryl of $R^{12}$ is independently optionally substituted with one or more halo or $C_{1-12}$ alkyl independently optionally substituted by one or more oxo, halo, hydroxyl or amino;

each $R^{20}$ and $R^{21}$ is independently hydrogen or $C_{1-12}$ alkyl independently optionally substituted with one or more oxo, halo, hydroxyl or amino; or $R^{20}$ and $R^{21}$ are taken together with the atoms to which they are attached to form heterocyclyl independently optionally substituted by one or more halo or $C_{1-12}$ alkyl independently optionally substituted by one or more oxo, halo, hydroxyl or amino; and each $R^{30}$ and $R^{31}$ is independently hydrogen or $C_{1-12}$ alkyl independently optionally substituted with one or more oxo, halo, hydroxyl or amino; or $R^{30}$ and $R^{31}$ are taken together with the atoms to which they are attached to form heterocyclyl independently optionally substituted by one or more halo or $C_{1-12}$ alkyl independently optionally substituted by one or more oxo, halo, hydroxyl or amino.

In certain embodiments, provided is a compound of Formula IA:

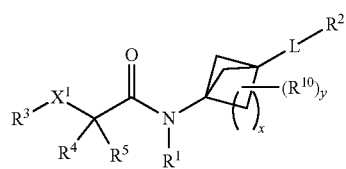

IA or a pharmaceutically acceptable salt, isotopically enriched analog, stereoisomer, mixture of stereoisomers or prodrug thereof, wherein:

L is a heteroalkylene optionally substituted with one to six $R^{10}$, or L is optionally substituted heterocyclyl or optionally substituted heteroaryl, provided that when L is optionally substituted heterocyclyl and bound to the bridged cycloalkyl via a nitrogen ring atom, a carbon atom on L adjacent to the point of attachment is not substituted with =O or =S;

x is 1 or 2;

$X^1$ is O, $NR^9$ or a bond;

$R^1$ is hydrogen, $C_{1-12}$ alkyl, $C_{2-12}$ alkenyl, $C_{2-12}$ alkynyl, $C_{3-10}$ cycloalkyl or heterocyclyl, each of which, other than hydrogen, is optionally substituted with one or more halo, oxo, acetyl, amino, hydroxyl or $C_{1-12}$ alkyl, or $R^1$ and $R^5$ together form a heterocyclyl ring;

$R^2$ is hydrogen, $C_{1-12}$ alkyl, $C_{2-12}$ alkenyl, $C_{2-12}$ alkynyl, $C_{1-12}$ alkoxy, $C_{3-10}$ cycloalkyl, $C_{3-10}$ cycloalkoxy, heterocyclyl, aryl or heteroaryl, each of which, other than hydrogen, is optionally substituted with one or more $R^{11}$, provided that when L is a heteroalkylene, $R^2$ is $C_{3-10}$ cycloalkyl, heterocyclyl, aryl or heteroaryl, each of which is optionally substituted with one or more $R^{11}$;

$R^3$ is hydrogen, $C_{1-12}$ alkyl, $C_{2-12}$ alkenyl, $C_{2-12}$ alkynyl, $C_{3-10}$ cycloalkyl, heterocyclyl, aryl or heteroaryl, each of which, other than hydrogen, is optionally substituted with one or more $R^{11}$;

each of $R^4$ and $R^5$ is independently hydrogen, $C_{1-12}$ alkyl, $C_{2-12}$ alkenyl or $C_{2-12}$ alkynyl, each of which, other than hydrogen, is independently optionally substituted with one or more halo, oxo, acetyl, amino, or hydroxyl;

or $R^3$ and $R^4$, together with the atoms to which they are attached, join to form a $C_{3-10}$ cycloalkyl, heterocyclyl, or heteroaryl, each of which is optionally substituted with one or more $R^{11}$;

or $R^4$ and $R^5$, together with the atoms to which they are attached, join to form a $C_{3-10}$ cycloalkyl or heterocyclyl, each of which is optionally substituted with one or more $R^{11}$;

each of $R^6$, $R^7$ and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$C(O)NR^{20}R^{21}$, —$S(O)_{1-2}R^{20}$ or —$S(O)_{1-2}NR^{20}$, wherein each alkyl, alkenyl, alkynyl, cycloalkyl, heterocyclyl, aryl and heteroaryl of $R^6$, $R^7$ and $R^8$ is independently optionally substituted with one or more $R^{12}$; or two of $R^6$, $R^7$ and $R^8$ are taken together with the atoms to which they are attached to form heterocyclyl independently optionally substituted by one or more halo, oxo, or $C_{1-12}$ alkyl independently optionally substituted by one or more oxo, halo, hydroxyl or amino;

$R^9$ is hydrogen. $C_{1-12}$ alkyl, $C_{2-12}$ alkenyl, $C_{2-12}$ alkynyl, $C_{3-10}$ cycloalkyl or heterocyclyl, each of which, other than hydrogen, is optionally substituted with one or more halo, oxo, acetyl, amino, hydroxyl or $C_{1-12}$ alkyl;

each $R^{10}$ is independently halo, $C_{1-12}$ alkyl, or $C_{1-12}$ haloalkyl;

y is 1, 2, 3, 4, 5, 6, 7, or 8;

each $R^{11}$ is independently halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$ or —$NR^6C$ (O)OR$^7$, wherein each alkyl, alkenyl, alkynyl, cycloalkyl, heterocyclyl, aryl and heteroaryl of R$^{11}$ is independently optionally substituted with one or more R$^{12}$;

each R$^{12}$ is independently halo, cyano, nitro, oxo, —OR$^{36}$, —SR$^{30}$, —SF$_5$, —NR$^{30}$R$^{31}$, C$_{1-12}$ alkyl, C$_{2-12}$ alkenyl, C$_{2-12}$ alkynyl, C$_{3-10}$ cycloalkyl, heterocyclyl, aryl, heteroaryl, —C(O)R$^{30}$, —C(O)OR$^{30}$, —OC(O)OR$^{30}$, —OC(O)OR$^{30}$, —C(O)NR$^{30}$R$^{31}$, —OC(O)NR$^{30}$R$^{31}$, —NR$^{30}$C(O)NR$^{30}$R$^{31}$, —S(O)$_{1-2}$R$^{30}$, —S(O)$_{1-2}$NR$^{30}$, —NR$^{30}$S(O)$_{1-2}$R$^{31}$, —NR$^{30}$S(O)$_{1-2}$NR$^{30}$R$^{31}$, —NR$^{30}$C(O)R$^{31}$ or —NR$^{30}$C(=O)OR$^{31}$, wherein each alkyl, alkenyl, alkynyl, cycloalkyl, heterocyclyl, aryl and heteroaryl of R$^{12}$ is independently optionally substituted with one or more halo or C$_{1-12}$ alkyl independently optionally substituted by one or more oxo, halo, hydroxyl or amino;

each R$^{20}$ and R$^{21}$ is independently hydrogen or C$_{1-12}$ alkyl independently optionally substituted with one or more oxo, halo, hydroxyl or amino; or R$^{20}$ and R$^{21}$ are taken together with the atoms to which they are attached to form heterocyclyl independently optionally substituted by one or more halo or C$_{1-12}$ alkyl independently optionally substituted by one or more oxo, halo, hydroxyl or amino; and each R$^{30}$ and R$^{31}$ is independently hydrogen or C$_{1-12}$ alkyl independently optionally substituted with one or more oxo, halo, hydroxyl or amino; or R$^{30}$ and R$^{31}$ are taken together with the atoms to which they are attached to form heterocyclyl independently optionally substituted by one or more halo or C$_{1-12}$ alkyl independently optionally substituted by one or more oxo, halo, hydroxyl or amino.

In certain embodiments, when R$^3$ is optionally substituted aryl or optionally substituted heteroaryl, z is 1, X$^1$ is O, and L is optionally substituted heteroaryl, L is not substituted with -L$^1$-R$^{14}$, wherein L$^1$ is an optionally substituted alkylene, optionally substituted heteroalkylene, or —O—, and R$^{14}$ is hydrogen, optionally substituted aryl, or optionally substituted heteroaryl.

In some embodiments, when z is 1, X$^1$ is O, R$^3$ is not optionally substituted aryl or optionally substituted heteroaryl.

In certain embodiments, when z is 0 and X$^1$ is a bond, then R$^3$ is not hydrogen or alkyl. In certain embodiments, when z is 0 and X$^1$ is O, then R$^3$ is not hydrogen or alkyl. In certain embodiments, when z is 0 and X$^1$ is O, then R$^3$ is not hydrogen or hydrogen. In certain embodiments, when z is 0 and X$^1$ is a bond, then R$^3$ is not hydrogen.

In certain embodiments, when R$^3$ is optionally substituted aryl or optionally substituted heteroaryl, z is 1, X$^1$ is O, and L is optionally substituted heteroaryl, L is not substituted with a group

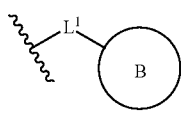

wherein:
L$^1$ is an C$_{1-6}$ alkylene, 2-7 membered heteroalkylene, or —O—, wherein each C$_{1-6}$ alkylene or 2-7 membered heteroalkylene is optionally substituted with 1-5 R$^x$;

B is hydrogen, phenyl, or 5-6-membered heteroaryl, wherein each phenyl or 5-6-membered heteroaryl is optionally substituted with 1-5 R$^Y$;

each R$^x$ is independently selected from the group consisting of C$_1$-C$_6$ alkyl, hydroxy-C$_1$-C$_6$ alkyl, halo-C$_1$-C$_6$ alkyl, amino-C$_1$-C$_6$ alkyl, cyano-C$_1$-C$_6$ alkyl, oxo, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, —SR$^B$, —S(O)R$^D$, and —S(O)$_2$R$^D$;

each R$^Y$ is independently selected from the group consisting of hydrogen, C$_1$-C$_6$ alkyl, hydroxy-C$_1$-C$_6$ alkyl, halo-C$_1$-C$_6$ alkyl, halo-C$_1$-C$_6$ alkoxy, amino-C$_1$-C$_6$ alkyl, cyano-C$_1$-C$_6$ alkyl, oxo, halo, cyano, —OR$^A$, —NR$^B$R$^C$, —NR$^B$C(O)R$^D$, —C(O)NR$^B$R$^C$, —C(O)R$^D$, —C(O)OH, —C(O)OR$^D$, —S(R$^F$)$_m$, —S(O)R$^D$, —S(O)$_2$R$^D$, and G$^1$;

or 2 R$^Y$ groups on adjacent atoms, together with the atoms to which they are attached form a 3-7-membered fused cycloalkyl, 3-7-membered fused heterocyclyl, aryl, or 5-6 membered fused heteroaryl optionally substituted with 1-5 R$^x$;

each G$^1$ is independently 3-7-membered cycloalkyl, 3-7-membered heterocyclyl, aryl, or 5-6-membered heteroaryl, wherein each 3-7-membered cycloalkyl, 3-7-membered heterocyclyl, aryl, or 5-6-membered heteroaryl is optionally substituted with 1-3 R$^z$;

each R$^Z$ is independently selected from the group consisting of C$_1$-C$_6$ alkyl, hydroxy-C$_1$-C$_6$ alkyl, halo-C$_1$-C$_6$ alkyl, halo, cyano, —OR$^A$, —NR$^B$R$^C$, —NR$^B$C(O)R$^D$, —C(O)NR$^B$R$^D$, —C(O)R$^D$, —C(O)OH, —C(O)OR$^D$, and —S(O)$_2$R$^D$; and R$^A$ is, at each occurrence, independently hydrogen, C$_1$-C$_6$ alkyl, halo-C$_1$-C$_6$ alkyl, —C(O)NR$^B$R$^C$, —C(O)R$^D$, —C(O)OH, or —C(O)OR$^D$ each of R$^B$ and R$^C$ is independently hydrogen or C$_1$-C$_6$ alkyl; or R$^B$ and R$^C$ together with the atom to which they are attached form a 3-7-membered heterocyclyl ring optionally substituted with 1-3 R$^z$;

each R$^D$ is independently C$_1$-C$_6$ alkyl or halo-C$_1$-C$_6$ alkyl;

each R$^E$ is independently hydrogen C$_1$-C$_6$ alkyl, or halo-C$_1$-C$_6$ alkyl;

each R$^F$ is independently hydrogen, C$_1$-C$_6$ alkyl, or halo; and m is 1, 3, or 5.

In certain embodiments, L is an optionally substituted heteroaryl ring.

In certain embodiments, L is an optionally substituted five membered C$_{2-4}$ heteroaryl ring.

In certain embodiments, L is an optionally substituted five membered C$_{2-4}$ heteroaryl ring having 1 to 3 nitrogen ring atoms.

In certain embodiments, L is an optionally substituted triazole, oxazole, imidazole, oxadiazole, or isoxazole.

In certain embodiments, L is an optionally substituted heterocyclyl ring.

In certain embodiments, L is an optionally substituted five membered C$_{2-4}$ heterocyclyl.

In certain embodiments, L is an optionally substituted five membered C$_{2-4}$ heterocyclyl ring having 1 to 3 nitrogen ring atoms.

In certain embodiments, L is an optionally substituted dihydroisoxazole or an optionally substituted oxazolidine.

In certain embodiments, L is further substituted with one to five R$^{13}$ where each R$^{13}$ is independently selected from halo, cyano, oxo, C$_{1-6}$alkyl, C$_{1-6}$ alkoxy, C$_{1-6}$ haloalkyl, or C$_{1-6}$ haloalkoxy.

In certain embodiments, L is heteroalkylene optionally substituted with one to six $R^{10}$.

In certain embodiments, L is a straight chain 2 to 4 atom heteroalkylene.

In certain embodiments, L is a straight chain heteroalkylene having 1 to 3 chain carbon atoms and one chain heteroatom selected from O, $NR^y$ and S.

In certain embodiments, L is —$CH_2O$—, —$CH_2OCH_2$—, —$CH_2CH_2O$—, or —$CF_2CH_2O$—.

In certain embodiments, when L is heteroalkylene, then the point of attachment of the heteroalkylene to the bridged cycloalkyl is through a carbon atom. In certain embodiments, when L is heteroalkylene, the point of attachment of the heteroalkylene to the bridged cycloalkyl may be through a carbon atom or a heteroatom. In certain embodiments, when L is heteroalkylene, the point of attachment of the heteroalkylene to —$R^2$ may be through a carbon atom or a heteroatom.

In certain embodiments, $R^3$ and $R^4$, together with the atoms to which they are attached, join to form a $C_{3-10}$ cycloalkyl or heterocyclyl, each of which is optionally substituted with one or more $R^{11}$.

In certain embodiments, provided is a compound of Formula II:

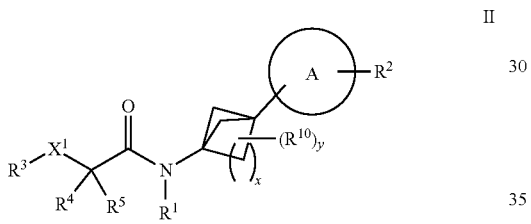

II or a pharmaceutically acceptable salt, isotopically enriched analog, stereoisomer, mixture of stereoisomers or prodrug thereof, wherein:

ring A is optionally substituted heterocyclyl or optionally substituted heteroaryl, provided that when ring A is optionally substituted heterocyclyl and bound to the bridged cycloalkyl via a nitrogen ring atom, a carbon atom on ring A adjacent to the point of attachment is not substituted with =O or =S;

x is 1 or 2;

$X^1$ is O, $NR^9$ or a bond;

$R^1$ is hydrogen, $C_{1-12}$ alkyl, $C_{2-12}$ alkenyl, $C_{2-12}$ alkynyl, $C_{3-10}$ cycloalkyl or heterocyclyl, each of which, other than hydrogen, is optionally substituted with one or more halo, oxo, acetyl, amino, hydroxyl or $C_{1-12}$ alkyl, or $R^1$ and $R^5$ together form a heterocyclyl ring;

$R^2$ is hydrogen, $C_{1-12}$ alkyl, $C_{2-12}$ alkenyl, $C_{2-12}$ alkynyl, $C_{1-12}$ alkoxy, $C_{3-10}$ cycloalkyl, $C_{3-10}$ cycloalkoxy, heterocyclyl, aryl or heteroaryl, each of which, other than hydrogen, is optionally substituted with one or more $R^{11}$;

$R^3$ is hydrogen, $C_{1-12}$ alkyl, $C_{2-12}$ alkenyl, $C_{2-12}$ alkynyl, $C_{3-10}$ cycloalkyl, heterocyclyl, aryl or heteroaryl, each of which, other than hydrogen, is optionally substituted with one or more $R^{11}$;

each of $R^4$ and $R^5$ is independently hydrogen, $C_{1-12}$ alkyl, $C_{2-12}$ alkenyl or $C_{2-12}$ alkynyl, each of which, other than hydrogen, is independently optionally substituted with one or more halo, oxo, acetyl, amino, or hydroxyl;

or $R^3$ and $R^4$, together with the atoms to which they are attached, join to form a $C_{3-10}$ cycloalkyl or heterocyclyl, each of which is optionally substituted with one or more $R^{11}$;

or $R^4$ and $R^5$, together with the atoms to which they are attached, join to form a $C_{3-10}$ cycloalkyl or heterocyclyl, each of which is optionally substituted with one or more $R^{11}$;

each of $R^6$, $R^7$ and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$C(O)NR^{20}R^{21}$, —$S(O)_{1-2}R^{20}$ or —$S(O)_{1-2}NR^{20}$, wherein each alkyl, alkenyl, alkynyl, cycloalkyl, heterocyclyl, aryl and heteroaryl of $R^6$, $R^7$ and $R^8$ is independently optionally substituted with one or more $R^{12}$; or two of $R^6$, $R^7$ and $R^8$ are taken together with the atoms to which they are attached to form heterocyclyl independently optionally substituted by one or more halo, oxo, or $C_{1-12}$ alkyl independently optionally substituted by one or more oxo, halo, hydroxyl or amino;

$R^9$ is hydrogen, $C_{1-12}$ alkyl, $C_{2-12}$ alkenyl, $C_{2-12}$ alkynyl, $C_{3-10}$ cycloalkyl or heterocyclyl, each of which, other than hydrogen, is optionally substituted with one or more halo, oxo, acetyl, amino, hydroxyl or $C_{1-12}$ alkyl;

each $R^{10}$ is independently halo, $C_{1-12}$ alkyl, or $C_{1-12}$ haloalkyl;

y is 1, 2, 3, 4, 5, 6, 7, or 8;

each $R^{11}$ is independently halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$ or —$NR^6C(O)OR^7$, wherein each alkyl, alkenyl, alkynyl, cycloalkyl, heterocyclyl, aryl and heteroaryl of $R^{11}$ is independently optionally substituted with one or more $R^{12}$;

each $R^{12}$ is independently halo, cyano, nitro, oxo, —$OR^{30}$, —$SR^{30}$, —$SF_5$, —$NR^{30}R^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{30}$, —$C(O)OR^{30}$, —$OC(O)OR^{30}$, —$OC(O)R^{30}$, —$C(O)NR^{30}R^{31}$, —$OC(O)NR^{30}R^{31}$, —$NR^{30}C(O)NR^{30}R^{31}$, —$S(O)_{1-2}R^{30}$, —$S(O)_{1-2}NR^{30}$, —$NR^{30}S(O)_{1-2}R^{31}$, —$NR^{30}S(O)_{1-2}NR^{30}R^{31}$, —$NR^{30}C(O)R^{31}$ or —$NR^{30}C(=O)OR^{31}$, wherein each alkyl, alkenyl, alkynyl, cycloalkyl, heterocyclyl, aryl and heteroaryl of $R^{12}$ is independently optionally substituted with one or more halo or $C_{1-12}$ alkyl independently optionally substituted by one or more oxo, halo, hydroxyl or amino;

each $R^{20}$ and $R^{21}$ is independently hydrogen or $C_{1-12}$ alkyl independently optionally substituted with one or more oxo, halo, hydroxyl or amino; or $R^{20}$ and $R^{21}$ are taken together with the atoms to which they are attached to form heterocyclyl independently optionally substituted by one or more halo or $C_{1-12}$ alkyl independently optionally substituted by one or more oxo, halo, hydroxyl or amino; and each $R^{30}$ and $R^{31}$ is independently hydrogen or $C_{1-12}$ alkyl independently optionally substituted with one or more oxo, halo, hydroxyl or amino; or $R^{30}$ and $R^{31}$ are taken together with the atoms to which they are attached to form heterocyclyl independently optionally substituted by one or more halo or $C_{1-12}$ alkyl independently optionally substituted by one or more oxo, halo, hydroxyl or amino.

In certain embodiments, $R^3$ is hydrogen, $C_{1-12}$ alkyl, $C_{2-12}$ alkenyl, $C_{2-12}$ alkynyl, $C_{3-10}$ cycloalkyl, heterocyclyl, aryl or heteroaryl, each of which, other than hydrogen, is optionally substituted with one or more $R^{11}$;

each of $R^4$ and $R^5$ is independently hydrogen, $C_{1-12}$ alkyl, $C_{2-12}$ alkenyl or $C_{2-12}$ alkynyl, each of which, other than hydrogen, is independently optionally substituted with one or more halo, oxo, acetyl, amino, or hydroxyl; and y is 1, 2, 3, 4, 5, or 6.

In certain embodiments is a compound of Formula IIA:

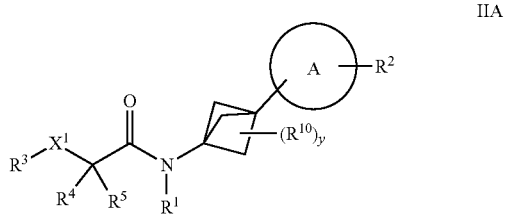

IIA or a pharmaceutically acceptable salt, isotopically enriched analog, stereoisomer, mixture of stereoisomers or prodrug thereof.

In certain embodiments is a compound of Formula IIB:

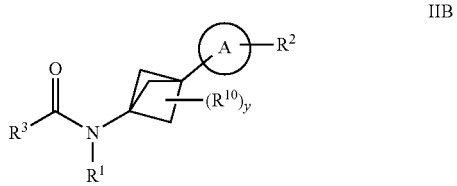

IIB or a pharmaceutically acceptable salt, isotopically enriched analog, stereoisomer, mixture of stereoisomers or prodrug thereof.

In certain embodiments of Formula II, IIA or IIB, $R^2$ is $C_{3-10}$ cycloalkyl optionally substituted with one or more $R^{11}$. In certain embodiments the cycloalkyl is cyclopropyl, cyclobutyl, cyclopentyl or cyclohexyl, each optionally substituted with one or more $R^{11}$. In certain embodiments of Formula II, IIA or IIB, each $R^{11}$ is independently halo, cyano, oxo, —$OR^6$, —$SR^6$, —$SF_5$, —$NR^6R^7$, $C_{1-12}$ alkyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$ or —$NR^6C(O)OR^7$, wherein each alkyl, alkenyl, alkynyl, cycloalkyl, heterocyclyl, aryl and heteroaryl of $R^{11}$ is independently optionally substituted with one or more $R^{12}$. In certain embodiments of Formula II, IIA or IIB, $R^2$ is $C_{3-10}$ cycloalkyl optionally substituted with —$OR^6$ and $R^6$ is $C_{1-12}$ alkyl optionally substituted with halo.

In certain embodiments of Formula II, IIA or IIB, $R^3$ is aryl or heteroaryl, each optionally substituted with one or more $R^{11}$. In certain embodiments of Formula II, IIA or IIB, $R^3$ is phenyl optionally substituted with one or more halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$ or —$NR^6C(O)OR^7$. In certain embodiments of Formula II, IIA or IIB, $R^3$ is phenyl optionally substituted with halo. In certain embodiments of Formula II, IIA or IIB, $R^2$ is $C_{3-10}$ cycloalkyl optionally substituted with —$OR^6$, $R^6$ is $C_{1-12}$ alkyl optionally substituted with halo, and $R^3$ is phenyl optionally substituted with one or more $R^{11}$.

In certain embodiments, ring A is an optionally substituted heteroaryl ring.

In certain embodiments, ring A is an optionally substituted five membered $C_{2-4}$ heteroaryl ring.

In certain embodiments, ring A is an optionally substituted five membered $C_{2-4}$ heteroaryl ring having 1 to 3 nitrogen ring atoms and optionally 1 or 2 oxygen and/or sulfur atoms. In certain embodiments, ring A is an optionally substituted five membered $C_{2-4}$ heteroaryl ring having 1 to 3 nitrogen ring atoms.

In certain embodiments, ring A is an optionally substituted triazole, oxazole, imidazole, oxadiazole, benzoxazole, pyrazole, triazole, thiadiazole, tetrazole, or isoxazole. In certain embodiments, ring A is an optionally substituted triazole, oxazole, imidazole, oxadiazole, or isoxazole.

In certain embodiments, ring A is an optionally substituted heterocyclyl ring.

In certain embodiments, ring A is an optionally substituted five membered $C_{2-4}$ heterocyclyl.

In certain embodiments, ring A is an optionally substituted five membered $C_{2-4}$ heterocyclyl ring having 1 to 3 nitrogen ring atoms and optionally 1 or 2 oxygen and/or sulfur atoms. In certain embodiments, ring A is an optionally substituted five membered $C_{2-4}$ heterocyclyl ring having 1 to 3 nitrogen ring atoms.

In certain embodiments, ring A is an optionally substituted pyrrolidine, imidazolidine, dihydropyrrole, oxathiazolidine, dihydroisoxazole or oxazolidine. In certain embodiments, ring A is an optionally substituted dihydroisoxazole or an optionally substituted oxazolidine.

In certain embodiments, ring A can be further substituted with one to five $R^{13}$ where each $R^{13}$ is independently selected from halo, cyano, oxo, thioxo, $C_{1-6}$ alkyl, $C_{1-6}$ alkoxy, $C_{1-6}$ haloalkyl, or $C_{1-6}$ haloalkoxy. In certain embodiments, ring A can be further substituted with one to five $R^{13}$ where each $R^{13}$ is independently selected from halo, cyano, oxo, $C_{1-6}$ alkyl, $C_{1-6}$alkoxy, $C_{1-6}$haloalkyl, or $C_{1-6}$ haloalkoxy.

In certain embodiments, ring A is unsubstituted (i.e., not further substituted other than by $R^2$). In certain embodiments, ring A is not further substituted and $R^2$ is $C_{3-10}$ cycloalkyl optionally substituted with one or more $R^{11}$. In certain embodiments, ring A is an unsubstituted five membered $C_{2-4}$ heteroaryl ring having 1 to 3 nitrogen ring atoms and optionally 1 or 2 oxygen and/or sulfur atoms. In certain embodiments, ring A is an unsubstituted five membered $C_{2-4}$ heteroaryl ring having 1 to 3 nitrogen ring atoms. In certain embodiments, ring A is an unsubstituted five membered $C_{2-4}$ heteroaryl ring having 1 to 3 nitrogen ring atoms and optionally 1 or 2 oxygen and/or sulfur atoms. In certain embodiments, ring A is an unsubstituted five membered $C_{2-4}$ heteroaryl ring having 1 to 3 nitrogen ring atoms.

In certain embodiments, $R^2$ is hydrogen or halo. In certain embodiments, $R^2$ is hydrogen.

In certain embodiments, $R^2$ is $C_{1-12}$ alkyl, $C_{1-12}$ alkoxy, $C_{3-10}$ cycloalkyl, $C_{3-10}$ cycloalkoxy, heterocyclyl, or aryl, each of which is optionally substituted with one to six $R^{11}$.

In certain embodiments, $R^2$ is $C_{3-10}$ cycloalkyl optionally substituted with one to six $R^{11}$.

In certain embodiments, $R^2$ is cyclopropyl, cyclobutyl, cyclopentyl, phenyl, azetidinyl, pyrrolidinyl, tetrahydrofuranyl, methyl, ethyl, propyl, methoxy, or cyclobutoxy, each which is optionally substituted with one to six $R^{11}$. In certain embodiments, $R^2$ is cyclopropyl, cyclobutyl, cyclopentyl, phenyl, azetidinyl, pyrrolidinyl, tetrahydrofuranyl, methyl, ethyl, propyl, methoxy, or cyclobutoxy, each which is optionally substituted with one to six $R^{10}$.

In certain embodiments, $R^2$ is substituted with one to six $R^{11}$. In certain embodiments, $R^2$ is substituted with at least one $R^{11}$.

In certain embodiments, $R^2$ is $C_{3-10}$ cycloalkyl substituted with $C_{1-6}$ haloalkoxy. In certain embodiments, $R^2$ is cycloalkyl substituted with trifluoromethoxy. In certain embodiments, $R^2$ is 3-(trifluoromethoxy)cyclobutyl.

In certain embodiments, $R^2$ is $C_{3-10}$ cycloalkyl substituted with ($C_{1-6}$haloalkoxy)methyl. In certain embodiments, $R^2$ is cycloalkyl substituted with (trifluoromethoxy)methyl. In certain embodiments, $R^2$ is 2-((trifluoromethoxy)methyl)cyclopropyl.

In certain embodiments, $R^{11}$ is hydroxyl, halo($C_{1-6}$ alkoxy), halo, cycloalkyl, cycloalkoxy, phenyl, $C_{1-6}$ alkoxycarbonyl, cyano, halo($C_{1-6}$ alkyl), halo($C_{1-6}$alkoxy)cycloalkoxy, halo($C_{1-6}$ alkoxy)alkyl, halo(heterocyclyl) or halophenoxy.

In certain embodiments, $R^{11}$ is 1,1,1-trifluoroethyl, 1,1-difluoroethyl, triazol-2-yl, trifluoromethylthio, trifluoromethoxy, (3,3-difluoropyrrolidin-1-yl)methyl, 2,2,2-trifluoro-1-methyl-ethyl, 2,2,2-trifluoroethyl, 2,2-difluoroethyl, 3-(trifluoromethyl)azetidin-1-yl, chloro, difluoromethoxy, difluoromethyl, fluoro, methyl, tort-butoxycarbonyl, trifluoro methoxymethyl, or cyclopropyl.

In certain embodiments, $R^2$ is (4-chloro-3-fluoro-phenoxy)methyl, 1-fluorocyclopropyl, 1,1,1-trifluoroethyl, 2-methylcyclopropyl, 2,2-difluorocyclopropyl, 3-(difluoromethoxy)cyclobutyl, 3-(trifluoromethoxy)cyclobutoxymethyl, 3-(trifluoromethoxy)cyclobutyl, 3-(trifluoromethoxy)propyl, 3-(trifluoromethyl)cyclobutyl, 3-cyanocyclobutyl, 3,3-difluoro-1-methyl-propyl, 4-chloro-3-fluoro-phenyl, 4-chlorophenyl, benzyl, cyanocyclobutyl, cyclobutoxymethyl, cyclobutyl, cyclobutylmethyl, cyclopentyl, cyclopropyl, cyclopropylethyl, cyclopropylmethyl, hydroxycyclobutyl, methyl, N-tert-butoxy(carbonyl)azetidin-3-yl, N-tert-butoxy(carbonyl)pyrrolidin-3-yl, tetrahydrofuranyl, trifluoroethyl, trifluoromethoxy, (thfluoromethoxy)cyclobutoxy, trifluoromethoxyethyl, or trifluoromethoxymethyl.

In certain embodiments, $R^2$ is (4-chloro-3-fluoro-phenoxy)methyl, 1-fluorocyclopropyl, 1,1,1-trifluoroethyl, 2-methylcyclopropyl, 2,2-difluorocyclopropyl, 3-(difluoromethoxy)cyclobutyl, 3-(trifluoromethoxy)cyclobutoxymethyl, 3-(trifluoromethoxy)cyclobutyl, 3-(trifluoromethoxy)propyl, 3-(trifluoromethyl)cyclobutyl, 3-cyanocyclobutyl, 3,3-difluoro-1-methyl-propyl, 4-chloro-3-fluoro-phenyl, 4-chlorophenyl, benzyl, cyanocyclobutyl, cyclobutoxymethyl, cyclobutyl, cyclobutylmethyl, cyclopentyl, cyclopropyl, cyclopropylethyl, cyclopropylmethyl, hydroxycyclobutyl, methyl, N-tert-butoxy(carbonyl)azetidin-3-yl, N-tert-butoxy(carbonyl)pyrrolidin-3-yl, tetrahydrofuranyl, trifluoroethyl, trifluoromethoxy, (trifluoromethoxy)cyclobutoxy, trifluoromethoxyethyl, trifluoromethoxymethyl, 3-(1,1-difluoroethyl)cyclobutyl, 3-(1,1,1-trifluoroethyl)azetidinyl, 3-(triazol-2-yl)cyclobutyl, 3-(trifluoromethylthio)cyclobutyl, or 3-(cyclopropyl)cyclobutyl.

In embodiments, $R^2$ is (4-chloro-3-fluoro-phenoxy)methyl, 1-fluorocyclopropyl, 1,1,1-trifluoroethyl, 2-methylcyclopropyl, 2,2-difluorocyclopropyl, 3-(difluoromethoxy)cyclobutyl, 3-(trifluoromethoxy)cyclobutoxymethyl, 3-(trifluoromethoxy)cyclobutyl, 3-(trifluoromethoxy)propyl, 3-(trifluoromethyl)cyclobutyl, 3-cyanocyclobutyl, 3,3-difluoro-1-methyl-propyl, 4-chloro-3-fluoro-phenyl, 4-chlorophenyl, benzyl, cyanocyclobutyl, cyclobutoxymethyl, cyclobutyl, cyclobutylmethyl, cyclopentyl, cyclopropyl, cyclopropylethyl, cyclopropylmethyl, hydroxycyclobutyl, methyl, N-tert-butoxy(carbonyl)azetidin-3-yl, N-tert-butoxy(carbonyl)pyrrolidin-3-yl, tetrahydrofuranyl, trifluoroethyl, trifluoromethoxy, (trifluoromethoxy)cyclobutoxy, trifluoromethoxyethyl, trifluoromethoxymethyl, 3-(1,1-difluoroethyl)cyclobutyl, 3-(1,1,1-trifluoroethyl)azetidinyl, 3-(triazol-2-yl)cyclobutyl, 3-(trifluoromethylthio)cyclobutyl, 3-(cyclopropyl)cyclobutyl, (3,3-difluoroazetidin-1-yl)methyl, (3,3-difluoropyrrolidin-1-yl)methyl, 1-(2,2,2-trifluoro-1-methyl-ethyl)azetidin-3-yl, 1-(2,2,2-trifluoroethyl)azetidin-3-yl, 1-(2,2,2-trifluoroethyl)pyrazol-3-yl, 1-(2,2,2-trifluoroethyl)pyrazol-4-yl, 1-(2,2-difluoroethyl)azetidin-3-yl, 1-tert-butoxycarbonyl-2-methylazetidin-3-yl, 2-(4-chloro-3-fluoro-phenyl, 2-(difluoromethyl)cyclopropyl, 2-(trifluoromethoxymethyl)cyclopropyl, 2,2-difluoro-1,1-dimethyl-ethyl, 2-methyl-1-(2,2,2-trifluoroethyl)azetidin-3-yl, 3-(trifluoromethoxymethyl)cyclobutyl, 3-(trifluoromethyl)azetidin-1-yl, 3-fluoro-1-(2,2,2-trifluoroethyl)azetidin-3-yl, 4-(2,2,2-trifluoroethyl)morpholin-2-yl, 4-tert-butoxycarbonyl-morpholin-2-yl, 5-(trifluoromethoxy)methyl)tetrahydrofuran-2-yl, 2-((trifluoromethoxy)methyl)cyclopropyl, or 5-fluoro-3-pyridyl.

In certain embodiments, $R^2$ is (4-chloro-3-fluoro-phenoxy)methyl, 1-fluorocyclopropyl, 1,1,1-trifluoroethyl, 2-methylcyclopropyl, 2,2-difluorocyclopropyl, 3-(difluoromethoxy)cyclobutyl, 3-(trifluoromethoxy)cyclobutoxymethyl, 3-(trifluoromethoxy)cyclobutyl, 3-(trifluoromethoxy)propyl, 3-(trifluoromethyl)cyclobutyl, 3-cyanocyclobutyl, 3,3-difluoro-1-methyl-propyl, 4-chloro-3-fluoro-phenyl, phenyl, 3-(trifluoromethyl)phenyl, 2-hydroxymethyl-4-(trifluoromethyl)phenyl, 2-fluoro-4-(trifluoromethyl)phenyl, 3-fluoro-4-(trifluoromethyl)phenyl, 4-(trifluoromethyl)phenyl, 2,4-difluorophenyl, 4-chloro-2,6-difluorophenyl, 4-chloro-2,3-difluorophenyl, 4-chloro-2,5-difluorophenyl, 3,4-difluorophenyl, 4-fluorophenyl, 3-fluorophenyl, 3,4-difluorophenyl, 3-fluoro-4-methylphenyl, 3-fluoro-2-methylphenyl, 4-fluoro-3-methylphenyl, 4-chloro-2-fluoro-phenyl, 5-(trifluoromethyl)-2-pyridyl, 6-(trifluoromethyl)-2-pyridyl, 2-(trifluoromethyl)pyrimidin-5-yl, 5-fluoropyridin-3-yl, 1,2,3-triazol-2-yl)cyclobut-3-yl, 1,2,3-triazol-2-yl)cyclobut-1-yl, 2-hydroxy-4-(trifluoromethyl)phenyl, 2-cyano-4-(trifluoromethyl)phenyl, 2,2-difluorobenzo[d][1,3]dioxol-5-yl, 3-((tert-butyldimethylsilyl)oxy)cyclobutyl, 5-(trifluoromethyl)-4,5-dihydrooxazol-2-yl, 2-methoxycarbonyl-4-(trifluoromethyl)phenyl, 2-(trifluoromethoxy)ethoxy, 4-chlorophenyl, benzyl, 2-cyanocyclobutyl, 2-hydroxycyclobutyl, cyclobutoxymethyl, cyclobutyl, cyclobutylmethyl, cyclopentyl, cyclopropyl, cyclopropylethyl, cyclopropylmethyl, hydroxycyclobutyl, methyl, N-tert-butoxy(carbonyl)azetidin-3-yl, N-tert-butoxy(carbonyl)pyrrolidin-3-yl, tetrahydrofuranyl, trifluoroethyl, trifluoromethoxy, (trifluoromethoxy)cyclobutoxy, trifluoromethoxyethyl, trifluoromethoxymethyl, 3-(1,1-difluoroethyl)cyclobutyl, 3-(1,1,1-trifluoroethyl)azetidinyl, 3-(triazol-2-yl)cyclobutyl, 3-(trifluoromethylthio)cyclobutyl, 3-(cyclopropyl)cyclobutyl, (3,3-difluoroazetidin-1-yl)methyl, (33-difluoropyrrolidin-1-yl)methyl, 1-(2,2,2-trifluoro-1-methyl-ethyl)azetidin-3-yl, 1-(2,2,2-trifluoroethyl)azetidin-3-yl, 1-(2,2,2-trifluoroethyl)pyrazol-3-yl, 1-(2,2,2-trifluoroethyl)pyrazol-4-yl, 1-(2,2- difluoroethyl)azetidin-3-yl, 1-tert-butoxycarbonyl-2-methylazetidin-3-yl, 2-(4-chloro-3-fluoro-phenyl, 2-(difluoromethyl)cyclopropyl, 2-(trifluoromethoxymethyl)cyclopropyl, 2,2-difluoro-1,1-dimethyl-ethyl, 2-methyl-1-(2,2,2-trifluoroethyl)azetidin-3-yl, -(trifluoromethoxymethyl)cyclobutyl, -(trifluoromethyl)azetidin-1-yl, 3-fluoro-1-(2,2,2-trifluoroethyl)azetidin-3-yl, 4-(2,2,2-trifluoroethyl)morpholin-2-yl, 4-tert-butoxycarbonyl-morpholin-2-yl, 5-(trifluoromethoxymethyl)tetrahydrofuran-2-yl, 2-((trifluoromethoxy)methyl)cyclopropyl or 5-fluoro-3-pyridyl.

In certain embodiments, $R^2$ is 3-(1,1-difluoroethyl)cyclobutyl, 3-(1,1,1-trifluoroethyl)azetidinyl, 3-(triazol-2-yl)cyclobutyl, 3-(trifluoromethylthio)cyclobutyl, or 3-(cyclopropyl)cyclobutyl.

In certain embodiments, L or ring A is (4-chloro-3-fluoro-phenoxy)methyl]-1,3,4-oxadiazol-2-yl, 1-(3-cyanocyclobutyl)triazol-4-yl, 1-(3-hydroxycyclobutyl)triazol-4-yl, 1-(4-chlorophenyl)triazol-4-yl, 1-benzyltriazol-4-yl, 1-cyclobutyltriazol-4-yl, 1H-1,2,3-triazol-4-yl, 2-(3-cyanocyclobutyl)triazol-4-yl, 2-(trifluoromethoxyethyl)-1,3,4-oxadiazol-2-yl, 2-cyclobutyltriazol-4-yl, 3-[(trifluoromethoxy)cyclobutoxy]-imidazol-1-yl, 3-cyanocyclobutyl)triazol-4-yl, 3-cyclobutylisoxazol-5-yl, 4-(cyclobutylmethyl)imidazol-1-yl, 4-[3-(trifluoromethoxy)cyclobutyl]imidazol-1-yl, 4-cyclobutylimidazol-1-yl, 4-cyclobutyloxazol-2-yl, 5-((4-chloro-3-fluorophenoxy)methyl)-4H-1,2,4-triazol-3-yl, 5-(1-fluorocyclopropyl)-1,3,4-oxadiazol-2-yl, 5-(2-cyclopropylethyl)-1,3,4-oxadiazol-2-yl, 5-(2,2-difluorocyclopropyl)-1,3,4-oxadiazol-2-yl, 5-(2,2,2-trifluoroethyl)-1,3,4-oxadiazol-2-yl, 5-(3-cyanocyclobutyl)-1,3,4-oxadiazol-2-yl, 5-(3,3-difluoro-1-methyl-propyl)-1,3,4-oxadiazol-2-yl, 5-(4-chloro-3-fluoro-phenyl)-1,3,4-oxadiazol-2-yl, 5-(cyclobutoxymethyl)-1,3,4-oxadiazol-2-yl, 5-(cyclobutylmethyl)-1,3,4-oxadiazol-2-yl, 5-(cyclopropylmethyl)-1,3,4-oxadiazol-2-yl, 5-(trifluoromethoxymethyl)-1,3,4-oxadiazol-2-yl, 5-[(4-chloro-3-fluoro-phenoxy)methyl]-1,3,4-oxadiazol-2-yl, 5-[[3-(trifluoromethoxy)cyclobutoxy]methyl]-1,3,4-oxadiazol-2-yl, 5-[2-methylcyclopropyl]-1,3,4-oxadiazol-2-yl, 5-[3-(trifluoromethoxy)cyclobutyl]-1,3,4-oxadiazol-2-yl, 5-[3-(trifluoromethoxy)propyl]-1,3,4-oxadiazol-2-yl, 5-[3-(trifluoromethyl)cyclobutyl]-1,3,4-oxadiazol-2-yl, 5-[N-(1,1,1-trifluoroethyl)azetidin-3-yl]-1,3,4-oxadiazol-2-yl, 5-[N-(1,1,1-trifluoroethyl)pyrrolidin-3-yl]-1,3,4-oxadiazol-2-yl, 5-[N-tert-butoxy(carbonyl)azetidin-3-yl]-1,3,4-oxadiazol-2-yl, 5-[N-tert-butoxy(carbonyl)pyrrolidin-3-yl]-1,3,4-oxadiazol-2-yl, 5-cyclobutyl-1,3,4-oxadiazol-2-yl, 5-cyclobutyl-4,5-dihydroisoxazol-3-yl, 5-cyclobutylisoxazol-3-yl, 5-cyclobutyloxazol-2-yl, 5-cyclopentyl-4,5-dihydroisoxazol-3-yl, or oxazolidin-2-one-5-yl.

In certain embodiments, when $R^2$ substituted cyclobutyl, the substituent on the cyclobutyl is cis. In certain embodiments, the substituent on the cyclobutyl is trans.

In certain embodiments, $X^1$ is O. In certain embodiments, $X^1$ is a bond.

In certain embodiments, z is 0 and $X^1$ is a bond.

In certain embodiments, z is 0, $X^1$ is a bond, and $R^3$ is $C_{1-12}$ alkyl, $C_{3-10}$ cycloalkyl, heterocyclyl, aryl or heteroaryl, each of which is optionally substituted with one or more $R^{11}$.

In certain embodiments, $R^3$ is $C_{1-12}$ alkyl, which is optionally substituted with one or more $R^{11}$.

In certain embodiments, z is 0. In certain embodiments, z is 1.

In certain embodiments, $R^3$ is $C_{3-10}$ cycloalkyl, heterocyclyl, aryl or heteroaryl, each of which is optionally substituted with one or more $R^{11}$.

In certain embodiments, $R^3$ is $C_{3-10}$ cycloalkyl, aryl, or heteroaryl, each of which is optionally substituted with one or more $R^{11}$.

In certain embodiments, $R^3$ is cyclobutyl, triazolyl or phenyl, each of which is optionally substituted with one or more $R^{11}$.

In certain embodiments, $R^3$ is cyclobutyl. In certain embodiments, $R^3$ is cyclobutyl and $R^{11}$ is trifluoromethoxy.

In certain embodiments, $R^3$ is optionally substituted phenyl.

In certain embodiments, $R^3$ is phenyl optionally substituted with one or more substituents independently selected from halo, cyano, $C_{1-12}$ alkyl optionally substituted with one or more halo and $C_{1-12}$ alkoxy optionally substituted with one or more halo.

In certain embodiments, $R^3$ is phenyl substituted with chloro, fluoro or a combination thereof.

In certain embodiments, $R^3$ is 4-chlorophenyl, 4-chloro-3-fluorophenyl or trifluoromethoxycyclobut-2-yl.

In certain embodiments, $R^3$ is 4-chlorophenyl, 4-chloro-3-fluorophenyl, trifluoromethoxycyclobut-2-yl(5-chloro-3-pyridyl)methyl, 1-(2,2,2-trifluoroethyl)azetidin-3-yl, 2-(trifluoromethoxy)ethyl, 2-spiro[2.3]hexan-5-yl, 3-(trifluoromethoxy)cyclobutyl, 3-(trifluoromethoxy)cyclobutyl]methyl, 3-(trifluoromethoxy)cyclopentyl, 3-(trifluoromethoxymethyl)cyclobutyl, 3-fluorophenyl, 4-cyclopropylphenoxy, 4-fluorophenyl, or 6,6-difluoro-3-bicyclo[3.1.0]hexanyl.

In certain embodiments, $R^3$ is 3,4-difluorophenyl, 2-(trifluoromethyl)pyridin-5-yl, 4-(trifluoromethyl)phenyl, 2-(4-fluoro-1H-pyrazol-1-yl)ethyl, 2-(trifluoromethoxy)ethyl, 1-(2,2,2-trifluoroethyl)piperidin-4-yl, 4-chlorophenyl, 3-chlorophenyl, 4-bromophenyl, 6-chlorochroman-2-yl, 6-fluorochroman-2-yl, 5-chlorobenzo[d]oxazol-2-yl, 6-(trifluoromethyl)quinolin-2-yl, 3-chloroquinolin-7-yl, 7-chloroquinolin-3-yl, 6-chloroquinolin-2-yl, 7-fluoroimidazo[1,2-a]pyridin-2-yl, 6-fluoropyrazolo[1,5-a]pyridin-2-yl, 3-(2H-1,2,3-triazol-2-yl)cyclobutyl, 3-(trifluoromethoxy)phenyl, 5-chlorobenzo[d]thiazol-2-yl, 7-chloro-[1,2,4]triazolo[1,5-a]pyridin-2-yl, 7-chloroimidazo[1,2-b]pyridazin-2-yl, 5-fluorobenzo[d]oxazol-2-yl, 7-bromoimidazo[1,2-a]pyridin-2-yl, 6-fluoroimidazo[1,2-a]pyridin-2-yl, 7-chloropyrrolo[1,2-c]pyrimidin-3-yl, 7-chloroisoquinolin-3-yl, 7-chlorocinnolin-3-yl, 7-bromoisoquinolin-3-yl, 7-(trifluoromethyl)imidazo[1,2-a]pyridin-2-yl, 6-(trifluoromethyl)imidazo[1,2-a]pyridin-2-yl, quinolin-2-yl, quinoxalin-2-yl, 6-fluoroquinolin-2-yl, 6-bromoquinolin-2-yl, quinazolin-2-yl, 6-chlorobenzo[d]thiazol-2-yl, 5-bromobenzo[d]oxazol-2-yl, 7-chloro-6-fluoroimidazo[1,2-a]pyridin-2-yl, 6-chloroquinazolin-2-yl, 6-chloro-7-fluoroquinolin-2-yl, 5-(trifluoromethyl)pyridin-2-yl, 1-(2-(trifluoromethoxy)ethyl)-1H-pyrazol-3-yl, 3-(trifluoromethoxy)cyclobutylmethyl, 3-(2-(trifluoromethoxy)ethoxy)cyclobutyl, 4-((trifluoromethoxy)methyl)cyclohexanyl, 1-(2,2,2-trifluoroethyl)azetidinyl, 3-ethoxycyclobutanyl, 3-cyanocyclobutyl, 2-(4-chlorophenyl)-1-hydroxyethyl, 4-chloro-3-(hydroxymethyl)phenyl, 2-(4-chlorophenyl)-2-hydroxyethyl, 3-(4-fluoro-1H-pyrazol-1-yl)cyclobutyl, 1-(trifluoromethoxy)propan-2-yl, 6-chloro-3,4-dihydroisoquinolin-2(1H)-yl, 2-(trifluoromethoxy)propyl, 1-(2-(trifluoromethoxy)ethyl)-1H-imidazol-4-yl, 4-chloro-3-fluorophenyl or trifluoromethoxycyclobut-2-yl.

In certain embodiments, $R^4$ and $R^5$ are H. In certain embodiments, $R^4$ and $R^5$ are each independently H, alkyl optionally substituted with hydroxy.

In certain embodiments, $R^1$ is H.

In certain embodiments, provided is a compound of Formula III:

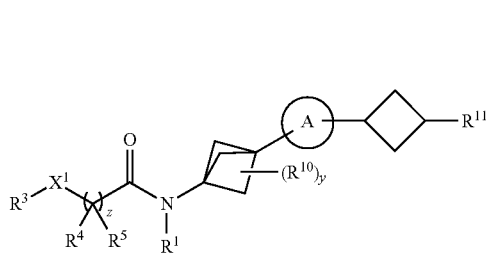

III wherein A, $X^1$, y, z, $R^1$, $R^3$, $R^4$, $R^5$, $R^{10}$ and $R^{11}$ are as defined herein.

In certain embodiments, provided is a compound of Formula IV:

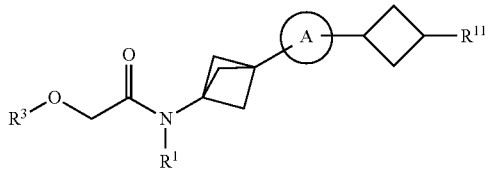

IV wherein A, $R^1$, $R^3$ and $R^{11}$ are as defined herein.

In certain embodiments, provided is a compound of Formula V:

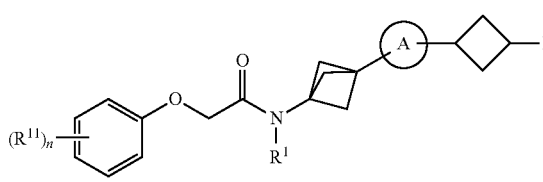

V wherein A, $R^1$ and $R^{11}$ are as defined herein, and n is 0, 1, 2 or 3.

In certain embodiments is a compound of Formula VI:

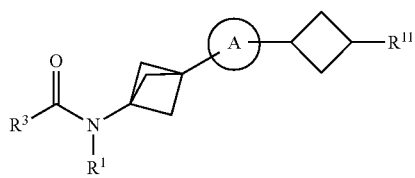

VI wherein A, $R^1$ and $R^{11}$ are as defined herein.

In certain embodiments, provided is a compound of Formula IIIA:

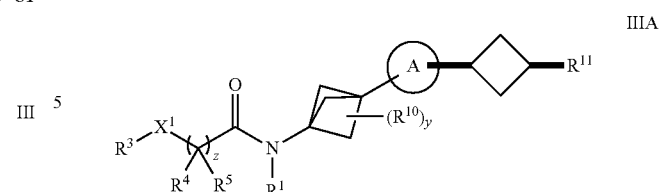

IIIA wherein A, $X^1$, y, z, $R^1$, $R^3$, $R^4$, $R^5$, $R^{10}$ and $R^{11}$ are as defined herein.

In certain embodiments, provided is a compound of Formula IVA:

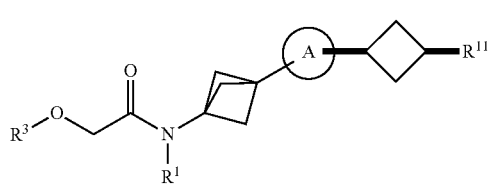

IVA wherein A, $R^1$, $R^3$ and $R^{11}$ are as defined herein.

In certain embodiments, provided is a compound of Formula VA:

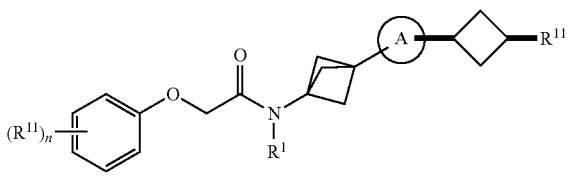

VA wherein A, $R^1$ and $R^{11}$ are as defined herein, and n is 0, 1, 2 or 3.

In certain embodiments is a compound of Formula VIA:

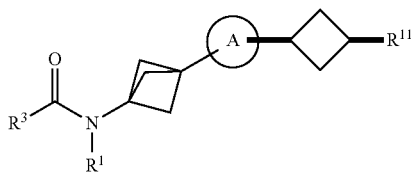

VIA wherein A, $R^1$, $R^3$ and $R^{11}$ are as defined herein.

In certain embodiments of Formula III, IV, V, VI, IIIA, IVA, VA or VIA, each $R^{11}$ is independently halo, cyano, oxo, —$OR^6$, —$SR^6$, —$SF_5$, —$NR^6R^7$, $C_{1-12}$ alkyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R$ or —$NR^6C(O)OR^7$, wherein each alkyl, alkenyl, alkynyl, cycloalkyl, heterocyclyl, aryl and heteroaryl of $R^{11}$ is independently optionally substituted with one or more $R^{12}$. In certain embodiments of Formula III, IV, V, VI, IIIA, IVA, VA or VIA, $R^2$ is $C_{3-10}$ cycloalkyl optionally substituted with —$OR^6$ and $R^6$ is $C_{1-12}$ alkyl optionally substituted with halo.

In certain embodiments of Formula III, IV, V, VI, IIIA, IVA, VA or VIA, R³ is aryl or heteroaryl, each optionally substituted with one or more R¹¹. In certain embodiments of Formula III, IV, V, VI, IIIA, WA, VA or VIA, R³ is phenyl optionally substituted with one or more halo, cyano, nitro, oxo, —OR⁶, —SR⁶, —SF₅, —NR⁶R⁷, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R⁶, —C(O)OR⁶, —OC(O)OR⁶, —OC(O)R⁶, —C(O)NR⁶R⁷, —OC(O)NR⁶R⁷, —NR⁶C(O)NR⁷R⁸, —S(O)$_{1-2}$R⁶, —S(O)$_{1-2}$NR⁶, —NR⁶S(O)$_{1-2}$R⁷, —NR⁶S(O)$_{1-2}$NR⁷R⁸, —NR⁶C(O)R⁷ or —NR⁶C(O)OR⁷. In certain embodiments of Formula III, IV, V, VI, IIIA, IVA, VA or VIA, R³ is phenyl optionally substituted with halo.

In certain embodiments, L or ring A is

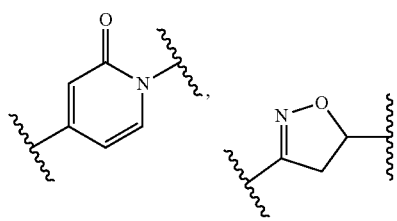

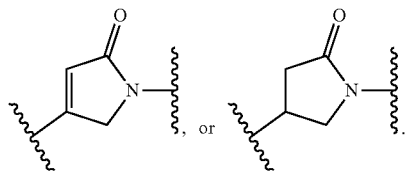

, or

In certain embodiments of Formulas I, IA or II, ring A is optionally substituted heteroaryl and R² is optionally substituted cycloalkyl.

In certain embodiments of Formulas I, IA or II, ring A is optionally substituted heteroaryl and R² is cyclopropyl, cyclobutyl or cyclopentyl, optionally substituted by halo, oxo, amino, hydroxyl, cyano, alkyl, alkenyl, alkynyl, or alkoxy, wherein the alkyl, alkenyl, alkynyl, and alkoxy are independently optionally substituted by oxo, halo, amino or hydroxyl.

In certain embodiments, provided is a compound selected from Table 1:

TABLE 1

| Ex. | Compound |
|---|---|
| 1 | |
| 2 | |

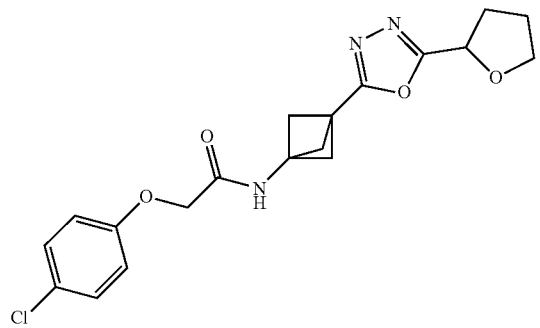 [SMILES: O=C(COc1ccc(Cl)cc1)NC12CC(c3nnc(C4CCCO4)o3)(C1)C2]

TABLE 1-continued
| Ex. | Compound |
|---|---|
| 3 | 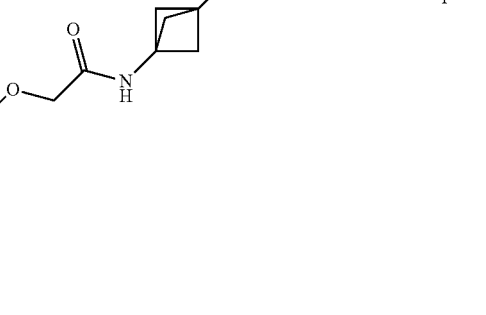 |
| 4 | 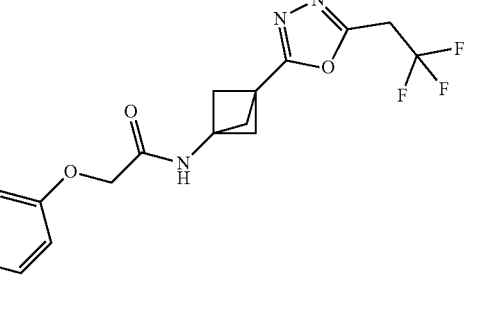 |
| 5 | 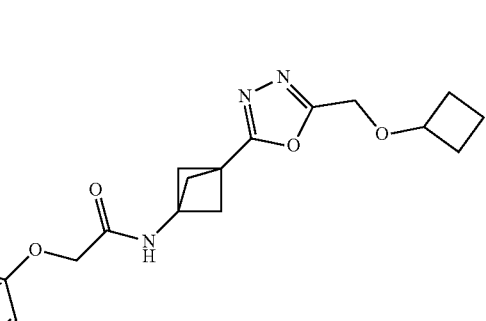 |
| 6 | 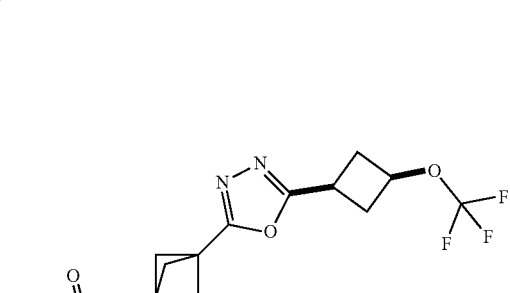 |

TABLE 1-continued
| Ex. | Compound |
|---|---|
| 7 | 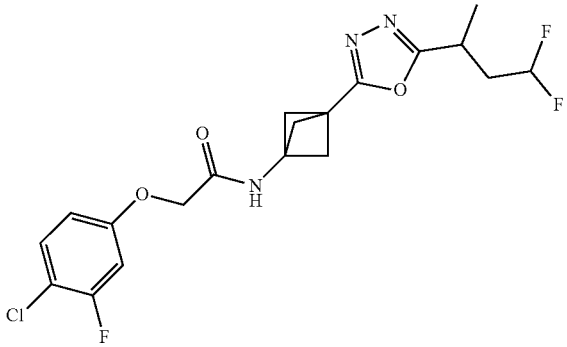 [SMILES: CC(CC(F)F)c1nnc(C23CC(NC(=O)COc4ccc(Cl)c(F)c4)(C2)C3)o1] |
| 8 | 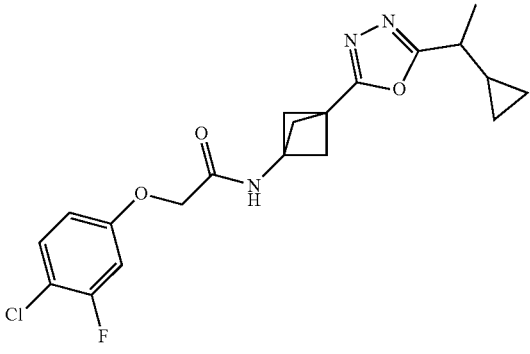 [SMILES: CC(c1nnc(C23CC(NC(=O)COc4ccc(Cl)c(F)c4)(C2)C3)o1)C1CC1] |
| 9 | 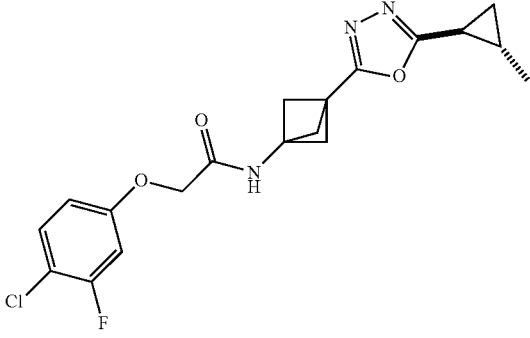 [SMILES: C[C@H]1C[C@@H]1c1nnc(C23CC(NC(=O)COc4ccc(Cl)c(F)c4)(C2)C3)o1] |
| 10 | 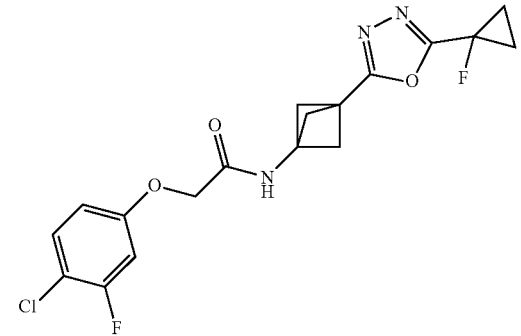 [SMILES: O=C(COc1ccc(Cl)c(F)c1)NC12CC(c3nnc(C4(F)CC4)o3)(C1)C2] |

TABLE 1-continued
| Ex. | Compound |
|---|---|
| 11 | 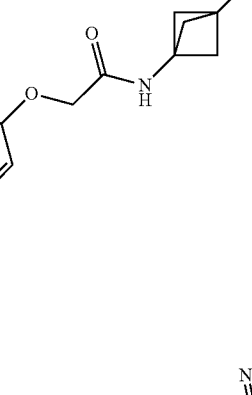 |
| 12 | 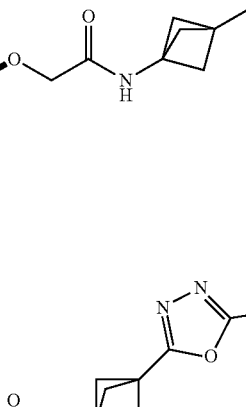 |
| 13 |  |
| 14 | 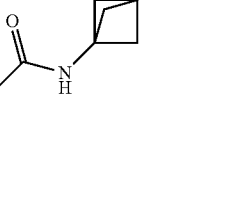 |

TABLE 1-continued
| Ex. | Compound |
|---|---|
| 15 | 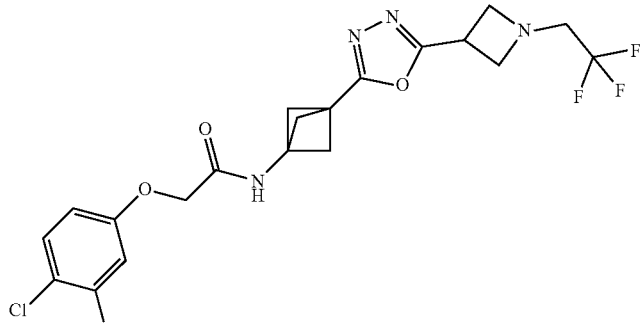 |
| 16 | 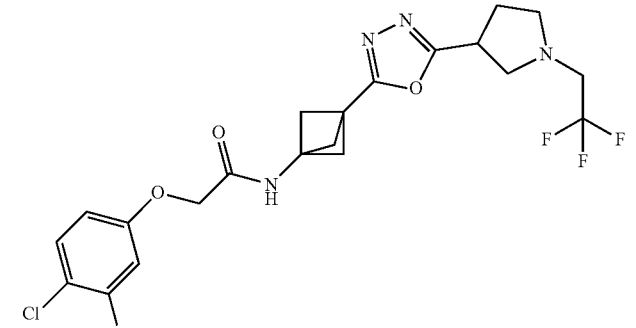 |
| 17 | 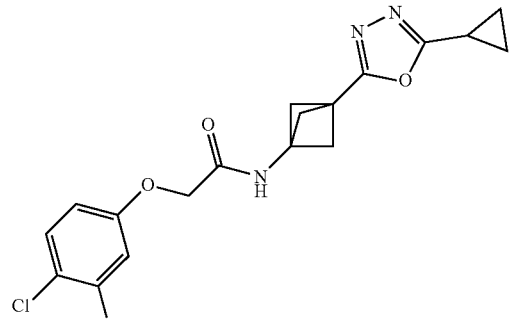 |
| 18 | 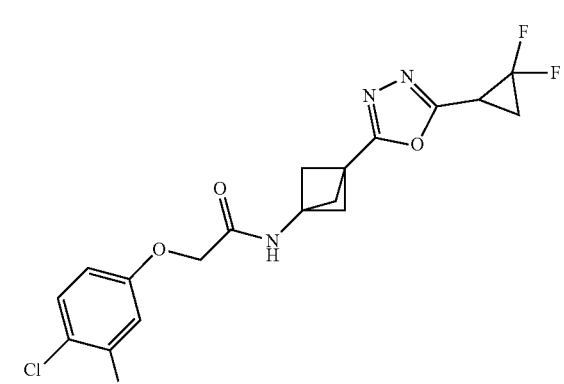 |

TABLE 1-continued
| Ex. | Compound |
|---|---|
| 19 | 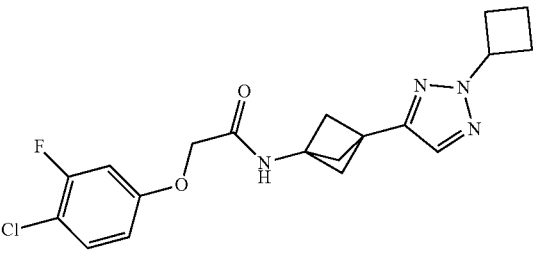 [SMILES: O=C(COc1ccc(Cl)c(F)c1)NC12CC(c3cnn(C4CCC4)n3)(C1)C2] |
| 20 | 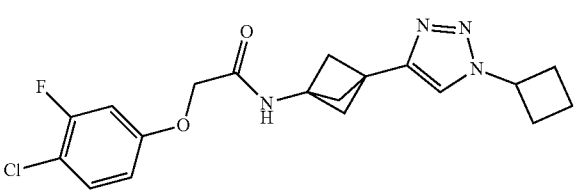 [SMILES: O=C(COc1ccc(Cl)c(F)c1)NC12CC(c3cn(C4CCC4)nn3)(C1)C2] |
| 21 | 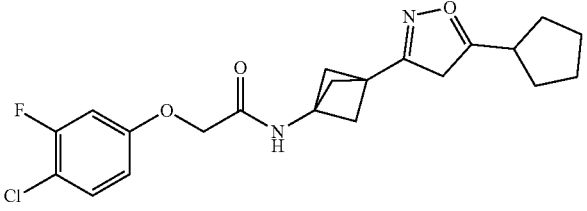 |
| 22 | 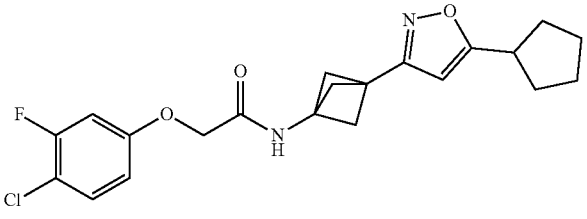 [SMILES: O=C(COc1ccc(Cl)c(F)c1)NC12CC(c3cc(C4CCCC4)on3)(C1)C2] |
| 23 | 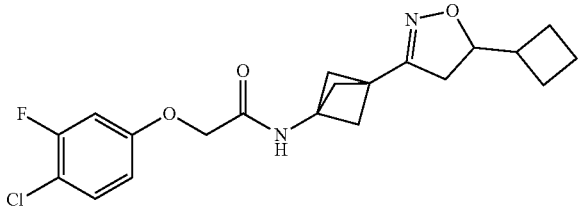 [SMILES: O=C(COc1ccc(Cl)c(F)c1)NC12CC(C3=NOC(C4CCC4)C3)(C1)C2] |
| 24 | 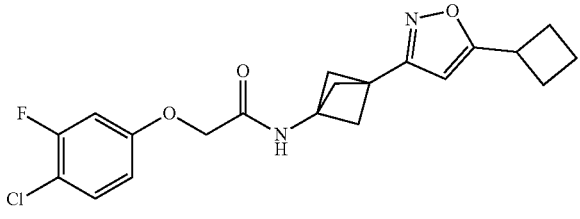 [SMILES: O=C(COc1ccc(Cl)c(F)c1)NC12CC(c3cc(C4CCC4)on3)(C1)C2] |

TABLE 1-continued

| Ex. | Compound |
|---|---|
| 25 | 2-(4-chloro-3-fluorophenoxy)-N-(3-(5-cyclobutyl-1,3,4-oxadiazol-2-yl)bicyclo[1.1.1]pentan-1-yl)acetamide |
| 26 | 2-(4-chloro-3-fluorophenoxy)-N-(3-(3-cyclobutylisoxazol-5-yl)bicyclo[1.1.1]pentan-1-yl)acetamide |
| 27 | 2-(4-chloro-3-fluorophenoxy)-N-(3-(4-cyclobutyloxazol-2-yl)bicyclo[1.1.1]pentan-1-yl)acetamide |
| 28 | N-(3-(1-(4-chlorophenyl)-1H-1,2,3-triazol-4-yl)bicyclo[1.1.1]pentan-1-yl)-2-cyclobutoxyacetamide |
| 29 | 3-(5-(3-(2-(4-chloro-3-fluorophenoxy)acetamido)bicyclo[1.1.1]pentan-1-yl)-1,3,4-oxadiazol-2-yl)cyclobutane-1-carbonitrile |

TABLE 1-continued

| Ex. | Compound |
|---|---|
| 31 | (structure) |
| 32 | (structure) |
| 33 | (structure) |
| 34 | (structure) |
| 35 | (structure) |

TABLE 1-continued
| Ex. | Compound |
|---|---|
| 36 | 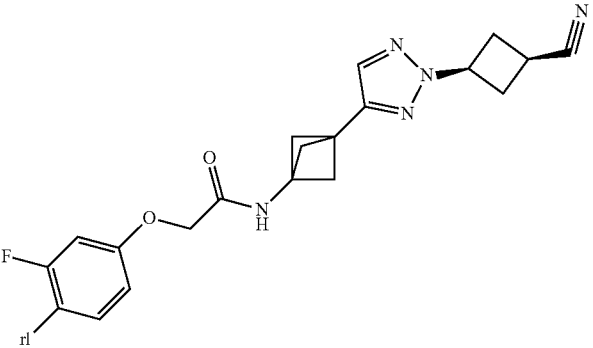 |
| 37 | 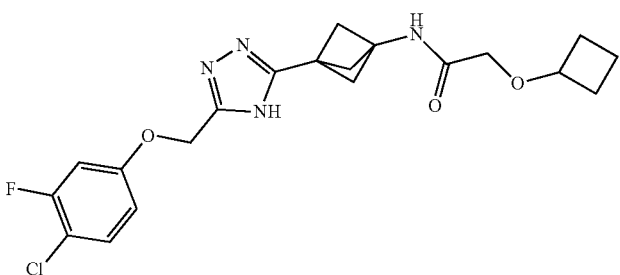 [SMILES: O=C(COC1CCC1)NC12CC(c3nnc(COc4ccc(Cl)c(F)c4)[nH]3)(C1)C2] |
| 38 | 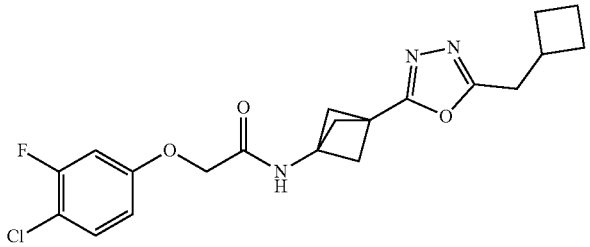 [SMILES: O=C(COc1ccc(Cl)c(F)c1)NC12CC(c3nnc(CC4CCC4)o3)(C1)C2] |
| 39 | 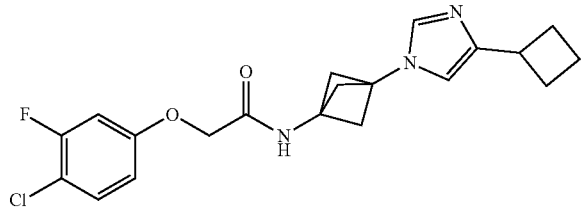 |
| 40 | 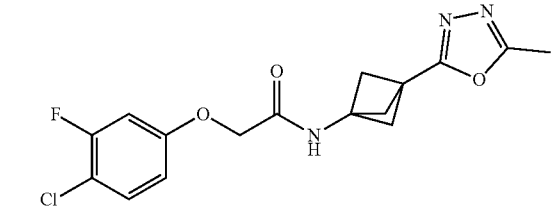 [SMILES: Cc1nnc(C23CC(NC(=O)COc4ccc(Cl)c(F)c4)(C2)C3)o1] |

TABLE 1-continued

| Ex. | Compound |
|---|---|
| 41 | |
| 42 | |
| 43 | |
| 44 | |
| 45 | |
| 46 | |

TABLE 1-continued
| Ex. | Compound |
|---|---|
| 47 | 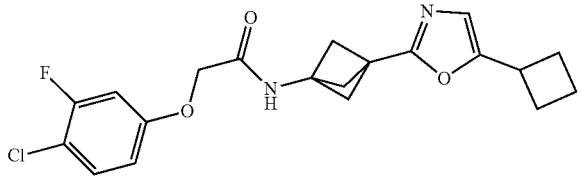 [SMILES: O=C(COc1ccc(Cl)c(F)c1)NC12CC(c3ncc(C4CCC4)o3)(C1)C2] |
| 48 | 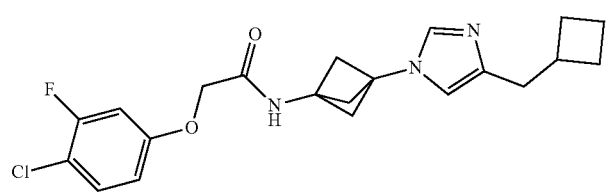 [SMILES: O=C(COc1ccc(Cl)c(F)c1)NC12CC(n3cnc(CC4CCC4)c3)(C1)C2] |
| 49 | 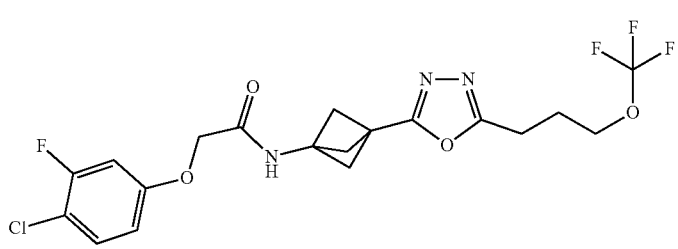 [SMILES: O=C(COc1ccc(Cl)c(F)c1)NC12CC(c3nnc(CCCOC(F)(F)F)o3)(C1)C2] |
| 50 | 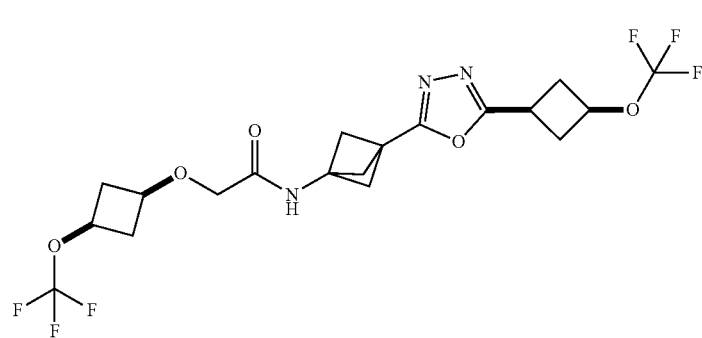 [SMILES: O=C(CO[C@H]1C[C@@H](OC(F)(F)F)C1)NC12CC(c3nnc([C@H]4C[C@@H](OC(F)(F)F)C4)o3)(C1)C2] |
| 51 | 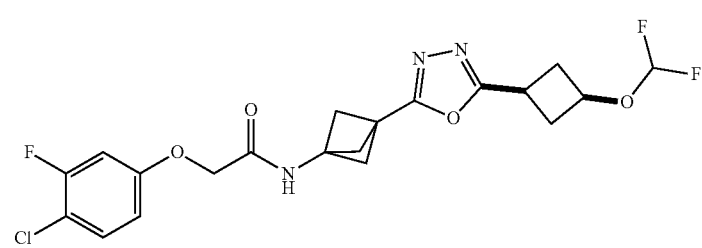 [SMILES: O=C(COc1ccc(Cl)c(F)c1)NC12CC(c3nnc([C@H]4C[C@@H](OC(F)F)C4)o3)(C1)C2] |
| 52 | 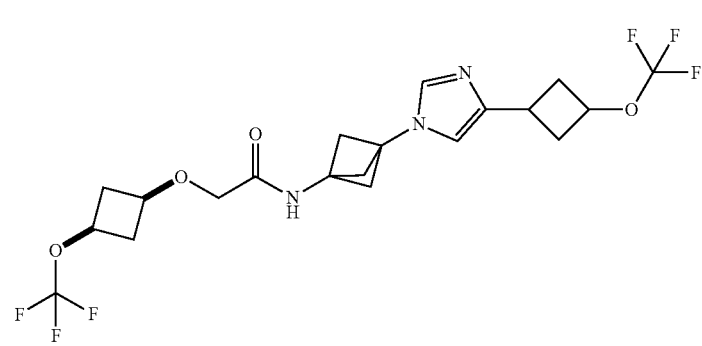 [SMILES: O=C(CO[C@H]1C[C@@H](OC(F)(F)F)C1)NC12CC(n3cnc(C4CC(OC(F)(F)F)C4)c3)(C1)C2] |

TABLE 1-continued

| Ex. | Compound |
|---|---|
| 53 | (structure) |
| 55 | (structure) |
| 56 | (structure) |
| 57 | (structure) |
| 58 | (structure) |
| 59 | (structure) |

TABLE 1-continued
| Ex. | Compound |
|---|---|
| 60 | 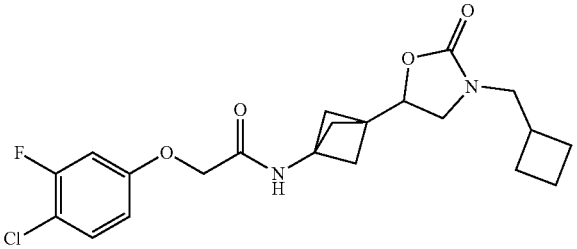 [SMILES: O=C(COc1ccc(Cl)c(F)c1)NC12CC(C3CN(CC4CCC4)C(=O)O3)(C1)C2] |
| 61 | 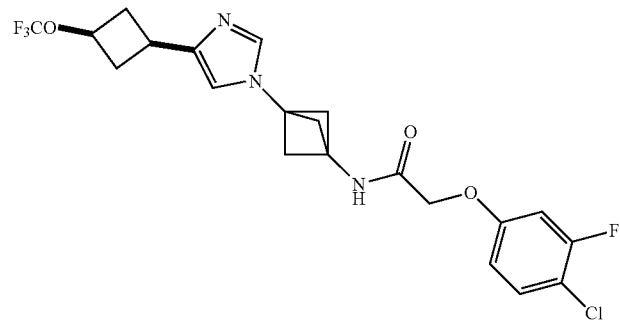 [SMILES: O=C(COc1ccc(Cl)c(F)c1)NC12CC(n3cnc([C@H]4C[C@@H](OC(F)(F)F)C4)c3)(C1)C2] |
| 62 | 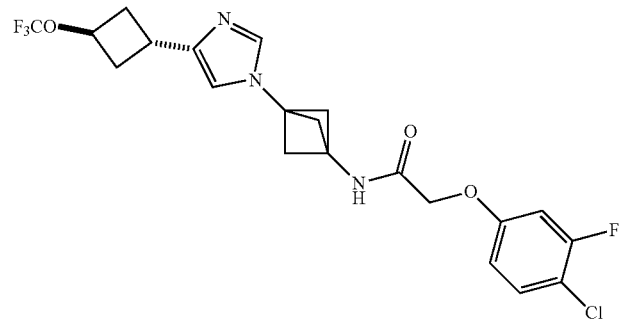 [SMILES: O=C(COc1ccc(Cl)c(F)c1)NC12CC(n3cnc([C@H]4C[C@H](OC(F)(F)F)C4)c3)(C1)C2] |
| 63 | 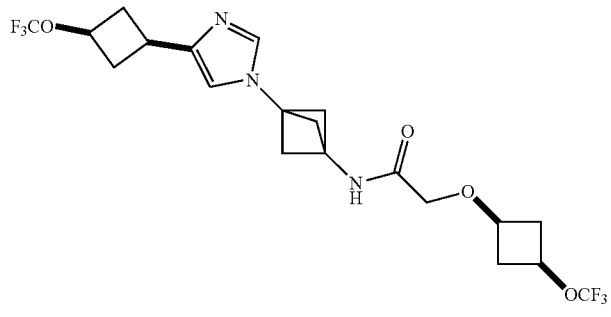 [SMILES: O=C(CO[C@H]1C[C@@H](OC(F)(F)F)C1)NC12CC(n3cnc([C@H]4C[C@@H](OC(F)(F)F)C4)c3)(C1)C2] |
| 64 | 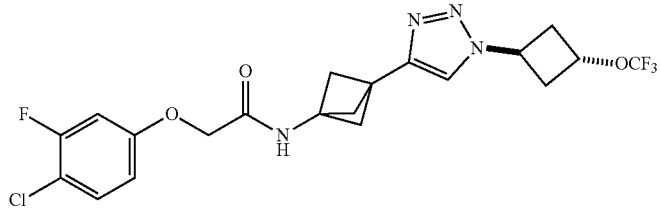 [SMILES: O=C(COc1ccc(Cl)c(F)c1)NC12CC(c3cn([C@H]4C[C@H](OC(F)(F)F)C4)nn3)(C1)C2] |

TABLE 1-continued

| Ex. | Compound |
|---|---|
| 65 | |
| 66 | |
| 67 | |
| 68 | |
| 69 | |

TABLE 1-continued

| Ex. | Compound |
|---|---|
| 70 | (structure) |
| 71 | (structure) |
| 72 | (structure) |
| 73 | (structure) |

TABLE 1-continued
| Ex. | Compound |
|---|---|
| 74 | 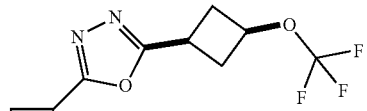 |
| 75 | 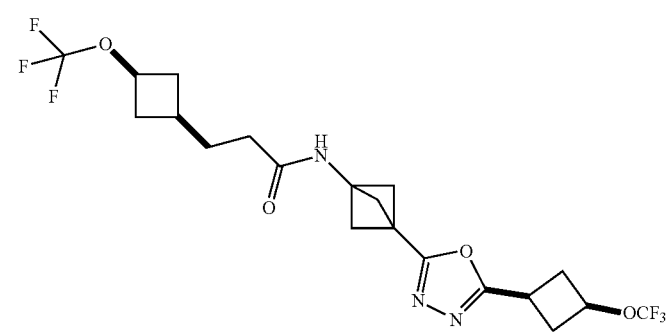 |
| 76 | 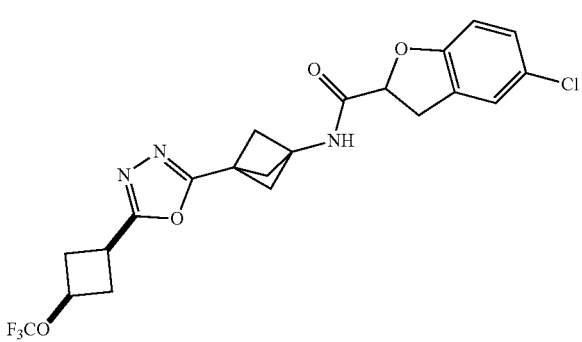 [SMILES: O=C(NC12CC(c3nnc([C@H]4C[C@@H](OC(F)(F)F)C4)o3)(C1)C2)C1Cc2cc(Cl)ccc2O1] |
| 77 | 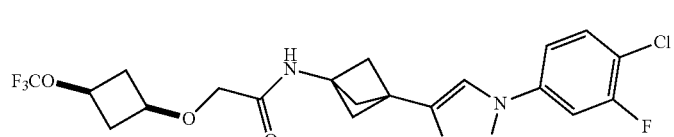 |
| 78 | 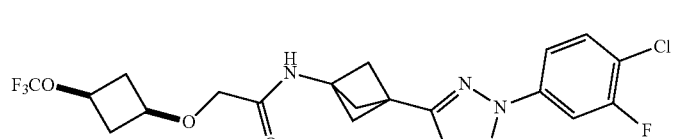 |

TABLE 1-continued
| Ex. | Compound |
|---|---|
| 79 | 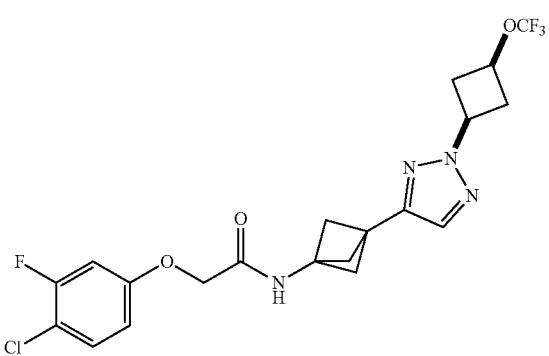 [SMILES: O=C(COc1ccc(Cl)c(F)c1)NC12CC(c3cnn([C@H]4C[C@@H](OC(F)(F)F)C4)n3)(C1)C2] |
| 80 | 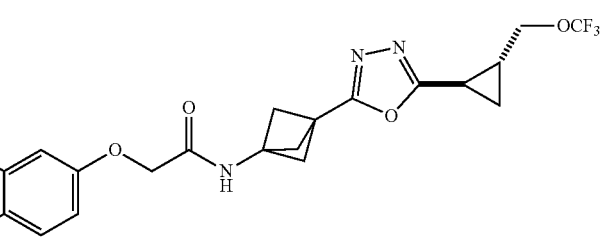 |
| 81 | 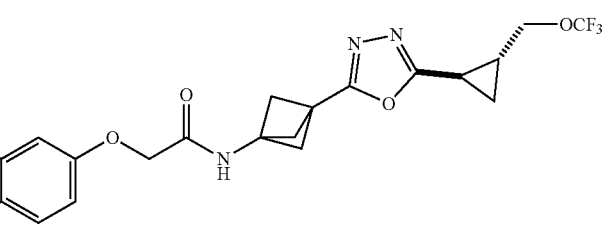 |
| 82 | 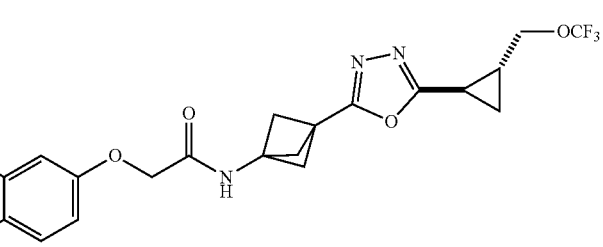 |
| 83 | 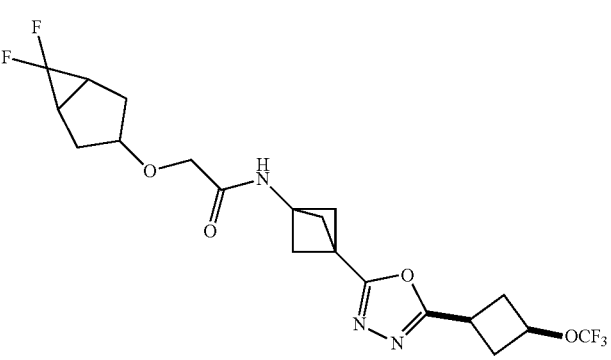 [SMILES: O=C(COC1CC2C(C1)C2(F)F)NC12CC(c3nnc([C@H]4C[C@@H](OC(F)(F)F)C4)o3)(C1)C2] |

TABLE 1-continued

| Ex. | Compound |
|---|---|
| 84 | (structure) |
| 85 | (structure) |
| 86 | (structure) |
| 87 | (structure) |
| 88 | (structure) |
| 89 | (structure) |
| 90 | (structure) |

TABLE 1-continued

| Ex. | Compound |
|---|---|
| 91 | (structure) |
| 92 | (structure) |
| 93 | (structure) |
| 94 | (structure) |
| 95 | (structure) |
| 96 | (structure) |

TABLE 1-continued
| Ex. | Compound |
|---|---|
| 97 | 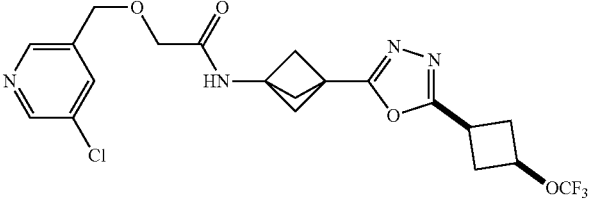 [SMILES: O=C(COCc1cncc(Cl)c1)NC12CC(c3nnc([C@H]4C[C@@H](OC(F)(F)F)C4)o3)(C1)C2] |
| 98 | 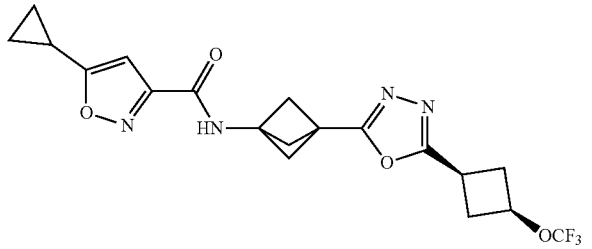 [SMILES: O=C(NC12CC(c3nnc([C@H]4C[C@@H](OC(F)(F)F)C4)o3)(C1)C2)c1cc(C2CC2)on1] |
| 99 | 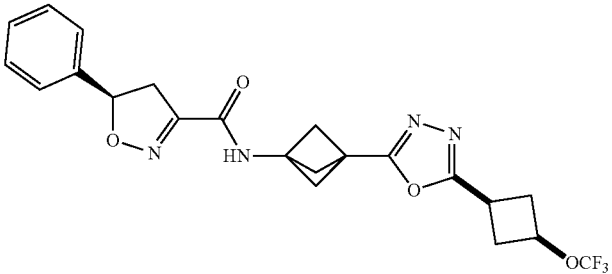 [SMILES: O=C(NC12CC(c3nnc([C@H]4C[C@@H](OC(F)(F)F)C4)o3)(C1)C2)C1=NO[C@@H](c2ccccc2)C1] |
| 100 | 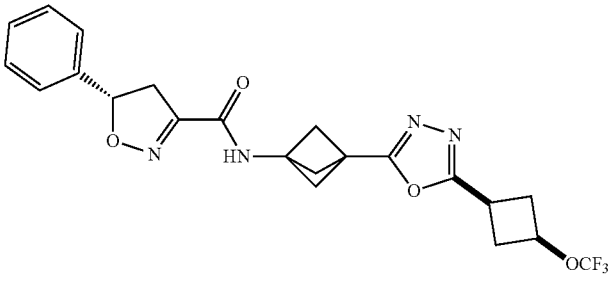 [SMILES: O=C(NC12CC(c3nnc([C@H]4C[C@@H](OC(F)(F)F)C4)o3)(C1)C2)C1=NO[C@H](c2ccccc2)C1] |
| 101 | 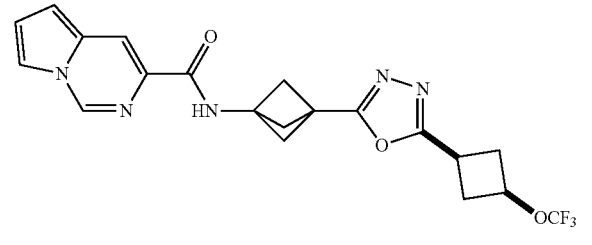 [SMILES: O=C(NC12CC(c3nnc([C@H]4C[C@@H](OC(F)(F)F)C4)o3)(C1)C2)c1cc2cccn2cn1] |
| 102 | 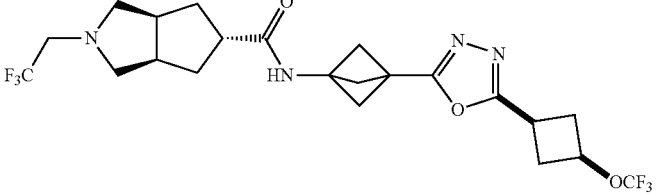 |

TABLE 1-continued
| Ex. | Compound |
|---|---|
| 103 |  |
| 104 | 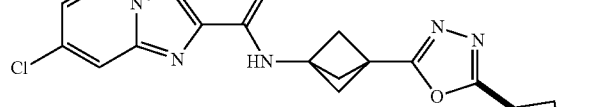 |
| 105 |  |
| 106 | 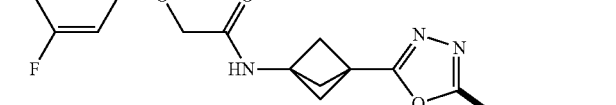 |
| 107 |  |
| 108 | 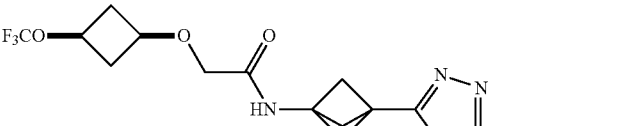 |
| 109 |  |

TABLE 1-continued

| Ex. | Compound |
|---|---|
| 110 | 4-chlorobenzyl (3-(5-(3-(trifluoromethoxy)cyclobutyl)-1,3,4-oxadiazol-2-yl)bicyclo[1.1.1]pentan-1-yl)carbamate |
| 111 | 4-chlorobenzyl (3-(5-(3-(trifluoromethoxy)cyclobutyl)-1,3,4-oxadiazol-2-yl)bicyclo[1.1.1]pentan-1-yl)carbamate |
| 112 | 2-(4-chloro-3-fluorophenoxy)-N-(3-(5-(2-methylcyclopropyl)-1,3,4-oxadiazol-2-yl)bicyclo[1.1.1]pentan-1-yl)acetamide (first eluting enantiomer) |
| 113 | 2-(4-chloro-3-fluorophenoxy)-N-(3-(5-(2-methylcyclopropyl)-1,3,4-oxadiazol-2-yl)bicyclo[1.1.1]pentan-1-yl)acetamide (second eluting enantiomer) |
| 114 | 2-((3-(trifluoromethoxy)cyclopentyl)oxy)-N-(3-(5-(3-(trifluoromethoxy)cyclobutyl)-1,3,4-oxadiazol-2-yl)bicyclo[1.1.1]pentan-1-yl)acetamide |
| 115 | 2-(spiro[2.3]hexan-5-yloxy)-N-(3-(5-(3-(trifluoromethoxy)cyclobutyl)-1,3,4-oxadiazol-2-yl)bicyclo[1.1.1]pentan-1-yl)acetamide |

TABLE 1-continued

| Ex. | Compound |
|---|---|
| 116 | (structure) |
| 117 | (structure) |
| 118 | (structure) |
| 119 | (structure) |
| 120 | (structure) |

TABLE 1-continued
| Ex. | Compound |
|---|---|
| 121 | 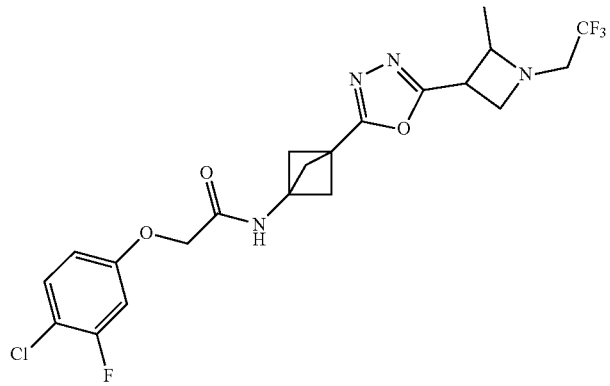 [SMILES: CC1C(c2nnc(C34CC(NC(=O)COc5ccc(Cl)c(F)c5)(C3)C4)o2)CN1CC(F)(F)F] |
| 122 | 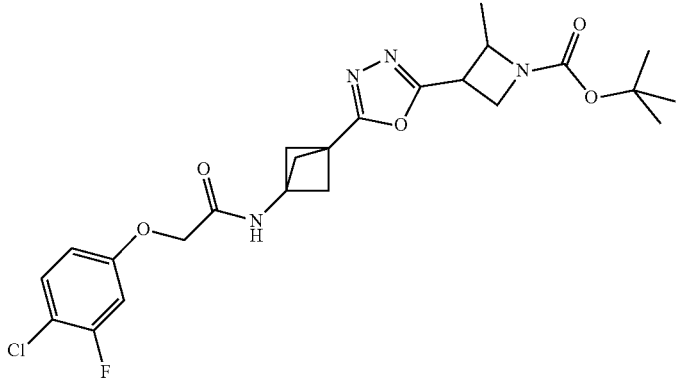 [SMILES: CC1C(c2nnc(C34CC(NC(=O)COc5ccc(Cl)c(F)c5)(C3)C4)o2)CN1C(=O)OC(C)(C)C] |
| 123 | 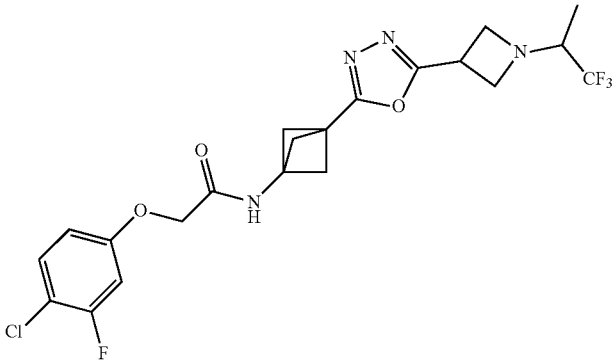 [SMILES: CC(N1CC(c2nnc(C34CC(NC(=O)COc5ccc(Cl)c(F)c5)(C3)C4)o2)C1)C(F)(F)F] |
| 124 | 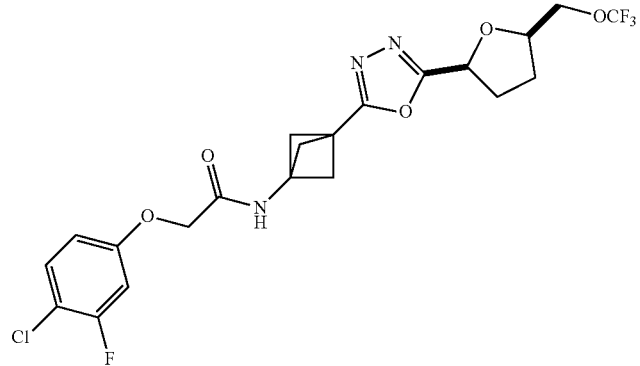 [SMILES: O=C(COc1ccc(Cl)c(F)c1)NC12CC(c3nnc([C@@H]4CC[C@H](COC(F)(F)F)O4)o3)(C1)C2] |

TABLE 1-continued
| Ex. | Compound |
|---|---|
| 125 | 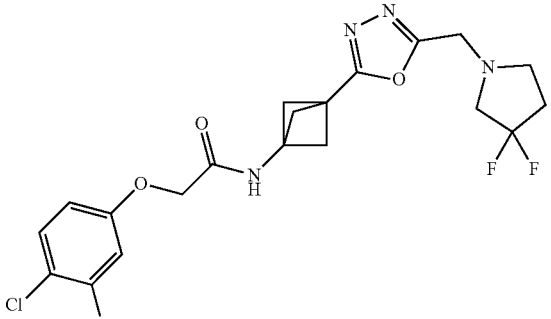 |
| 126 | 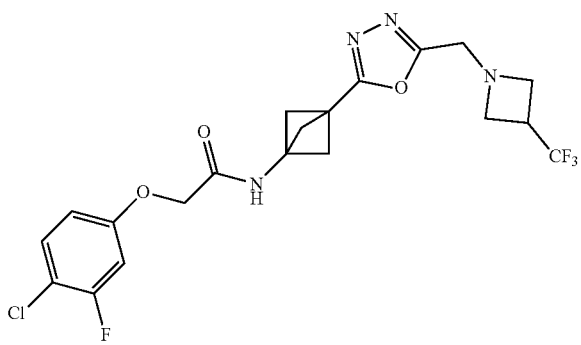 [SMILES: O=C(COc1ccc(Cl)c(F)c1)NC12CC(c3nnc(CN4CC(C(F)(F)F)C4)o3)(C1)C2] |
| 127 | 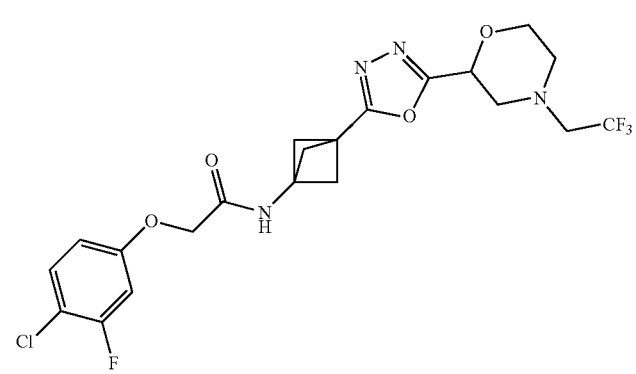 [SMILES: O=C(COc1ccc(Cl)c(F)c1)NC12CC(c3nnc(C4CN(CC(F)(F)F)CCO4)o3)(C1)C2] |
| 128 | 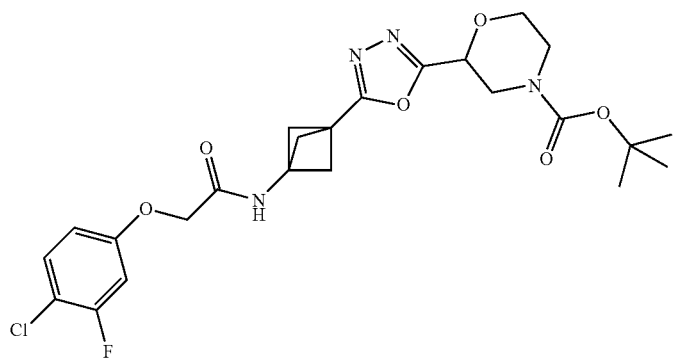 [SMILES: CC(C)(C)OC(=O)N1CCOC(c2nnc(C34CC(NC(=O)COc5ccc(Cl)c(F)c5)(C3)C4)o2)C1] |

TABLE 1-continued

| Ex. | Compound |
|---|---|
| 129 | |
| 130 | |
| 131 | |
| 132 | |

TABLE 1-continued

| Ex. | Compound |
|---|---|
| 133 | (structure: 4-chloro-3-fluorophenoxyacetamide-N-bicyclo[1.1.1]pentyl-NH-CH₂CH₂-O-cyclobutyl-OCF₃) |
| 134 | (structure: 3-(trifluoromethoxy)cyclobutyl-O-CH₂-C(=O)-NH-bicyclo[1.1.1]pentyl-imidazol-1-yl-4-(3-(trifluoromethyl)phenyl)) |
| 135 | (structure: 3-(trifluoromethoxy)cyclobutyl-O-CH₂-C(=O)-NH-bicyclo[1.1.1]pentyl-imidazol-1-yl-4-(2,4-difluorophenyl)) |
| 136 | (structure: 3-(trifluoromethoxy)cyclobutyl-O-CH₂-C(=O)-NH-bicyclo[1.1.1]pentyl-imidazol-1-yl-4-(4-fluorophenyl)) |
| 137 | (structure: 3-(trifluoromethoxy)cyclobutyl-O-CH₂-C(=O)-NH-bicyclo[1.1.1]pentyl-imidazol-1-yl-4-(3-fluorophenyl)) |

TABLE 1-continued
| Ex. | Compound |
|---|---|
| 138 | 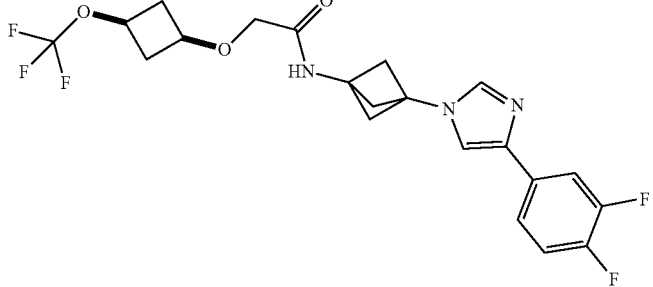 |
| 139 | 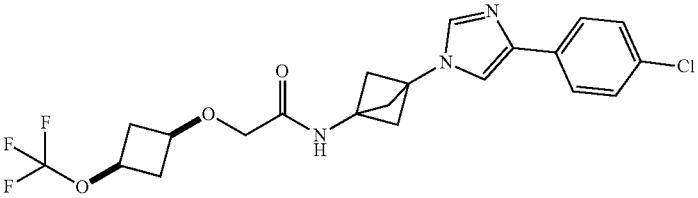 [SMILES: O=C(CO[C@H]1C[C@@H](OC(F)(F)F)C1)NC12CC(n3cnc(-c4ccc(Cl)cc4)c3)(C1)C2] |
| 140 | 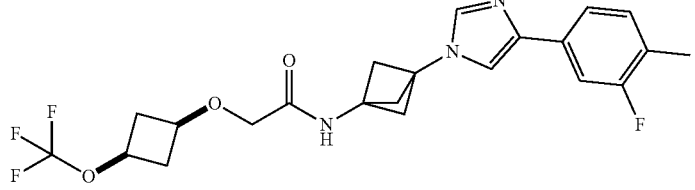 |
| 141 | 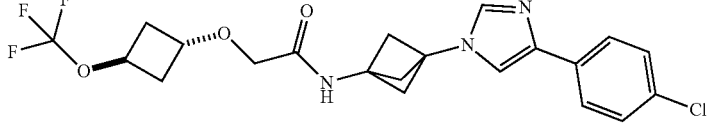 |
| 142 | 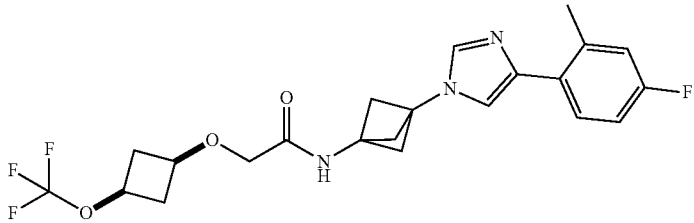 [SMILES: Cc1cc(F)ccc1-c1cn(C23CC(NC(=O)CO[C@H]4C[C@@H](OC(F)(F)F)C4)(C2)C3)cn1] |
| 143 | 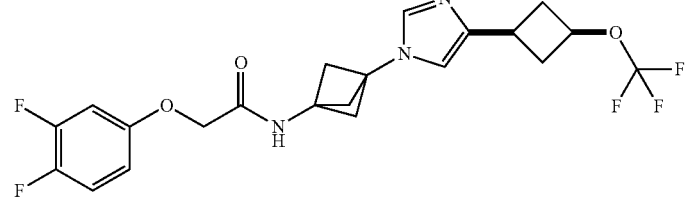 |
| 144 | 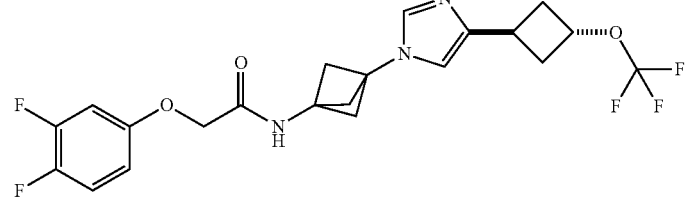 |

TABLE 1-continued

| Ex. | Compound |
|---|---|
| 145 | |
| 146 | |
| 147 | |
| 148 | |
| 149 | |
| 150 | |

TABLE 1-continued

| Ex. | Compound |
|---|---|
| 151 | (structure) |
| 152 | (structure) |
| 153 | (structure) |
| 154 | (structure) |
| 155 | (structure) |
| 156 | (structure) |
| 157 | (structure) First eluting enantiomer |
| 158 | (structure) second eluting enantiomer |

TABLE 1-continued
| Ex. | Compound |
|---|---|
| 159 | 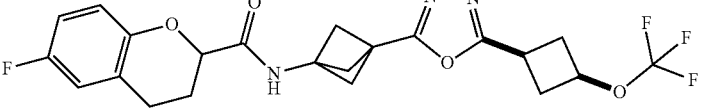<br>first eluting enantiomer |
| 160 | 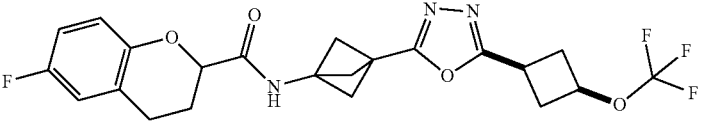 [SMILES: O=C(NC12CC(c3nnc([C@H]4C[C@@H](OC(F)(F)F)C4)o3)(C1)C2)C1CCc2cc(F)ccc2O1]<br>Second eluting enantiomer |
| 161 | 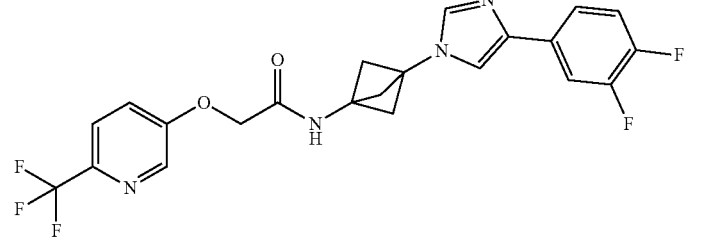 |
| 162 | 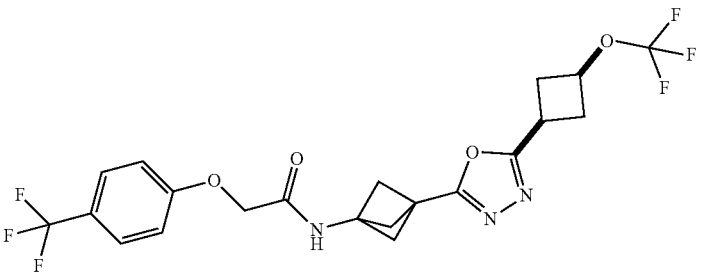 [SMILES: O=C(COc1ccc(C(F)(F)F)cc1)NC12CC(c3nnc([C@H]4C[C@@H](OC(F)(F)F)C4)o3)(C1)C2] |
| 163 | 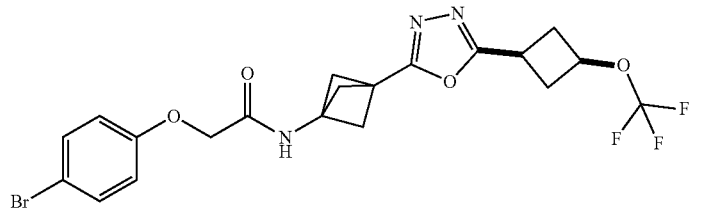 [SMILES: O=C(COc1ccc(Br)cc1)NC12CC(c3nnc([C@H]4C[C@@H](OC(F)(F)F)C4)o3)(C1)C2] |
| 164 | 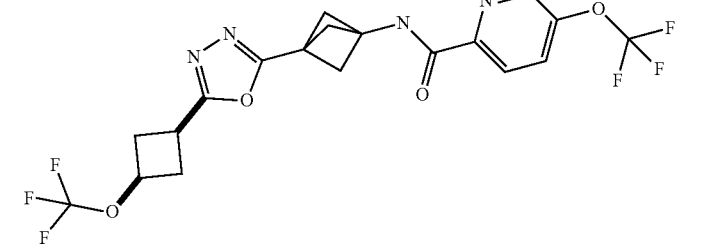 |

TABLE 1-continued
| Ex. | Compound |
|---|---|
| 165 | 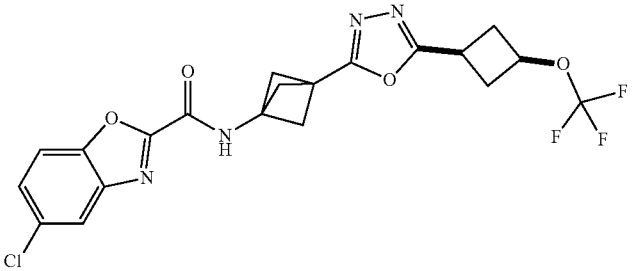 |
| 166 | 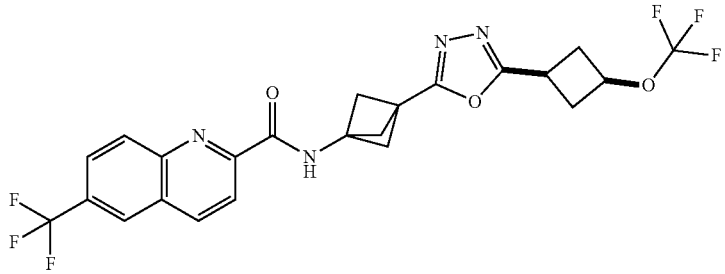 [SMILES: O=C(NC12CC(c3nnc([C@H]4C[C@@H](OC(F)(F)F)C4)o3)(C1)C2)c1ccc2cc(C(F)(F)F)ccc2n1] |
| 167 | 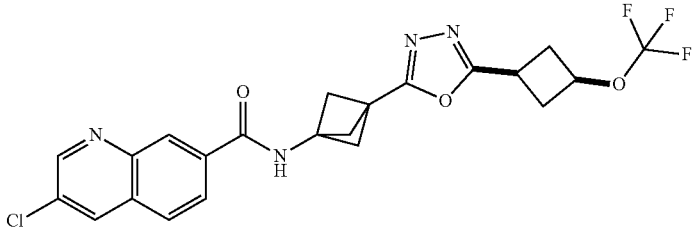 [SMILES: O=C(NC12CC(c3nnc([C@H]4C[C@@H](OC(F)(F)F)C4)o3)(C1)C2)c1ccc2cc(Cl)cnc2c1] |
| 168 | 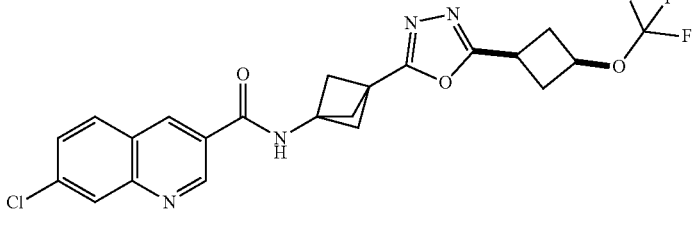 |
| 169 | 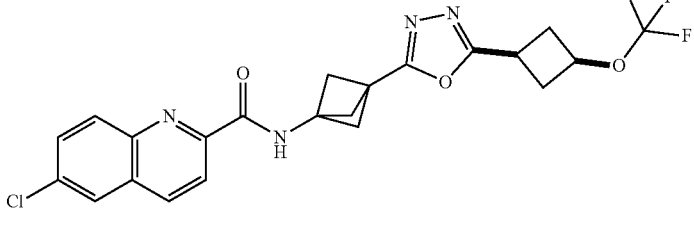 |
| 170 | 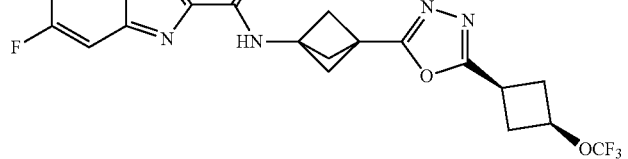 |

TABLE 1-continued

| Ex. | Compound |
|---|---|
| 171 | |
| 172 | |
| 173 | |
| 174 | |
| 175 | |
| 176 | |

TABLE 1-continued

| Ex. | Compound |
|---|---|
| 177 | 7-chloroimidazo[1,2-b]pyridazine-2-carboxamide linked via N-H to bicyclo[1.1.1]pentane substituted with 1,3,4-oxadiazole bearing trans-4-(trifluoromethoxy)cyclobutyl |
| 178 | 5-fluorobenzo[d]oxazole-2-carboxamide linked via N-H to bicyclo[1.1.1]pentane substituted with 1,3,4-oxadiazole bearing trans-4-(trifluoromethoxy)cyclobutyl |
| 179 | 6-bromoimidazo[1,2-a]pyridine-2-carboxamide linked via N-H to bicyclo[1.1.1]pentane substituted with 1,3,4-oxadiazole bearing trans-4-(trifluoromethoxy)cyclobutyl |
| 180 | 6-fluoroimidazo[1,2-a]pyridine-2-carboxamide linked via N-H to bicyclo[1.1.1]pentane substituted with 1,3,4-oxadiazole bearing trans-4-(trifluoromethoxy)cyclobutyl |
| 181 | 7-chloropyrrolo[1,2-c]pyrimidine-3-carboxamide linked via N-H to bicyclo[1.1.1]pentane substituted with 1,3,4-oxadiazole bearing trans-4-(trifluoromethoxy)cyclobutyl |
| 182 | 7-chloroisoquinoline-3-carboxamide linked via N-H to bicyclo[1.1.1]pentane substituted with 1,3,4-oxadiazole bearing trans-4-(trifluoromethoxy)cyclobutyl |
| 183 | 7-chlorocinnoline-3-carboxamide linked via N-H to bicyclo[1.1.1]pentane substituted with 1,3,4-oxadiazole bearing trans-4-(trifluoromethoxy)cyclobutyl |

TABLE 1-continued
| Ex. | Compound |
|---|---|
| 184 | 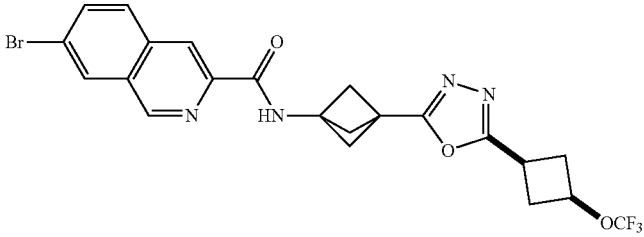 |
| 185 | 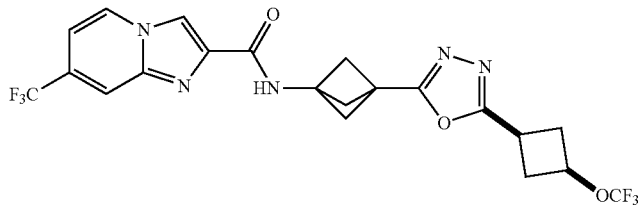 [SMILES: O=C(NC12CC(c3nnc([C@H]4C[C@@H](OC(F)(F)F)C4)o3)(C1)C2)c1cn2ccc(C(F)(F)F)cc2n1] |
| 186 | 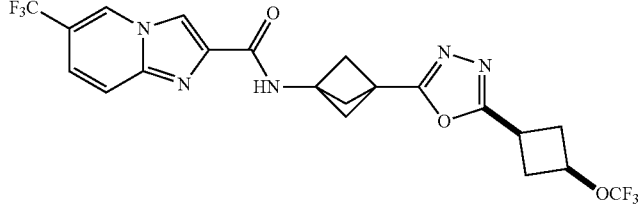 [SMILES: O=C(NC12CC(c3nnc([C@H]4C[C@@H](OC(F)(F)F)C4)o3)(C1)C2)c1cn2cc(C(F)(F)F)ccc2n1] |
| 187 | 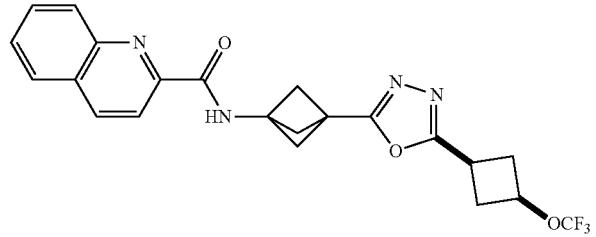 [SMILES: O=C(NC12CC(c3nnc([C@H]4C[C@@H](OC(F)(F)F)C4)o3)(C1)C2)c1ccc2ccccc2n1] |
| 188 | 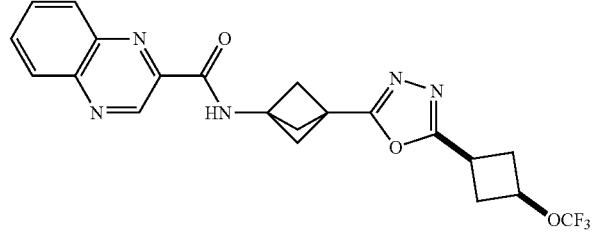 |
| 189 | 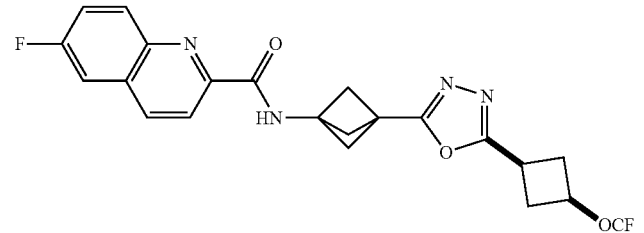 |

TABLE 1-continued

| Ex. | Compound |
|---|---|
| 190 | 6-bromoquinoline-2-carboxamide-N-(bicyclo[1.1.1]pentyl)-1,3,4-oxadiazole-cyclobutyl-OCF3 |
| 191 | quinazoline-2-carboxamide-N-(bicyclo[1.1.1]pentyl)-1,3,4-oxadiazole-cyclobutyl-OCF3 |
| 192 | 6-chlorobenzothiazole-2-carboxamide-N-(bicyclo[1.1.1]pentyl)-1,3,4-oxadiazole-cyclobutyl-OCF3 |
| 193 | 5-bromobenzoxazole-2-carboxamide-N-(bicyclo[1.1.1]pentyl)-1,3,4-oxadiazole-cyclobutyl-OCF3 |
| 194 | 6-fluoro-7-chloroimidazo[1,2-a]pyridine-2-carboxamide-N-(bicyclo[1.1.1]pentyl)-1,3,4-oxadiazole-cyclobutyl-OCF3 |
| 195 | 6-chloroquinazoline-2-carboxamide-N-(bicyclo[1.1.1]pentyl)-1,3,4-oxadiazole-cyclobutyl-OCF3 |

TABLE 1-continued

| Ex. | Compound |
|---|---|
| 196 | (6-chloro-7-fluoroquinoline-2-carboxamide linked via NH to bicyclo[1.1.1]pentyl-1,3,4-oxadiazole-cyclobutyl-OCF₃) |
| 197 | (4-chloro-3-fluorophenoxy-acetamide-NH-bicyclopentyl-NH-ethoxy-cyclobutyl-triazole) |
| 198 | (F₃CO-cyclobutyl-O-CH₂-C(O)NH-bicyclopentyl-N-oxazolone-4-chlorophenyl) |
| 199 | (5-(trifluoromethyl)pyridin-2-yl-oxadiazole-bicyclopentyl-NHC(O)CH₂O-cyclobutyl-OCF₃) |
| 200 | (4-chloro-3-fluorophenoxy-acetamide-NH-bicyclopentyl-tetrazole) |
| 201 | (trifluoromethoxy-cyclobutyl-O-CH₂-C(O)NH-bicyclopentyl-oxadiazole-(4-chloro-3-fluorophenyl)) |

TABLE 1-continued
| Ex. | Compound |
|---|---|
| 202 | 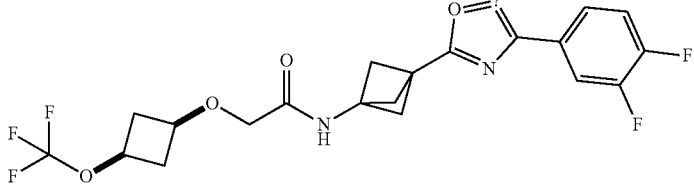 |
| 203 | 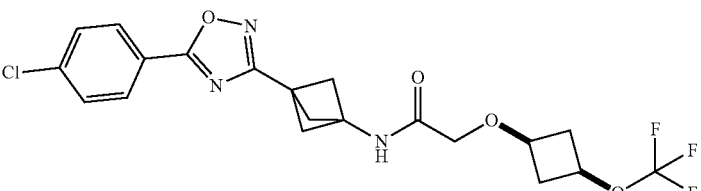 |
| 204 | 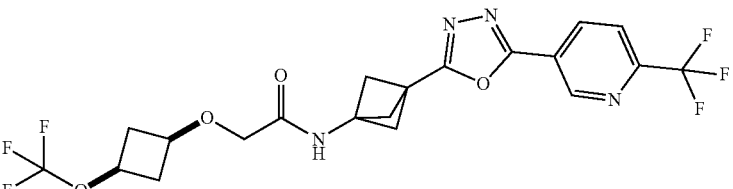 |
| 205 | 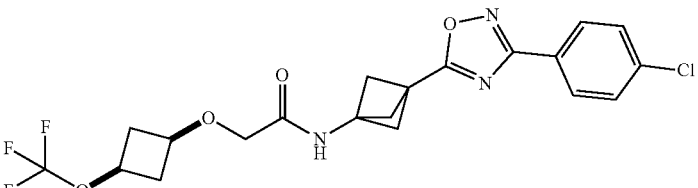 |
| 206 | 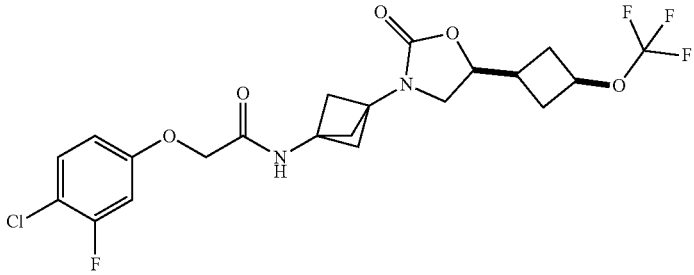<br>first eluting enantiomer |
| 207 | 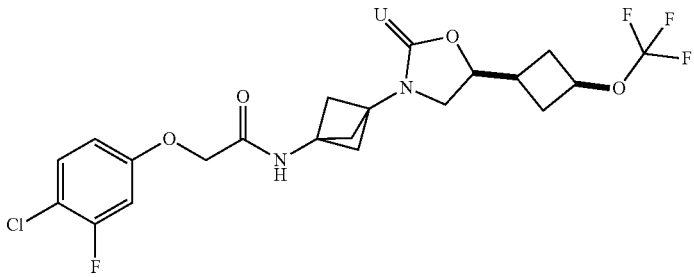<br>second eluting enantiomer |

TABLE 1-continued
| Ex. | Compound |
|---|---|
| 208 | 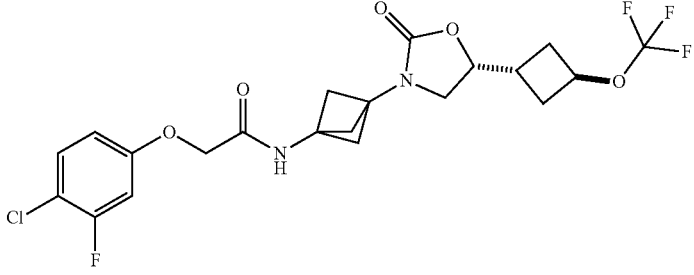 first eluting enantiomer |
| 209 | 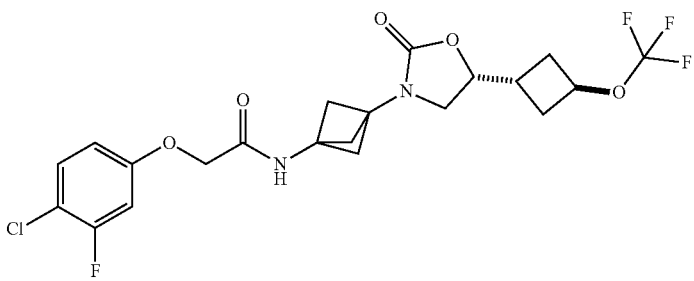 second eluting enantiomer |
| 210 | 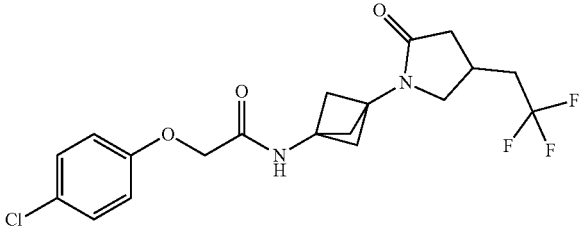 [SMILES: O=C(COc1ccc(Cl)cc1)NC12CC(N3CC(CC(F)(F)F)CC3=O)(C1)C2] |
| 211 | 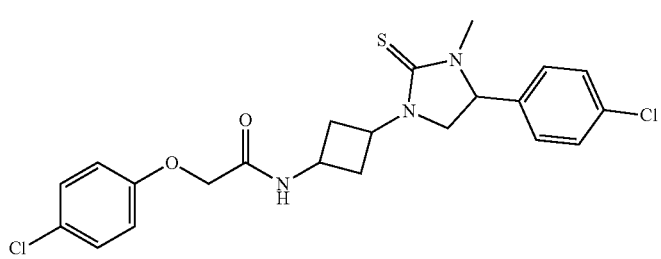 [SMILES: CN1C(=S)N(C2CC(NC(=O)COc3ccc(Cl)cc3)C2)CC1c1ccc(Cl)cc1] |
| 212 | 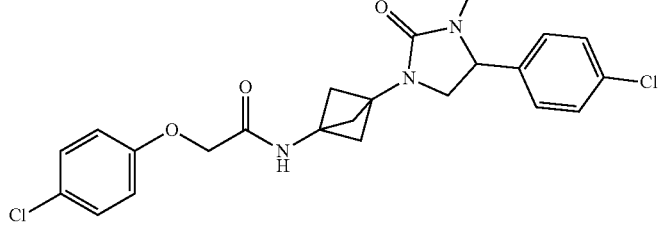 |

TABLE 1-continued

| Ex. | Compound |
|---|---|
| 213 | 4-chlorophenoxy-N-{3-[3-cyclobutyl-2-oxopyrrolidin-1-yl]bicyclo[1.1.1]pentan-1-yl}acetamide |
| 214 | 4-chlorophenoxy-N-{3-[4-cyclobutyl-2-oxo-2,5-dihydro-1H-pyrrol-1-yl]bicyclo[1.1.1]pentan-1-yl}acetamide |
| 215 | 2-(4-chloro-3-fluorophenoxy)-N-{3-[3-(cyclobutylmethyl)-2-oxoimidazolidin-1-yl]bicyclo[1.1.1]pentan-1-yl}acetamide |
| 216 | 2-(4-chloro-3-fluorophenoxy)-N-{3-[5-cyclobutyl-2-oxo-1,3-oxazolidin-3-yl]bicyclo[1.1.1]pentan-1-yl}acetamide |
| 217 | 2-(4-chloro-3-fluorophenoxy)-N-{3-[5-(3-cyanocyclobutyl)-2-oxo-1,3-oxazolidin-3-yl]cyclobutyl}acetamide<br>first eluting enantiomer |
| 218 | 2-(4-chloro-3-fluorophenoxy)-N-{3-[5-(3-cyanocyclobutyl)-2-oxo-1,3-oxazolidin-3-yl]bicyclo[1.1.1]pentan-1-yl}acetamide<br>second eluting enantiomer |

TABLE 1-continued

| Ex. | Compound |
|---|---|
| 219 | |
| 220 | |
| 221 | |
| 222 | |
| 223 | |
| 224 | |

TABLE 1-continued

| Ex. | Compound |
|---|---|
| 225 | |
| 226 | |
| 227 | |
| 228 | |
| 229 | |
| 230 | |
| 231 | |

TABLE 1-continued
| Ex. | Compound |
|---|---|
| 232 | 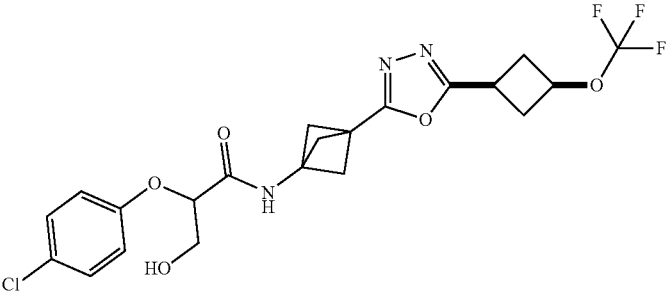 |
| 233 | 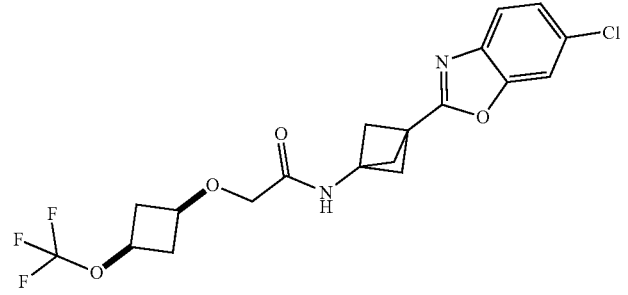 [SMILES: O=C(CO[C@H]1C[C@@H](OC(F)(F)F)C1)NC12CC(c3nc4ccc(Cl)cc4o3)(C1)C2] |
| 234 | 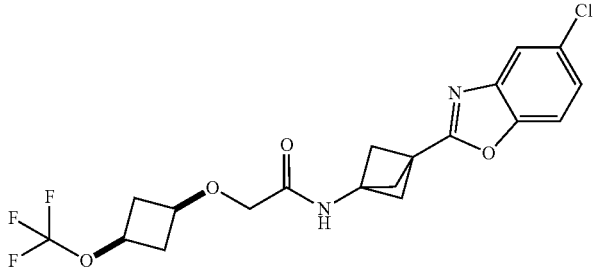 [SMILES: O=C(CO[C@H]1C[C@@H](OC(F)(F)F)C1)NC12CC(c3nc4cc(Cl)ccc4o3)(C1)C2] |
| 235 | 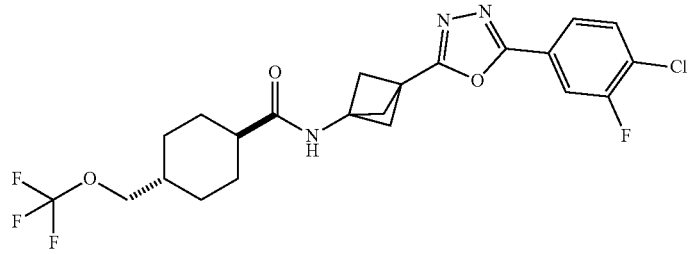 [SMILES: O=C(NC12CC(c3nnc(-c4ccc(Cl)c(F)c4)o3)(C1)C2)[C@H]1CC[C@H](COC(F)(F)F)CC1] |
| 236 | 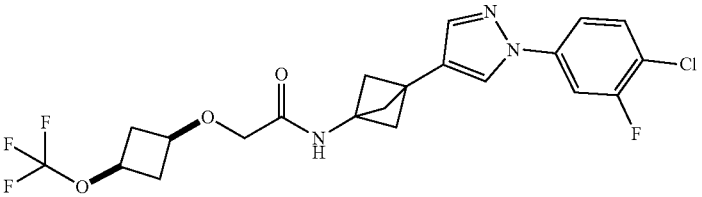 [SMILES: O=C(CO[C@H]1C[C@@H](OC(F)(F)F)C1)NC12CC(c3cnn(-c4ccc(Cl)c(F)c4)c3)(C1)C2] |
| 237 | 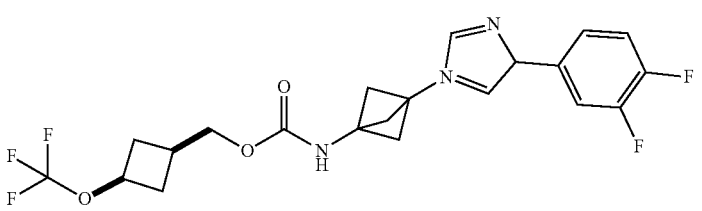 |

TABLE 1-continued

| Ex. | Compound |
|---|---|
| 238 | |
| 239 | |
| 240 | |
| 241 | |
| 242 | |
| 243 | |
| 244 | |

TABLE 1-continued

| Ex. | Compound |
|---|---|
| 245 | |
| 246 | |
| 247 | |
| 248 | |
| 249 | |
| 250 | |
| 251 | |

TABLE 1-continued
| Ex. | Compound |
|---|---|
| 252 | 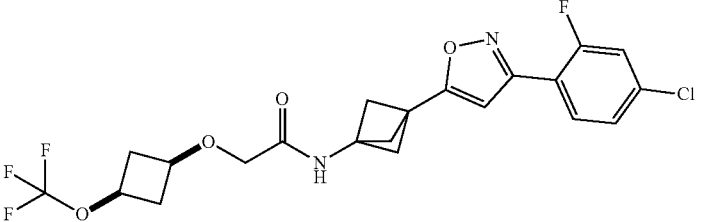 [SMILES: O=C(CO[C@H]1C[C@@H](OC(F)(F)F)C1)NC12CC(c3cc(-c4ccc(Cl)cc4F)no3)(C1)C2] |
| 253 | 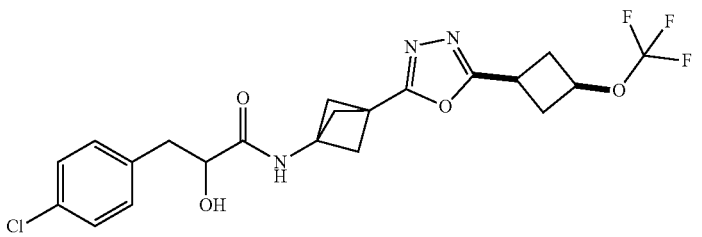 [SMILES: O=C(NC12CC(c3nnc([C@H]4C[C@@H](OC(F)(F)F)C4)o3)(C1)C2)C(O)Cc1ccc(Cl)cc1] |
| 254 | 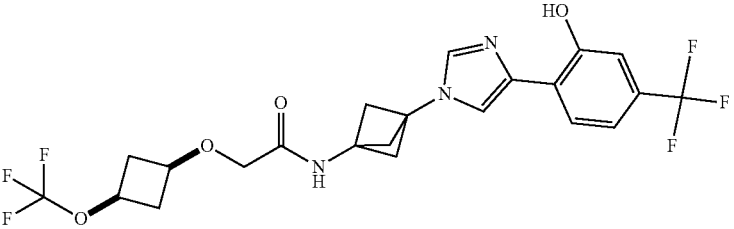 [SMILES: O=C(CO[C@H]1C[C@@H](OC(F)(F)F)C1)NC12CC(n3cnc(-c4ccc(C(F)(F)F)cc4O)c3)(C1)C2] |
| 255 | 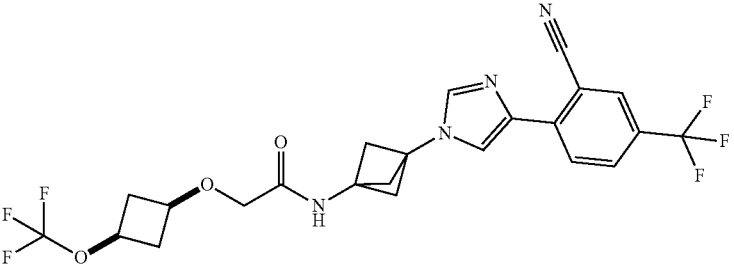 [SMILES: N#Cc1cc(C(F)(F)F)ccc1-c1cn(C23CC(NC(=O)CO[C@H]4C[C@@H](OC(F)(F)F)C4)(C2)C3)cn1] |
| 256 | 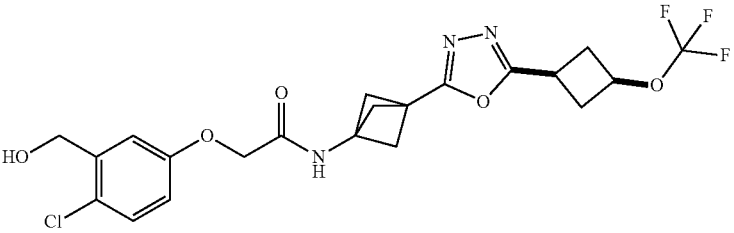 [SMILES: O=C(COc1ccc(Cl)c(CO)c1)NC12CC(c3nnc([C@H]4C[C@@H](OC(F)(F)F)C4)o3)(C1)C2] |
| 257 | 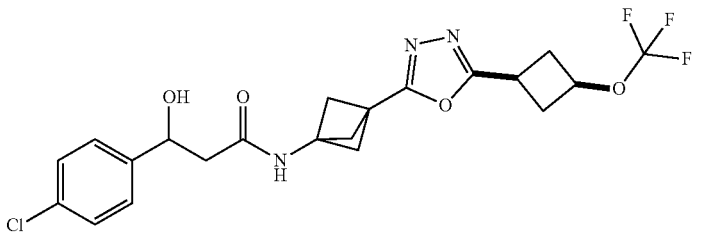 [SMILES: O=C(CC(O)c1ccc(Cl)cc1)NC12CC(c3nnc([C@H]4C[C@@H](OC(F)(F)F)C4)o3)(C1)C2] |

TABLE 1-continued

| Ex. | Compound |
|---|---|
| 258 | |
| 259 | |
| 260 | |
| 261 | |
| 262 | |
| 263 | |
| 264 | |

TABLE 1-continued
| Ex. | Compound |
|---|---|
| 265 | 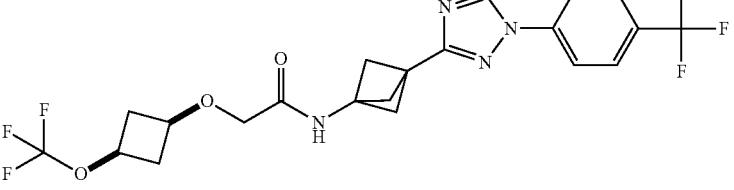 |
| 266 | 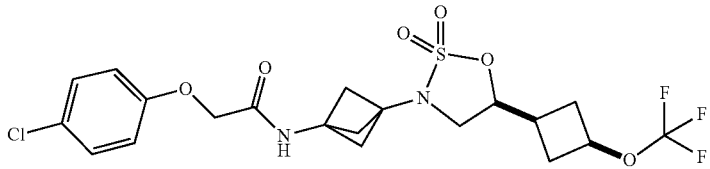 |
| 267 | 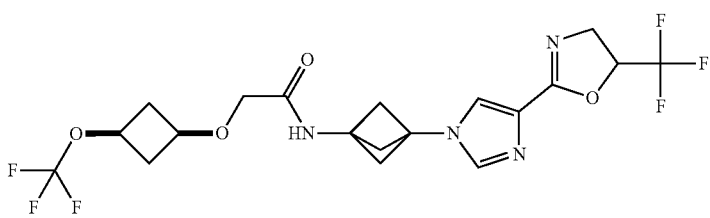 [SMILES: O=C(CO[C@H]1C[C@@H](OC(F)(F)F)C1)NC12CC(n3cnc(C4=NCC(C(F)(F)F)O4)c3)(C1)C2] |
| 268 | 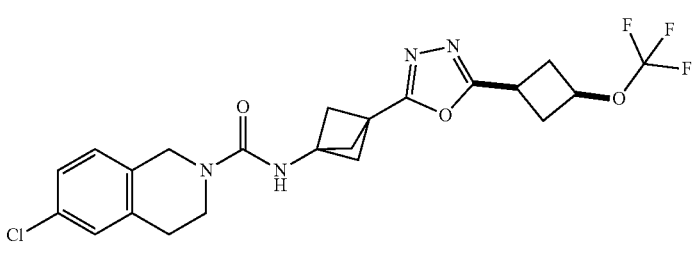 [SMILES: O=C(NC12CC(c3nnc([C@H]4C[C@@H](OC(F)(F)F)C4)o3)(C1)C2)N1CCc2cc(Cl)ccc2C1] |
| 269 | 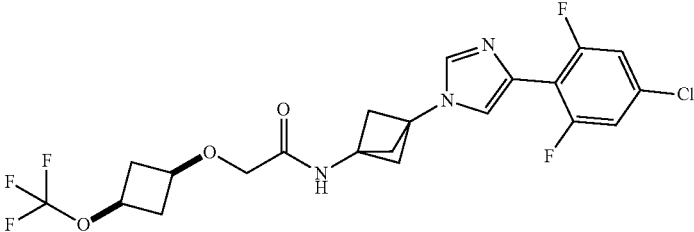 [SMILES: O=C(CO[C@H]1C[C@@H](OC(F)(F)F)C1)NC12CC(n3cnc(-c4c(F)cc(Cl)cc4F)c3)(C1)C2] |
| 270 | 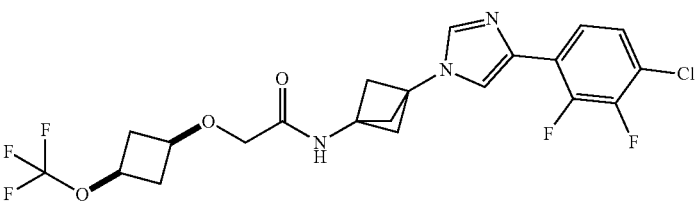 [SMILES: O=C(CO[C@H]1C[C@@H](OC(F)(F)F)C1)NC12CC(n3cnc(-c4ccc(Cl)c(F)c4F)c3)(C1)C2] |
| 271 | 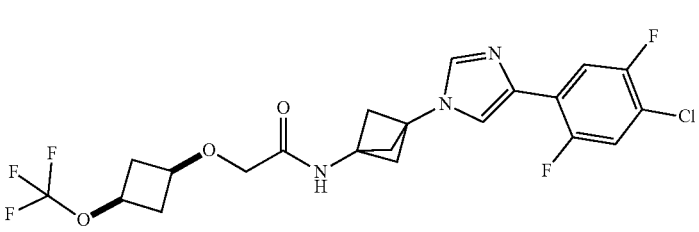 [SMILES: O=C(CO[C@H]1C[C@@H](OC(F)(F)F)C1)NC12CC(n3cnc(-c4cc(F)c(Cl)cc4F)c3)(C1)C2] |

TABLE 1-continued
| Ex. | Compound |
|---|---|
| 272 | 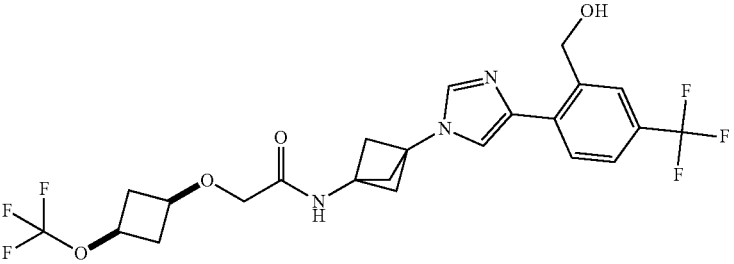 [SMILES: O=C(CO[C@H]1C[C@@H](OC(F)(F)F)C1)NC12CC(n3cnc(-c4ccc(C(F)(F)F)cc4CO)c3)(C1)C2] |
| 273 | 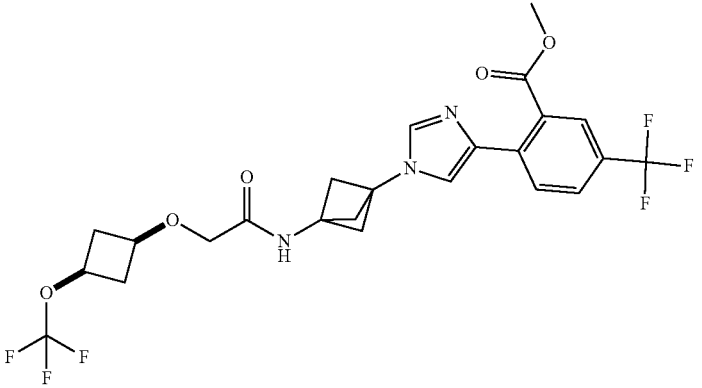 [SMILES: COC(=O)c1cc(C(F)(F)F)ccc1-c1cn(C23CC(NC(=O)CO[C@H]4C[C@@H](OC(F)(F)F)C4)(C2)C3)cn1] |
| 274 | 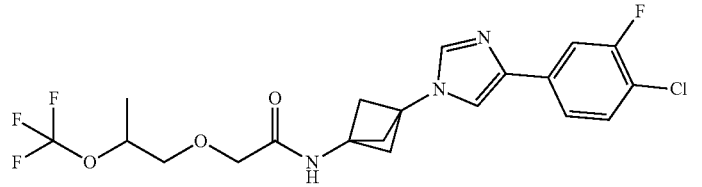 [SMILES: CC(COCC(=O)NC12CC(n3cnc(-c4ccc(Cl)c(F)c4)c3)(C1)C2)OC(F)(F)F] |
| 275 | 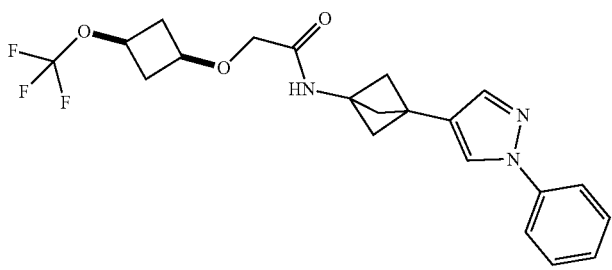 [SMILES: O=C(CO[C@H]1C[C@@H](OC(F)(F)F)C1)NC12CC(c3cnn(-c4ccccc4)c3)(C1)C2] |
| 276 | 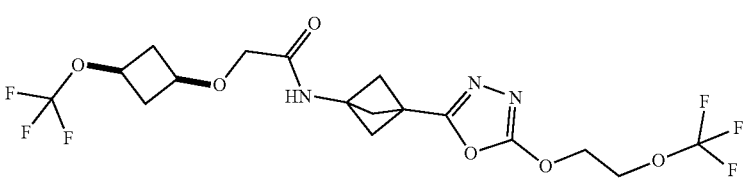 [SMILES: O=C(CO[C@H]1C[C@@H](OC(F)(F)F)C1)NC12CC(c3nnc(OCCOC(F)(F)F)o3)(C1)C2] |

TABLE 1-continued
| Ex. | Compound |
|---|---|
| 277 | 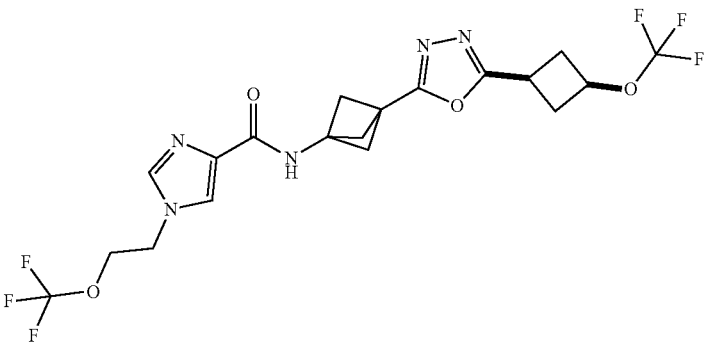 [SMILES: O=C(NC12CC(c3nnc([C@H]4C[C@@H](OC(F)(F)F)C4)o3)(C1)C2)c1cn(CCOC(F)(F)F)cn1] |
or a pharmaceutically acceptable salt, isotopically enriched analog, prodrug, stereoisomer, or a mixture of stereoisomers thereof.
In certain embodiments, provided is a compound selected from Table 2:
TABLE 2
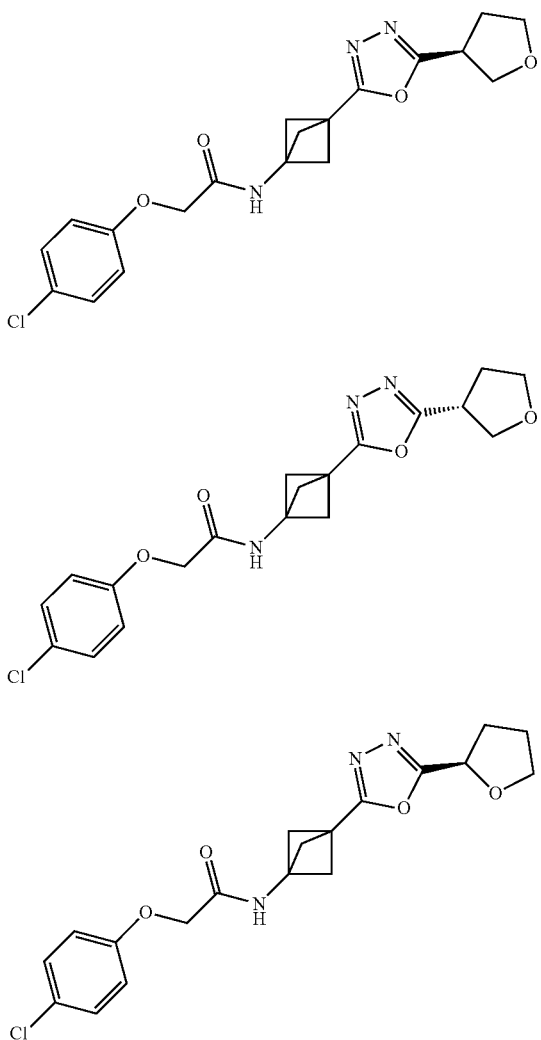

TABLE 2-continued
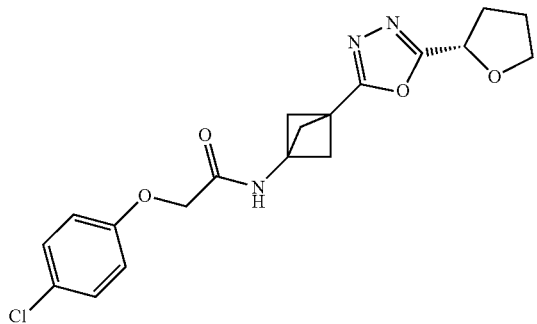 [SMILES: O=C(COc1ccc(Cl)cc1)NC12CC(c3nnc([C@@H]4CCCO4)o3)(C1)C2]
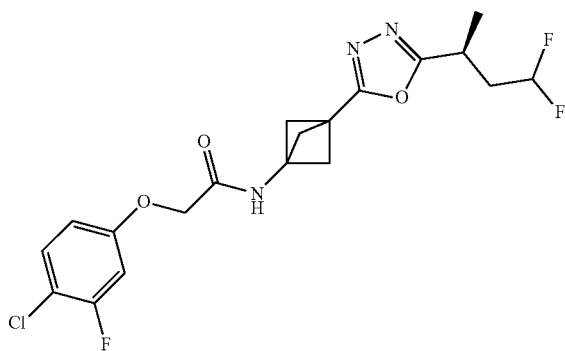 [SMILES: C[C@@H](CC(F)F)c1nnc(C23CC(NC(=O)COc4ccc(Cl)c(F)c4)(C2)C3)o1]
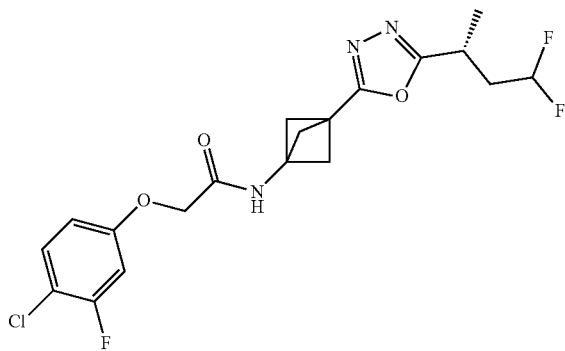 [SMILES: C[C@H](CC(F)F)c1nnc(C23CC(NC(=O)COc4ccc(Cl)c(F)c4)(C2)C3)o1]
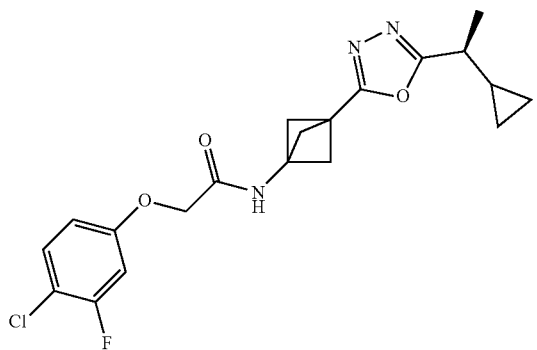 [SMILES: C[C@H](c1nnc(C23CC(NC(=O)COc4ccc(Cl)c(F)c4)(C2)C3)o1)C1CC1]

TABLE 2-continued
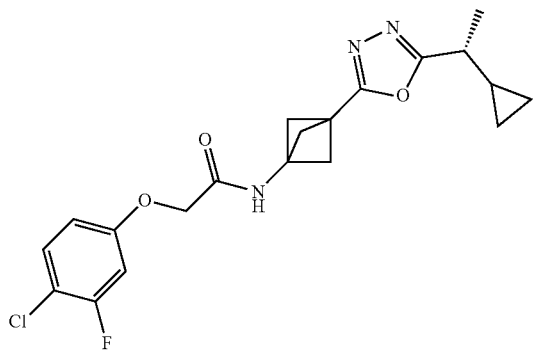 [SMILES: C[C@@H](c1nnc(C23CC(NC(=O)COc4ccc(Cl)c(F)c4)(C2)C3)o1)C1CC1]
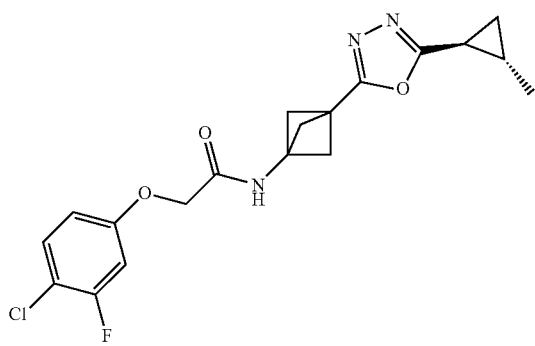 [SMILES: C[C@H]1C[C@@H]1c1nnc(C23CC(NC(=O)COc4ccc(Cl)c(F)c4)(C2)C3)o1]
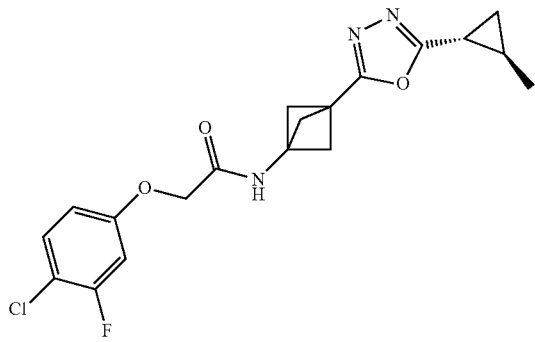 [SMILES: C[C@@H]1C[C@H]1c1nnc(C23CC(NC(=O)COc4ccc(Cl)c(F)c4)(C2)C3)o1]
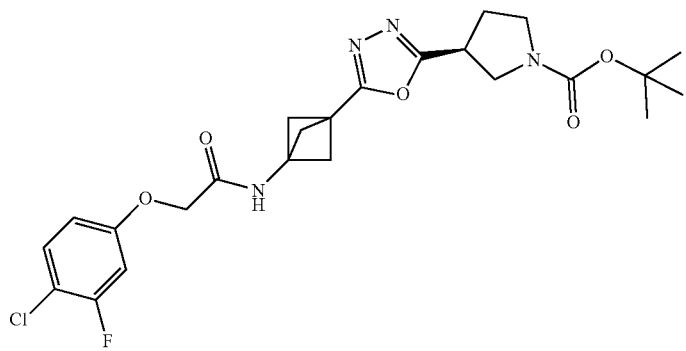 [SMILES: CC(C)(C)OC(=O)N1CC[C@H](c2nnc(C34CC(NC(=O)COc5ccc(Cl)c(F)c5)(C3)C4)o2)C1]

TABLE 2-continued
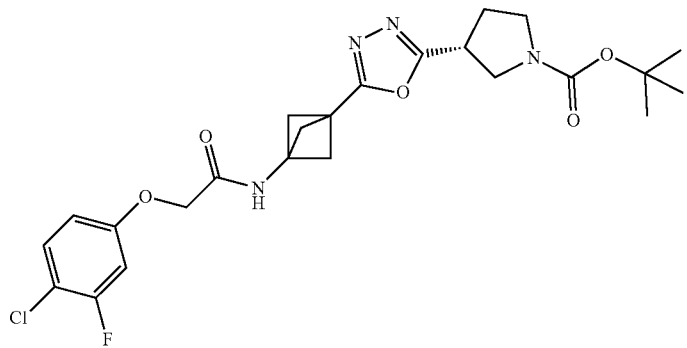 [SMILES: CC(C)(C)OC(=O)N1CC[C@@H](c2nnc(C34CC(NC(=O)COc5ccc(Cl)c(F)c5)(C3)C4)o2)C1]
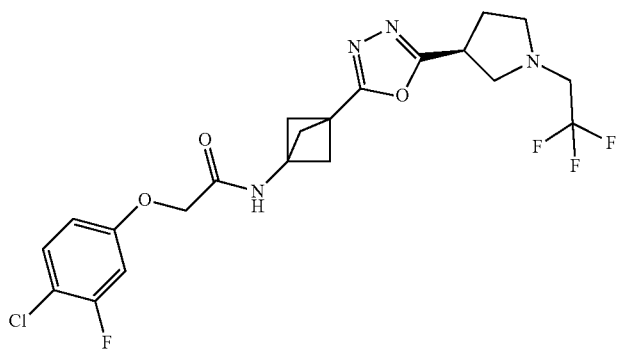 [SMILES: O=C(COc1ccc(Cl)c(F)c1)NC12CC(c3nnc([C@H]4CCN(CC(F)(F)F)C4)o3)(C1)C2]
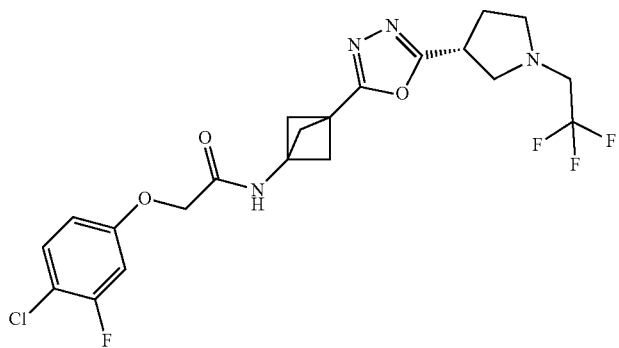 [SMILES: O=C(COc1ccc(Cl)c(F)c1)NC12CC(c3nnc([C@@H]4CCN(CC(F)(F)F)C4)o3)(C1)C2]
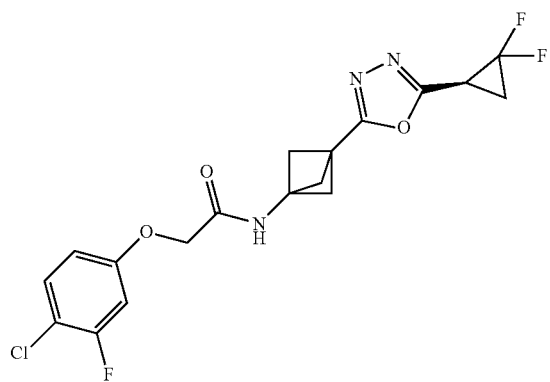 [SMILES: O=C(COc1ccc(Cl)c(F)c1)NC12CC(c3nnc([C@@H]4CC4(F)F)o3)(C1)C2]

TABLE 2-continued
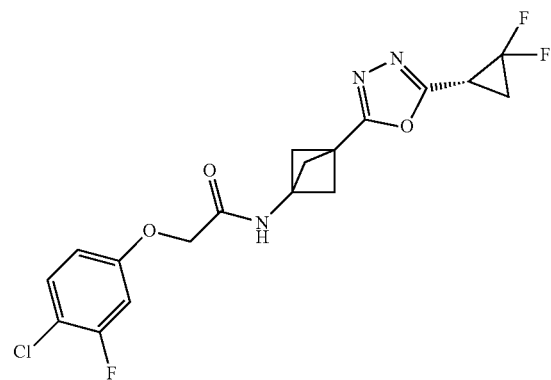 [SMILES: O=C(COc1ccc(Cl)c(F)c1)NC12CC(c3nnc([C@H]4CC4(F)F)o3)(C1)C2]
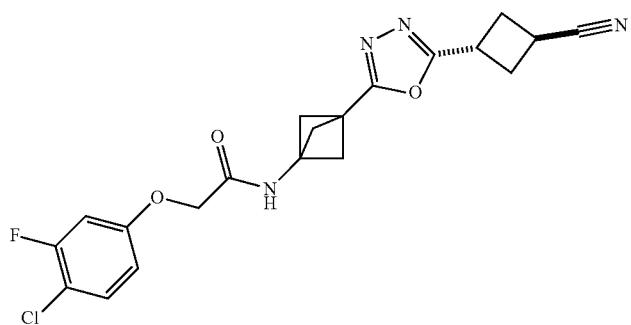
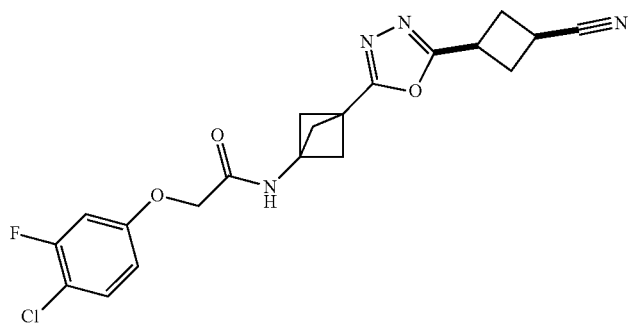
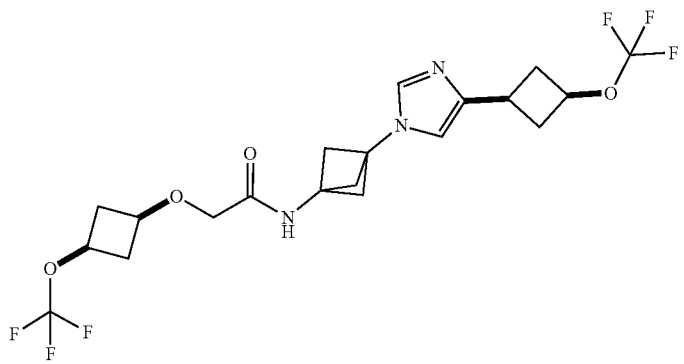

TABLE 2-continued
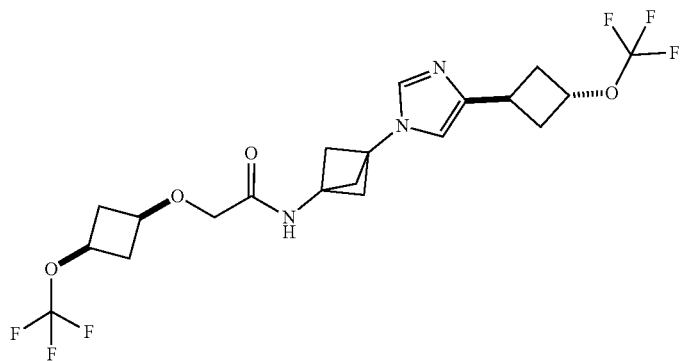
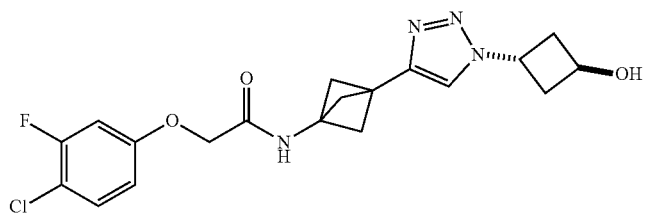
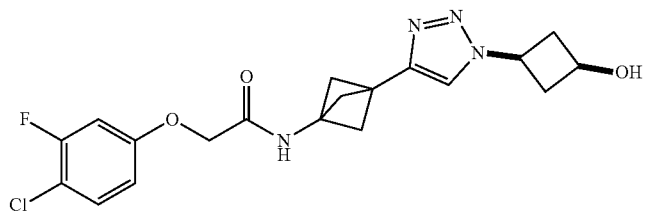
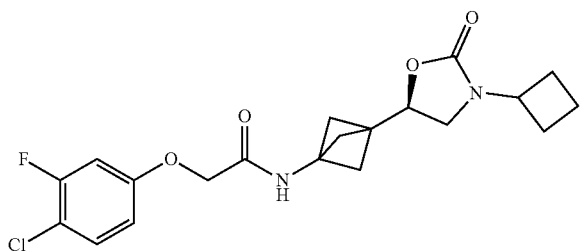 [SMILES: O=C(COc1ccc(Cl)c(F)c1)NC12CC([C@@H]3CN(C4CCC4)C(=O)O3)(C1)C2]
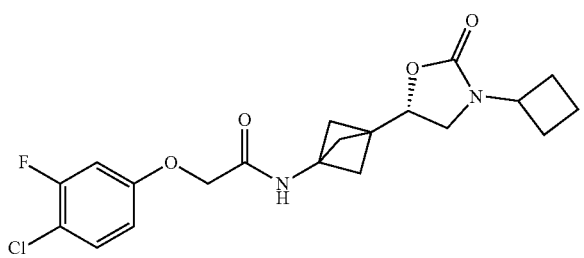 [SMILES: O=C(COc1ccc(Cl)c(F)c1)NC12CC([C@H]3CN(C4CCC4)C(=O)O3)(C1)C2]
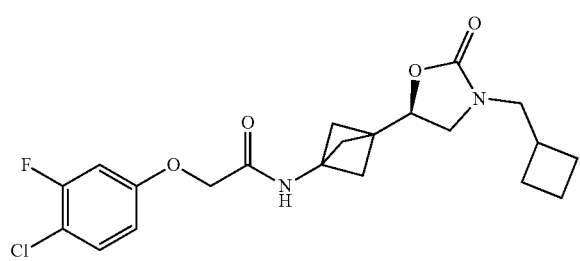 [SMILES: O=C(COc1ccc(Cl)c(F)c1)NC12CC([C@@H]3CN(CC4CCC4)C(=O)O3)(C1)C2]

TABLE 2-continued
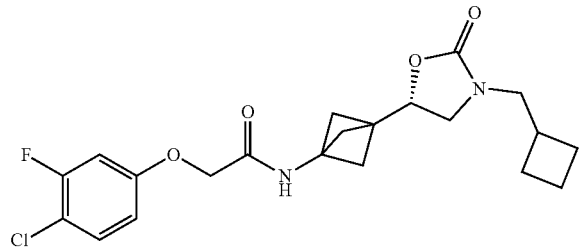 [SMILES: O=C(COc1ccc(Cl)c(F)c1)NC12CC([C@H]3CN(CC4CCC4)C(=O)O3)(C1)C2]
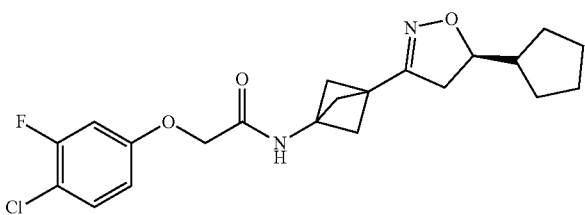 [SMILES: O=C(COc1ccc(Cl)c(F)c1)NC12CC(C3=NO[C@@H](C4CCCC4)C3)(C1)C2]
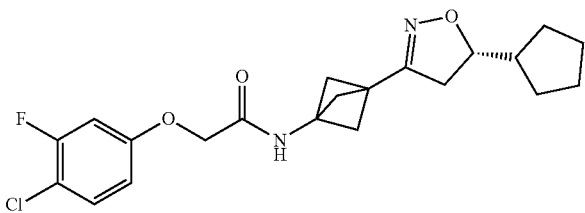 [SMILES: O=C(COc1ccc(Cl)c(F)c1)NC12CC(C3=NO[C@H](C4CCCC4)C3)(C1)C2]
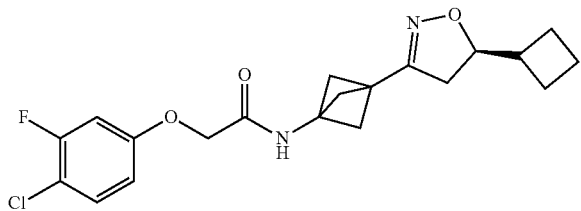 [SMILES: O=C(COc1ccc(Cl)c(F)c1)NC12CC(C3=NO[C@@H](C4CCC4)C3)(C1)C2]
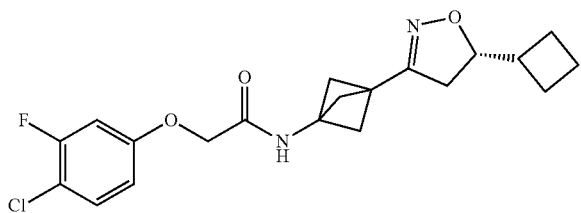 [SMILES: O=C(COc1ccc(Cl)c(F)c1)NC12CC(C3=NO[C@H](C4CCC4)C3)(C1)C2]
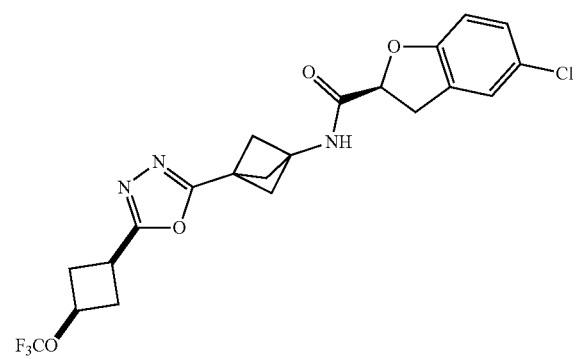

TABLE 2-continued
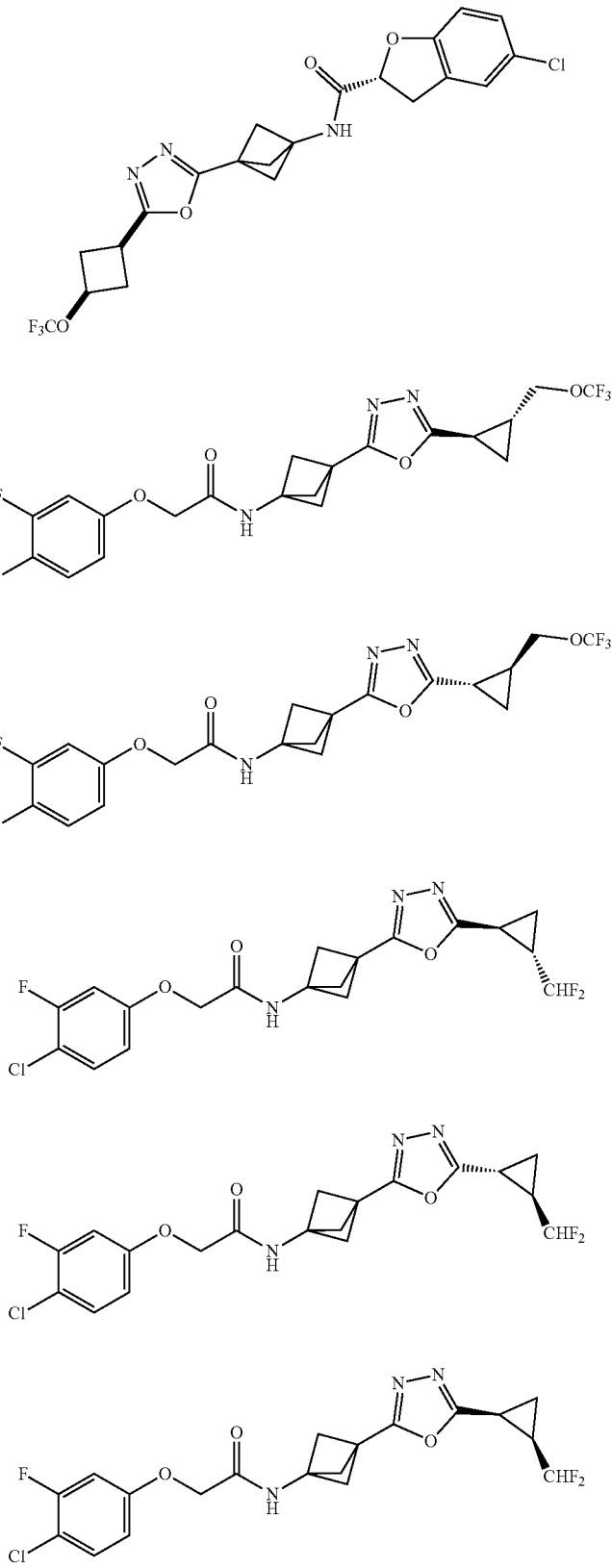

TABLE 2-continued
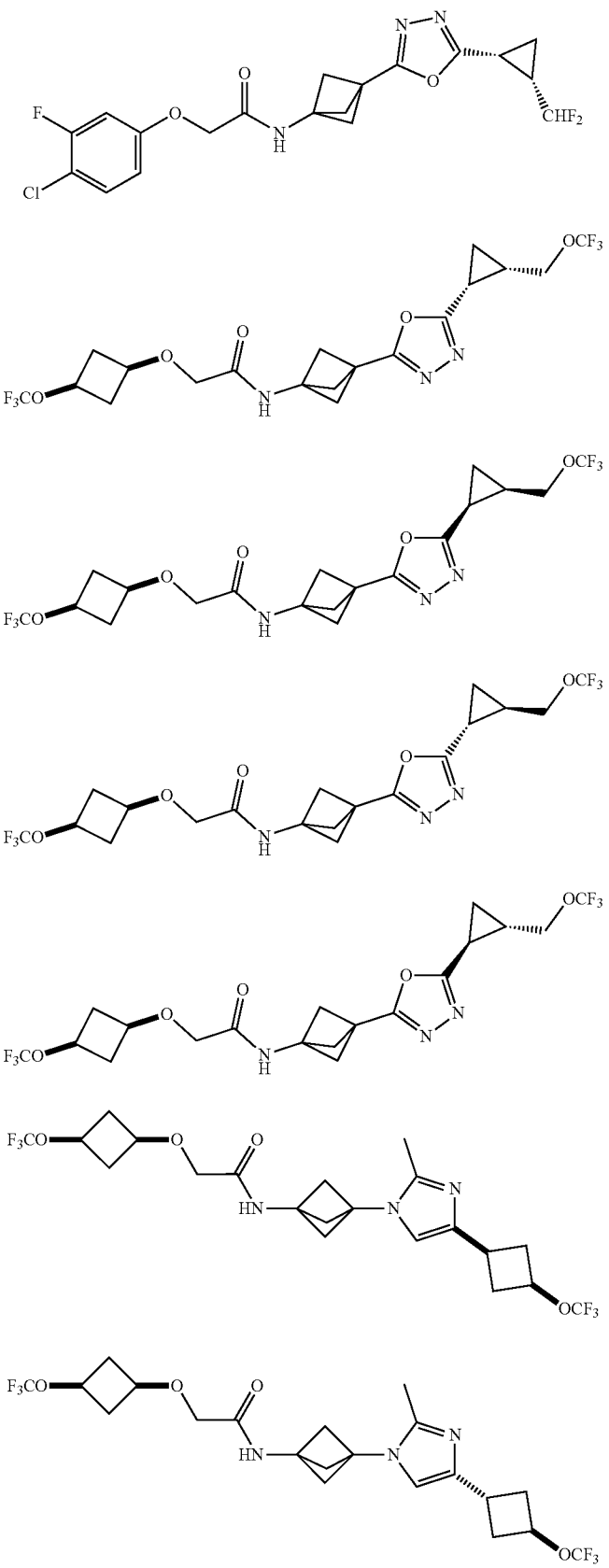

TABLE 2-continued
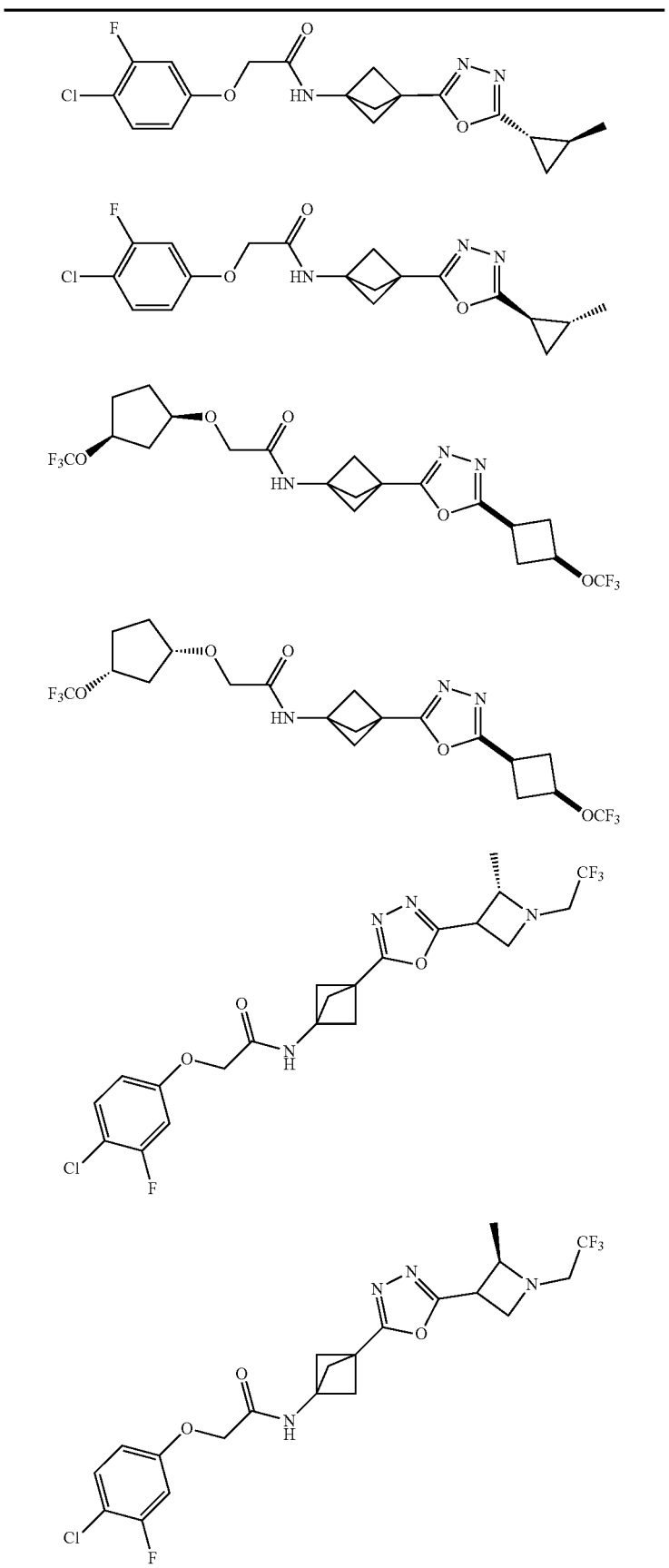

TABLE 2-continued
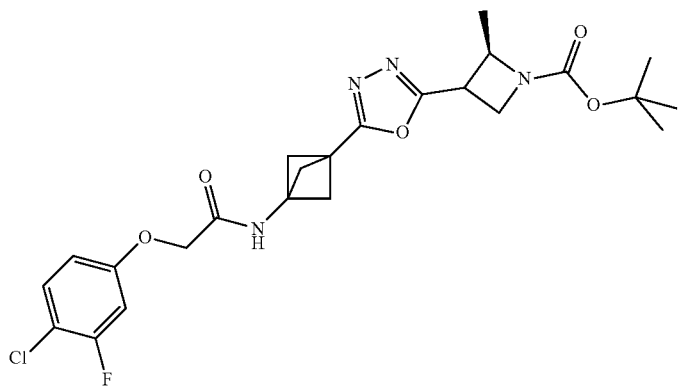 [SMILES: C[C@@H]1C(c2nnc(C34CC(NC(=O)COc5ccc(Cl)c(F)c5)(C3)C4)o2)CN1C(=O)OC(C)(C)C]
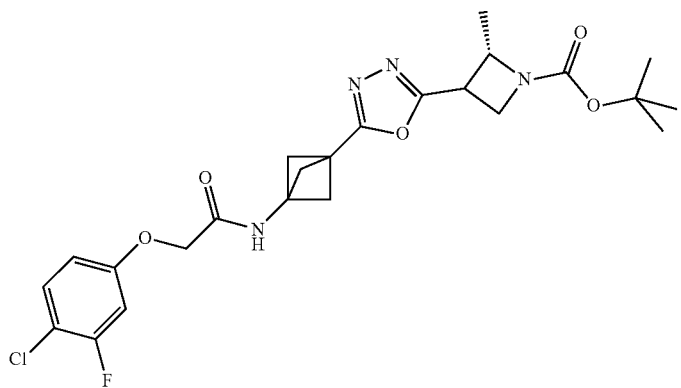 [SMILES: C[C@H]1C(c2nnc(C34CC(NC(=O)COc5ccc(Cl)c(F)c5)(C3)C4)o2)CN1C(=O)OC(C)(C)C]
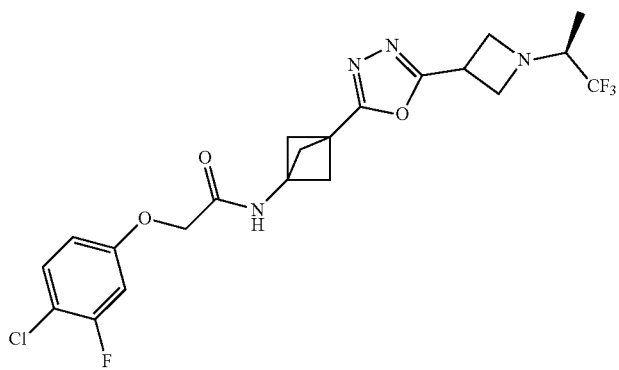 [SMILES: C[C@H](N1CC(c2nnc(C34CC(NC(=O)COc5ccc(Cl)c(F)c5)(C3)C4)o2)C1)C(F)(F)F]
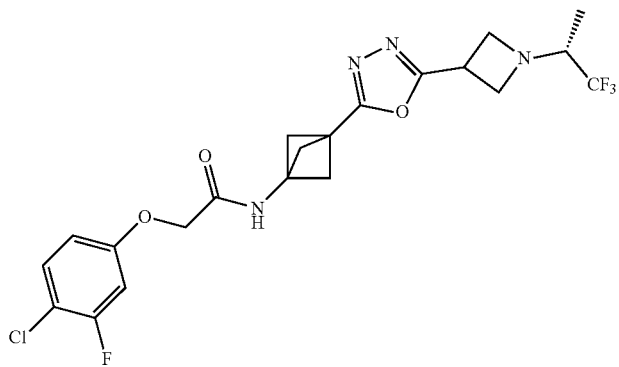 [SMILES: C[C@@H](N1CC(c2nnc(C34CC(NC(=O)COc5ccc(Cl)c(F)c5)(C3)C4)o2)C1)C(F)(F)F]

TABLE 2-continued
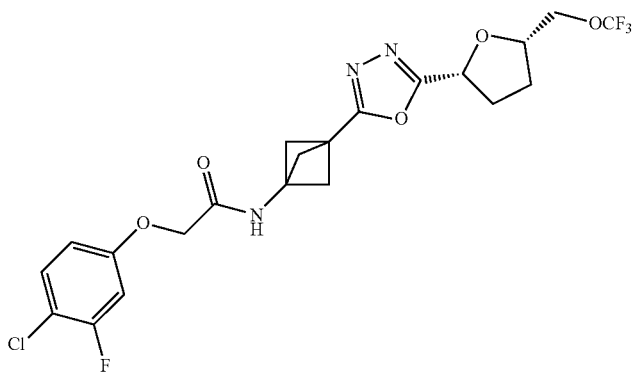 [SMILES: O=C(COc1ccc(Cl)c(F)c1)NC12CC(c3nnc([C@H]4CC[C@@H](COC(F)(F)F)O4)o3)(C1)C2]
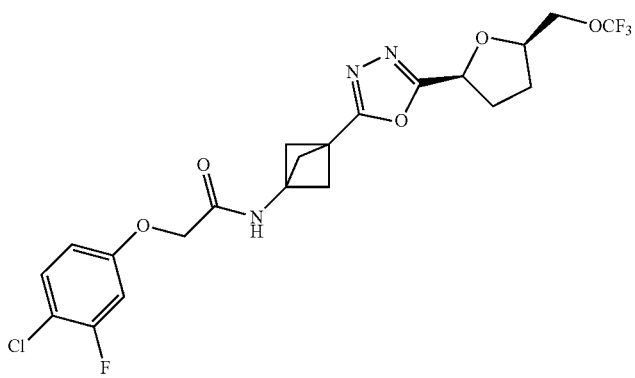 [SMILES: O=C(COc1ccc(Cl)c(F)c1)NC12CC(c3nnc([C@@H]4CC[C@H](COC(F)(F)F)O4)o3)(C1)C2]
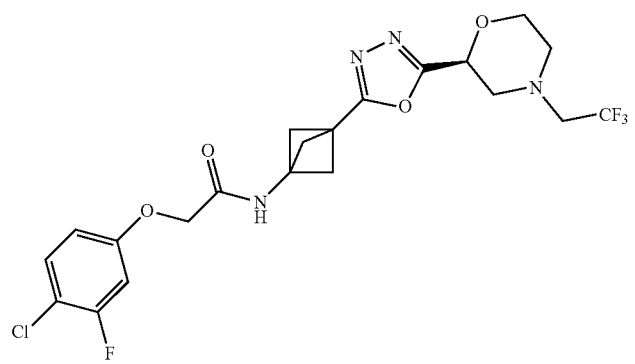 [SMILES: O=C(COc1ccc(Cl)c(F)c1)NC12CC(c3nnc([C@@H]4CN(CC(F)(F)F)CCO4)o3)(C1)C2]
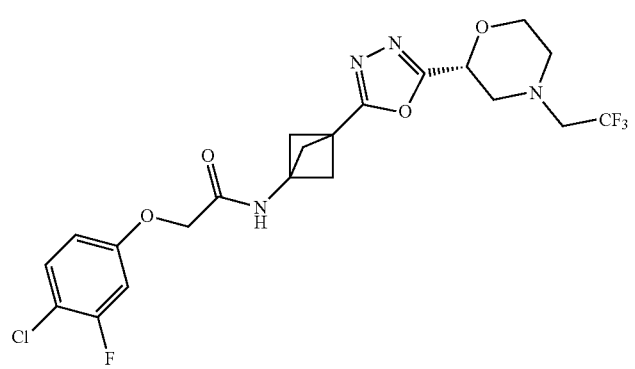 [SMILES: O=C(COc1ccc(Cl)c(F)c1)NC12CC(c3nnc([C@H]4CN(CC(F)(F)F)CCO4)o3)(C1)C2]

TABLE 2-continued
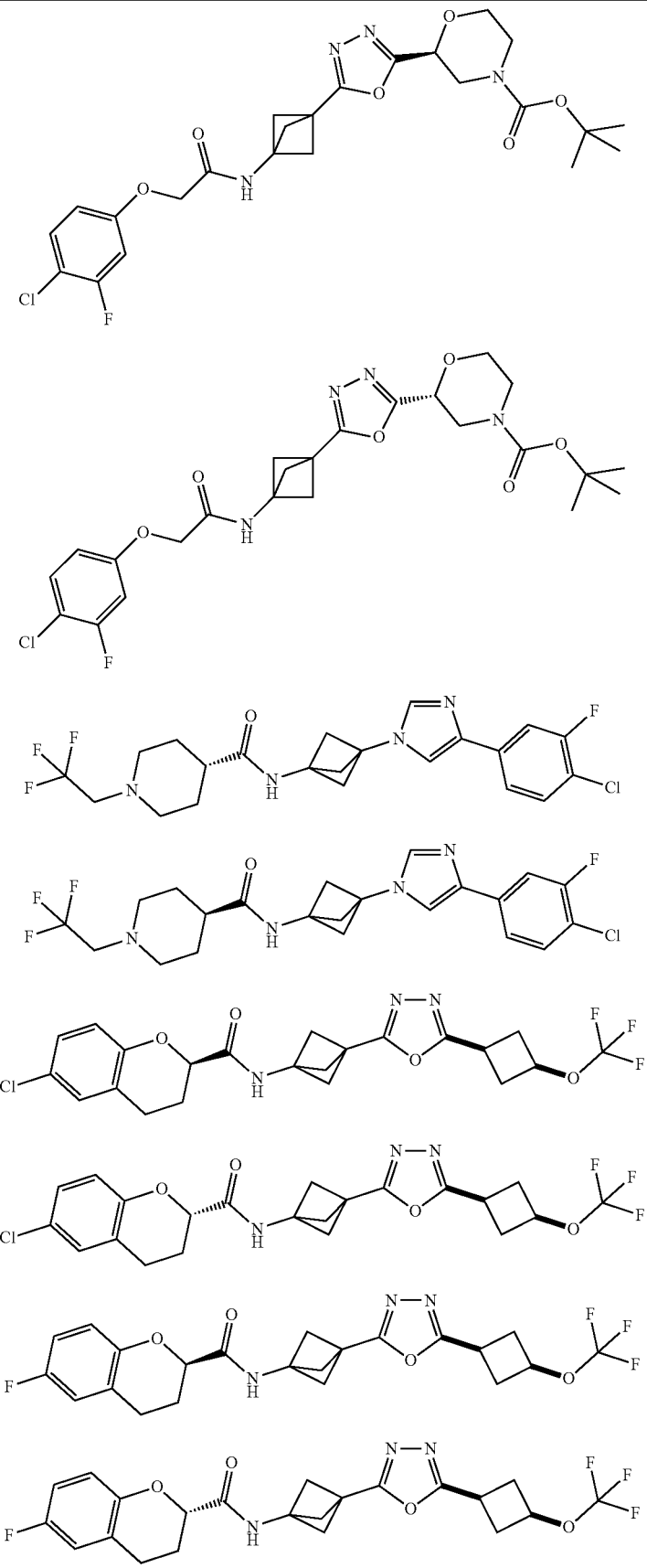

TABLE 2-continued
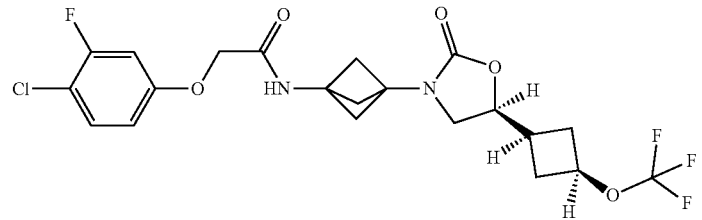 [SMILES: O=C(COc1ccc(Cl)c(F)c1)NC12CC(N3C[C@H]([C@H]4C[C@@H](OC(F)(F)F)C4)OC3=O)(C1)C2]
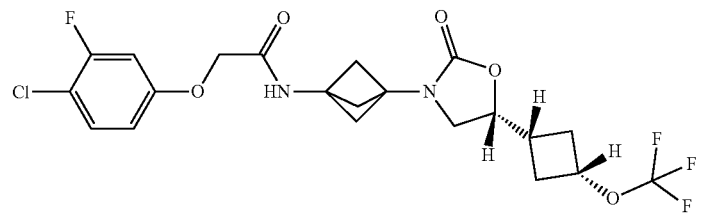 [SMILES: O=C(COc1ccc(Cl)c(F)c1)NC12CC(N3C[C@@H]([C@H]4C[C@@H](OC(F)(F)F)C4)OC3=O)(C1)C2]
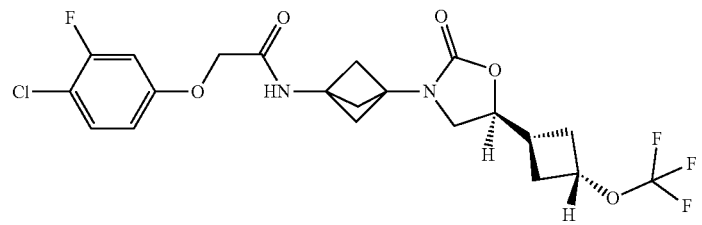
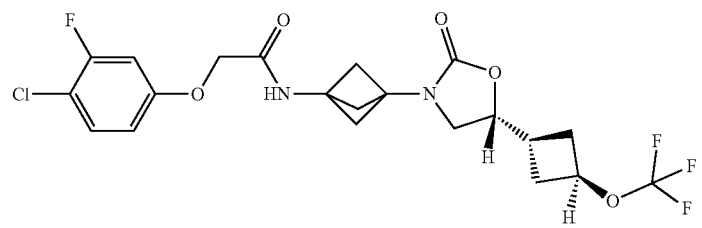
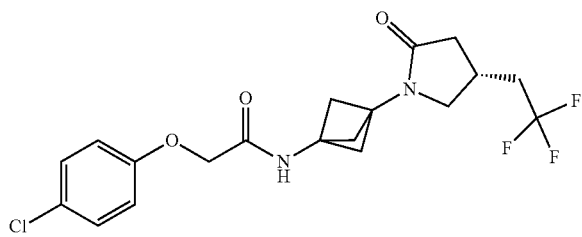 [SMILES: O=C(COc1ccc(Cl)cc1)NC12CC(N3C[C@@H](CC(F)(F)F)CC3=O)(C1)C2]
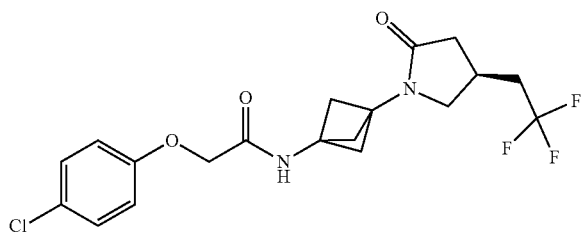 [SMILES: O=C(COc1ccc(Cl)cc1)NC12CC(N3C[C@H](CC(F)(F)F)CC3=O)(C1)C2]

TABLE 2-continued
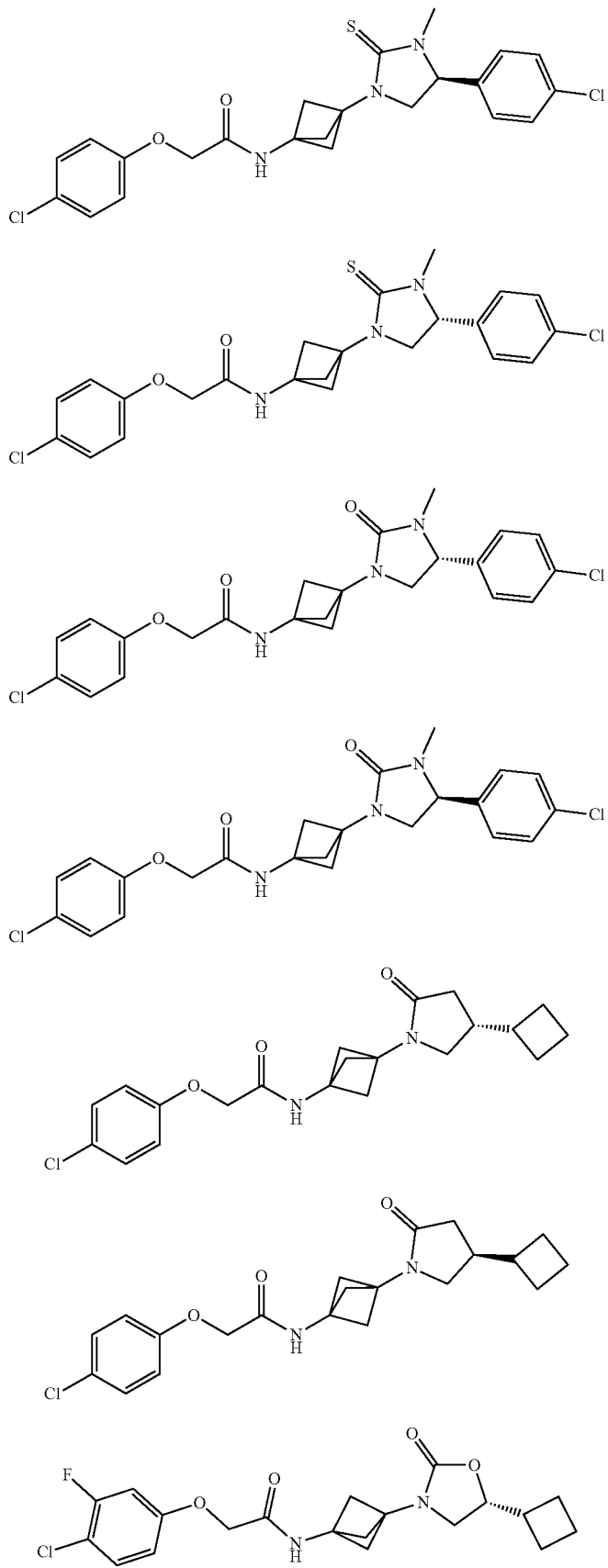

TABLE 2-continued
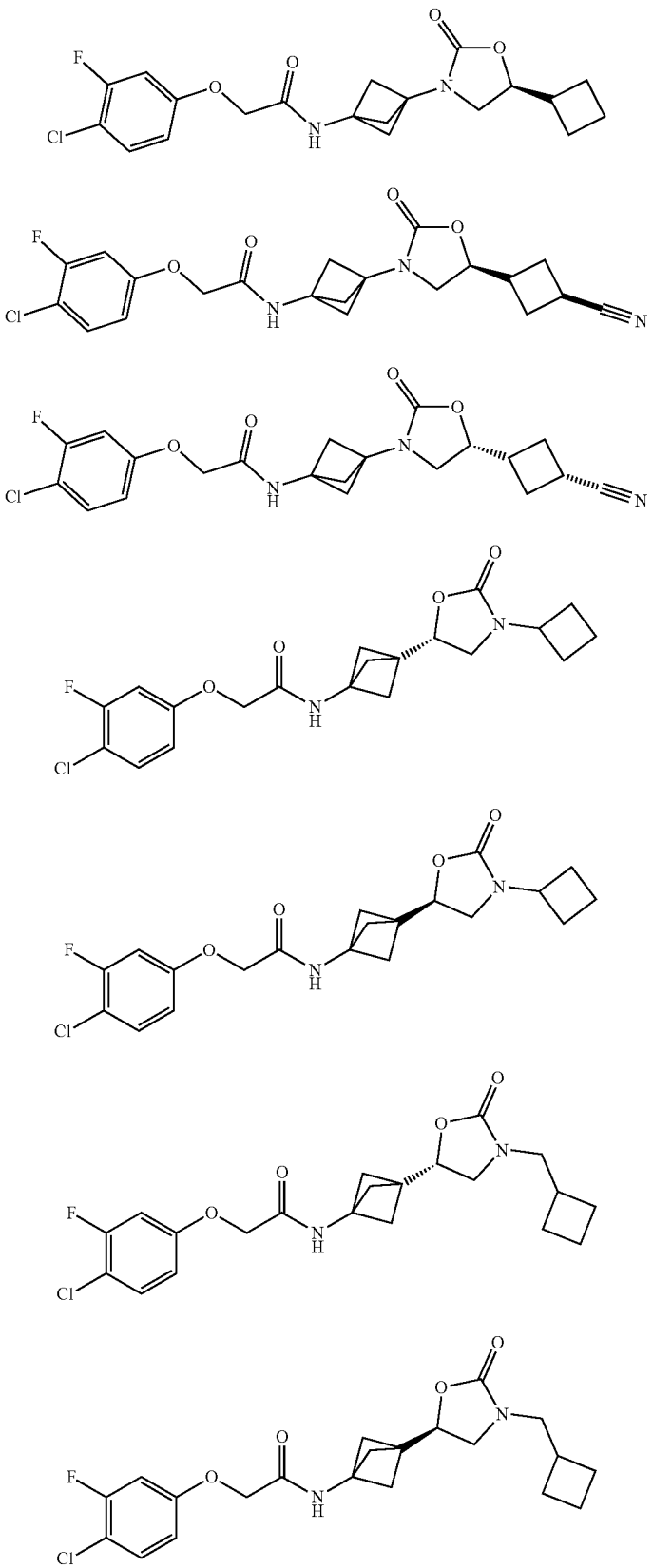

TABLE 2-continued
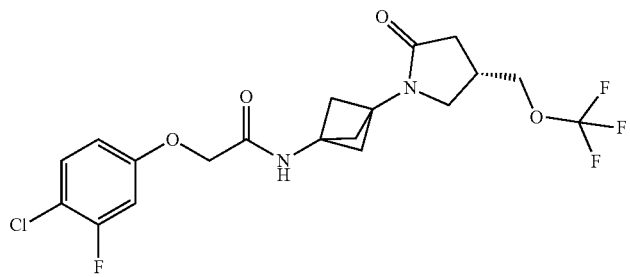 [SMILES: O=C(COc1ccc(Cl)c(F)c1)NC12CC(N3C[C@@H](COC(F)(F)F)CC3=O)(C1)C2]
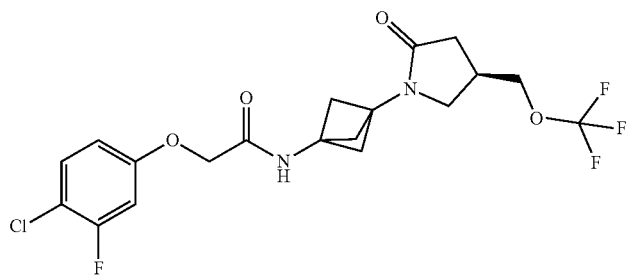 [SMILES: O=C(COc1ccc(Cl)c(F)c1)NC12CC(N3C[C@H](COC(F)(F)F)CC3=O)(C1)C2]
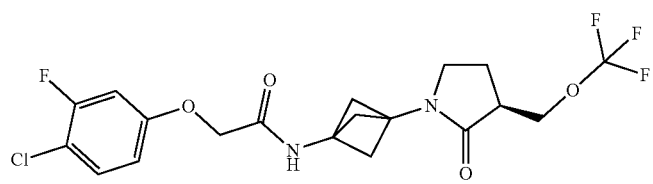 [SMILES: O=C(COc1ccc(Cl)c(F)c1)NC12CC(N3CC[C@@H](COC(F)(F)F)C3=O)(C1)C2]
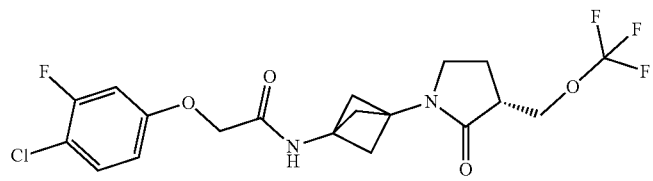 [SMILES: O=C(COc1ccc(Cl)c(F)c1)NC12CC(N3CC[C@H](COC(F)(F)F)C3=O)(C1)C2]
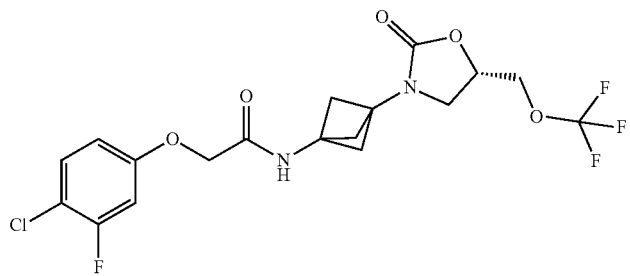 [SMILES: O=C(COc1ccc(Cl)c(F)c1)NC12CC(N3C[C@@H](COC(F)(F)F)OC3=O)(C1)C2]
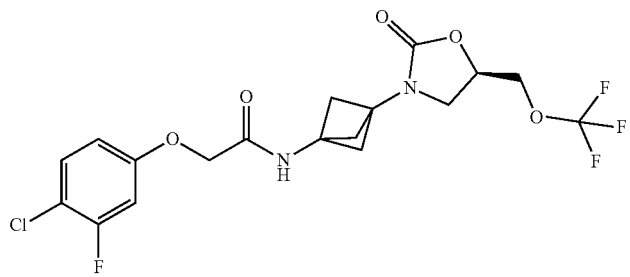 [SMILES: O=C(COc1ccc(Cl)c(F)c1)NC12CC(N3C[C@H](COC(F)(F)F)OC3=O)(C1)C2]

TABLE 2-continued
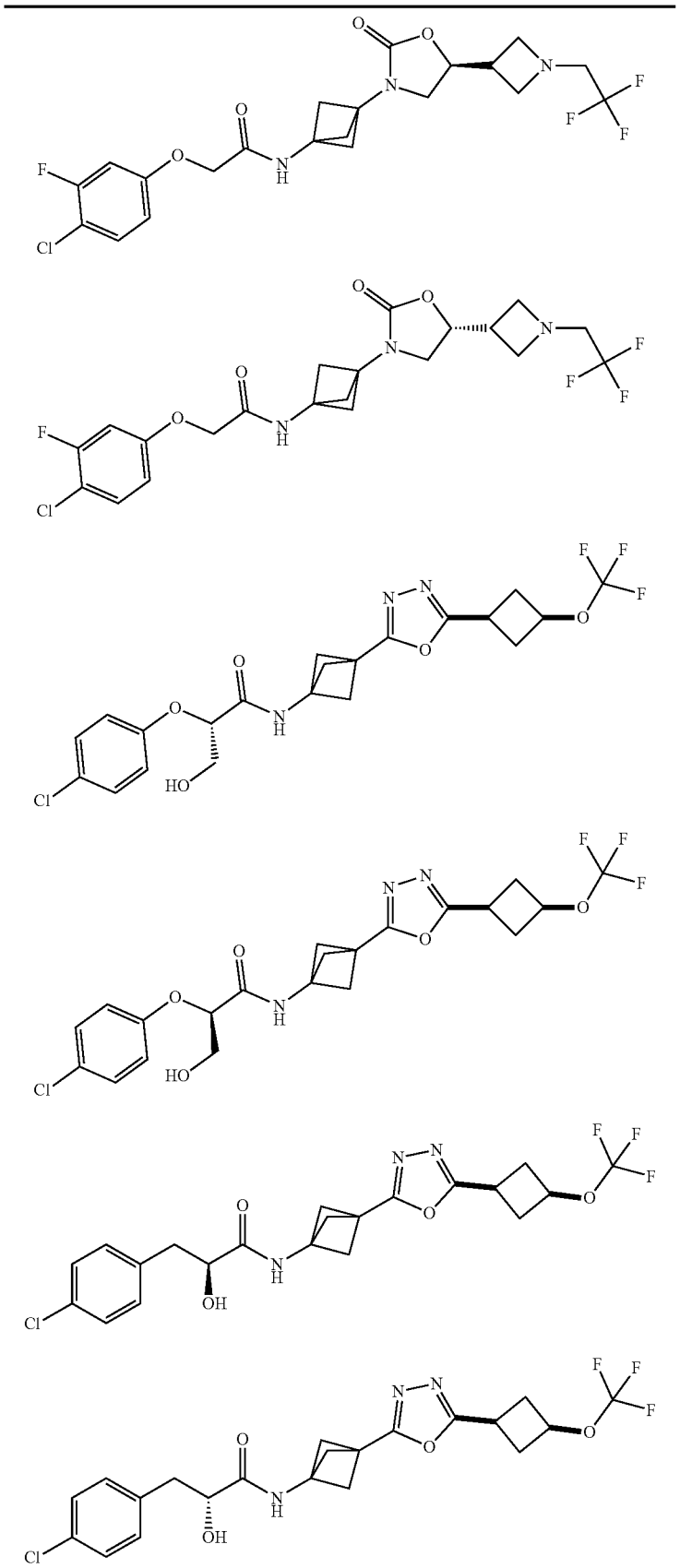

TABLE 2-continued
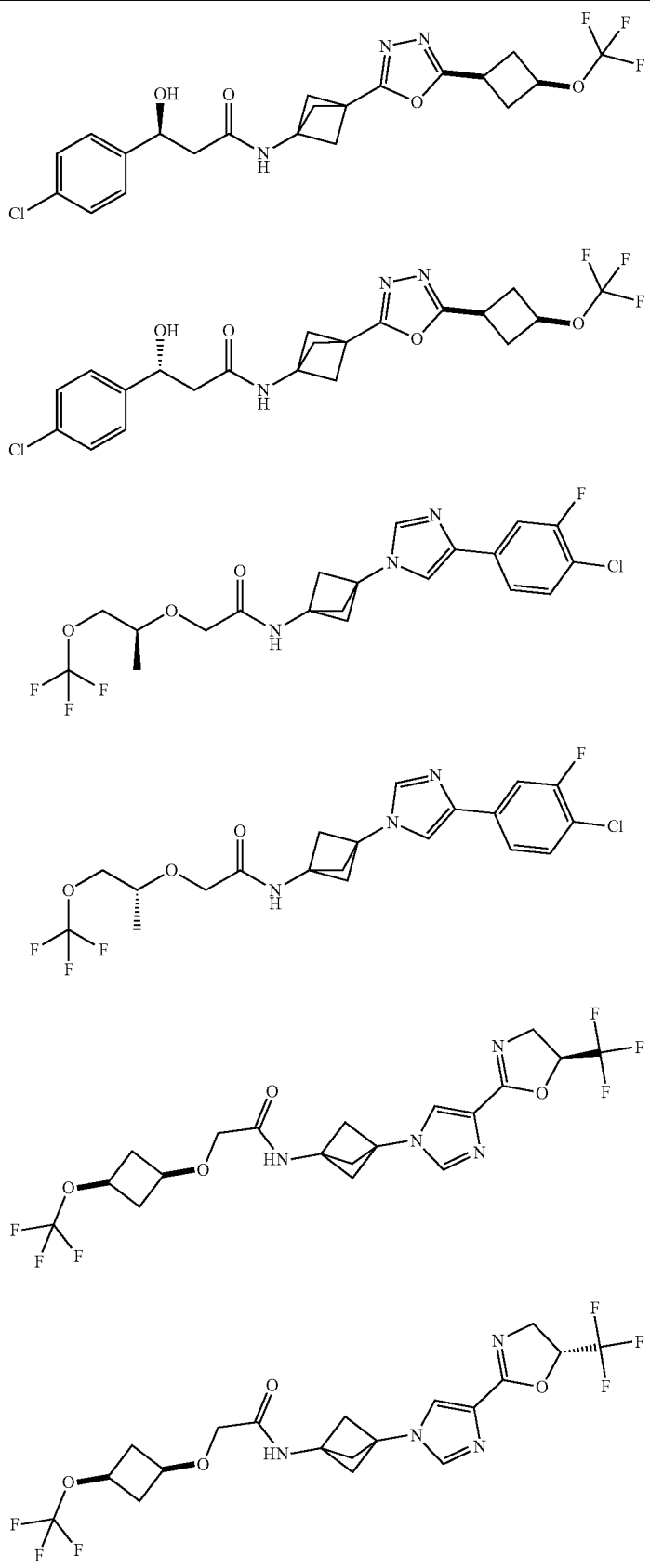

TABLE 2-continued

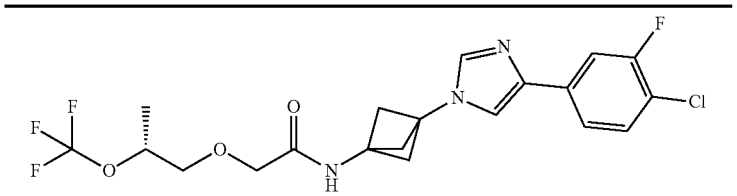

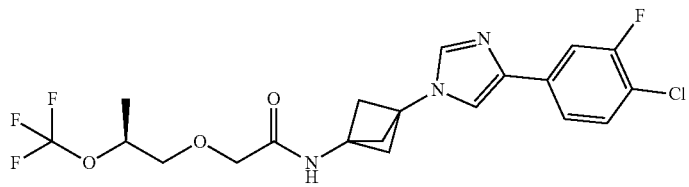 [SMILES: C[C@@H](COCC(=O)NC12CC(n3cnc(-c4ccc(Cl)c(F)c4)c3)(C1)C2)OC(F)(F)F]

or a pharmaceutically acceptable salt, isotopically enriched analog, or prodrug thereof.

In certain embodiments, provided is a compound of having the structure

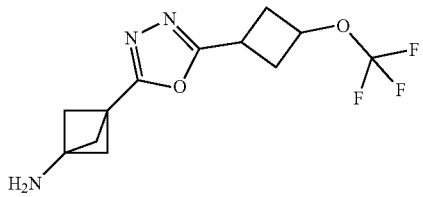

or a salt, isotopically enriched analog, stereoisomer, or a mixture of stereoisomers thereof. In certain embodiments, the salt is the HCl salt.

In certain embodiments, provided is a compound of having the structure

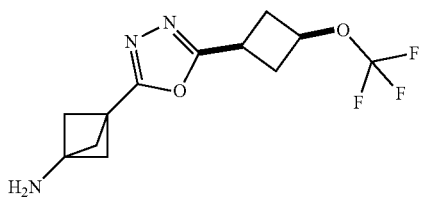

or a salt thereof. In certain embodiments, the salt is the HCl salt.

In certain embodiments, provided is a compound of having the structure

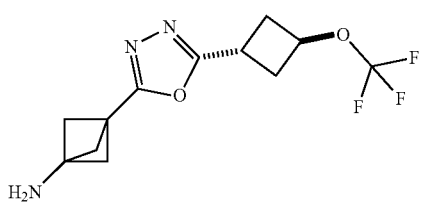

or a salt thereof. In certain embodiments, the salt is the HCl salt.

3. Methods

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In certain embodiments, the subject is a human.

The term "therapeutically effective amount" or "effective amount" of a compound described herein or a pharmaceutically acceptable salt, isotopically enriched analog, stereoisomer, mixture of stereoisomers or prodrug thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

In certain embodiments, the compounds disclosed herein can be used to treat cellular proliferative disorders, including both cancerous and non-cancerous cellular proliferative disorders. Treatment of cellular proliferative disorders may comprise, but is not limited to, inhibiting cellular proliferation, including rapid proliferation. It is contemplated that the compounds described herein can be used to treat any type of cancer, including, but not limited to, carcinomas, sarcomas, lymphomas, leukemias and germ cell tumors. Exemplary cancers include, but are not limited to, adrenocortical carcinoma, anal cancer, appendix cancer, basal cell carcinoma, cholangiocarcinoma, bladder cancer, bone cancer, osteosarcoma or malignant fibrous histiocytoma, brain cancer (e.g., brain stem glioma, astrocytoma (e.g., cerebellar, cerebral, etc.), atypical teratoid/rhabdoid tumor, central nervous system embryonal tumors, malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors, etc.), breast cancer, bronchial tumors, carcinoid tumor (e.g., gastrointestinal, etc. carcinoma of unknown primary, cervical cancer, chordoma, chronic myeloproliferative disorders, colon cancer, colorectal cancer, embryonal tumors, cancers of the central nervous system, endometrial cancer, ependymoma, esophageal cancer, Ewing family of tumors, eye cancer (e.g., intraocular melanoma, retinoblastoma, etc.), gallbladder cancer, gastric cancer, gastrointestinal tumor (e.g., carcinoid tumor, stromal tumor (gist), stromal cell tumor, etc.), germ cell tumor (e.g., extracranial, extragonadal, ovarian, etc.), gestational trophoblastic tumor, head and neck cancer, hepatocellular cancer, hypopharyngeal cancer, hypothalamic and visual pathway glioma, intraocular melanoma, islet cell tumors, Kaposi sarcoma, kidney cancer, large cell tumors, laryngeal cancer (e.g., acute lymphoblastic, acute myeloid, etc.), leukemia (e.g., myeloid, acute myeloid, acute lymphoblastic, chronic lymphocytic, chronic myelogenous, multiple myelogenous, hairy cell, etc.), lip and/or oral cavity cancer, liver cancer, lung cancer (e.g., non-small cell, small cell, etc.), lymphoma (e.g., AIDS-related, Burkitt, cutaneous Tcell, Hodgkin, non-Hodgkin, primary central nervous system, cutaneous T-cell, Waldenström macroglobulinemia, etc.), malignant fibrous histiocytoma of bone and/or osteosarcoma, medulloblastoma, medulloepithelioma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases (e.g., myeloproliferative disorders, chronic, etc.) nasal cavity and/or paranasal sinus cancer, nasopharyngeal cancer, neuroblastoma, oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor, etc.), pancreatic cancer (e.g., islet cell tumors, etc.), papillomatosis, paranasal sinus and/or nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, prostate cancer, rectal cancer, renal cell cancer, transitional cell cancer, respiratory tract carcinoma involving the nut gene on chromosome 15, retinoblastoma, rhabdomyosarcoma, salivary gland cancer, sarcoma (e.g., Ewing family of tumors, Kaposi, soft tissue, uterine, etc.), Sézary syndrome, skirt cancer (e.g., non-melanoma, melanoma, merkel cell, etc.), small intestine cancer, squamous cell carcinoma, squamous neck cancer with occult primary, metastatic, stomach cancer, supratentorial primitive neuroectodermal tumors, testicular cancer, throat cancer, thymoma and/or thymic carcinoma, thyroid cancer, transitional cell cancer of the renal, pelvis and/or ureter (e.g., trophoblastic tumor, unknown primary site carcinoma, urethral cancer, uterine cancer, endometrial, uterine sarcoma, etc.), vaginal cancer, visual pathway and/or hypothalamic glioma, vulvar cancer. Wilms tumor, and the like. Examples of noncancerous cellular proliferative disorders include, but are not limited to, fibroadenoma adenoma, intraductal papilloma, nipple adenoma, adenosis, fibrocystic disease or changes of breast, plasma cell proliferative disorder (PCPD), restenosis, atherosclerosis, rheumatoid arthritis, myofibromatosis, fibrous hamartoma, granular lymphocyte proliferative disorders, benign hyperplasia of prostate, heavy chain diseases (HCDs), lymphoproliferative disorders, psoriasis, idiopathic pulmonary fibrosis, scleroderma, cirrhosis of the liver, IgA nephropathy, mesangial proliferative glomerulonephritis, membranoproliferative glomerulonephritis, hemangiomas, vascular and non-vascular intraocular proliferative disorders, and the like.

In certain embodiments, the compounds disclosed herein can be used to treat lung injury and/or lung inflammation.

In certain embodiments, the compounds disclosed herein can be used to treat cancer, pre-cancerous syndromes and diseases/injuries associated with activated unfolded protein response pathways, such as Alzheimer's disease, neuropathic pain, spinal cord injury, traumatic brain injury, ischemic stroke, stroke, Parkinson's disease, diabetes, metabolic syndrome, metabolic disorders, Huntington's disease, Creutzfeldt-Jakob Disease, fatal familial insomnia, Gerstmann-Straussler-Scheinker syndrome, and related prion diseases, amyotrophic lateral sclerosis, progressive supranuclear palsy, myocardial infarction, cardiovascular disease, inflammation, organ fibrosis, chronic and acute diseases of the liver, fatty liver disease, liver steatosis, liver fibrosis, chronic and acute diseases of the lung, lung fibrosis, chronic and acute diseases of the kidney, kidney fibrosis, chronic traumatic encephalopathy (CTE), neurodegeneration, dementias, frontotemporal dementias, tauopathies, Pick's disease, Neimann-Pick's disease, amyloidosis, cognitive impairment, atherosclerosis, ocular diseases, arrhythmias, in organ transplantation and in the transportation of organs for transplantation.

In embodiments, the compounds disclosed herein can be used to treat or lessen the severity of cancer, Alzheimer's disease, stroke, Type 1 diabetes, Parkinson disease, Huntington's disease, amyotrophic lateral sclerosis, myocardial infarction, cardiovascular disease, atherosclerosis, arrhythmias, or age-related macular degeneration.

In certain embodiments, the compounds disclosed herein can be used to treat neuropathic pain.

In certain embodiments, the compounds disclosed herein can be used to treat or lessen the severity of ocular diseases/angiogenesis. In certain embodiments, the ocular disease includes vascular leakage (e.g., edema or neovascularization for any occlusive or inflammatory retinal vascular disease, such as rubeosis irides, neovascular glaucoma, pterygium, vascularized glaucoma filtering blebs, conjunctival papilloma), choroidal neovascularization (e.g., neovascular age-related macular degeneration (AMD), myopia, prior uveitis, trauma, or idiopathic), macular edema (e.g., post surgical macular edema, macular edema secondary to uveitis including retinal and/or choroidal inflammation, macular edema secondary to diabetes, and macular edema secondary to retinovascular occlusive disease (i.e. branch and central retinal vein occlusion)), retinal neovascularization due to diabetes (e.g., retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease), and genetic disorders (e.g., VonHippel-Lindau syndrome). In certain embodiments, the neovascular age-related macular degeneration is wet age-related macular degeneration. In certain embodiments, the neovascular age-related macular degeneration is dry age-related macular degeneration and the patient is characterized as being at increased risk of developing wet age-related macular degeneration.

In certain embodiments, the compounds disclosed herein can be used to treat viral infections (e.g., to prevent the initiation of viral protein synthesis). Exemplary viruses which can be treated using the compounds disclosed herein include, but are not limited to, picornaviridae (e.g., polioviruses), reoviridae (e.g., rotaviruses), togaviridae (e.g., encephalitis viruses, yellow fever virus, rubella virus, etc.), orthomyxoviridae (e.g., influenza viruses), paramyxoviridae (e.g., respiratory syncytial virus, measles virus, mumps virus, parainfluenza virus, etc.), rhabdoviridae (e.g., rabies virus), coronaviridae, bunyaviridae, flaviviridae, filoviridae, arenaviridae, bunyaviridae and retroviridae (e.g., human T-cell lymphotropic viruses (HTLV), human immunodeficiency viruses (HIV), etc.), papovaviridae (e.g., papilloma viruses), adenoviridae adenovirus), herpesviridae (e.g., herpes simplex viruses) and poxyiridae (e.g., variola viruses). In certain embodiments, the viral infection is caused by hepatitis B virus, hepatitis C virus and/or HIV.

In certain embodiments, the compounds disclosed herein can be used to treat disorders associated with viral infections. Such disorders include, but are not limited to neurological symptoms (e.g., encephalitis, meningoencephalitis paralysis, myelopathy, neuropathy, aseptic meningitis, hemiparesis, dementia, dysphagia, lack of muscular coordination, impaired vision, coma, etc.), wasting symptoms (e.g., inflammatory cell infiltration, perivascular cuffing of blood vessels, demyelination, necrosis, reactive gliosis, etc.), gastroenteritis symptoms (e.g., diarrhea, vomiting, cramps, etc.), hepatitis symptoms (nausea, vomiting, right upper quadrant pain, raised liver enzyme levels (e.g., AST, ALT, etc.), jaundice, etc.), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure, etc.), oncogenic symptoms (e.g., sarcomas, leukemias and the like, as well as "rare" malignancies, e.g., Kaposi's sarcoma, oral hairy leukoplasia, lymphomas etc.), immunodeficiency symptoms (e.g., opportunistic infections, wasting, rare malignancies, neurological disease, fever, diarrhea, skin rashes, etc.), lesions (e.g., warts (e.g., common wart, flat wart, deep hyperkeratotic palmoplantar wart, superficial mosaic type palmoplantar wart, etc.)), epidermodysplasia, mucosal lesions, ulcers and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopathy, arthritis, ulcers, photosensitivity, weight loss, irritability, restlessness, anxiety, coma, death, etc.).

In certain embodiments, the compounds disclosed herein can be used to treat disorders characterized by unwanted synthesis and/or abnormal accumulation of one or more mutant and/or wild-type proteins. It is contemplated that the compounds disclosed herein that can inhibit translation initiation and thus can reduce the load on the protein-folding machinery and, accordingly, may reduce the severity of the disorder. Disorders associated with unwanted synthesis and/or abnormal accumulation of one or more mutant and/or wild-type proteins include, but are not limited to, Tay-Sachs disease, cystic fibrosis, phenylketonuria, Fabry disease, Alzheimer's disease, Huntington's disease, Parkinson's disease, frontotemporal dementia, congophilic angiopathy, prion related disorders (i.e., transmissible spongiform encephalopathies such as Creutzfeldt-Jacob disease, kuru, fatal familial insomnia, scrapie, bovine spongiform encephalopathy, etc.), and the like.

It is contemplated that the compounds and compositions disclosed herein are capable of inhibiting neuronal cell death, such as in prion disease. Generally, the method includes administering a therapeutically effective amount of a compound or composition as described herein, to a patient in need of.

In some embodiments, the disorder is a neurodegenerative disease. The term "neurodegenerative disease" refers to a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, insulin resistance or Tabes dorsalis.

Other embodiments include use of the presently disclosed compounds in therapy. Some embodiments include their use in the treatment of a neurodegenerative disease.

In other embodiments, provided are the presently disclosed compounds for use in the treatment of Alzheimer's disease, Parkinson's disease, dementia, or ALS.

In other embodiments, provided is the use of the presently disclosed compounds for the manufacture of a medicament for treating a neurodegenerative disease.

In other embodiments, provided is the use of the presently disclosed compounds for the manufacture of a medicament for treating Alzheimer's disease, Parkinson's disease, dementia, or ALS.

4. Kits

Provided herein are also kits that include a compound of the disclosure, or a pharmaceutically acceptable salt, isotopically enriched analog, stereoisomer, mixture of stereoisomers or prodrug thereof, and suitable packaging. In certain embodiments, a kit further includes instructions for use. In one aspect, a kit includes a compound of the disclosure, or a pharmaceutically acceptable salt, isotopically enriched analog, stereoisomer, mixture of stereoisomers or prodrug thereof, and a label and/or instructions for use of the compounds in the treatment of the indications, including the diseases or conditions, described herein.

Provided herein are also articles of manufacture that include a compound described herein or a pharmaceutically acceptable salt, isotopically enriched analog, stereoisomer, mixture of stereoisomers or prodrug thereof in a suitable container. The container may be a vial, jar, ampoule, preloaded syringe and intravenous bag.

5. Pharmaceutical Compositions and Modes of Administration

Compounds provided herein are usually administered in the form of pharmaceutical compositions. Thus, provided herein are also pharmaceutical compositions that contain one or more of the compounds described herein a pharmaceutically acceptable salt, stereoisomer, mixture of stereoisomers or prodrug thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, isotopically enriched analog, stereoisomer, mixture of stereoisomers or prodrug thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include lubricating agents such as talc, magnesium stearate and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, isotopically enriched analog, stereoisomer, mixture of stereoisomers or prodrug thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, isotopically enriched analog, stereoisomer, mixture of stereoisomers or prodrug thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation may include solutions and suspensions in pharmaceutically acceptable, aqueous or organic solvents, or mixtures thereof and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

6. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

7. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents and starting materials may be purchased commercially, e.g., from Sigma Aldrich or other chemical suppliers.

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

General Synthesis

In certain embodiments, provided is a method of preparing a compound of Formula I, comprising coupling a compound of Formula 1-A:

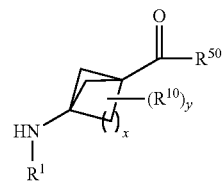

1-A with a compound of Formula 2-A:

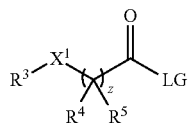

2-A under conditions suitable to provide a compound of Formula 3-A:

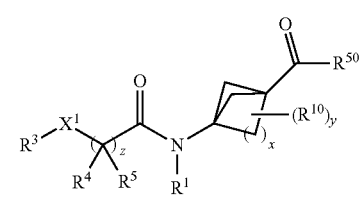

3-A and coupling a compound of Formula 3-A with a suitable reagent in combination with an acid of Formula $R^2$—C(O)$_2$H under ring forming reaction conditions (when L is a ring) or coupling reaction conditions, optionally in combination with reduction (when L is heteroalkylene) to provide the compound of Formula I, wherein $R^1$, $R^3$, $R^4$, $R^5$, $R^{10}$, x, y, z and $X^1$ are as defined herein, $R^{50}$ is H, —NHNH$_2$ or a leaving group and LG is leaving group (e.g., $C_{1-6}$ alkoxy or halo). In addition, compounds of Formula I where L is heteroalkylene can be provided by coupling a compound of Formula 3A with a suitably functionalized compound of Formula $R^2$—OH (e.g., when L comprises an O), optionally in combination with a reduction step.

The following reaction shown in Scheme I illustrates a general method which can be employed for the synthesis of compounds disclosed herein. In Scheme I, $R^1$, $R^3$, $R^4$, $R^5$, $R^{10}$, x, y and $X^1$ are as defined herein, $R^{50}$ is H or a leaving group, PG is a protecting group, and LG is leaving group (e.g., $C_{1-6}$alkoxy or halo).

Scheme I

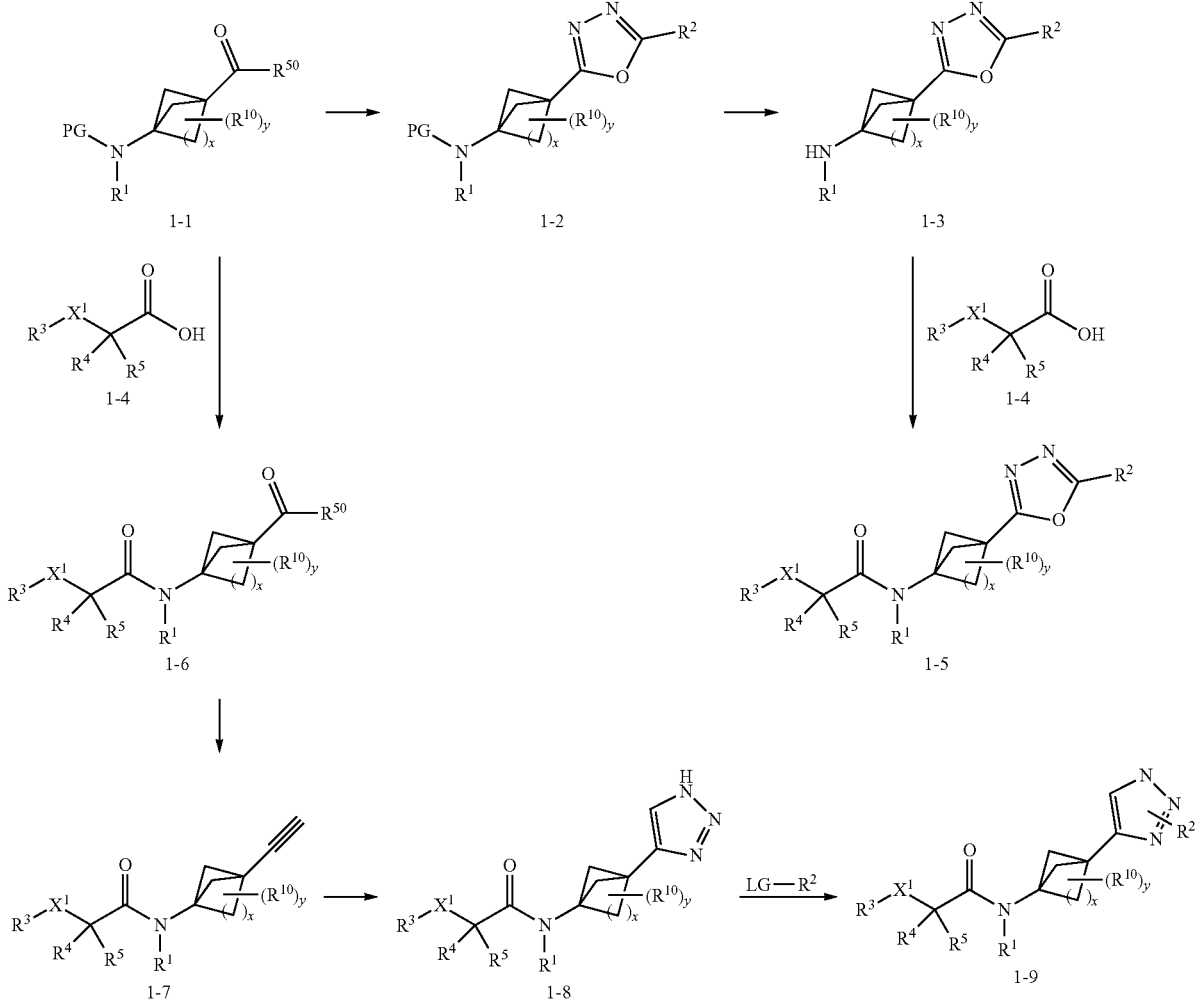

Referring to Scheme I, compound 1-2 can be prepared by reacting compound 1-1, where $R^{50}$ is —NHNH$_2$, with a suitable reagent under ring forming reaction conditions with a suitably substituted carboxylic acid, to provide the oxadiazole 1-2. Deprotection of compound 1-2 provides compound 1-3, followed by coupling with a suitably substituted compound of Formula 1-4 to provides compound 1-5. In certain embodiments, compound 1-3 is converted to a salt (e.g., the HCl salt) prior to coupling with a suitably substituted compound of Formula 1-4. Compound of Formula I where L is triazole can be prepared from compound 1-1 where $R^{50}$ is hydrogen. Deprotecting compound 1-1 and coupling with compound 1-4 under standard amide bond forming reaction conditions provides compound 1-6. The coupling typically employs a suitable reagent, such as a carbodiimide (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), anhydrides (e.g., symmetric, mixed, or cyclic anhydrides), an activated ester (e.g., phenyl activated ester derivatives, p-hydroxamic activated ester, hexafluoroacetone (HFA), etc.), acylazoles (acylimidazoles using CDI, acylbenzotriazoles, etc.), acyl azides, acid halides, phosphonium salts (HOBt, PyBOP, HOAt, etc.), aminium/uronium salts (e.g., tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.), an organophosphorus reagent (e.g., phosphinic and phosphoric acid derivatives, such as propylphosphonic anhydride), organosulfur reagents (e.g., sulfonic acid derivatives), a triazine coupling reagent (e.g., 2-chloro-4,6-dimethoxy-1,3,5-triazine, 4-(4,6-dimethoxy-1,3,5-triazin-2-yl)-4 methylmorpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), and the like (see, e.g., El-Faham, et al. Chem. Rev., 2011, 111(11): 6557-6602; Han, et al. Tetrahedron, 2004, 60:2447-2467). Conversion of compound 1-6 to acetylene intermediate 1-7 allows for triazole formation using standard click-chemistry reaction conditions. Triazole 1-8 can be functionalized with an $R^2$ moiety under standard coupling reaction conditions to provide compound 1-9.

Appropriate starting materials and reagents (i.e., diamines, esters and acids) can be purchased or prepared by methods known to one of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure; appreciate that many changes can be made in the specific embodiments which are disclosed and still obtain a like or similar result without departing from the spirit and scope of the disclosure.

General Experimental Methods

All solvents used were commercially available and were used without further purification. Reactions were typically run using anhydrous solvents under an inert atmosphere of nitrogen.

NMR Spectroscopy: $^1$H Nuclear magnetic resonance (NMR) spectroscopy was carried out using a Bruker Avance III equipped with a BBFO 300 MHz probe operating at 300 MHz or one of the following instruments: a Bruker Avance 400 instrument equipped with probe DUAL 400 MHz S1, a Bruker Avance 400 instrument equipped with probe 6 S1 400 MHz 5 mm $^1$H-1-$^{13}$C ID, a Bruker Avance III 400 instrument equipped with nanobay equipped with probe Broadband BBFO 5 mm direct, a Bruker Mercury Plus 400 NMR spectrometer equipped with a Bruker 400 BBO probe with all operating at 400 MHz. All deuterated solvents contained typically 0.03% to 0.05% v/v tetramethylsilane, which was used as the reference signal (set at δ 0.00 for both $^1$H and $^{13}$C). In certain cases, $^1$H Nuclear magnetic resonance (NMR) spectroscopy was carried out using a Bruker Advance 400 instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Thin Layer Chromatography: Where thin layer chromatography (TLC) has been used it refers to silica gel TLC using silica gel F254 (Merck) plates, Rf is the distance travelled by the compound divided by the distance travelled by the solvent on a TLC plate. Column chromatography was performed using an automatic flash chromatography system over silica gel cartridges or in the case of reverse phase chromatography over C18 cartridges. Alternatively, thin layer chromatography (TLC) was performed on Alugram® (Silica gel 60 F254) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24} \cdot 4H_2O$, 5 g $(NH_4)_2Ce(IV)(NO_3)_6$ in 450 mL water and 50 mL concentrated $H_2SO_4$) to visualize the compound.

Liquid Chromatography-Mass Spectrometry and HPLC Analysis: HPLC analysis was performed on Shimadzu 20AB HPLC system with a photodiode array detector and Luna-C18(2) 2.0×50 mm, 5 μm column at a flow rate of 1.2 mL/min with a gradient solvent Mobile phase A (MPA, $H_2O+0.037\%$ (v/v) TFA): Mobile phase B (MPB, ACN+ 0.018 (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral conditions. Acidic: Luna C18 100×30 mm, 5 μm; MPA: HCl/$H_2O=0.04\%$, or formic acid/$H_2O=0.2\%$ (v/v); MPB: ACN. Neutral: Waters Xbridge 150×25, 5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector. SFC analysis was performed on Thar analytical SFC system with a UV/Vis detector and series of chiral columns including AD-3, AS-H, OJ-3, OD-3, AY-3 and IC-3, 4.6×100 mm, 3 µm column at a flow rate of 4 mL/min with a gradient solvent Mobile phase A (MPA, $CO_2$): Mobile phase B (MPB, MeOH+0.05% (v/v) IPAm) (0.01 min, 10% MPB; 3 min, 40% MPB; 3.5 min, 40% MPB; 3.56-5 min, 10% MPB). SFC preparative was performed on Thar 80 preparative SFC system with a UV/Vis detector and series of chiral preparative columns including AD-H, AS-H, OJ-H, OD-H, AY-H and IC-H, 30×250 mm, 5 µm column at a flow rate of 65 mL/min with a gradient solvent Mobile phase A (MPA, $CO_2$): Mobile phase B (MPB, MeOH+0.1% (v/v) $NH_3H_2O$) (0.01 min, 10% MPB; 5 min, 40% MPB; 6 min, 40% MPB; 6.1-10 min, 10% MPB). LC-MS data were also collected using an UPLC-MS Acquity™ system equipped with PDA detector and coupled to a Waters single quadrupole mass spectrometer operating in alternated positive and negative electrospray ionization mode. The column used was a Cortecs UPLC C18, 1.6 µm, 2.1×50 mm. A linear gradient was applied, starting at 95% A (A: 0.1% formic acid in water) and ending at 95% B (B: 0.1% formic acid in MeCN) over 2.0 min with a total run time of 2.5 min. The column temperature was at 40° C. with the flow rate of 0.8 mL/min.

General procedure A, T3P Coupling: To a flask containing amine (1 eq), and carboxylic acid (1.5 eq) in DMF or EtOAc (0.1 M-0.2 M) were added either N-methylimidazole, diisopropylethylamine, or triethylamine (3.0-5.0 eq) followed by T3P solution (1.5-3.0 eq., 50% in EtOAc). The resulting reaction mixture was stirred at rt for 4 h, at which point 1M NaOH solution was added followed by EtOAc. The layers were separated, and the aqueous layer was extracted with EtOAc (3×). The combined organic layers were dried over anhydrous $MgSO_4$, filtered and concentrated under reduced pressure. The crude reaction mixture was purified employing silica flash chromatography or reverse-phase HPLC to provide the desired product.

The following compounds were prepared using General Procedure A and were used to prepare compounds disclosed herein: tert-butyl (3-(2-(3,4-difluorophenoxy)acetamido)bicyclo[1.1.1]pentan-1-yl)carbamate and tert-butyl N-[1-[[2-[3-cis-(trifluoromethoxy)cyclobutoxy]acetyl]amino]-3-bicyclo[1.1.1]pentanyl]carbamate.

General procedure B, Hydrazide Formation: To a suspension of the methyl ester (1 eq) in EtOH (0.25-0.1M) was added hydrazine hydrate (3-5 eq) and the reaction mixture was heated at 90° C. overnight. The reaction mixture was cooled to rt often causing the product to crystallize out of solution. This solid was collected by removal of the supernatant. If the product did not crystallize, the solution was concentrated, and the crude product was sufficiently pure to use in subsequent steps.

General procedure C, Oxadiazole Formation: To a solution of hydrazide (1 eq) and carboxylic acid (1.5 eq) in EtOAc or MeCN (0.1M) was added $NEt_3$ (5 eq) followed by T3P solution (3 eq). The resulting reaction mixture was heated at 100° C. in a sealed vial overnight. The reaction mixture was diluted with sat $NaHCO_3$ solution and EtOAc. The layers were separated and the aqueous layer was extracted with EtOAc (3×). The combined organic layers were dried over anhydrous $MgSO_4$, filtered, and concentrated under reduced pressure. The crude reaction mixture was purified employing reverse-phase HPLC.

General procedure D, Acyl Chloride: To a flask containing carboxylic acid (1 eq), and DMF (0.05 eq) in DCM (0.1 M-0.2 M) was added oxalyl chloride (1.2 eq) at 0° C. The resulting reaction mixture was stirred at 0° C. for 2 h. The reaction mixture was concentrated under reduced pressure. The crude product was used directly.

Or: The solution of acid (1 eq) in $SOCl_2$ (0.5 M) was stirred at 85° C. for 3 h. The reaction mixture was concentrated under reduced pressure to give the crude product which was used directly.

General procedure E, α-bromoketone: To a solution of acyl chloride (1 eq) in MeCN (0.1 M) and THF (0.1 M) was added $TMSCHN_2$ (1.5 eq) in DCM (0.1 M) at 0° C. and the reaction mixture was stirred at 0° C. for 1 h. To the mixture was added aq. HBr (1.1 eq, 48% solution), at which point $H_2O$ was added followed by EtOAc. The layers were separated, and the aqueous layer was extracted with EtOAc (3×). The combined organic layers were dried over anhydrous $Na_2SO_4$, filtered and concentrated under reduced pressure. The crude reaction mixture was used directly or purified employing silica flash chromatography to provide the desired product.

General procedure F, Bromoketone Alkylation: To a flask containing primary amine (1 eq), and α-bromoketone (1 eq) in MeCN (0.1 M-0.2 M) was added $Na_2CO_3$ (4 eq). The resulting reaction mixture was heated at 40° C. for 2 h. The reaction mixture was cooled to rt and $H_2O$ was added followed by EtOAc. The layers were separated, and the aqueous layer was extracted with EtOAc (3×). The combined organic layers were dried over anhydrous $Na_2SO_4$, filtered and concentrated under reduced pressure. The crude reaction mixture was used directly or purified employing silica flash chromatography to provide the desired product.

The following compounds were prepared using General Procedure F and were used to prepare compounds disclosed herein: N-(3-((2-oxo-2-(3-(trifluoromethyl)phenyl)ethyl)amino)bicyclo[1.1.1]pentan-1-yl)-2-(3-cis-(trifluoromethoxy)cyclobutoxy)acetamide, N-(3-((2-(2,4-difluorophenyl)-2-oxoethyl)amino)bicyclo[1.1.1]pentan-1-yl)-2-(3-cis-(trifluoromethoxy)cyclobutoxy)acetamide, N-(3-((2-(4-fluorophenyl)-2-oxoethyl)amino)bicyclo[1.1.1]pentan-1-yl)-2-(3-cis-(trifluoromethoxy)cyclobutoxy)acetamide, N-(3-((2-(3-fluorophenyl)-2-oxoethyl)amino)bicyclo[1.1.1]pentan-1-yl)-2-(3-cis-(trifluoromethoxy)cyclobutoxy)acetamide, N-(3-((2-(3,4-difluorophenyl)-2-oxoethyl)amino)bicyclo[1.1.1]pentan-1-yl)-2-(3-cis-(trifluoromethoxy)cyclobutoxy)acetamide, N-(3-((2-(4-chlorophenyl)-2-oxoethyl)amino)bicyclo[1.1.1]pentan-1-yl)-2-(3-cis-(trifluoromethoxy)cyclobutoxy)acetamide, N-(3-((2-(3-fluoro-4-methylphenyl)-2-oxoethyl)amino)bicyclo[1.1.1]pentan-1-yl)-2-(3-cis-(trifluoromethoxy)cyclobutoxy)acetamide, N-(3-((2-(4-chlorophenyl)-2-oxoethyl)amino)bicyclo[1.1.1]pentan-1-yl)-2-(3-trans-(trifluoromethoxy)cyclobutoxy)acetamide, N-(3-((2-(4-fluoro-2-methylphenyl)-2-oxoethyl)amino)bicyclo[1.1.1]pentan-1-yl)-2-(3-cis-(trifluoromethoxy)cyclobutoxy)acetamide, 2-(3,4-difluorophenoxy)-N-(3-((2-oxo-2-(3-(trifluoromethoxy)cyclobutyl)ethyl)amino)bicyclo[1.1.1]pentan-1-yl)acetamide, N-(3-((2-(4-chloro-2-fluorophenyl)-2-oxoethyl)amino)bicyclo[1.1.1]pentan-1-yl)-2-(3-cis-(trifluoromethoxy)cyclobutoxy)acetamide, N-(3-((2-oxo-2-(3-(trifluoromethyl)phenyl)ethyl)amino)bicyclo[1.1.1]pentan-1-yl)-2-(3-cis-(trifluoromethoxy)cyclobutoxy)acetamide, N-(3-((2-(2-fluoro-4-(trifluoromethyl)phenyl)-2-oxoethyl)amino)bicyclo[1.1.1]pentan-1-yl)-2-(3-cis-(trifluoromethoxy)cyclobutoxy)acetamide, N-(3-((2-(3-fluoro-4-(trifluoromethyl)phenyl)-2-oxoethyl)amino)bicyclo[1.1.1]pentan-1-yl)-2-(3-cis-(trifluoromethoxy)cyclobutoxy)acetamide, N-(3-((2-oxo-2-(4-(trifluoromethyl)phenyl)ethyl)amino)bicyclo[1.1.1]pentan-1-yl)-2-(3-cis-(trifluoromethoxy)cyclobutoxy)acetamide, and N-(3-((2-oxo-2-(3-cis-(trifluoromethoxy)cyclobutyl)

ethyl)amino)bicyclo[1.1.1]pentan-1-yl)-2-((6-(trifluoromethyl)pyridin-3-yl)oxy)acetamide.

General procedure G, Formylation: To a solution of Ac$_2$O (2 eq) in formic acid (0.1 M) was added secondary amine (1 eq) in DCM (0.1 M) at 0° C. and the reaction mixture was stirred at 0° C. for 1 h, at which point sat. NaHCO$_3$ was added followed by EtOAc. The layers were separated, and the aqueous layer was extracted with EtOAc (3×). The combined organic layers were dried over anhydrous Na$_2$SO$_4$, filtered and concentrated under reduced pressure. The crude reaction mixture was used directly or purified employing silica flash chromatography to provide the desired product.

The following compounds were prepared using General Procedure G and were used to prepare compounds disclosed herein: N-(3-(N-(2-oxo-2-(3-(trifluoromethyl)phenyl)ethyl) formamido)bicyclo[1.1.1]pentan-1-yl)-2-(3-cis-(trifluoromethoxy)cyclobutoxy)acetamide, N-(3-(N-(2-(2,4-difluorophenyl)-2-oxoethyl)formamido)bicyclo[1.1.1]pentan-1-yl)-2-(3-cis-(trifluoromethoxy)cyclobutoxy)acetamide, N-(3-(N-(2-(4-fluorophenyl)-2-oxoethyl)formamido)bicyclo[1.1.1]pentan-1-yl)-2-(3-cis-(trifluoromethoxy)cyclobutoxy)acetamide, N-(3-(N-(2-(3-fluorophenyl)-2-oxoethyl)formamido)bicyclo[1.1.1]pentan-1-yl)-2-(3-cis-(trifluoromethoxy)cyclobutoxy)acetamide, N-(3-(N-(2-(3,4-difluorophenyl)-2-oxoethyl)formamido)bicyclo[1.1.1]pentan-1-yl)-2-(3-cis-(trifluoromethoxy)cyclobutoxy)acetamide, N-(3-(N-(2-(4-chlorophenyl)-2-oxoethyl)formamido)bicyclo[1.1.1]pentan-1-yl)-2-(3-cis-(trifluoromethoxy)cyclobutoxy)acetamide, N-(3-(N-(2-(3-fluoro-4-methylphenyl)-2-oxoethyl)formamido)bicyclo[1.1.1]pentan-1-yl)-2-(3-cis-(trifluoromethoxy)cyclobutoxy)acetamide, N-(3-(N-(2-(4-chlorophenyl)-2-oxoethyl)formamido)bicyclo[1.1.1]pentan-1-yl)-2-(3-trans-(trifluoromethoxy)cyclobutoxy)acetamide, N-(3-(N-(2-(4-fluoro-2-methylphenyl)-2-oxoethyl)formamido)bicyclo[1.1.1]pentan-1-yl)-2-(3-cis-(trifluoromethoxy)cyclobutoxy)acetamide, 2-(3,4-difluorophenoxy)-N-(3-(N-(2-oxo-2-(3-(trifluoromethoxy)cyclobutyl)ethyl)formamido)bicyclo[1.1.1]pentan-1-yl)acetamide, tert-butyl (3-((2-(4-chlorophenyl)-2-oxoethyl)amino)bicyclo[1.1.1]pentan-1-yl)carbamate, N-(3-(N-(2-(4-chloro-2-fluorophenyl)-2-oxoethyl)formamido)bicyclo[1.1.1]pentan-1-yl)-2-(3-cis-(trifluoromethoxy)cyclobutoxy)acetamide, N-(3-(N-(2-(4-fluoro-3-methylphenyl)-2-oxoethyl)formamido) bicyclo[1.1.1]pentan-1-yl)-2-(3-cis-(trifluoromethoxy) cyclobutoxy)acetamide, N-(3-(N-(2-(2-fluoro-4-(trifluoromethyl)phenyl)-2-oxoethyl)formamido)bicyclo[1.1.1]pentan-1-yl)-2-(3-cis-(trifluoromethoxy) cyclobutoxy)acetamide, N-(3-(N-(2-(3-fluoro-4-(trifluoromethyl)phenyl)-2-oxoethyl)formamido)bicyclo[1.1.1]pentan-1-yl)-2-(3-cis-(trifluoromethoxy) cyclobutoxy)acetamide, N-(3-(N-(2-oxo-2-(4-(trifluoromethyl)phenyl)ethyl)formamido)bicyclo[1.1.1]pentan-1-yl)-2-(3-cis-(trifluoromethoxy)cyclobutoxy) acetamide, and N-(3-(N-(2-oxo-2-(3-cis-(trifluoromethoxy)cyclobutyl)ethyl)formamido)bicyclo[1.1.1]pentan-1-yl)-2-((6-(trifluoromethyl)pyridin-3-yl)oxy)acetamide.

General procedure H, Formate Cyclization: To a solution of tertiary amine (1 eq) in AcOH (0.1 M) was added CH$_3$COONH$_4$ (5 eq) and the reaction mixture was heated at 110° C. for 15 h, at which point sat. NaHCO$_3$ was added followed by EtOAc. The layers were separated, and the aqueous layer was extracted with EtOAc (3×). The combined organic layers were dried over anhydrous Na$_2$SO$_4$, filtered and concentrated under reduced pressure. The crude reaction mixture was purified employing p-HPLC.

The following compound was prepared using General Procedure H and were used to prepare compounds disclosed herein: tert-butyl (3-(4-(4-chlorophenyl)-1H-imidazol-1-yl) bicyclo[1.1.1]pentan-1-yl)carbamate.

Intermediate 1

Methyl 3-[[2-(4-chlorophenoxy)acetyl]amino]bicyclo[1.1.1]pentane-1-carboxylate

Prepared using General Procedure A employing methyl 3-aminobicyclo[1.1.1]pentane-1-carboxylate trifluoroacetate salt (255 mg, 1.0 mmol), 2-(4-chlorophenoxy)acetic acid (224 mg, 1.2 mmol), N-methylimidazole (246 mg, 3.0 mmol), and T3P (382 mg, 1.2 mmol) in DMF (2 mL). LC-MS m/z:=310.1 [M+H]$^+$. $^1$H-NMR (400 MHz, CDCl$_3$): δ 7.24-7.30 (m, 2H), 6.89-6.96 (m, 1H), 6.81-6.88 (m, 2H), 4.39 (s, 2H), 3.66-3.74 (m, 3H), 2.36-2.47 (m, 6H).

Intermediate 2

Methyl 3-[[2-(4-chloro-3-fluoro-phenoxy)acetyl] amino]bicyclo[1.1.1]pentane-1-carboxylate Prepared using General Procedure A employing methyl 3-aminobicyclo[1.1.1]pentane-1-carboxylate trifluoroacetate salt (1.06 g, 4.14 mmol), 2-(4-chloro-3-fluoro-phenoxy)acetic acid (1.02 g, 4.97 mmol), DIPEA (1.61 g, 12.4 mmol), and T3P (1.58 g, 4.97 mmol) in DMF 8.3 mL). $^1$H-NMR (400 MHz, DMSO-d6): δ ppm 7.33 (t, J=8.60 Hz, 1H), 6.84 (br s, 1H), 6.76 (dd, J=10.14, 2.87 Hz, 1H), 6.64-6.71 (m, 1H), 4.40 (s, 2H), 3.71 (s, 3H), 2.44 (s, 6H).

Intermediate 3

2-(4-chlorophenoxy)-N-[1-(hydrazinecarbonyl)-3-bicyclo[1.1.1]pentanyl]acetamide

Prepared using General Procedure B employing methyl 3-[[2-(4-chlorophenoxy)acetyl]amino]bicyclo[1.1.1]pentane-1-carboxylate (270 mg, 0.87 mmol), hydrazine hydrate (131 mg, 2.6 mmol) in EtOH (3.5 mL). LC-MS m/z:=310.1 [M+H]$^+$.

Intermediate 4

2-(4-chloro-3-fluoro-phenoxy)-N-[1-(hydrazinecarbonyl)-3-bicyclo[1.1.1]pentanyl]acetamide Prepared using General Procedure B employing methyl 3-[[2-(4-chloro-3-fluoro-phenoxy)acetyl]amino]bicyclo[1.1.1]pentane-1-carboxylate (1.46 g, 4.5 mmol), hydrazine hydrate (669 mg, 13.3 mmol) in EtOH (18 mL). LC-MS m/z:=328.1 [M+H]$^+$.

Intermediate 5 tert-butyl 3-cis-hydroxycyclobutanecarboxylate

A mixture of tert-butyl 3-oxocyclobutanecarboxylate (70.0 g, 411 mmol) in MeOH (700 mL) was added NaBH$_4$ (15.6 g, 411 mmol) at −30° C. under N$_2$ over 2 h. The reaction mixture was stirred at −30° C. for 0.5 h. The reaction mixture was quenched by the addition of with ice with sat. NH$_4$Cl (700 mL) slowly at 0° C. over 30 min. The reaction mixture was concentrated under reduced pressure to leave the aqueous phase that was extracted with EtOAc (3×300 mL). The combined organics were washed with brine (300 mL), dried over anhydrous $Na_2SO_4$, filtered, and concentrated. Isolated as a mixture of diastereomers in favor of the cis-product. $^1$H-NMR (400 MHz, CDCl$_3$): δ 4.23-4.04 (m, 1H), 2.79 (br s, 1H), 2.60-2.43 (m, 3H), 2.14-2.05 (m, 2H), 1.43 (s, 9H).

tert-butyl 3-cis-(trifluoromethoxy)cyclobutanecarboxylate

To a reaction flask equipped with a stir bar and covered with aluminum foil in a water bath were added AgOTf (134.3 g, 523 mmol), Selectfluor (92.6 g, 261 mmol), KF (40.5 g, 697 mmol) and tert-butyl 3-cis-hydroxycyclobutanecarboxylate (30.0 g, 174 mmol) under $N_2$. Then EtOAc (1000 mL), 2-fluoropyridine (50.7 g, 523 mmol) and TMSCF$_3$ (74.3 g, 523 mmol) were added dropwise successively while keeping the inner temperature below 30° C. using a water bath. The reaction mixture was stirred at 25° C. for 12 h. The reaction mixture was filtered through a plug of silica and the filtrate was concentrated under reduced pressure. The residue was washed with MTBE (800 mL) and filtered. The filtrate was washed with 1 N CuSO$_4$ (3×300 mL) and the organics were dried over $Na_2SO_4$, filtered, and concentrated under reduced pressure. The residue was purified by silica gel column chromatography. $^1$H-NMR (400 MHz, CDCl$_3$): δ 4.60-4.48 (m, 1H) 2.69-2.53 (m, 3H), 2.52-2.37 (m, 2H), 1.46 (s, 9H).

3-cis-(trifluoromethoxy)cyclobutanecarboxylic acid

To a solution of tert-butyl 3-cis-(trifluoromethoxy)cyclobutanecarboxylate (24.0 g, 100.0 mmol) in DCM (250 mL) was added TFA (77.0 g, 675 mmol). The reaction mixture was stirred at 40° C. for 2 h. The reaction mixture was concentrated under reduced pressure. The residue was dissolved in DCM (50 mL), washed with H$_2$O (3×30 mL), dried over Na$_2$SO$_4$, filtered, and concentrated under reduced pressure. $^1$H-NMR (400 MHz. DMSO-d6): δ 12.39 (s, 1H), 4.74 (quin, J=7.44 Hz, 1H), 2.76-2.64 (m, 1H), 2.63-2.53 (m, 2H), 2.33-2.21 (m. 2H).

Intermediate 6

3-cis-(benzyloxy)cyclobutanol

A mixture of 3-benzyloxycyclobutanone (100.0 g, 567 mmol) in MeOH (1000 mL) was added NaBH$_4$ (21.5 g, 567 mmol) at −30° C. under N$_2$ over 2 h. The reaction mixture was stirred at −30° C. for 0.5 h. The reaction mixture was quenched by the addition of ice and sat. NH$_4$Cl (600 mL) slowly at 0° C. over 0.5 h. The reaction mixture was concentrated under reduced pressure to leave the aqueous phase that was extracted with EtOAc (3×200 mL). The combined organics were washed with brine (200 mL), dried over anhydrous Na$_2$SO$_4$, filtered, and concentrated under reduced pressure to provide a mixture of diastereomers in favor of the cis-product. $^1$H-NMR (400 MHz, CDCl$_3$): δ 7.32-7.18 (m, 5H), 4.35 (s, 2H), 3.83 (quin, J=7.17 Hz, 1H), 3.56 (quin, J=6.95 Hz, 1H), 2.69-2.60 (m, 2H), 1.91-1.82 (m, 2H).

tert-butyl 2-(3-cis-(benzyloxy)cyclobutoxy)acetate

To a mixture of 3-cis-(benzyloxy)cyclobutanol (19.7 g, 110 mmol), tert-butyl 2-bromoacetate (32.3 g, 165 mmol), tetrabutylammonium hydrogen sulfate (1.9 g, 5.5 mmol), and water (10 mL) in toluene (400 mL) was added NaOH (66.3 g, 1.6 mol) in water (120 mL). The reaction mixture was stirred at 25° C. for 4 h. The reaction mixture was quenched by addition of ice-water (120 mL) and extracted with MTBE (3×50 mL). The combined organics were washed with brine (100 mL), dried over anhydrous Na$_2$SO$_4$, filtered, and concentrated under reduced pressure. The crude product was used directly. $^1$H-NMR (400 MHz. CDCl$_3$): δ 7.39-7.27 (m, 5H), 4.42 (s, 2H), 3.89 (s, 2H), 3.75-3.62 (m, 2H), 2.65 (dtd, J=9.26, 6.28, 6.28, 3.31 Hz, 2H), 2.09-2.00 (m, 2H), 1.48 (s, 9H).

tert-butyl 2-(3-cis-hydroxycyclobutoxy)acetate

To a solution of tert-butyl 2-(3-cis-(benzyloxy)cyclobutoxy)acetate (27.0 g, 92.4 mmol) in MeOH (350 mL) was added Pd/C (3.0 g, 10 weight % Pd on carbon) under N$_2$. The reaction mixture was degassed under vacuum, purged with H$_2$ three times, and stirred under H$_2$ (50 psi) at 50° C. for 12 h. The reaction mixture was filtered through a pad of celite and concentrated under reduced pressure to afford the crude product, which was used directly. $^1$H-NMR (400 MHz, CDCl$_3$): δ 3.94-3.89 (m, 1H), 3.88 (s, 2H), 3.67 (quin, J=6.89 Hz, 1H), 2.78-2.69 (m, 2H), 2.01-1.92 (m, 2H), 1.80 (br d, J=6.39 Hz, 1H), 1.47 (s, 9H).

tert-butyl 2-(3-cis-(trifluoromethoxy)cyclobutoxy)acetate

To a reaction flask equipped with a stir bar and covered with aluminum foil in a water bath were added AgOTf (57.2 g, 222 mmol), Selectfluor (39.4 g, 111 mmol), KF (17.2 g, 297 mmol), and tert-butyl 2-(3-cis-hydroxycyclobutoxy)acetate (15.0 g, 74.2 mmol) under N$_2$. And then EtOAc (600 mL), 2-fluoropyridine (21.6 g, 222 mmol) and TMSCF$_3$ (31.6 g, 222 mmol) were added dropwise successively while keeping the inner temperature below 30° C. using a water bath. The reaction mixture was stirred at 25° C. for 12 h. The reaction mixture was filtered through a plug of silica and the filtrate was concentrated under reduced pressure. The residue was washed with MTBE (800 mL) and filtered. The residue was purified by silica gel column chromatography. $^1$H-NMR (400 MHz, CDCl$_3$): δ 4.35-4.22 (m, 1H), 3.90 (s, 2H), 3.81-3.69 (m, 1H), 2.86-2.72 (m, 2H), 2.40-2.23 (m, 2H), 1.49 (s, 9H).

2-(3-cis-(trifluoromethoxy)cyclobutoxy)acetic acid

To a solution of tert-butyl 2-(3-cis-(trifluoromethoxy)cyclobutoxy)acetate (11.5 g, 42.6 mmol) in DCM (100 mL) was added TFA (30.8 g, 270 mmol) under N$_2$. The reaction mixture was stirred at 40° C. for 2 h and then was concentrated under reduced pressure. The residue was dissolved in DCM (30 mL), washed with H$_2$O (3×30 mL), dried over Na$_2$SO$_4$, filtered, and concentrated under reduced pressure. The crude product was used directly. $^1$H-NMR (400 MHz, CDCl$_3$): δ 4.26-4.19 (m, 1H), 4.00 (s, 2H), 3.73-3.70 (m, 1H), 2.77-2.74 (m, 2H), 2.27-2.24 (m. 2H).

Intermediate 7

N-methoxy-N-methyl-2-[3-cis-(trifluoromethoxy) cyclobutoxy]acetamide

To a solution of 2-[3-cis-(trifluoromethoxy)cyclobutoxy] acetic acid (1.6 g, 7.7 mmol) in EtOAc (50 mL) was added N,N-diisopropylethylamine (4.47 mL. 25.7 mmol) followed by T3P (2.4 g, 7.7 mmol, 50% in EtOAc). The resulting reaction mixture was stirred 10 min and N,O-dimethylhydoxylamine hydrochloride (500 mg, 5.13 mmol) was added. The reaction mixture was stirred at 23° C. for 4 h. The reaction mixture was quenched by the addition of sat. $NH_4Cl$ and extracted with EtOAc (3×25 mL) The combined organic layers are dried over $MgSO_4$, filtered, and concentrated under reduced pressure. The crude reaction mixture was sufficiently pure and was used directly. $^1$H-NMR (400 MHz; $CDCl_3$): δ 4.29 (t, J=7.3 Hz, 1H), 4.21 (s, 2H), 3.83 (td, J=7.0, 1.1 Hz, 1H), 3.71 (s, 3H), 3.21 (s, 3H), 2.83 (dtd, J=9.8, 6.6, 3.2 Hz, 2H), 2.38-2.32 (m, 2H).

2-[3-cis-(trifluoromethoxy)cyclobutoxy]acetaldehyde

To a cooled solution of N-methoxy-N-methyl-2-[3-cis-(trifluoromethoxy)cyclobutoxy]acetamide (100 mg, 0.39 mmol) in THF (3.9 mL) at −78° C. was added diisobutylaluminum hydride (0.78 mL, 0.78 mmol, 1 M in hexane). The reaction mixture was stirred at −78° C. for 2 h. The reaction mixture was quenched by the addition of anhydrous EtOAc (1.0 mL) and sat. $NH_4Cl$ (3 mL) and then removed from the cooling bath and allowed to stir for 15 min. The reaction mixture was then dilute with water (20 mL) and extracted with $Et_2O$ (3×15 mL). The combined organics were dried over $Na_2SO_4$, filtered and concentrated under reduced pressure. The crude aldehyde was used immediately and without further purification.

Intermediate 8

1-[5-[3-cis-(trifluoromethoxy)cyclobutyl]-1,3,4-oxadiazol-2-yl]bicyclo[1.1.1]pentan-3-amine tert-butyl (3-(hydrazinecarbonyl)bicyclo[1.1.1]pentan-1-yl) carbamate To a solution of methyl 3-((tert-butoxycarbonyl)amino) bicyclo[1.1.1]pentane-1-carboxylate (1.0 eq) in 2-propanol (1.0 M) was added $NH_2NH_2·H_2O$ (3.0 eq) in one portion at 0° C. The mixture was stirred at 85° C. for 12 h. The reaction mixture was cooled to 25° C. and filtered. The filter cake was washed with 2-propanol and dried under reduced pressure to provide the desired product. LC-MS: m/z: 242.1 $[M+H]^+$.

tert-butyl(3-(2-(3-cis-(trifluoromethoxy)cyclobutane-1-carbonyl)hydrazine-1-carbonyl)bicyclo[1.1.1]pentan-1-yl)carbamate To a suspension of 3-cis-(trifluoromethoxy)cyclobutane-1-carboxylic acid (1.1 eq; 8:1 to 10:1 ratio of cis- to trans-) in anhydrous N,N-dimethylformamide (DMF) (1.1 M) were added TEA (4.0 eq) and T3P (2.0 eq, 50% in EtOAc) dropwise at 0° C. The reaction mixture was warmed to 20° C. and stirred for 1 h. The reaction mixture was then cooled to 0° C. and tert-butyl (3-(hydrazinecarbonyl)bicyclo[1.1.1] pentan-1-yl)carbamate (275 g, 1.14 mol, 1 eq) was added into the reaction mixture portionwise at 0° C. The reaction mixture was stirred for 12 h at 25° C. The reaction was quenched by the addition of sat. $NaHCO_3$. The mixture was further stirred at 40° C. for 10 min and filted immediately. The filter cake was washed with water and dried under reduced pressure at 45° C. The crude product was used directly. LC-MS: m/z: 408.1 $[M+H]^+$.

tert-butyl(3-(5-(3-cis-(trifluoromethoxy)cyclobutyl)-1,3,4-oxadiazol-2-yl)bicyclo[1.1.1]pentan-1-yl)carbamate To a suspension of tert-butyl (3-(2-(3-cis-(trifluoromethoxy)cyclobutane-1-carbonyl)hydrazine-1-carbonyl) bicyclo[1.1.1]pentan-1-yl)carbamate (1.0 eq) in MeCN (0.25 M) were added $K_2CO_3$ (powdered, 325 mesh, 5.0 eq) [note: $Cs_2CO_3$ may be used in place of the powdered $K_2CO_3$], 4 Å Molecular Sieves (1:1 w/w), and p-toluenesulfonyl chloride (TsCl) (2.5 eq) at 25° C. The resulting reaction mixture was heated to 80° C. and stirred for 3 h. The reaction mixture was cooled to 25° C. and the mixture was filtered. The filtrate was concentrated under reduced pressure. The residue was dissolved in MeCN (0.6 M) at 70° C. and water (0.4 M) was added into the solution in one portion. The mixture was stirred for 15 min at 20° C. and filtered. The filter cake was washed by water and was dissolved in dichloromethane. The solution was dried over $Na_2SO_4$, filtered, and concentrated under reduced pressure. The crude residue was dissolved in dichloromethane (1 M) at 20° C., and hexane (0.3 M) was added into the solution in one portion. The mixture was stirred for 30 min and was filtered. The filter cake was washed by hexane and dried under reduced pressure to provide the desired product. LC-MS: m/z: 390.1 $[M+H]^+$.

1-[5-[3-cis-(trifluoromethoxy)cyclobutyl]-1,3,4-oxadiazol-2-yl]bicyclo[1.1.1]pentan-3-amine HCl Salt To tert-butyl (3-(5-(3-cis-(trifluoromethoxy)cyclobutyl)-1,3,4-oxadiazol-2-yl)bicyclo[1.1.1]pentan-1-yl)carbamate (1.0 eq) was added into HCl (20 eq, 4 M in EtOAc) in one portion at 0° C. The reaction mixture was stirred at 25° C. for 12 h. The reaction mixture was concentrated under reduced pressure to provide an 8:1 to 10:1 diastereomeric mixture of 1-[5-[3-(trifluoromethoxy)cyclobutyl]-1,3,4-oxadiazol-2-yl]bicyclo[1.1.1]pentan-3-amine favoring 1-[5-[3-cis-(trifluoromethoxy)cyclobutyl]-1,3,4-oxadiazol-2-yl]bicyclo[1.1.1]pentan-3-amine. The crude residue was used directly. LC-MS: m/z: 290.0 $[M+H]^+$.

Intermediate 9

N-(3-ethynylbicyclo[1.1.1]pentan-1-yl)-2-(3-cis-(trifluoromethoxy)cyclobutoxy)acetamide N-(3-formylbicyclo[1.1.1]pentan-1-yl)-2-(3-cis-(trifluoromethoxy)cyclobutoxy)acetamide To a solution of N-(3-(hydroxymethyl)bicyclo[1.1.1]pentan-1-yl)-2-(3-cis-(trifluoromethoxy)cyclobutoxy)acetamide (430 mg, 1.39 mmol) in DCM (5.0 mL) at 0° C. was added DMP (649 mg, 1.53 mmol) in portions. The mixture was warmed to 15° C. and was stirred for 12 h. The mixture was filtered through a pad of Celite and the filtrate was concentrated under reduced pressure. The residue was purified by silica gel column chromatography. $^1$H-NMR (400 MHz, $CDCl_3$): δ 9.66 (s, 1H), 6.88 (br s, 1H), 4.37-4.25 (m, 1H), 3.80 (s, 2H), 3.73-3.70 (m, 1H), 2.83-2.80 (m, 2H), 2.40 (s, 6H), 2.30-2.20 (m, 2H).

N-(3-ethynylbicyclo[1.1.1]pentan-1-yl)-2-(3-cis-(trifluoromethoxy)cyclobutoxy)acetamide To a solution of N-(3-formylbicyclo[1.1.1]pentan-1-yl)-2-(3-cis-(trifluoromethoxy)cyclobutoxy)acetamide (240 mg, 0.78 mmol) in MeOH (5.0 mL) at 0° C. was added K₂CO₃ (324 mg, 2.34 mmol) and dimethyl (1-diazo-2-oxopropyl) phosphonate (210 mg, 1.09 mmol), and the mixture was warmed to 15° C. and stirred for 4 h. The reaction mixture was diluted with water (10 mL) and was concentrated under reduced pressure to remove MeOH. The aqueous phase was extracted with EtOAc (3×5 mL), the combined organics were washed with brine (10 mL), dried over anhydrous Na₂SO₄, filtered and concentrated under reduced pressure. The residue was purified by silica gel column chromatography to deliver the title compound. ¹H-NMR (400 MHz, CDCl₃): δ 6.80 (br s, 1H), 4.36-4.31 (m, 1H), 3.79 (s, 2H), 3.76-3.65 (m, 1H), 2.83-2.80 (m, 2H), 2.41 (s, 6H), 2.31-2.20 (m, 2H), 2.17 (s, 1H).

Example 1

2-(4-Chlorophenoxy)-N-[3-(5-tetrahydrofuran-3-yl-1,3,4-oxadiazol-2-yl)-1-bicyclo[1.1.1]pentanyl]acetamide Prepared using General Procedure C employing 2-(4-chlorophenoxy)-N-[1-(hydrazinecarbonyl)-3-bicyclo[1.1.1]pentanyl]acetamide (20 mg, 0.06 mmol), tetrahydro-3-furoic acid (11 mg, 0.1 mmol), NEt₃ (33 mg, 0.32 mmol), and T3P (62 mg, 0.19 mmol) in EtOAc (0.5 mL). ¹H-NMR (400 MHz; CDCl₃): δ 7.26-7.22 (m, 2H), 6.97-6.92 (m, 1H), 6.84-6.80 (m, 2H), 4.38-4.34 (m, 2H), 4.12-4.05 (m, 1H), 4.00-3.57 (m, 4H), 2.59-2.47 (m. 6H), 2.36-2.29 (m. 2H). LC-MS: m/z: 390.2 [M+H]⁺.

Example 2

2-(4-Chlorophenoxy)-N-[3-(5-tetrahydrofuran-2-yl-1,3,4-oxadiazol-2-yl)-1-bicyclo[1.1.1]pentanyl]acetamide Prepared using General Procedure C employing 2-(4-chlorophenoxy)-N-[1-(hydrazinecarbonyl)-3-bicyclo[1.1.1]pentanyl]acetamide (20 mg, 0.06 mmol), tetrahydro-2-furoic acid (11 mg, 0.1 mmol), NEt₃ (33 mg, 0.32 mmol), and T3P (62 mg, 0.19 mmol) in EtOAc (0.5 mL). ¹H-NMR (400 MHz; CDCl₃): δ 7.27-7.23 (m, 2H), 6.95 (s, 1H), 6.85-6.81 (m, 2H), 5.10-5.07 (m, 1H), 4.38 (s, 2H), 4.00-3.89 (m, 2H), 2.61 (s, 6H), 2.35-2.29 (m, 2H), 2.16-1.95 (m, 2H). LC-MS: m/z: 390.2 [M+H]⁺.

Example 3

2-(4-chlorophenoxy)-N-[3-[5-[cis-3-(trifluoromethoxy)cyclobutyl]-1,3,4-oxadiazol-2-yl]-1-bicyclo[1.1.1]pentanyl]acetamide 2-(4-chlorophenoxy)-N-[1-(hydrazinecarbonyl)-3-bicyclo[1.1.1]pentanyl]acetamide (200 mg, 0.65 mmol), 3-cis-(trifluoromethoxy)cyclobutanecarboxylic acid (131 mg, 0.71 mmol; 8:1 to 10:1 ratio of cis- to trans-) and triethylamine (NEt₃) (0.45 mL, 3.23 mmol) were dissolved in EtOAc (2.6 mL) and T3P solution (0.58 mL, 1.94 mmol, 50% in EtOAc) was added. The resulting reaction mixture was heated to 100° C. overnight, cooled to rt and was diluted with sat. aq. NaHCO₃ solution (10 mL) and EtOAc (10 mL). The layers were separated and the aqueous layer was extracted with EtOAc (3×10 mL). The combined organic layers were dried over anhydrous MgSO₄, filtered, and concentrated under reduced pressure. The crude reaction mixture was purified employing reverse-phase prep-HPLC to deliver the desired product as a clear oil. ¹H-NMR (400 MHz; CDCl₃): δ 7.33-7.29 (m, 2H), 7.03 (s, 1H), 6.91-6.87 (m, 2H), 4.76-4.69 (m, 1H), 4.44 (s, 2H), 3.39-3.30 (m, 1H), 2.92-2.84 (m, 2H), 2.74-2.68 (m, 2H), 2.67 (s, 6H). LC-MS m/z:=458.20 [M+H]⁺.

Alternatively, a mixture of 2-(4-chlorophenoxy)acetic acid (50 mg. 0.27 mmol), 2-(4-chlorophenoxy)acetic acid (50 mg, 0.27 mmol), NEt₃ (123 mg, 1.21 mmol) and T3P (185 mg, 0.29 mmol, 50% purity) in DCM (1 mL) was stirred at 0° C. for 1 h. To the mixture was added 1-[5-[3-cis-(trifluoromethoxy)cyclobutyl]-1,3,4-oxadiazol-2-yl]bicyclo[1.1.1]pentan-3-amine HCl salt (8:1 to 10:1 favoring the cis-diastereomer) (70 mg, 0.24 mmol) at 0° C. The mixture was stirred at 25° C. for 12 h. To the reaction was added sat. aq. NaHCO₃ (4 mL). The aqueous phase was extracted with DCM (5 mL, 3 mL). The combined organic phase was washed with brine (10 mL), dried with anhydrous Na₂SO₄, filtered and concentrated under reduced pressure to provide the title compound.

Example 4

2-(4-chlorophenoxy)-N-[3-[5-(2,2,2-trifluoroethyl)-1,3,4-oxadiazol-2-yl]-1-bicyclo[1.1.1]pentanyl]acetamide Prepared using General Procedure C employing 2-(4-chlorophenoxy)-N-[1-(hydrazinecarbonyl)-3-bicyclo[1.1.1]pentanyl]acetamide (25 mg, 0.08 mmol), 3,3,3-trifluoropropanoic acid (16 mg, 0.12 mmol), NEt₃ (41 mg, 0.40 mmol), and T3P (77 mg, 0.24 mmol) in EtOAc (0.8 mL). ¹H-NMR (400 MHz; CDCl₃): δ 7.33-7.29 (m, 2H), 7.03 (s, 1H), 6.91-6.87 (m, 2H), 4.45 (s, 2H), 3.77 (q, J=9.6 Hz, 2H), 2.69 (s, 6H). LC-MS m/z:=402.11 [M+H]⁻.

Example 5

2-(4-Chlorophenoxy)-N-[1-[5-(cyclobutoxymethyl)-1,3,4-oxadiazol-2-yl]-3-bicyclo[1.1.1]pentanyl]acetamide Prepared using General Procedure C employing 2-(4-chlorophenoxy)-N-[1-(hydrazinecarbonyl)-3-bicyclo[1.1.1]pentanyl]acetamide (25 mg, 0.08 mmol), 2-(cyclobutoxy)acetic acid (16 mg, 0.12 mmol), NEt₃ (41 mg, 0.40 mmol), and T3P (77 mg, 0.24 mmol) in EtOAc (0.8 mL). ¹H-NMR (400 MHz; CDCl₃): δ 7.34-7.30 (m, 2H), 7.01 (s, 1H), 6.91-6.87 (m, 2H), 4.60 (s, 2H), 4.44 (s, 2H), 4.12-4.05 (m, 1H), 2.68 (s, 6H), 2.28-2.20 (m, 2H), 2.04-1.93 (m, 2H), 1.79-1.70 (m, 1H), 1.57-1.50 (m, 1H). LC-MS m/z:=404.21 [M+H]⁺.

Example 6

2-(4-chloro-3-fluoro-phenoxy)-N-[1-[5-[cis-3-(trifluoromethoxy)cyclobutyl]-1,3,4-oxadiazol-2-yl]-3-bicyclo[1.1.1]pentanyl]acetamide 3-cis-(trifluoromethoxy)cyclobutanecarboxylic acid (138 mg, 0.75 mmol; 8:1 to 10:1 ratio of cis- to trans-), 2-(4-chloro-3-fluoro-phenoxy)-N-[1-(hydrazinecarbonyl)-3-bicyclo[1.1.1]pentanyl]acetamide (164 mg, 0.50 mmol), and NEt₃ (0.35 mL, 2.5 mmol) were dissolved in MeCN (4.0 mL) and T3P solution (0.45 mL, 1.5 mmol) was added. The resulting reaction mixture was stirred at 100° C. for 72 h. The reaction mixture was diluted with saturated NaHCO₃ solution (10 mL) and EtOAc (10 mL). The layers were separated and the aqueous layer was extracted with EtOAc (3×10 mL). The combined organic layers were dried over anhydrous MgSO$_4$, filtered, and concentrated under reduced pressure. The crude reaction mixture was purified employing silica gel column chromatography and then by reverse phase HPLC to provide the desired product. $^1$H-NMR (400 MHz; CDCl$_3$): δ 7.36 (t, J=8.6 Hz, 1H), 6.99 (s, 1H), 6.79 (dd, J=10.2, 2.9 Hz, 1H), 6.71 (ddd, J=8.9, 2.9, 1.3 Hz, 1H), 4.76-4.69 (m, 1H), 4.44 (s, 2H), 3.39-3.30 (m, 1H), 2.88 (dddt, J=9.8, 7.3, 4.8, 2.5 Hz, 2H), 2.71-2.66 (m, 8H). LC-MS m/z:=476.27 [M+H]$^+$.

Example 7

2-(4-chloro-3-fluoro-phenoxy)-N-[1-[5-(3,3-difluoro-1-methyl-propyl)-1,3,4-oxadiazol-2-yl]-3-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 4,4-difluoro-2-methyl-butanoic acid (26 mg, 0.18 mmol), NEt$_3$ (62 mg. 0.61 mmol), and T3P (117 mg, 0.37 mmol) in EtOAc (1.0 mL). $^1$H-NMR (400 MHz; CDCl$_3$): δ 7.36 (t, J=8.6 Hz, 1H), 6.98 (s, 1H), 6.79 (dd, J=10.2, 2.9 Hz, 1H), 6.71 (ddd, J=8.9, 2.9, 1.3 Hz, 1H), 6.03 (tdd, J=56.3, 5.3, 4.0 Hz, 1H), 4.46-4.42 (m, 2H), 3.39-3.30 (m, 1H), 2.67 (s, 6H), 2.50 (ddddd, J=21.6, 14.6, 13.4, 8.1, 4.0 Hz, 1H), 2.26-2.12 (m, 1H), 1.48 (d, J=7.1 Hz, 3H). LC-MS m/z:=430.18 [M+H]$^+$.

Example 8

2-(4-chloro-3-fluoro-phenoxy)-N-[1-[5-(1-cyclopropylethyl)-1,3,4-oxadiazol-2-yl]-3-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 2-cyclopropylpropanoic acid (21 mg, 0.18 mmol), NEt$_3$ (62 mg, 0.61 mmol), and T3P (117 mg, 0.37 mmol) in EtOAc (1.0 mL). $^1$H-NMR (400 MHz; CDCl$_3$): δ 7.36 (t, J=8.6 Hz, 1H), 6.99 (s, 1H). 6.79 (dd, J=10.2, 2.8 Hz, 1H), 6.71 (ddd, J=8.9, 2.9, 1.3 Hz, 1H), 4.44 (s, 2H), 2.66 (s, 6H), 2.34 (dq, J=9.4, 7.1 Hz, 1H), 1.47 (d, J=7.1 Hz, 3H), 1.11-1.02 (m, 1H), 0.67-0.53 (m, 2H), 0.40-0.34 (m, 1H), 0.29-0.23 (m, 1H). LC-MS m/z:=406.27 [M+H]$^+$.

Example 9

2-(4-chloro-3-fluoro-phenoxy)-N-[1-[5-[(trans)-2-methylcyclopropyl]-1,3,4-oxadiazol-2-yl]-3-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), trans-2-methylcyclopropanecarboxylic acid (18 mg, 0.18 mmol), NEt$_3$ (62 mg, 0.61 mmol), and T3P (117 mg, 0.37 mmol) in EtOAc (1.0 mL). $^1$H-NMR (400 MHz; CDCl$_3$): δ 7.36 (t, J=8.6 Hz, 1H), 6.95 (s, 1H), 6.81-6.78 (m, 1H), 6.71 (ddd, J=8.9, 2.8, 1.3 Hz, 1H), 4.44 (s, 2H), 2.63 (s, 6H), 1.85 (dd, J=8.8, 4.4 Hz, 1H), 1.54-1.48 (m, 1H), 1.34-1.29 (m, 1H), 1.23 (d, J=6.0 Hz, 3H), 0.95 (ddd, J=8.6, 6.1, 4.9 Hz, 1H). LC-MS m/z:=392.15 [M+H]$^+$.

Example 10

2-(4-chloro-3-fluoro-phenoxy)-N-[1-[5-(1-fluorocyclopropyl)-1,3,4-oxadiazol-2-yl]-3-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 1-fluorocyclopropanecarboxylic acid (19 mg, 0.18 mmol), NEt$_3$ (62 mg, 0.61 mmol), and T3P (117 mg, 0.37 mmol) in EtOAc (1.0 mL). $^1$H-NMR (400 MHz; CDCl$_3$): δ 7.36 (t, J=8.6 Hz, 1H), 6.98 (s, 1H), 6.80 (dd, J=10.2, 2.8 Hz, 1H), 6.71 (ddd, J=8.9, 2.9, 1.3 Hz, 1H), 4.45 (s, 2H), 2.70 (s, 6H), 1.68-1.60 (m, 2H), 1.49-1.43 (m, 2H). LC-MS m/z:=396.2 [M+H]$^+$.

Example 11

2-(4-chloro-3-fluoro-phenoxy)-N-[1-[5-(cyclopropylmethyl)-1,3,4-oxadiazol-2-yl]-3-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 2-cyclopropylacetic acid (18 mg, 0.18 mmol), NEt$_3$ (62 mg, 0.61 mmol), and T3P (117 mg, 0.37 mmol) in EtOAc (1.0 mL). $^1$H-NMR (400 MHz; CDCl$_3$): δ 7.36 (t, J=8.6 Hz, 1H), 6.96 (s, 1H), 6.80 (dd, J=10.2, 2.8 Hz, 1H), 6.71 (ddd, J=8.9, 2.9, 1.3 Hz, 1H), 4.44 (s, 2H), 2.76 (d, J=7.1 Hz, 2H), 2.67 (s, 6H), 1.21-1.11 (m, 1H), 0.66-0.61 (m, 2H), 0.34-0.30 (m, 2H). LC-MS m/z:=392.2 [M+H]$^+$.

Example 12

N-[3-[5-(4-chloro-3-fluoro-phenyl)-1,3,4-oxadiazol-2-yl]-1-bicyclo[1.1.1]pentanyl]-2-[cis-3-(trifluoromethoxy)cyclobutoxy]acetamide Step 1: tert-butyl N-[1-(hydrazinecarbonyl)-3-bicyclo[1.1.1]pentanyl]carbamate Prepared using General Procedure B employing methyl 3-(tert-butoxy carbonylamino)bicyclo[1.1.1]pentane-1-carboxylate (241 mg, 1.0 mmol), hydrazine hydrate (150 mg, 3.0 mmol) in EtOH (5.0 mL).

Step 2: tert-butyl N-[1-[5-(4-chloro-3-fluoro-phenyl)-1,3,4-oxadiazol-2-yl]-3-bicyclo[1.1.1]pentanyl]carbamate Prepared using General Procedure C employing tert-butyl N-[1-(hydrazinecarbonyl)-3-bicyclo[1.1.1]pentanyl]carbamate (30 mg, 0.12 mmol), 4-chloro-3-fluoro-benzoic acid (33 mg, 0.19 mmol), NEt$_3$ (63 mg, 0.62 mmol), and T3P (119 mg, 0.37 mmol) in EtOAc (1.2 mL).

Step 3: 1-[5-(4-chloro-3-fluoro-phenyl)-1,3,4-oxadiazol-2-yl]bicyclo[1.1.1]pentan-3-amine; 2,2,2-trifluoroacetic acid tert-butyl N-[1-[5-(4-chloro-3-fluoro-phenyl)-1,3,4-oxadiazol-2-yl]-3-bicyclo[1.1.1]pentanyl]carbamate (35. mg, 0.09 mmol) was dissolved in CH$_2$Cl$_2$ (0.9 mL) at rt and trifluoroacetic acid (105 mg, 0.92 mmol) was added. The reaction mixture was stirred at rt for 2 h and was concentrated. The crude was used directly.

Step 4: N-[3-[5-(4-chloro-3-fluoro-phenyl)-1,3,4-oxadiazol-2-yl]-1-bicyclo[1.1.1]pentanyl]-2-[cis-3-(trifluoromethoxy)cyclobutoxy]acetamide Prepared using General Procedure A employing methyl 3-aminobicyclo[1.1.1]pentane-1-carboxylate trifluoroacetate salt (35 mg, 0.09 mmol), 2-[3-cis-(trifluoromethoxy)cyclobutoxy]acetic acid (23 mg, 0.11 mmol), NEt$_3$ (27 mg, 0.27 mmol), and T3P (34 mg, 0.27 mmol) in EtOAc (0.9 mL). $^1$H-NMR (400 MHz; CDCl$_3$): δ 7.86-7.80 (m, 2H), 7.58-7.55 (m, 1H), 6.98 (s, 1H), 4.36 (quintet, J=7.1 Hz, 1H), 3.86 (s, 2H), 3.75 (quintet, J=6.8 Hz, 1H), 2.89-2.82 (m, 2H), 2.70 (s, 6H), 2.34-2.26 (m, 2H). LC-MS m/z:=476.4 [M+H]$^-$.

Example 13 tert-Butyl 3-[5-[3-[[2-(4-chloro-3-fluoro-phenoxy)acetyl]amino]-1-bicyclo[1.1.1]pentanyl]-1,3,4-oxadiazol-2-yl]azetidine-1-carboxylate Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 1-tert-butoxycarbonylazetidine-3-carboxylic acid (37 mg, 0.18 mmol), NEt$_3$ (62 mg, 0.61 mmol), and T3P (117 mg, 0.37 mmol) in EtOAc (1.2 mL). $^1$H-NMR (400 MHz; CDCl$_3$): δ 7.36 (t, J=8.6 Hz, 1H), 6.98 (s, 1H), 6.80 (dd, J=10.2, 2.8 Hz, 1H), 6.71 (ddd, J=8.9, 2.9, 1.3 Hz, 1H), 4.45 (s, 2H), 4.34 (t, J=8.8 Hz, 2H), 4.27-4.23 (m, 2H), 4.03-3.96 (m, 1H), 2.68 (s, 6H), 1.48 (s, 9H). LC-MS m/z:=437.2 [M+H−t-Bu]

Example 14 tert-butyl 3-[5-[3-[[2-(4-chloro-3-fluoro-phenoxy)acetyl]amino]-1-bicyclo[1.1.1]pentanyl]-1,3,4-oxadiazol-2-yl]pyrrolidine-1-carboxylate Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 1-tert-butoxycarbonylpyrrolidine-3-carboxylic acid (39 mg, 0.18 mmol), NEt$_3$ (62 mg, 0.61 mmol), and T3P (117 mg, 0.37 mmol) in EtOAc (1.2 mL). $^1$H-NMR (400 MHz; CDCl$_3$): δ 7.36 (t, J=8.6 Hz, 1H), 6.97 (s, 1H), 6.79 (dd, J=10.2, 2.8 Hz, 1H), 6.71 (ddd, J=8.9, 2.9, 1.3 Hz, 1H), 4.44 (s, 2H), 3.86-3.80 (m, 1H), 3.67-3.61 (m, 3H), 3.51-3.46 (m, 1H), 2.66 (s, 6H), 2.40-2.25 (m, 2H), 1.49 (s, 9H). LC-MS m/z:=451.2 [M+H−t-Bu]

Example 15

2-(4-chloro-3-fluoro-phenoxy)-N-[1-[5-[1-(2,2,2-trifluoroethyl)azetidin-3-yl]-1,3,4-oxadiazol-2-yl]-3-bicyclo[1.1.1]pentanyl]acetamide tert-Butyl 3-[5-[3-[[2-(4-chloro-3-fluoro-phenoxy)acetyl]amino]-1-bicyclo[1.1.1]pentanyl]-1,3,4-oxadiazol-2-yl]azetidine-1-carboxylate (34 mg, 0.07 mmol) was dissolved in CH$_2$Cl$_2$ (0.7 mL) at ambient temperature followed by cooling of the reaction mixture to 0° C. Subsequently, trifluoroacetic acid (118 mg, 1.03 mmol) was added dropwise. After 4 h, the reaction was quenched by the addition of sat NaHCO$_3$ and the resulting biphasic reaction mixture was then further diluted with sat NaHCO$_3$ and CH$_2$Cl$_2$. The layers were separated and the aqueous layer was extracted with CH$_2$Cl$_2$ (3×). The combined organic layers were dried over anhydrous MgSO$_4$, filtered, and concentrated under reduced pressure. The crude product was used in the next transformation without further purification.

The crude residue was dissolved in EtOAc (0.9 mL). H$_2$O (0.5 mL) and NaHCO$_3$ (29 mg, 0.34 mmol) were then added sequentially and the reaction was cooled to 0° C. 2,2,2-Trifluoroethyl trifluoromethanesulfonate (19 mg, 0.08 mmol) was then added dropwise. After 6 h, the reaction mixture was diluted with EtOAc and sat NaHCO$_3$. The layers were separated and the aqueous layer was extracted with EtOAc (3×). The combined organic layers were dried over anhydrous MgSO$_4$, filtered, and concentrated under reduced pressure. The crude reaction mixture was purified employing reverse-phase HPLC. $^1$H NMR (400 MHz; CDCl$_3$): δ 7.37 (t, J=8.6 Hz, 1H), 6.96 (s, 1H), 6.80 (dd, J=10.2, 2.9 Hz, 1H), 6.71 (ddd, J=8.9, 2.9, 1.2 Hz, 1H), 4.45 (s, 2H), 4.06-3.94 (m, 3H), 3.65 (t, J=6.7 Hz, 2H), 3.11 (q, J=9.3 Hz, 2H), 2.67 (s, 6H). LC-MS m/z:=475.30 [M+H]$^+$.

Example 16

2-(4-chloro-3-fluoro-phenoxy)-N-[1-[5-[1-(2,2,2-trifluoroethyl)pyrrolidin-3-yl]-1,3,4-oxadiazol-2-yl]-3-bicyclo[1.1.1]pentanyl]acetamide tert-Butyl 3-[5-[3-[[2-(4-chloro-3-fluoro-phenoxy)acetyl]amino]-1-bicyclo[1.1.1]pentanyl]-1,3,4-oxadiazol-2-yl]pyrrolidine-1-carboxylate (38 mg, 0.07 mmol) was dissolved in CH$_2$Cl$_2$ (0.7 mL) at ambient temperature followed by cooling of the reaction mixture to 0° C. Subsequently, trifluoroacetic acid (128 mg, 1.12 mmol) was added dropwise. After 4 h, the reaction was quenched by the addition of sat NaHCO$_3$ and the resulting biphasic reaction mixture was then further diluted with sat NaHCO$_3$ and CH$_2$Cl$_2$. The layers were separated and the aqueous layer was extracted with CH$_2$Cl$_2$ (3×). The combined organic layers were dried over anhydrous MgSO$_4$, filtered, and concentrated under reduced pressure. The crude product was used in the next transformation without further purification.

The crude residue was dissolved in EtOAc (0.9 mL). H$_2$O (0.5 mL) and NaHCO$_3$ (32 mg, 0.38 mmol) were then added sequentially and the reaction mixture was cooled to 0° C. 2,2,2-Trifluoroethyl trifluoromethanesulfonate (21 mg, 0.08 mmol) was then added dropwise. After 6 h, the reaction mixture was diluted with EtOAc and sat NaHCO$_3$. The layers were separated and the aqueous layer was extracted with EtOAc (3×). The combined organic layers were dried over anhydrous MgSO$_4$, filtered, and concentrated under reduced pressure. The crude reaction mixture was purified employing reverse-phase HPLC. $^1$H-NMR (400 MHz; CDCl$_3$): δ 7.36 (t, J=8.6 Hz, 1H), 6.95 (s, 1H), 6.80 (dd, J=10.2, 2.9 Hz, 1H), 6.71 (ddd, J=8.9, 2.9, 1.2 Hz, 1H), 4.44 (s, 2H), 3.65 (dq, J=9.7, 7.2 Hz, 1H), 3.34 (t, J=8.6 Hz, 1H), 3.18 (dtt, J=14.3, 9.5, 4.8 Hz, 2H), 3.07 (td, J=8.4, 5.4 Hz, 1H), 3.00 (dd, J=9.3, 7.4 Hz, 1H), 2.86 (q, J=7.7 Hz, 1H), 2.66 (s, 6H), 2.38 (dddd, J=13.0, 9.7, 7.7, 6.8 Hz, 1H), 2.26 (dddd, J=13.1, 8.0, 6.4, 5.3 Hz, 1H). LC-MS m/z:=489.34 [M+H]$^+$.

Example 17

2-(4-chloro-3-fluoro-phenoxy)-N-[3-(5-cyclopropyl-1,3,4-oxadiazol-2-yl)-1-bicyclo[1.1.1]pentanyl]acetamide 2-(4-Chloro-3-fluoro-phenoxy)-N-[1-(hydrazinecarbonyl)-3-bicyclo[1.1.1]pentanyl]acetamide (40 mg, 0.12 mmol) was dissolved in EtOAc (1.2 mL) at ambient temperature followed by the addition of NEt$_3$ (62 mg, 0.61 mmol) and cyclopropanecarbonyl chloride (19 mg, 0.18 mmol). After 30 min, the consumption of starting material was complete by HPLC analysis and T3P (233 mg, 0.37 mmol) was added. The resulting reaction mixture was heated at 100° C. in a sealed vial overnight. The reaction mixture was diluted with sat NaHCO$_3$ solution and EtOAc. The layers were separated and the aqueous layer was extracted with EtOAc (3×). The combined organic layers were dried over anhydrous MgSO$_4$, filtered, and concentrated under reduced pressure. The crude reaction mixture was purified employing reverse-phase HPLC. $^1$H NMR (400 MHz; CDCl$_3$): δ 7.36 (t, J=8.6 Hz, 1H), 6.95 (s, 1H), 6.79 (dd, J=10.2, 2.8 Hz, 1H), 6.71 (ddd, J=8.9, 2.8, 1.2 Hz, 1H), 4.44 (s, 2H), 2.64 (s, 6H), 2.18-2.11 (m, 1H), 1.16 (s, 4H). LC-MS m/z:=378.24 [M+H]$^+$.

Example 18

2-(4-chloro-3-fluoro-phenoxy)-N-[3-[5-(2,2-difluorocyclopropyl)-1,3,4-oxadiazol-2-yl]-1-bicyclo [1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg. 0.12 mmol), 2,2-difluorocyclopropanecarboxylic acid (22 mg, 0.18 mmol), NEt$_3$ (62 mg, 0.61 mmol), and T3P (233 mg, 0.37 mmol) in EtOAc (1.2 mL). $^1$H NMR (400 MHz; CDCl$_3$): δ 7.36 (t, J=8.6 Hz, 1H), 6.96 (s, 1H), 6.80 (dd, J=10.2, 2.8 Hz, 1H), 6.71 (ddd, J=8.9, 2.9, 1.2 Hz, 1H), 4.45 (s, 2H), 2.95 (ddd, J=11.5, 10.0, 7.9 Hz, 1H), 2.67 (s, 6H), 2.25 (dtd, J=12.3, 8.1, 5.4 Hz, 1H), 2.13-2.05 (m, 1H). LC-MS m/z:=414.12 [M+H]$^+$.

Example 19 and 20

2-(4-Chloro-3-fluoro-phenoxy)-N-[1-(2-cyclobutyltriazol-4-yl)-3-bicyclo[1.1.1]pentanyl]acetamide and 2-(4-chloro-3-fluoro-phenoxy)-N-[1-(1-cyclobutyltriazol-4-yl)-3-bicyclo[1.1.1]pentanyl]acetamide Step 1: 2-(4-chloro-3-fluoro-phenoxy)-N-(1-ethynyl-3-bicyclo[1.1.1]pentanyl)acetamide To a mixture of 2-(4-chloro-3-fluoro-phenoxy)-N-(1-formyl-3-bicyclo[1.1.1]pentanyl)acetamide (900 mg, 3.02 mmol) and 1-diazo-1-dimethoxyphosphoryl-propan-2-one (813 mg, 4.23 mmol) in MeOH (20 mL) was added K$_2$CO$_3$ (1.25 g, 9.07 mmol) at 20° C. under N$_2$. The mixture was stirred at 20° C. for 16 h. The mixture was poured into ice-water (20 mL) and extracted with EtOAc (3×15 mL). The combined organic phase was washed with brine (15 mL), dried over anhydrous Na$_2$SO$_4$, filtered and concentrated under reduced pressure. The residue was purified by silica gel column chromatography (PE:MTBE=1:0 to 3:1) to give the desired product. $^1$H-NMR (400 MHz, CDCl$_3$): δ 7.33 (t, J=8.60 Hz, 1H), 6.82 (br s, 1H), 6.75 (dd, J=10.29, 2.89 Hz, 1H), 6.67 (ddd, J=8.88, 2.85, 1.19 Hz, 1H), 4.38 (s, 2H), 2.43-2.47 (m, 6H), 2.19 (s, 1H).

Step 2: 2-(4-chloro-3-fluoro-phenoxy)-N-[1-(1H-triazol-4-yl)-3-bicyclo[1.1.1]pentanyl]acetamide To a mixture of 2-(4-chloro-3-fluoro-phenoxy)-N-(1-ethynyl-3-bicyclo[1.1.1]pentanyl)acetamide (80 mg, 0.27 mmol) and CuSO$_4$ (0.4 mg, 0.003 mmol) in t-BuOH (3 mL) and H$_2$O (1 mL) was added TMSN$_3$ (33 mg, 0.29 mmol), benzoic acid (3 mg, 0.027 mmol) and sodium ascorbate (1 mg, 0.005 mmol) at 20° C. under N$_2$. The mixture was stirred at 80° C. for 32 h. The mixture was cooled to 20° C. and poured into ice-water (5 mL) and extracted with EtOAc (3×2 mL). The combined organic phase was washed with brine (2 mL), dried over anhydrous Na$_2$SO$_4$, filtered and concentrated under reduced pressure. The crude product 2-(4-chloro-3-fluoro-phenoxy)-N-[1-(1H-triazol-4-yl)-3-bicyclo[1.1.1]pentanyl]acetamide was used in the next step without further purification. LC-MS m/z:=337.1 [M+H]$^+$.

Step 3: 2-(4-chloro-3-fluoro-phenoxy)-N-[1-(2-cyclobutyltriazol-4-yl)-3-bicyclo[1.1.1]pentanyl]acetamide and 2-(4-chloro-3-fluoro-phenoxy)-N-[1-(1-cyclobutyltriazol-4-yl)-3-bicyclo[1.1.1]pentanyl] acetamide To a mixture of 2-(4-chloro-3-fluoro-phenoxy)-N-[1-(1H-triazol-4-yl)-3-bicyclo[1.1.1]pentanyl]acetamide (71 mg, 211 μmol) and bromocyclobutane (43 mg, 316 μmol, 30 uL) in DMF (1 mL) was added Cs$_2$CO$_3$ (206 mg, 633 μmol) at 20° C. under N$_2$. The mixture was stirred at 80° C. for 6 h. The mixture was poured into ice-water (3 mL) and extracted with EtOAc (3×1 mL). The combined organic phase was washed with brine (3×1 mL), dried over anhydrous Na$_2$SO$_4$, filtered and concentrated under reduced pressure. The residue was purified by prep-HPLC to give 2-(4-chloro-3-fluoro-phenoxy)-N-[1-(2-cyclobutyltriazol-4-yl)-3-bicyclo [1.1.1]pentanyl]acetamide as the first eluting isomer. $^1$H-NMR (400 MHz, CDCl$_3$): δ 7.41 (s, 1H), 7.34 (t, J=8.53 Hz, 1H), 6.90 (br s, 1H), 6.79 (dd, J=10.29, 2.89 Hz, 1H), 6.71 (br d, J=9.16 Hz, 1H), 5.06 (quin, J=8.28 Hz, 1H), 4.42 (s, 2H), 2.64-2.76 (m, 2H), 2.45-2.55 (m, 8H), 1.82-1.98 (m, 2H). LC-MS m/z:=391.3 [M+H]$^+$.

2-(4-Chloro-3-fluoro-phenoxy)-N-[1-(1-cyclobutyltriazol-4-yl)-3-bicyclo[1.1.1]pentanyl]acetamide as the second eluting isomer. $^1$H-NMR (400 MHz, CDCl$_3$): δ 7.42 (s, 1H), 7.34 (t, J=8.53 Hz, 1H), 6.94 (br s, 1H), 6.78 (dd, J=10.29, 2.76 Hz, 1H), 6.70 (br d, J=8.91 Hz, 1H), 5.03 (quin, J=8.47 Hz, 1H), 4.43 (s, 2H), 2.59 (br t, J=8.66 Hz, 4H), 2.53 (s, 6H), 1.90-2.02 (m, 2H). LC-MS m/z:=391.3 [M+H]$^+$.

Example 21

2-(4-chloro-3-fluorophenoxy)-N-(3-(5-cyclopentyl-4,5-dihydroisoxazol-3-yl)bicyclo[1.1.1]pentan-1-yl) acetamide Step 1: 2-(4-chloro-3-fluoro-phenoxy)-N-[3-(hydroxymethyl)-1-bicyclo[1.1.1]pentanyl]acetamide To a solution of methyl 3-[[2-(4-chloro-3-fluoro-phenoxy)acetyl]amino]bicyclo[1.1.1]pentane-1-carboxylate (795 mg, 2.43 mmol) in THF (30 mL) was added LiBH$_4$ (159 mg, 7.28 mmol) at 0° C. under N$_2$, then the mixture was stirred at 20° C. for 16 h. The reaction mixture was quenched with sat. NH$_4$Cl (10 mL) and extracted with EtOAc (3×15 mL). The combined organic layers were washed with brine (10 mL), dried over Na$_2$SO$_4$, filtered and concentrated under reduced pressure. The residue was purified by silica gel column chromatography to give the desired product. $^1$H-NMR (400 MHz; CDCl$_3$): δ 7.33 (t, J=8.60 Hz, 1H), 6.84 (br s, 1H), 6.77 (dd, J=10.29, 2.89 Hz, 1H), 6.68 (ddd, J=8.88, 2.79, 1.13 Hz, 1H), 4.39 (s, 2H), 3.74 (br d, J=3.76 Hz, 2H), 2.10 (s, 6H).

Step 2: 2-(4-chloro-3-fluorophenoxy)-N-(3-formyl-bicyclo[1.1.1]pentan-1-yl)acetamide To a solution of 2-(4-chloro-3-fluoro-phenoxy)-N-[1-(hydroxymethyl)-3-bicyclo[1.1.1]pentanyl]acetamide (450 mg, 1.50 mmol) in anhydrous CH$_2$Cl$_2$ (20 mL) was added DMP (669 mg, 1.58 mmol) at 0° C., the mixture was stirred at 10° C. for 5 h. The reaction solution was quenched with addition of sat. NaHCO$_3$ and extracted with CH$_2$Cl$_2$ (3×10 mL). The organic layers were combined, washed with brine (10 mL), dried over Na$_2$SO$_4$, filtered and concentrated under reduced pressure to give the desired product. $^1$H-NMR (400 MHz; CDCl$_3$): δ 9.68 (s, 1H), 7.32-7.36 (m, 1H), 6.87 (br s, 1H), 6.75-6.78 (m, 1H), 6.68-6.70 (m, 1H), 4.40 (s, 2H), 2.44 (s, 6H).

Step 3: (E)-2-(4-chloro-3-fluorophenoxy)-N-(3-((hydroxyimino)methyl)bicyclo[1.1.1]pentan-1-yl)acetamide To a solution of 2-(4-chloro-3-fluoro-phenoxy)-N-(1-formyl-3-bicyclo[1.1.1]pentanyl)acetamide (500 mg, 1.68 mmol) in EtOH (3 mL) was added NH$_2$OH·HCl (210 mg, 3.02 mmol) and NaOAc (234 mg, 2.86 mmol). After addition, the mixture was stirred at 85° C. for 3 h. The reaction mixture was quenched with addition of sat. NaHCO$_3$ (10 mL) at 0° C., and then concentrated under reduced pressure. The residue was diluted with H$_2$O (10 mL) and extracted with EtOAc (3×5 mL). The combined organic layers were washed with brine (5 mL), dried over Na$_2$SO$_4$, filtered and concentrated under reduced pressure to give the desired product. $^1$H-NMR (400 MHz; CDCl$_3$): δ 7.50 (s, 1H), 7.34 (t, J=8.60 Hz, 1H), 6.85 (br s, 1H), 6.73-6.79 (m, 1H), 6.64-6.71 (m, 1H), 4.40 (s, 2H), 2.50 (s, 1H) 2.34 (s, 4H). LC-MS m/z:=313.3 [M+H]$^+$.

Step 4: (Z)-3-(2-(4-chloro-3-fluorophenoxy)acetamido)-N-hydroxybicyclo[1.1.1]pentane-1-carbimidoyl chloride To a solution of 2-(4-chloro-3-fluorophenoxy)-N-[1-[(E)-hydroxyiminomethyl]-3-bicyclo[1.1.1]pentanyl]acetamide (50 mg, 0.16 mmol) in DMF (1 mL) was added NCS (23 mg, 0.18 mmol) at 0° C. The reaction mixture was stirred at 0° C. for 1 h, and then stirred at 20° C. for 1 h. The mixture was used for the next step without further purification.

Step 5: 2-(4-chloro-3-fluorophenoxy)-N-(3-(5-cyclopentyl-4,5-dihydroisoxazol-3-yl)bicyclo[1.1.1]pentan-1-yl)acetamide To a solution of (Z)-3-[[2-(4-chloro-3-fluoro-phenoxy)acetyl]amino]-N-hydroxybicyclo[1.1.1]pentane-1-carboximidoyl chloride (56 mg, 0.16 mmol) in DMF (1 mL) was added dropwise vinylcyclopentane (19 mg, 0.19 mmol) and NEt$_3$ (23 mg, 0.22 mmol) at 0° C. After addition, the mixture was stirred at 0° C. for 30 min, and then stirred at 20° C. for 30 min. The reaction mixture was quenched with H$_2$O (0.2 mL) at 0° C., and then concentrated under reduced pressure. The residue was purified by prep-HPLC to give the desired product. $^1$H-NMR (400 MHz; CDCl$_3$): δ 7.33 (t, J=8.60 Hz, 1H), 6.88 (br s, 1H), 6.77 (dd, J=10.25, 2.76 Hz, 1H), 6.69 (br d, J=8.82 Hz, 1H), 4.41-4.49 (m, 1H), 4.40 (s, 2H), 2.94 (dd, J=16.87, 10.25 Hz, 1H), 2.58 (dd, J=16.76, 8.60 Hz, 1H), 2.39 (s, 6H), 2.01-2.12 (m, 1H), 1.76-1.90 (m, 1H), 1.54-1.74 (m, 5H) 1.31-1.42 (m, 1H), 1.14-1.29 (m, 1H). LC-MS m/z:=407.3 [M+H]$^+$.

Example 22

2-(4-chloro-3-fluorophenoxy)-N-(3-(5-cyclopentyl-isoxazol-3-yl)bicyclo[1.1.1]pentan-1-yl)acetamide To a solution of (Z)-3-[[2-(4-chloro-3-fluoro-phenoxy)acetyl]amino]-N-hydroxybicyclo[1.1.1]pentane-1-carboximidoyl chloride (56 mg, 0.16 mmol) in DMF (1 mL) was added dropwise ethynylcyclopentane (18 mg, 0.19 mmol) and NEt$_3$ (23 mg, 0.22 mmol) at 0° C. After addition, the mixture was stirred at 0° C. for 30 min, and then stirred at 20° C. for 30 min. The mixture was added to a sealed tube and then stirred at 70° C. for 11 h. The reaction mixture was quenched with H$_2$O (0.2 mL) at 0° C., and then concentrated under reduced pressure. The residue was purified by prep-HPLC to give the desired product. $^1$H-NMR (400 MHz; CDCl$_3$): δ 7.34 (t, J=8.60 Hz, 1H), 6.90 (s, 1H), 6.78 (dd, J=10.25, 2.76 Hz, 1H), 6.66-6.73 (m, 1H), 5.83 (s, 1H), 4.42 (s, 2H), 3.12-3.22 (m, 1H), 2.50 (s, 6H), 2.08 (br d, J=8.60 Hz, 2H), 1.64-1.83 (m, 6H). LC-MS m/z:=405.3 [M+H]$^+$.

Example 23

2-(4-chloro-3-fluorophenoxy)-N-(3-(5-cyclobutyl-4,5-dihydroisoxazol-3-yl)bicyclo[1.1.1]pentan-1-yl)acetamide To a solution of (E)-2-(4-chloro-3-fluorophenoxy)-N-(3-((hydroxyimino)methyl)bicyclo[1.1.1]pentan-1-yl)acetamide (50 mg, 0.16 mmol) in dry 1,4-dioxane (5 mL) was added vinylcyclobutane (131 mg, 1.60 mmol), t-BuOCl (35 mg, 0.32 mmol), NaI (48 mg, 0.32 mmol) and 2,6-lutidine (0.037 mL, 0.32 mmol) at 20° C., then the mixture was stirred at 20° C. for 48 h. The mixture was quenched with sat. NH$_4$Cl (5 mL), and extracted with EtOAc (3×5 mL). The organic layer was washed with brine (5 mL), then dried over Na$_2$SO$_4$ and concentrated under reduced pressure. The crude was purified by prep-TLC to give the desired product. LC-MS m/z:=393.4 [M+H]$^+$.

Example 24

2-(4-chloro-3-fluorophenoxy)-N-(3-(5-cyclobutyl-isoxazol-3-yl)bicyclo[1.1.1]pentan-1-yl)acetamide To a solution of 2-(4-chloro-3-fluorophenoxy)-N-(3-(5-cyclobutyl-4,5-dihydroisoxazol-3-yl)bicyclo[1.1.1]pentan-1-yl)acetamide (20 mg, 0.05 mmol) in 1,4-dioxane (3 mL) was added DDQ (23.1 mg, 0.1 mmol), the reaction was heated at reflux for 12 h under O$_2$. The reaction was cooled down, filtered over a plug of celite and washed with EtOAc (2×5 mL). The solvent was removed under reduced pressure. The residue was purified by prep-HPLC to give the desired product. $^1$H-NMR (400 MHz; CDCl$_3$): δ 7.34 (t, J=8.60 Hz, 1H), 6.91 (s, 1H), 6.78 (dd, J=10.29, 2.76 Hz, 1H), 6.67-6.73 (m, 1H), 5.88 (s, 1H), 4.42 (s, 2H), 3.61 (quin, J=8.56 Hz, 1H), 2.51 (s, 6H), 2.33-2.43 (m, 2H), 2.20-2.32 (m, 2H), 1.91-2.11 (m, 2H). LC-MS m/z:=391.3 [M+H]$^+$.

Example 25

2-(4-chloro-3-fluoro-phenoxy)-N-[1-(5-cyclobutyl-1,3,4-oxadiazol-2-yl)-3-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (45 mg, 0.14 mmol), cyclobutanecarboxylic acid (17 mg, 0.16 mmol), NEt₃ (56 mg, 0.55), and T3P (87.5 mg, 0.27 mmol) in EtOAc (2 mL). ¹H-NMR (400 MHz, CDCl₃): δ 7.34 (t, J=8.60 Hz, 1H), 6.98 (s, 1H), 6.78 (dd, J=10.23, 2.82 Hz, 1H), 6.69 (ddd, J=8.88, 2.79, 1.13 Hz, 1H), 4.43 (s, 2H), 3.72 (quin, J=8.41 Hz, 1H), 2.65 (s, 6H), 2.38-2.53 (m, 4H), 1.95-2.23 (m, 2H). LC-MS m/z:=392.3 [M+H]⁺.

Example 26

2-(4-Chloro-3-fluorophenoxy)-N-(3-(3-cyclobutyl-isoxazol-5-yl)bicyclo[1.1.1]pentan-1-yl)acetamide Step 1: Cyclobutanecarbaldehyde oxime To a solution of cyclobutanecarbaldehyde (500 mg, 5.94 mmol) in EtOH (20 mL) was added NaOAc (829 mg, 10.1 mmol) and NH₂OH·HCl (744 mg, 10.7 mmol). The mixture was stirred at 80° C. for 5 h. The reaction mixture was diluted with H₂O (40 mL) and extracted with EtOAc (3×20 mL). The combined organic layers were washed with brine (40 mL), dried over Na₂SO₄, filtered and concentrated under reduced pressure to give cyclobutanecarbaldehyde oxime which was used for the next step directly. ¹H-NMR (400 MHz, CDCl₃): δ 1.82-1.93 (m, 4H) 1.95-2.03 (m, 5H) 2.06-2.12 (m, 9H) 2.13-2.23 (m, 5H) 2.24-2.33 (m, 2H) 2.97-3.20 (m, 2H) 3.72 (q, J=7.06 Hz, 1H) 6.82 (d, J=6.39 Hz, 1H) 7.50 (d, J=6.39 Hz, 3H).

Step 2: N-hydroxycyclobutanecarbimidoyl chloride

To a solution of cyclobutanecarbaldehyde oxime (200 mg, 2.02 mmol) in DMF (8 mL) was added NCS (323 mg, 2.42 mmol) at 0° C. The mixture was stirred at 20° C. for 2 h. The reaction solution was used for the next step directly.

Step 3: 2-(4-chloro-3-fluorophenoxy)-N-(3-(3-cyclobutylisoxazol-5-yl)bicyclo[1.1.1]pentan-1-yl) acetamide To a solution of N-hydroxycyclobutanecarboximidoyl chloride (73 mg, 0.54 mmol) in DMF (3.5 mL) was added 2-(4-chloro-3-fluoro-phenoxy)-N-(1-ethynyl-3-bicyclo [1.1.1]pentanyl)acetamide (80 mg, 0.27 mmol) and NEt₃ (41 mg, 0.41 mmol). The mixture was stirred at 60° C. for 5 h. After the reaction was complete, the reaction mixture was purified by prep-HPLC to give the desired product. ¹H-NMR (400 MHz, CDCl₃): δ 1.83-2.06 (m, 2H) 2.09-2.21 (m, 2H) 2.23-2.35 (m, 2H) 2.46 (s, 6H) 3.51 (quin, J=8.38 Hz, 1H) 4.34 (s, 2H) 5.89 (s, 1H) 6.62 (dd, J=8.93, 1.65 Hz, 1H) 6.70 (dd, J=10.14, 2.87 Hz, 1H) 6.82 (s, 1H) 7.26 (t, J=8.60 Hz, 1H). LC-MS m/z:=391.3 [M+H]⁺.

Example 27

2-(4-chloro-3-fluoro-phenoxy)-N-[1-(4-cyclobutyloxazol-2-yl)-3-bicyclo[1.1.1]pentanyl]acetamide To a mixture of 3-[[2-(4-chloro-3-fluoro-phenoxy)acetyl] amino]bicyclo[1.1.1]pentane-1-carboxamide (0.1 g, 0.32 mmol) in DMPU (5 mL) was added 2-bromo-1-cyclobutyl-ethanone (113 mg, 0.64 mmol) at 20° C. under N₂. The mixture was stirred at 150° C. for 5 h. The mixture was poured into ice-water (10 mL). The aqueous phase was extracted with EtOAc (3×5 mL). The combined organic phase was washed with brine (5×5 mL), dried over anhydrous Na₂SO₄, filtered and concentrated under reduced pressure. The residue was purified by prep-HPLC to give the desired product. ¹H-NMR (400 MHz; CDCl₃): δ 7.30-7.40 (m, 2H), 6.91 (s, 1H), 6.78 (dd, J=10.29, 2.89 Hz, 1H), 6.66-6.72 (m, 1H), 4.41 (s, 2H), 3.41 (quin, J=8.41 Hz, 1H), 2.59 (s, 6H) 2.25-2.36 (m, 2H), 2.08-2.20 (m, 2H), 1.83-2.06 (m, 2H). LC-MS m/z:=391.3 [M+H]⁺.

Example 28

N-[1-[1-(4-Chlorophenyl)triazol-4-yl]-3-bicyclo [1.1.1]pentanyl]-2-(cyclobutoxy)acetamide Step 1: Methyl 3-[[2-(cyclobutoxy)acetyl]amino] bicyclo[1.1.1]pentane-1-carboxylate To a mixture of 2-(cyclobutoxy)acetic acid (967 mg, 7.43 mmol) in CH₂Cl₂ (20 mL) was added T3P (6.45 g, 10.13 mmol, 50% in EtOAc) and NEt₃ (3.42 g, 33.78 mmol) at 0° C. under N₂. After 1 h, methyl 3-aminobicyclo[1.1.1]pentane-1-carboxylate HCl salt (1.2 g, 6.76 mmol) was added to the solution at 0° C., then the mixture was stirred at 20° C. for 15 h. The reaction mixture was adjusted to pH=7-8 with sat. NaHCO₃ and extracted with EtOAc (3×20 mL). The combined organic layers were washed with brine (20 mL), dried over Na₂SO₄, filtered and concentrated under reduced pressure to provide a residue. The residue was purified by silica gel column chromatography to give the desired product. ¹H-NMR (400 MHz, CDCl₃): δ 6.89 (s, 1H), 3.91-4.02 (m, 1H), 3.77 (s, 2H), 3.69 (s, 3H), 2.47-2.48 (m, 1H), 2.41 (s, 6H), 2.17-2.27 (m, 2H), 1.88-2.01 (m, 2H), 1.68-1.79 (m, 1H), 1.46-1.59 (m, 1H).

Step 2: 2-(cyclobutoxy)-N-[1-(hydroxymethyl)-3-bicyclo[1.1.1]pentanyl]acetamide

To a mixture of methyl 3-[[2-(cyclobutoxy)acetyl]amino] bicyclo[1.1.1]pentane-1-carboxylate (0.7 g, 2.76 mmol) in THF (20 mL) was added LiBH₄ (120 mg, 5.53 mmol) at 0° C. under N₂, then the mixture was stirred at 20° C. for 16 h. The reaction mixture was quenched with sat. NH₄Cl (50 mL) and extracted with EtOAc (3×20 mL). The combined organic layers were washed with brine (50 mL), dried over Na₂SO₄, filtered and concentrated under reduced pressure. The residue was purified by silica gel column chromatography (PE:MTBE=100:1 to 0:1) to give the desired product. ¹H-NMR (400 MHz, CDCl₃): δ 6.88 (s, 1H), 3.90-4.04 (m, 1H), 3.78 (s, 2H), 3.73 (s, 2H), 3.22 (s, 1H), 2.18-2.27 (m, 2H), 2.05-2.09 (m, 6H), 1.86-2.01 (m, 2H), 1.67-1.80 (m, 1H), 1.42-1.60 (m, 2H).

Step 3: 2-(cyclobutoxy)-N-(1-formyl-3-bicyclo [1.1.1]pentanyl)acetamide

To a mixture of 2-(cyclobutoxy)-N-[1-(hydroxymethyl)-3-bicyclo[1.1.1]pentanyl]acetamide (0.35 g, 1.55 mmol) in CH₂Cl₂ (10 mL) was added Dess-Martin reagent (692 mg, 1.63 mmol) at 0° C. under N₂, then the mixture was stirred at 20° C. for 4 h. The mixture was adjusted to pH=7-8 with sat. NaHCO₃. The aqueous phase was extracted with EtOAc (3×10 mL). The combined organic layers were washed with brine (20 mL), dried over anhydrous Na₂SO₄, filtered and concentrated under reduced pressure. The residue was slurried with MTBE, then filtered and the filtrate was concentrated under reduced pressure to give the desired product. ¹H-NMR (400 MHz, CDCl₃): δ 9.68 (s, 1H), 3.87-4.13 (m, 1H), 3.79 (s, 3H), 2.41 (s, 6H), 2.22 (s, 3H), 1.97 (d, J=7.78 Hz, 3H), 1.66-1.82 (m, 2H), 1.26 (s, 8H), 1.20 (s, 5H).

Step 4: 2-(cyclobutoxy)-N-(1-ethynyl-3-bicyclo [1.1.1]pentanyl)acetamide

To a mixture of 2-(cyclobutoxy)-N-(1-formyl-3-bicyclo [1.1.1]pentanyl)acetamide (300 mg, 1.34 mmol) in MeOH (6 mL) was added $K_2CO_3$ (557 mg, 4.03 mmol) and 1-diazo-1-dimethoxyphosphoryl-propan-2-one (361 mg, 1.88 mmol) at 20° C. under $N_2$, then the mixture was stirred at 20° C. for 16 h. The reaction mixture was diluted with $H_2O$ (10 mL) and extracted with EtOAc (3×8 mL). The combined organic layers were washed with brine (10 mL), dried over $Na_2SO_4$, filtered and concentrated under reduced pressure. The residue was purified by prep-TLC to give the desired product. $^1$H-NMR (400 MHz, $CDCl_3$): δ 6.86 (s, 1H), 3.96 (quin, J=7.22 Hz, 1H), 3.76 (s, 2H), 2.41 (s, 6H), 2.18-2.27 (m, 2H), 2.16 (s, 1H), 1.88-2.00 (m, 2H), 1.73 (q, J=10.14 Hz, 1H), 1.44-1.61 (m, 1H).

Step 5: N-[1-[1-(4-chlorophenyl)triazol-4-yl]-3-bicyclo[1.1.1]pentanyl]-2-(cyclobutoxy)acetamide To a mixture of 2-(cyclobutoxy)-N-(1-ethynyl-3-bicyclo [1.1.1]pentanyl)acetamide (50 mg, 0.23 mmol) and 1-azido-4-chloro-benzene (53 mg, 0.34 mmol) in t-BuOH (1 mL) and $H_2O$ (2 mL) was added sodium ascorbate (0.9 mg, 0.0046 mmol), benzoic acid (3 mg, 0.023 mmol) and $CuSO_4$ (364 mg, 0.0023 mmol) at 20° C., then the mixture was stirred at 80° C. for 5 h. The reaction mixture was diluted with $H_2O$ (5 mL) and extracted with EtOAc (3×5 mL). The combined organic layers were washed with brine (5 mL), dried over $Na_2SO_4$, filtered and concentrated under reduced pressure. The residue was purified by prep-HPLC to give the desired product. $^1$H-NMR (400 MHz, $CDCl_3$): δ 7.75 (s, 1H), 7.62-7.70 (m, 2H), 7.45-7.54 (m, 2H), 6.99 (s, 1H), 3.99 (quin, J=7.18 Hz, 1H), 3.81 (s, 2H), 2.54 (s, 6H), 2.17-2.31 (m, 2H), 1.89-2.06 (m, 2H), 1.75 (q, J=10.04 Hz, 1H), 1.48-1.63 (m, 1H). LC-MS m/z:=373.3 $[M+H]^+$.

Example 29

2-(4-chloro-3-fluoro-phenoxy)-N-[1-[5-(3-cyanocyclobutyl)-1,3,4-oxadiazol-2-yl]-3-bicyclo[1.1.1]pentanyl]acetamide To a mixture of 2-(4-chloro-3-fluoro-phenoxy)-N-[1-(hydrazinecarbonyl)-3-bicyclo[1.1.1]pentanyl]acetamide (0.07 g, 0.21 mmol) and 3-cyanocyclobutanecarboxylic acid (32 mg, 0.26 mmol) in EtOAc (3 mL) was added T3P (272 mg, 0.43 mmol, 50% in EtOAc) and $NEt_3$ (86 mg, 0.85 mmol) at 20° C. under $N_2$. The mixture was stirred at 80° C. for 16 h. After that $NEt_3$ (108 mg, 1.07 mmol) and p-TsCl (81 mg, 0.43 mmol) were added to the solution at 20° C., then the mixture was stirred at 80° C. for 16 h. The reaction mixture was concentrated under reduced pressure. The residue was purified by prep-HPLC to deliver the desired product. $^1$H-NMR (400 MHz, $CDCl_3$): 7.35 (t, J=8.60 Hz, 1H), 7.04 (s, 1H), 6.79 (dd, J=10.25, 2.76 Hz, 1H), 6.66-6.73 (m, 1H), 4.47 (s, 2H), 3.80 (quip, J=9.10 Hz, 1H), 3.16-3.39 (m, 1H), 2.82-2.91 (m, 4H), 2.64-2.71 (m, 6H). LC-MS m/z:=417.3 $[M+H]^+$.

Example 31

2-(4-chloro-3-fluorophenoxy)-N-(3-ethynylbicyclo [1.1.1]pentan-1-yl)acetamide

Step 1: 3-cyanocyclobutyl methanesulfonate

To a solution of 3-hydroxycyclobutanecarbonitrile (0.2 g, 2.06 mmol) in $CH_2Cl_2$ (2 mL) was added MsCl (283 mg, 2.47 mmol) and $NEt_3$ (312 mg, 3.09 mmol) at 0° C. The mixture was stirred at 0° C. for 3 h. The reaction mixture was diluted with $CH_2Cl_2$ (60 mL) and then washed with sat. $NaHCO_3$ (3×20 mL) and brine (20 ml), dried over $Na_2SO_4$, filtered and concentrated under reduced pressure to give the desired product. $^1$H-NMR (400 MHz, $CDCl_3$): δ 5.00-4.90 (m, 1H), 3.03 (s, 3H). 2.96-2.67 (m, 5H).

Step 2: 2-(4-chloro-3-fluorophenoxy)-N-(3-(hydroxymethyl)bicyclo[1.1.1]pentan-1-yl)acetamide To a solution of methyl 3-[[2-(4-chloro-3-fluoro-phenoxy)acetyl]amino]bicyclo[1.1.1]pentane-1-carboxylate (500 mg, 1.53 mmol) in THF (10 mL) was added $LiBH_4$ (99 mg, 4.58 mmol) at 0° C. The mixture was stirred at 20° C. for 20 h. The reaction mixture was quenched with sat. $NH_4Cl$ (60 mL) at 0° C., and then extracted with EtOAc (3×20 mL). The combined organic layers were washed with brine (20 mL), dried over $Na_2SO_4$, filtered and concentrated under reduced pressure to give a residue. The residue was purified by silica gel column chromatography to give the desired product. $^1$H-NMR (400 MHz, $CDCl_3$): δ 7.33 (t, J=8.6 Hz, 1H), 6.82 (s, 1H), 6.77 (dd, J=2.9, 10.4 Hz, 1H), 6.72-6.65 (m, 1H), 4.39 (s, 2H), 3.74 (s, 2H), 2.10 (s, 6H). LC-MS m/z:=300.1 $[M+H]^+$.

Step 3: 2-(4-chloro-3-fluorophenoxy)-N-(3-formyl-bicyclo[1.1.1]pentan-1-yl)acetamide To a mixture of 2-(4-chloro-3-fluoro-phenoxy)-N-[1-(hydroxymethyl)-3-bicyclo[1.1.1]pentanyl]acetamide (370 mg, 1.23 mmol) in $CH_2Cl_2$ (10 mL) was added DMP (549 mg, 1.30 mmol) at 0° C. under $N_2$. The mixture was stirred at 20° C. for 4 h. The reaction mixture was quenched with sat. $NaHCO_3$ (60 mL) at 0° C., and extracted with $CH_2Cl_2$ (3×20 mL). The combined organic layers were washed with brine (20 mL), dried over $Na_2SO_4$, filtered and concentrated under reduced pressure to give the desired product. $^1$H-NMR (400 MHz, $CDCl_3$): δ 9.68 (s, 1H), 7.34 (t, J=8.6 Hz, 1H), 6.90 (br s, 1H), 6.77 (dd, J=2.8, 10.2 Hz, 1H), 6.68 (ddd, J=1.2, 2.8, 8.9 Hz, 1H), 4.41 (s, 2H), 2.49-2.41 (m, 6H).

Step 4: 2-(4-chloro-3-fluorophenoxy)-N-(3-ethynyl-bicyclo[1.1.1]pentan-1-yl)acetamide To a solution of 2-(4-chloro-3-fluoro-phenoxy)-N-(1-formyl-3-bicyclo[1.1.1]pentanyl)acetamide (450 mg, 1.51 mmol) in MeOH (10 mL) was added 1-diazo-1-dimethoxyphosphoryl-propan-2-one (406 mg, 2.12 mmol) and $K_2CO_3$ (626, 4.53 mmol). The mixture was stirred at 20° C. for 15 h. The mixture was filtered and concentrated under reduced pressure to give a residue. The residue was purified by silica gel column chromatography to give the desired product. $^1$H-NMR (400 MHz, $CDCl_3$): δ 7.33 (t, J=8.7 Hz, 1H), 6.82 (br s, 1H), 6.75 (dd, J=2.9, 10.3 Hz, 1H), 6.67 (ddd, J=1.2, 2.8, 8.9 Hz, 1H), 4.38 (s, 2H), 2.49-2.39 (m, 6H), 2.19 (s, 1H). LC-MS m/z:=294.3 $[M+H]^+$.

Example 32

N-(3-(1H-1,2,3-triazol-4-yl)bicyclo[1.1.1]pentan-1-yl)-2-(4-chloro-3-fluorophenoxy)acetamide A mixture of 2-(4-chloro-3-fluoro-phenoxy)-N-(1-ethynyl-3-bicyclo[1.1.1]pentanyl)acetamide (120 mg, 0.408 mmol), TMSN$_3$ (70 mg, 0.612 mmol), sodium ascorbate (0.2 mg, 0.008 mmol), CuSO$_4$ (1 mg, 0.008 mmol) and benzoic acid (5 mg, 0.041 mmol) in t-BuOH (0.5 mL) and H$_2$O (1 mL) was stirred at 80° C. for 40 h under N$_2$ in a pressure vessel. To the reaction mixture was added H$_2$O (60 mL), and then extracted with EtOAc (3×20 mL). The combined organic layers were washed with brine (20 mL), dried over Na$_2$SO$_4$, filtered and concentrated under reduced pressure to give a residue. The residue was purified by prep-HPLC to give the desired product. $^1$H-NMR (400 MHz, CD$_3$OD): δ 7.69 (s, 1H), 7.39 (t, J=8.7 Hz, 1H), 6.95 (dd, J=2.6, 11.0 Hz, 1H), 6.84 (dd, J=2.8, 8.9 Hz, 1H), 4.50 (s, 2H), 2.47 (s, 6H). LC-MS m/z:=337.3 [M+H]$^+$.

Example 33

2-(4-chloro-3-fluorophenoxy)-N-(3-(2-((trans)-3-cyanocyclobutyl)-2H-1,2,3-triazol-4-yl)bicyclo[1.1.1]pentan-1-yl)acetamide A mixture of 2-(4-chloro-3-fluoro-phenoxy)-N-[1-(1H-triazol-4-yl)-3-bicyclo[1.1.1]pentanyl]acetamide (40 mg, 0.118 mmol), cis-(3-cyanocyclobutyl) methanesulfonate (41 mg, 0.13 mmol) and K$_2$CO$_3$ (32 mg, 0.23 mmol) in DMF (2 mL) was stirred at 100° C. for 13 h in a pressure vessel. The mixture was filtered through a pad of celite and purified by prep-HPLC (TFA) to give the desired product. $^1$H-NMR (400 MHz, CDCl$_3$): δ 7.44 (s, 1H), 7.37-7.31 (m, 1H), 6.91 (s, 1H), 6.78 (dd, J=2.8, 10.2 Hz, 1H), 6.74-6.67 (m, 1H), 5.43-5.29 (m, 1H), 4.42 (s, 2H), 3.44-3.32 (m, 1H), 3.14-3.03 (m, 2H), 2.99-2.90 (m, 2H), 2.50 (s, 6H). LC-MS m/z:=416.6 [M+H]$^+$.

Example 34

2-(4-chloro-3-fluorophenoxy)-N-(3-(1-((trans)-3-cyanocyclobutyl)-1H-1,2,3-triazol-4-yl)bicyclo[1.1.1]pentan-1-yl)acetamide

Step 1: 3-azidocyclobutanecarbonitrile

A solution of PPh$_3$ (405 mg, 1.54 mmol) and DIAD (312 mg, 1.54 mmol) in THF (3 mL) was stirred at 0° C. for 0.5 h. A solution of 3-hydroxycyclobutanecarbonitrile (100 mg, 1.03 mmol) and DPPA (340 mg, 1.24 mmol) in THF (1 mL) was added dropwise to the solution. The mixture was warmed to 25° C. and then stirred at 25° C. for 15 h. To the reaction mixture was added H$_2$O (2 mL), and then extracted with EtOAc (2 mL). The combined organic layers were washed with brine (2 mL) to give a solution of 3-azidocyclobutanecarbonitrile in THF (4 mL) and EtOAc (2 mL).

Step 2: 2-(4-chloro-3-fluorophenoxy)-N-(3-(1-((trans)-3-cyanocyclobutyl)-1H-1,2,3-triazol-4-yl)bicyclo[1.1.1]pentan-1-yl)acetamide A mixture of 2-(4-chloro-3-fluoro-phenoxy)-N-(1-ethynyl-3-bicyclo[1.1.1]pentanyl)acetamide (40 mg, 0.13 mmol), sodium ascorbate (1 mg, 0.005 mmol), CuSO$_4$ (1 mg, 0.002 mmol), benzoic acid (3 mg, 0.03 mmol) and 3-azidocyclobutanecarbonitrile (49 mg, 0.408 mmol, above solution in THF and EtOAc) in t-BuOH (0.5 mL) and H$_2$O (1 mL) was stirred at 80° C. for 40 h in a sealed tube. To the reaction mixture was added H$_2$O (30 mL), and then extracted with EtOAc (3×10 mL). The combined organic layers were washed with brine (10 mL), dried over Na$_2$SO$_4$, filtered and concentrated under reduced pressure to give a residue. The residue was purified by prep-TLC (PE:EtOAc=1:2) to give crude product. The crude product was purified by prep-HPLC to provide the desired product. $^1$H-NMR (400 MHz, CDCl$_3$): δ 7.39-7.31 (m, 2H), 6.92 (s, 1H), 6.78 (dd, J=2.9, 10.3 Hz, 1H), 6.70 (td, J=1.4, 8.9 Hz, 1H), 5.29-5.15 (m, 1H), 4.42 (s, 2H), 3.49-3.38 (m, 1H), 3.21-3.10 (m, 2H), 3.05-2.93 (m, 2H), 2.52 (s, 6H). LC-MS m/z:=416.4 [M+H]$^+$.

Example 35

2-(4-chloro-3-fluorophenoxy)-N-(3-(1-((cis)-3-cyanocyclobutyl)-1H-1,2,3-triazol-4-yl)bicyclo[1.1.1]pentan-1-yl)acetamide

Step 1: 3-iodocyclobutanecarbonitrile

A mixture of (3-cyanocyclobutyl)methanesulfonate (300 mg, 1.71 mmol) and NaI (769 mg, 5.14 mmol) in DMF (2 mL) was stirred at 110° C. for 15 h. To the reaction mixture was added H$_2$O (60 mL), and then extracted with EtOAc (3×20 mL). The combined organic layers were washed with brine (20 mL), dried over Na$_2$SO$_4$, filtered and concentrated under reduced pressure to give 3-iodocyclobutanecarbonitrile. $^1$H-NMR (400 MHz, CDCl$_3$): δ 4.72-4.63 (m, 1H), 4.46-4.35 (m, 1H), 3.53-3.42 (m, 1H), 3.21-3.03 (m, 4H), 3.00-2.91 (m, 3H), 2.88-2.80 (m, 1H).

Step 2: 3-azidocyclobutanecarbonitrile

A mixture of 3-iodocyclobutanecarbonitrile (300 mg, 1.45 mmol) and NaN$_3$ (188 mg, 2.90 mmol) in DMF (2 mL) was stirred at 80° C. for 15 h under N$_2$. To the reaction mixture was added H$_2$O (8 mL), and then extracted with EtOAc (2×4 mL). The combined organic layers were washed with brine (2×4 mL) to give 3-azidocyclobutanecarbonitrile as a yellow liquid in EtOAc.

Step 3: 2-(4-chloro-3-fluorophenoxy)-N-(3-(1-((cis)-3-cyanocyclobutyl)-1H-1,2,3-triazol-4-yl)bicyclo[1.1.1]pentan-1-yl)acetamide A mixture of 2-(4-chloro-3-fluoro-phenoxy)-N-(1-ethynyl-3-bicyclo[1.1.1]pentanyl)acetamide (60 mg, 0.204 mmol), sodium ascorbate (2 mg, 0.008 mmol), CuSO$_4$ (1 mg, 0.004 mmol), benzoic acid (5 mg, 0.041 mmol) and 3-azidocyclobutanecarbonitrile (74 mg, 0.612 mmol) in t-BuOH (0.5 mL) and H$_2$O (1 mL) was stirred at 80° C. for 40 h in a microwave tube. To the reaction mixture was added H$_2$O (30 mL), and then extracted with EtOAc (3×10 mL). The combined organic layers were washed with brine (10 mL), dried over Na$_2$SO$_4$, filtered and concentrated under reduced pressure to give a residue. The residue was separated by SFC to provide the desired product. $^1$H-NMR (400 MHz, CD$_3$OD): δ 8.80 (s, 1H), 7.97 (s, 1H), 7.38 (t, J=8.7 Hz, 1H), 6.94 (dd, J=2.9, 11.0 Hz, 1H), 6.83 (ddd, J=1.2, 2.9, 8.9 Hz, 1H), 5.15-5.08 (m, 1H), 4.49 (s, 2H), 3.28-3.19 (m, 1H), 3.06-2.93 (m, 4H), 2.44 (s, 6H). LC-MS m/z:=416.4 [M+H]$^+$.

Example 36

2-(4-chloro-3-fluorophenoxy)-N-(3-(2-((cis)-3-cyanocyclobutyl)-2H-1,2,3-triazol-4-yl)bicyclo[1.1.1]pentan-1-yl)acetamide A mixture of 2-(4-chloro-3-fluoro-phenoxy)-N-[1-(1H-triazol-4-yl)-3-bicyclo[1.1.1]pentanyl]acetamide (120 mg, 0.35 mmol), 3-iodocyclobutanecarbonitrile (110 mg, 0.53 mmol) and $Cs_2CO_3$ (348 mg, 1.07 mmol) in DMF (2 mL) was stirred at 80° C. for 15 h under $N_2$. To the mixture was added $H_2O$ (30 mL), and then extracted with EtOAc (3×10 mL). The combined organic layers were washed with brine (10 mL), dried over $Na_2SO_4$, filtered and concentrated under reduced pressure to give a residue. The residue was purified by prep-HPLC (TFA) to give the desired product. $^1$H-NMR (400 MHz, $CDCl_3$): δ 7.44 (s, 1H), 7.35 (t, J=8.6 Hz, 1H), 6.92 (s, 1H), 6.79 (dd, J=2.9, 10.3 Hz, 1H), 6.71 (dd, J=2.3, 8.4 Hz, 1H), 5.12-4.97 (m, 1H), 4.43 (s, 2H), 3.20-3.07 (m, 2H), 3.05-2.91 (m, 3H), 2.51 (s, 6H). LC-MS m/z:=416.4 [M+H]$^+$.

Example 37

N-(3-(5-((4-chloro-3-fluorophenoxy)methyl)-4H-1,2,4-triazol-3-yl)bicyclo[1.1.1]pentan-1-yl)-2-cyclobutoxyacetamide

Step 1: tert-butyl 2-cyclobutoxyacetate

To a solution of cyclobutanol (20 g, 277 mmol) in THF (400 mL) was added NaH (12.20 g, 305 mmol, 60% purity) at 0° C. under $N_2$. The mixture was stirred at 0° C. for 1 h. To the mixture was added tert-butyl 2-bromoacetate (59.5 g, 305 mmol) at 0° C. under $N_2$. The mixture was stirred at 20° C. for 4 h. The reaction mixture was quenched with sat. $NH_4Cl$ (600 mL) at 0° C., and extracted with EtOAc (3×200 mL). The combined organic layers were washed with brine (300 mL), dried over $Na_2SO_4$, filtered and concentrated under reduced pressure to give tert-butyl 2-(cyclobutoxy)acetate.

Step 2: 2-cyclobutoxyacetic acid

To a solution of tert-butyl 2-(cyclobutoxy)acetate (20 g, 107 mmol) in $CH_2Cl_2$ (300 mL) was added TFA (48.98 g, 429 mmol). The mixture was stirred at 40° C. for 4 h. To the reaction mixture was added sat. $NaHCO_3$ at 0° C. to pH=9 and then extracted with MTBE (3×200 mL). The water layer was adjusted to pH=3 with 2M HCl, then extracted with EtOAc (3×200 mL), then washed with brine (200 mL), dried over $Na_2SO_4$, filtered and concentrated under reduced pressure to give 2-(cyclobutoxy)acetic acid. $^1$H-NMR (400 MHz, $CDCl_3$): δ 4.11-4.00 (m, 3H), 2.30-2.19 (m, 2H), 2.07-1.95 (m, 2H), 1.79-1.67 (m, 1H), 1.59-1.46 (m, 1H).

Step 3: methyl 3-(2-cyclobutoxyacetamido)bicyclo[1.1.1]pentane-1-carboxylate A mixture of 2-(cyclobutoxy)acetic acid (879 mg, 6.76 mmol), T3P (5.37 g, 8.44 mmol, 50% in EtOAc) and $NEt_3$ (2.85 g, 28.2 mmol) in $CH_2Cl_2$ (20 mL) was stirred at 0° C. for 1 h. To the mixture was added methyl 3-aminobicyclo[1.1.1]pentane-1-carboxylate, HCl salt (1 g, 5.63 mmol). The mixture was stirred at 20° C. for 16 h. The reaction mixture was quenched with sat. $NaHCO_3$ (120 mL), and then extracted with $CH_2Cl_2$ (3×40 mL). The combined organic layers were washed with brine (40 mL), dried over $Na_2SO_4$, filtered and concentrated under reduced pressure to give a residue. The residue was purified by silica gel column chromatography (PE:MTBE=1:0 to 0:1) to give the desired product. $^1$H-NMR (400 MHz, $CDCl_3$): δ 6.89 (s, 1H), 4.01-3.92 (m, 1H), 3.77 (s, 2H), 3.71-3.68 (m, 3H), 2.41 (s, 6H), 2.27-2.17 (m, 2H), 2.00-1.87 (m, 2H), 1.78-1.69 (m, 1H), 1.59-1.46 (m, 1H). LC-MS m/z:=254.3 [M+H]$^+$.

Step 4: 2-cyclobutoxy-N-(3-(hydrazinecarbonyl)bicyclo[1.1.1]pentan-1-yl)acetamide To a mixture of methyl 3-[[2-(cyclobutoxy)acetyl]amino]bicyclo[1.1.1]pentane-1-carboxylate (200 mg, 0.79 mmol) in EtOH (5 mL) was added $NH_2NH_2 \cdot H_2O$ (403 mg, 7.90 mmol) at 0° C. The mixture was stirred at 80° C. for 12 h. The mixture was concentrated under reduced pressure to give the desired product. $^1$H-NMR (400 MHz, $CD_3OD$): δ 3.99 (quin, J=7.3 Hz. 1H), 3.77 (s, 2H), 2.31 (s, 6H), 2.25-2.17 (m, 2H), 2.01-1.90 (m, 2H), 1.71 (q, J=10.3 Hz, 1H), 1.61-1.59 (m, 1H), 1.60-1.49 (m, 1H). LC-MS m/z:=254.3 [M+H]$^+$.

Step 5: 2-(4-chloro-3-fluorophenoxy)acetimidamide

To a mixture of $NH_4Cl$ (2.30 g, 43.0 mmol) in Toluene (15 mL) was added $AlMe_3$ (2.5 M, 8.60 mL). The mixture was stirred at 25° C. for 1 h. To the mixture was added ethyl 2-(4-chloro-3-fluoro-phenoxy)acetate (1.0 g, 4.30 mmol) in toluene (5 mL). The mixture was stirred at 90° C. for 14 h. The reaction mixture was quenched with MeOH (60 mL) at 0° C. The mixture was stirred at 20° C. for 2 h then filtered and the filtrate concentrated under reduced pressure to give a residue. The residue was dissolved in $CH_2Cl_2$:MeOH (60 mL, v:v=10:1), and stirred at 25° C. for 1 h. The mixture was filtered and the filtrate concentrated under reduced pressure to give the desired product. $^1$H-NMR (400 MHz, $CD_3OD$): δ 7.48-7.41 (m, 1H), 7.06-7.00 (m, 1H), 6.95-6.87 (m, 1H), 4.98 (s, 2H). LC-MS m/z:=203.1 [M+H]$^+$.

Step 6: N-(3-(5-((4-chloro-3-fluorophenoxy)methyl)-4H-1,2,4-triazol-3-yl)bicyclo[1.1.1]pentan-1-yl)-2-cyclobutoxyacetamide A mixture of 2-(cyclobutoxy)-N-[1-(hydrazinecarbonyl)-3-bicyclo[1.1.1]pentanyl]acetamide (50 mg, 0.197 mmol), 2-(4-chloro-3-fluoro-phenoxy)acetamidine (80 mg, 0.394 mmol) and $K_2CO_3$ (54.56 mg, 0.394 mmol) in MeOH (3 mL) was stirred at 70° C. for 15 h. The reaction mixture was filtered and the filtrate concentrated under reduced pressure to give a residue. The residue was purified by prep-HPLC (TFA) to give the desired product. $^1$H-NMR (400 MHz, $CDCl_3$): δ 7.31-7.27 (m, 1H), 7.25 (d, J=3.7 Hz, 1H), 6.84 (dd, J=2.9, 10.6 Hz, 1H), 6.76 (ddd, J=1.1, 2.8, 8.9 Hz, 1H), 5.17 (s, 2H), 4.05-3.98 (m, 1H), 3.92 (s, 2H), 2.70 (s, 6H), 2.29-2.22 (m, 2H), 2.03-1.94 (m, 2H), 1.77 (br d, J=9.9 Hz, 1H), 1.62-1.53 (m, 1H). LC-MS m/z:=421.4 [M-41]$^+$.

Example 38

2-(4-chloro-3-fluoro-phenoxy)-N-[1-[5-(cyclobutylmethyl)-1,3,4-oxadiazol-2-yl]-3-bicyclo[1.1.1]pentanyl]acetamide To a mixture of 2-(4-chloro-3-fluoro-phenoxy)-N-[1-(hydrazinecarbonyl)-3-bicyclo[1.1.1]pentanyl]acetamide (100 mg, 0.31 mmol) and 2-cyclobutylacetic acid (42 mg, 0.37 mmol) in EtOAc (5 mL) was added T3P (388 mg, 0.62 mmol, 50% in EtOAc) and NEt₃ (124 mg, 1.22 mmol) at 20° C., then the mixture was stirred at 80° C. for 16 h, then T3P (194 mg, 0.61 mmol, 50% in EtOAc) was added to the mixture and the mixture was stirred at 80° C. for 16 h. The mixture was adjusted to pH=7-8 with sat. NaHCO₃. The aqueous phase was extracted with EtOAc (3×8 mL). The combined organic layers were washed with brine (10 mL), dried over anhydrous Na₂SO₄, filtered and concentrated under reduced pressure. The residue was purified by prep-HPLC (TFA) to give the desired product. ¹H-NMR (400 MHz, CDCl₃): 7.34 (t, J=8.60 Hz, 1H), 6.98 (s, 1H), 6.77 (dd, J=10.23, 2.82 Hz, 1H), 6.69 (ddd, J=8.85, 2.82, 1.25 Hz, 1H), 4.43 (s, 2H), 2.87-2.96 (m, 2H), 2.76 (sept, J=7.76 Hz, 1H), 2.63 (s, 6H), 2.09-2.22 (m, 2H), 1.85-1.98 (m, 2H), 1.74-1.84 (m, 2H). LC-MS m/z:=406.3 [M+H]⁺.

Example 39

2-(4-chloro-3-fluoro-phenoxy)-N-[3-(4-cyclobutyl-imidazol-1-yl)-1-bicyclo[1.1.1]pentanyl]acetamide Step 1: 2-(4-chloro-3-fluoro-phenoxy)-N-[1-[(2-cyclobutyl-2-oxo-ethyl)amino]-3-bicyclo[1.1.1]pentanyl]acetamide To a mixture of N-(1-amino-3-bicyclo[1.1.1]pentanyl)-2-(4-chloro-3-fluoro-phenoxy)acetamide·HCl (300 mg, 934.07 mop and 2-bromo-1-cyclobutyl-ethanone (330 mg, 1.87 mmol) in CH₃CN (10 mL) was added Na₂CO₃ (396 mg, 3.74 mmol) at 20° C. under N₂. The mixture was heated to 40° C. and stirred for 7 h. The mixture was added with water (15 mL). The aqueous phase was extracted with EtOAc (3×8 mL). The combined organic phase was washed with brine (5 mL), dried over anhydrous Na₂SO₄, filtered and concentrated under reduced pressure. The residue was purified by silica gel column chromatography (CH₂Cl₂:MeOH=100:0 to 10:1) to give the desired product. ¹H-NMR (400 MHz, CDCl₃): δ 7.30-7.35 (m, 1H), 6.80 (br s, 1H), 6.74-6.77 (m, 1H), 6.67 (ddd, J=8.93, 2.87, 1.21 Hz, 1H), 4.39 (s, 2H), 3.46 (s, 2H), 3.23-3.32 (m, 1H), 2.15-2.32 (m, 7H), 2.13 (s, 6H), 1.81-2.10 (m, 4H). LC-MS m/z:=381.2 [M+H]⁺.

Step 2: 2-(4-chloro-3-fluoro-phenoxy)-N-[3-(4-cyclobutylimidazol-1-yl)-1-bicyclo[1.1.1]pentanyl]acetamide 2-(4-chloro-3-fluoro-phenoxy)-N-[1-[(2-cyclobutyl-2-oxo-ethyl)amino]-3-bicyclo[1.1.1]pentanyl]acetamide (40 mg, 105.03 μmol) and NEt₃ (15 mg, 157.55 μmol, 21.93 uL) were taken up into a microwave tube in formamide (6.78 g, 150.53 mmol, 6.00 mL) under N₂. The sealed tube was heated at 100° C. for 30 min under microwave. The reaction was purified by prep-HPLC (TFA) to give the desired product. ¹H-NMR (400 MHz, CDCl₃): δ 8.96 (d, J=1.54 Hz, 1H), 7.54-7.57 (m, 1H), 7.39 (t, J=8.71 Hz, 1H), 6.95 (dd, J=11.03, 2.87 Hz, 1H), 6.84 (ddd, J=8.99, 2.92, 1.32 Hz, 1H), 4.54 (s, 2H), 3.61 (quin, J=8.54 Hz, 1H), 2.71 (s, 6H), 2.38-2.47 (m, 2H), 2.08-2.28 (m, 3H), 1.92-2.02 (m, 1H). LC-MS m/z:=390.4 [M+H]⁺.

Example 40

2-(4-chloro-3-fluoro-phenoxy)-N-[1-(5-methyl-1,3,4-oxadiazol-2-yl)-3-bicyclo[1.1.1]pentanyl]acetamide Step 1: N-[1-(acetamidocarbamoyl)-3-bicyclo[1.1.1]pentanyl]-2-(4-chloro-3-fluoro-phenoxy)acetamide To a mixture of 2-(4-chloro-3-fluoro-phenoxy)-N-[1-(hydrazinecarbonyl)-3-bicyclo[1.1.1]pentanyl]acetamide (100 mg, 0.31 mmol) and acetic acid (22 mg, 0.37 mmol) in EtOAc (3 mL) was added T3P (388 mg, 0.62 mmol, 50% in EtOAc) and NEt₃ (124 mg, 1.22 mmol) at 20° C., then the mixture was stirred at 80° C. for 16 h. The mixture was adjusted to pH=7-8 with sat. NaHCO₃. The aqueous phase was extracted with EtOAc (3×10 mL). The combined organic layers were washed with brine (10 mL), dried over anhydrous Na₂SO₄, filtered and concentrated under reduced pressure to give the desired product. LC-MS m/z:=370.1 [M+H]⁺.

Step 2: 2-(4-chloro-3-fluoro-phenoxy)-N-[1-(5-methyl-1,3,4-oxadiazol-2-yl)-3-bicyclo[1.1.1]pentanyl]acetamide To a mixture of N-[1-(acetamidocarbamoyl)-3-bicyclo[1.1.1]pentanyl]-2-(4-chloro-3-fluoro-phenoxy)acetamide (90 mg, 0.24 mmol) in CH₂Cl₂ (3 mL) was added NEt₃ (99 mg, 0.97 mmol) and p-TsCl (93 mg, 0.49 mmol) at 25° C., then the mixture was stirred at 25° C. for 16 h. The mixture was adjusted to pH=7-8 with sat. NaHCO₃ and concentrated. The aqueous phase was extracted with EtOAc (3×10 mL). The combined organic layers were washed with brine (10 mL), dried over anhydrous Na₂SO₄, filtered and concentrated under reduced pressure. The residue was purified by prep-HPLC (TFA) to give the desired product. ¹H-NMR (400 MHz, CDCl₃): 7.34 (t, J=8.60 Hz, 1H), 7.01 (s, 1H), 6.77 (dd, J=10.14, 2.87 Hz, 1H), 6.69 (dt, J=8.93, 1.27 Hz, 1H), 4.43 (s, 2H), 2.64 (s, 6H), 2.54 (s, 3H). LC-MS m/z:=352.3 [M+H]⁺.

Example 41

N-[1-[5-[(4-chloro-3-fluoro-phenoxy)methyl]-1,3,4-oxadiazol-2-yl]-3-bicyclo[1.1.1]pentanyl]-2-cis-[3-(trifluoromethoxy)cyclobutoxy]acetamide Step 1: 3-(tert-butoxycarbonylamino)bicyclo[1.1.1]pentane-1-carboxylic acid To a mixture of methyl 3-(tert-butoxycarbonylamino)bicyclo[1.1.1]pentane-1-carboxylate (500 mg, 2.07 mmol) in THF (10 mL) and water (2 mL) was added LiOH·H₂O (173 mg, 4.14 mmol) at 25° C. under N₂. The mixture was stirred at 25° C. for 12 h. To the mixture was added water (10 mL). The aqueous phase was extracted with MTBE (5 mL). The combined organic phase was adjusted to pH=2 by HCl (2M) and extracted with CH₂Cl₂:MeOH (3×10 mL, v:v=3:1) and washed with brine (10 mL), dried over Na₂SO₄, filtered and concentrated under reduced pressure to give the desired product. ¹H-NMR (400 MHz, DMSO-d₆): δ 7.54 (s, 1H), 2.05 (s, 6H), 1.34 (s, 9H).

Step 2: tert-butyl N-[1-[[[2-(4-chloro-3-fluoro-phenoxy)acetyl]amino]carbamoyl]-3-bicyclo[1.1.1]pentanyl]carbamate To a mixture of 3-(tert-butoxycarbonylamino)bicyclo[1.1.1]pentane-1-carboxylic acid (50 mg, 0.22 mmol) and 2-(4-chloro-3-fluoro-phenoxy)acetohydrazide (48 mg, 0.22 mmol in EtOAc (5 mL) was added T3P (420 mg, 0.66 mmol, 50% in EtOAc) and NEt₃ (89 mg, 0.88 mmol) at 20° C. under N₂. The mixture was stirred at 80° C. for 12 h. The mixture was poured into aq. NaHCO₃ (10 mL). The aqueous phase was extracted with EtOAc (3×5 mL). The combined organic phase was washed with brine (5 mL), dried over Na₂SO₄, filtered and concentrated under reduced pressure to give the desired product.

Step 3: tert-butyl N-[1-[5-[(4-chloro-3-fluoro-phenoxy)methyl]-1,3,4-oxadiazol-2-yl]-3-bicyclo[1.1.1]pentanyl]carbamate To a mixture of tert-butyl N-[1-[[[2-(4-chloro-3-fluorophenoxy)acetyl]amino]carbamoyl]-3-bicyclo[1.1.1]pentanyl]carbamate (94 mg, 0.22 mmol) and NEt₃ (89 mg, 0.88 mmol) in CH₂Cl₂ (5 mL) was added p-TsCl (83 mg, 0.44 mmol) at 0° C. under N₂. The mixture was stirred at 25° C. for 12 h. The mixture was poured into aq. NaHCO₃ (10 mL). The aqueous phase was extracted with CH₂Cl₂ (3×5 mL). The combined organic phase was washed with brine (10 mL), dried over anhydrous Na₂SO₄, filtered and concentrated under reduced pressure. The residue was purified by silica gel column chromatography (PE:MTBE=100:1 to 0:1) to give the desired product. ¹H-NMR (400 MHz, CDCl₃): δ 7.32 (t, J=8.60 Hz, 1H), 6.85 (dd, J=10.36, 2.87 Hz, 1H), 6.75-6.81 (m, 1H), 5.20 (s, 2H), 5.05 (s, 1H), 2.53 (s, 6H), 1.47 (s, 9H).

Step 5: 1-[5-[(4-chloro-3-fluoro-phenoxy)methyl]-1,3,4-oxadiazol-2-yl]bicyclo[1.1.1]pentan-3-amine A mixture of tert-butyl N-[1-[5-[(4-chloro-3-fluoro-phenoxy)methyl]-1,3,4-oxadiazol-2-yl]-3-bicyclo[1.1.1]pentanyl]carbamate (64 mg, 0.16 mmol) in HCl/EtOAc (5 mL) was stirred at 25° C. for 3 h. The mixture was concentrated under reduced pressure at 40° C. to give the desired product as the HCl salt.

Step 6: N-[1-[5-[(4-chloro-3-fluoro-phenoxy)methyl]-1,3,4-oxadiazol-2-yl]-3-bicyclo[1.1.1]pentanyl]-2-cis-[3-(trifluoromethoxy)cyclobutoxy]acetamide To a mixture of cis-2-[3-(trifluoromethoxy)cyclobutoxy]acetic acid (44 mg, 0.2 mmol) and 1-[5-[(4-chloro-3-fluoro-phenoxy)methyl]-1,3,4-oxadiazol-2-yl]bicyclo[1.1.1]pentan-3-amine (53 mg, 0.15 mmol, HCl) in DMF (5 mL) was added HATU (117 mg, 0.31 mmol) and DIEA (132 mg, 1.03 mmol) at 25° C. under N₂. The mixture was stirred at 25° C. for 12 h. The mixture was poured into ice-water (20 mL). The aqueous phase was extracted with EtOAc (3×5 mL). The combined organic phase was washed with brine (4×5 mL), dried over Na₂SO₄, filtered and concentrated under reduced pressure. The residue was purified by prep-HPLC (NH₄HCO₃) to give the desired product. ¹H-NMR (400 MHz, CDCl₃): δ 7.32 (t, J=8.66 Hz, 1H), 6.92 (s, 1H), 6.86 (dd, J=10.29, 2.51 Hz, 1H), 6.79 (d, J=8.66 Hz, 1H), 5.21 (s, 2H), 4.34 (t, J=7.03 Hz, 1H), 3.83 (s, 2H), 3.65-3.77 (m, 1H), 2.83 (dd, J=6.84, 3.20 Hz, 2H), 2.65 (s, 6H), 2.28 (d, J=6.53 Hz, 2H). LC-MS m/z:=506.4 [M+H]⁺.

Example 42

N-[1-[[(4-chloro-3-fluoro-benzoyl)amino]carbamoyl]-3-bicyclo[1.1.1]pentanyl]-2-(cyclobutoxy)acetamide To a solution of 4-chloro-3-fluoro-benzoic acid (83 mg, 0.474 mmol) in EtOAc (3 mL) was added Et₃N (160 mg, 1.58 mmol), T3P (502 mg, 0.79 mmol, 50% in EtOAc) and 2-(cyclobutoxy)-N-[1-(hydrazinecarbonyl)-3-bicyclo[1.1.1]pentanyl]acetamide (100 mg, 0.395 mmol). After addition, the mixture was stirred at 25° C. for 12 h. The mixture was concentrated under reduced pressure to give the desired product. LC-MS m/z:=410.2 [M+H]⁺.

N-[1-[5-(4-chloro-3-fluoro-phenyl)-1,3,4-oxadiazol-2-yl]-3-bicyclo[1.1.1]pentanyl]-2-(cyclobutoxy)acetamide To a solution of N-[1-[[(4-chloro-3-fluoro-benzoyl)amino]carbamoyl]-3-bicyclo[1.1.1]pentanyl]-2-(cyclobutoxy)acetamide (130 mg, 0.317 mmol) in CH₂Cl₂ (2 mL) was added Et₃N (128.39 mg, 1.27 mmol) and TsCl (121 mg, 0.634 mmol). The mixture was stirred at 20° C. for 12 h. The mixture was diluted with H₂O 10 mL and extracted with EtOAc (3×5 mL). The combined organic layers were washed with brine 10 mL, dried over Na₂SO₄, filtered and concentrated under reduced pressure. The residue was purified by prep-HPLC (TFA) to give the desired product. ¹H-NMR (400 MHz, CDCl₃): δ 7.77-7.86 (m, 2H), 7.55 (t, J=7.78 Hz, 1H), 7.05 (s, 1H), 3.99 (quin, J=7.25 Hz, 1H), 3.82 (s, 2H), 2.68 (s, 6H), 2.19-2.30 (m, 2H), 1.90-2.05 (m, 4H), 1.75 (q, J=10.29 Hz, 1H), 1.48-1.62 (m, 1H). LC-MS m/z:=392.3 [M+H]⁺.

Example 43

2-(4-chloro-3-fluorophenoxy)-N-(3-(5-((cis)-3-(trifluoromethyl)cyclobutyl)-1,3,4-oxadiazol-2-yl)bicyclo[1.1.1]pentan-1-yl)acetamide To a solution of 2-(4-chloro-3-fluoro-phenoxy)-N-[1-(hydrazinecarbonyl)-3-bicyclo[1.1.1]pentanyl]acetamide (100 mg, 0.31 mmol) and cis-3-(trifluoromethyl)cyclobutanecarboxylic acid (62 mg, 0.37 mmol) in EtOAc (3 mL) was added T3P (388 mg, 0.61 mmol, 50% in EtOAc) and NEt₃ (123 mg, 1.22 mmol) in a sealed tube. The mixture was stirred at 80° C. for 16 h. The reaction mixture was diluted with sat.NaHCO₃ (10 mL) at 0° C., and then extracted with EtOAc (3×5 mL). The combined organic layers were washed with brine (3 mL), dried over Na₂SO₄, filtered and concentrated under reduced pressure to give 2-(4-chloro-3-fluorophenoxy)-N-(3-(2-((cis)-3-(trifluoromethyl)cyclobutanecarbonyl)hydrazinecarbonyl)bicyclo[1.1.1]pentan-1-yl)acetamide. The crude product was used for the next step without further purification.

The mixture of 2-(4-chloro-3-fluorophenoxy)-N-(3-(2-((cis)-3-(trifluoromethyl)cyclobutanecarbonyl)hydrazinecarbonyl)bicyclo[1.1.1]pentan-1-yl)acetamide (150 mg, 0.31 mmol), 4-methylbenzenesulfonyl chloride (120 mg, 0.63 mmol), NEt₃ (127 mg, 1.26 mmol) in CH₂Cl₂ (5 mL) was stirred at 25° C. for 16 h under N₂ atmosphere. The reaction mixture was quenched with H₂O (10 mL) at 0° C., and then extracted with EtOAc (3×10 mL). The combined organic layers were washed with brine (5 mL), dried over Na₂SO₄, filtered and concentrated under reduced pressure. The residue was purified by prep-HPLC (TFA) to give the desired product. ¹H-NMR (400 MHz, CD₃OD): δ 7.38 (t, J=8.71 Hz, 1H), 6.94 (dd, J=11.03, 2.87 Hz, 1H), 6.83 (ddd, J=8.93, 2.87, 1.21 Hz, 1H), 4.50 (s, 2H), 3.78 (quin, J=9.10 Hz, 1H), 3.15-3.28 (m, 1H), 2.46-2.70 (m, 10H). LC-MS m/z:=460.4 [M+H]⁺.

Example 44

2-(4-chloro-3-fluoro-phenoxy)-N-[1-[5-trans-[3-(trifluoromethyl)cyclobutyl]-1,3,4-oxadiazol-2-yl]-3-bicyclo[1.1.1]pentanyl]acetamide To a mixture of 2-(4-chloro-3-fluoro-phenoxy)-N-[1-(hydrazinecarbonyl)-3-bicyclo[1.1.1]pentanyl]acetamide (100 mg, 0.31 mmol) and tran-3-(trifluoromethyl)cyclobutanecarboxylic acid (62 mg, 0.37 mmol) in EtOAc (3 mL) was added T3P (388 mg, 0.61 mmol, 50% in EtOAc) and NEt$_3$ (124 mg, 1.22 mmol) at 25° C., and the mixture was stirred at 80° C. for 16 h. The mixture was adjusted to pH=7-8 with sat. NaHCO$_3$. The aqueous phase was extracted with EtOAc (4×10 mL). The combined organic layers were washed with brine (10 mL), dried over anhydrous Na$_2$SO$_4$, filtered and concentrated under reduced pressure to give 2-(4-chloro-3-fluoro-phenoxy)-N-[1-[[[3-(trifluoromethyl)cyclobutanecarbonyl]amino]carbamoyl]-3-bicyclo[1.1.1]pentanyl]acetamide.

To a mixture of 2-(4-chloro-3-fluoro-phenoxy)-N-[1-[[[trans-3-(trifluoromethyl)cyclobutanecarbonyl]amino]carbamoyl]-3-bicyclo[1.1.1]pentanyl]acetamide (130 mg, 0.27 mmol) in CH$_2$Cl$_2$ (5 mL) was added NEt$_3$ (110 mg, 1.09 mmol) and p-TsCl (104 mg, 0.54 mmol) at 25° C., then the mixture was stirred at 25° C. for 16 h. The mixture was adjusted to pH=7-8 with sat. NaHCO$_3$. The aqueous phase was extracted with EtOAc (3×20 mL). The combined organic layers were washed with brine (20 mL), dried over anhydrous Na$_2$SO$_4$, filtered and concentrated under reduced pressure. The residue was purified by prep-HPLC (TFA) to give the desired product. $^1$H-NMR (400 MHz, CD$_3$OD): δ 7.38 (t, J=8.78 Hz, 1H), 6.94 (dd, J=10.92, 2.76 Hz, 1H), 6.77-6.86 (m, 1H), 4.50 (s, 2H), 3.84 (quin, J=8.03 Hz, 1H), 3.16-3.28 (m, 1H), 2.67 (t, J=7.91 Hz, 4H), 2.59 (s, 6H). LC-MS m/z:=460.4 [M+H]$^+$.

Example 45

2-(4-chloro-3-fluoro-phenoxy)-N-[1-[5-(trifluoromethoxymethyl)-1,3,4-oxadiazol-2-yl]-3-bicyclo[1.1.1]pentanyl]acetamide Step 1: 2-(4-chloro-3-fluoro-phenoxy)-N-[1-[[[2-(trifluoromethoxy)acetyl]amino]carbamoyl]-3-bicyclo[1.1.1]pentanyl]acetamide To a mixture of 2-(4-chloro-3-fluoro-phenoxy)-N-[1-(hydrazinecarbonyl)-3-bicyclo[1.1.1]pentanyl]acetamide (100 mg, 305.12 μmol) and 2-(trifluoromethoxy)acetic acid (52 mg, 366.15 μmop in EtOAc (3 mL) was added T3P (388 mg, 610.24 μmol, 362.93 μL, 50% in EtOAc) and Et$_3$N (123 mg, 1.22 mmol, 169.88 uL) at 25° C. under N$_2$. The mixture was heated to 80° C. and stirred for 15 h. The mixture was quenched by sat. NaHCO$_3$ (5 mL). The aqueous phase was extracted with EtOAc (3×5 mL). The combined organic phase was washed with brine (5 mL), dried over anhydrous Na$_2$SO$_4$, filtered and concentrated under reduced pressure to give the desired product. $^1$H-NMR (400 MHz, CDCl$_3$): δ 8.46 (br s, 2H), 7.31-7.37 (m, 1H), 6.91 (s, 1H), 6.77 (dd, J=10.16, 2.76 Hz, 1H), 6.69 (dd, J=9.03, 1.76 Hz, 1H), 4.62 (s, 2H), 4.58 (s, 2H), 4.38-4.44 (m, 2H), 2.45-2.53 (m, 6H). LC-MS m/z:=454.1 [M+H]$^+$.

Step 2: 2-(4-chloro-3-fluoro-phenoxy)-N-[1-[5-(trifluoromethoxymethyl)-1,3,4-oxadiazol-2-yl]-3-bicyclo[1.1.1]pentanyl]acetamide To a mixture of 2-(4-chloro-3-fluoro-phenoxy)-N-[1-[[[2-(trifluoromethoxy)acetyl]amino]carbamoyl]-3-bicyclo[1.1.1]pentanyl]acetamide (100 mg, 220.37 μmol) in CH$_2$Cl$_2$ (5 mL) was added NEt$_3$ (89 mg, 882 μmol) and 4-methylbenzenesulfonyl chloride (84 mg, 441 μmol) at 25° C. under N$_2$, then the reaction was stirred for 15 h. The mixture was quenched by sat. NaHCO$_3$. The aqueous phase was extracted with EtOAc (3×5 mL). The combined organic phase was washed with brine (5 mL), dried over anhydrous Na$_2$SO$_4$, filtered and concentrated under reduced pressure. The residue was purified by prep-HPLC (TFA) to give the desired product. $^1$H-NMR (400 MHz, CDCl$_3$): δ 7.35 (t, J=8.53 Hz, 1H), 6.97 (s, 1H), 6.78 (dd, J=10.23, 2.82 Hz, 1H), 6.70 (dd, J=8.85, 1.69 Hz, 1H), 5.16 (s, 2H), 4.43 (s, 2H), 2.69 (s, 6H). LC-MS m/z:=436.3 [M+H]$^+$.

Examples 46-48

The following Examples as shown in Table 1 were synthesized via procedures similar to those described throughout.

| Example | LC/MS (m/z, [M = H]$^+$) |
|---|---|
| 46 | 422.00 |
| 47 | 391.30 |
| 48 | 404.20 |

Example 49

2-(4-chloro-3-fluorophenoxy)-N-(3-(5-(3-(trifluoromethoxy)propyl)-1,3,4-oxadiazol-2-yl)bicyclo[1.1.1]pentan-1-yl)acetamide benzyl 4-(trifluoromethoxy)butanoate To a solution of AgOTf (2.65 g, 10.30 mmol) in EtOAc (25 mL) were added 1-(chloromethyl)-4-fluoro-1,4-diazoniabicyclo[2.2.2]octane ditetrafluoroborate (2.74 g, 7.72 mmol), KF (897 mg, 15.5 mmol), benzyl 4-hydroxybutanoate (1.0 g, 5.15 mmol) in a foil-wrapped flask under N$_2$. To the mixture were added 2-fluoropyridine (1.00 g, 10.3 mmol) and trimethyl(trifluoromethyl)silane (1.46 g, 10.3 mmol), and the reaction mixture was stirred at 25° C. for 12 h. The mixture was filtered through a pad of celite and was concentrated under reduced pressure to give a residue, which was purified by silica gel column chromatography. $^1$H NMR (400 MHz, MeOD): δ 7.47-7.29 (m, 5H), 5.15 (s, 2H), 4.03 (t, J=6.1 Hz, 2H), 2.52 (t, J=7.3 Hz, 2H), 2.05 (quin, J=6.7 Hz, 2H).

4-(trifluoromethoxy)butanehydrazide

To a solution of benzyl 4-(trifluoromethoxy)butanoate (200 mg, 0.76 mmol) in 1,4-dioxane (8 mL) was added hydrazine hydrate (0.38 mL, 7.63 mmol), and the solution was heated to 80° C. for 12 h. The reaction mixture was cooled to rt, and was concentrated under reduced pressure to give a residue that was used directly. LC-MS: m/z: 187.1 [M+H]$^+$.

2-(4-chloro-3-fluorophenoxy)-N-(3-(2-(4-(trifluoromethoxy)butanoyl)hydrazinecarbonyl)bicyclo[1.1.1]pentan-1-yl)acetamide To a solution of 4-(trifluoromethoxy)butanehydrazide (120 mg, 0.64 mmol) in THF (5 mL) was added 3-[[2-(4- chloro-3-fluoro-phenoxy)acetyl]amino]bicyclo[1.1.1]pentane-1-carboxylic acid (182 mg, 0.58 mmol), HATU (270 mg, 0.71 mmol) and DIEA (0.34 mL, 1.93 mmol) at 0° C. The mixture was stirred at 20° C. for 2 h. The reaction mixture was poured onto ice-water (10 mL) and was extracted with EtOAc (3×10 mL). The organic layers were washed with brine (10 mL), dried over anhydrous $Na_2SO_4$, filtered and concentrated under reduced pressure to give a residue, which was purified by prep-TLC. LC-MS: m/z: 482.3 $[M+H]^+$.

2-(4-chloro-3-fluorophenoxy)-N-(3-(5-(3-(trifluoromethoxy)propyl)-1,3,4-oxadiazol-2-yl)bicyclo[1.1.1]pentan-1-yl)acetamide To a mixture of 2-(4-chloro-3-fluorophenoxy)-N-(3-(2-(4-(trifluoromethoxy)butanoyl)hydrazinecarbonyl)bicyclo[1.1.1]pentan-1-yl)acetamide (120 mg, 0.25 mmol) in DCM (6 mL) was added $NEt_3$ (0.14 mL, 0.10 mmol) and TsCl (95 mg, 0.50 mmol), and the mixture was stirred at 25° C. for 16 h. The reaction mixture was poured onto ice-water (6 mL) and was extracted with DCM (3×6 mL). The combined organic layers were washed with brine (20 mL), dried over anhydrous $Na_2SO_4$, filtered and concentrated under reduced pressure to give a residue, which was purified by prep-HPLC to provide the title compound. LC-MS: m/z: 464.3 $[M+H]^+$. $^1H$ NMR (400 MHz, $CDCl_3$): δ 7.35 (t, J=8.60 Hz, 1H), 6.94 (s, 1H), 6.78 (dd, J=10.25, 2.76 Hz, 1H), 6.70 (dt, J=8.88, 1.41 Hz, 1H), 4.43 (s, 2H), 4.11 (t, J=5.95 Hz, 2H), 2.98 (t, J=7.39 Hz, 2H), 2.65 (s, 6H), 2.23 (quin, J=6.73 Hz, 2H).

Examples 50-60

The following Examples as shown in Table 1 were synthesized via procedures similar to those described throughout.

| Example | LC/MS (m/z, $[M = H]^+$) |
|---|---|
| 50 | 486.10 |
| 51 | 458.30 |
| 52 | 484.40 |
| 53 | 506.10 |
| 55 | 450.30 |
| 56 | 458.90 |
| 57 | 407.30 |
| 58 | 427.30 |
| 59 | 409.3 |
| 60 | 423.3 |

Examples 61 and 62

2-(4-chloro-3-fluoro-phenoxy)-N-[3-[4-[3-cis-(trifluoromethoxy)cyclobutyl]imidazol-1-yl]-1-bicyclo[1.1.1]pentanyl]acetamide and 2-(4-chloro-3-fluorophenoxy)-N-[3-[4-[3-trans-(trifluoromethoxy)cyclobutyl]imidazol-1-yl]-1-bicyclo[1.1.1]pentanyl]acetamide cis-3-(trifluoromethoxy)cyclobutanecarbonyl chloride To a solution of 3-cis-(trifluoromethoxy)cyclobutanecarboxylic acid (2.0 g, 10.9 mmol; 8:1 to 10:1 ratio of cis- to trans-) and DMF (79 mg, 1.1 mmol) in DCM (30 mL) was added $(COCl)_2$ (4.14 g, 32.6 mmol) at 0° C. and the mixture was stirred at 0° C. for 2 h. The solution was concentrated under reduced pressure to provide 3-cis-(trifluoromethoxy)cyclobutanecarbonyl chloride as a mixture of diastereomers in favor of the cis-configuration, which was used for the next step without further purification.

2-bromo-1-(3-cis-(trifluoromethoxy)cyclobutyl)ethanone

To a solution of 3-cis-(trifluoromethoxy)cyclobutanecarbonyl chloride (2.5 g, 12.3 mmol) in $CH_3CN$ (20 mL) and THF (20 mL) was added $TMSCHN_2$ (2 M, 6.17 mL) dropwise at 0° C. over 10 min. The resulting reaction mixture was stirred at 0° C. for 20 min, and then at 25° C. for 1 h. HBr (7.5 g, 37.0 mmol, 5.0 mL, 40% in water) was added dropwise at 0° C., and the mixture was stirred at 25° C. for 2 h. The reaction mixture was diluted with $H_2O$ (50 mL) at 0° C., and then was extracted with EtOAc (3×50 mL). The combined organic layers were washed with brine (30 mL), dried over anhydrous $Na_2SO_4$, filtered and concentrated under reduced pressure to provide 2-bromo-1-(3-cis-(trifluoromethoxy)cyclobutyl)ethanone as a mixture of diastereomers in favor of the cis-configuration, which was used directly without further purification. $^1H$-NMR (400 MHz, $CDCl_3$): δ 4.78-4.86 (m, 0.2H), 4.57-4.70 (m, 1H), 4.07-4.11 (m, 1H), 3.86-3.94 (m, 1H), 3.10-3.26 (m, 1H), 2.59-2.71 (m, 2H), 2.43-2.58 (m, 2H).

2-(4-chloro-3-fluorophenoxy)-N-(3-((2-oxo-2-(3-cis-(trifluoromethoxy)cyclobutyl)ethyl)amino)bicyclo[1.1.1]pentan-1-yl)acetamide To a solution of N-(1-amino-3-bicyclo[1.1.1]pentanyl)-2-(4-chloro-3-fluoro-phenoxy)acetamide HCl salt (1.2 g, 3.74 mmol) and 2-bromo-1-(3-cis-(trifluoromethoxy)cyclobutyl)ethanone (1.95 g, 7.47 mmol) in $CH_3CN$ (20 mL) was added $Na_2CO_3$ (1.58 g, 14.95 mmol). The mixture was stirred at 40° C. for 7 h. The reaction mixture was filtered and concentrated under reduced pressure. The residue was diluted with $H_2O$ (20 mL) and extracted with EtOAc (3×10 mL). The combined organic layers were washed with brine (5 mL), dried over anhydrous $Na_2SO_4$, filtered and concentrated under reduced pressure. The residue was purified by silica gel column chromatography to provide 2-(4-chloro-3-fluorophenoxy)-N-(3-((2-oxo-2-(3-cis-(trifluoromethoxy)cyclobutyl)ethyl)amino)bicyclo[1.1.1]pentan-1-yl)acetamide (as a ca. 5:1 mixture of diastereomers in favor of the cis-configuration). The product was used into the next step directly. LC-MS m/z=465.3 $[M+H]^+$.

2-(4-chloro-3-fluorophenoxy)-N-(3-(N-(2-oxo-2-(cis-3-(trifluoromethoxy)cyclobutyl)ethyl)formamido)bicyclo[1.1.1]pentan-1-yl)acetamide To a solution of formic acid (4.88 g, 106 mmol, 4 mL) was added $Ac_2O$ (703 mg, 6.88 mmol) at 0° C. and then a solution of 2-(4-chloro-3-fluorophenoxy)-N-(3-((2-oxo-2-(cis-3-(trifluoromethoxy)cyclobutyl)ethyl)amino)bicyclo[1.1.1]pentan-1-yl)acetamide (0.8 g, 1.72 mmol) in DCM (4 mL) was added at 0° C. The mixture was stirred at 0° C. for 2 h. The reaction mixture was diluted with $H_2O$ (10 mL) and the pH was adjusted to 8-9 with sat. $NaHCO_3$ (20 mL) at 0° C. and extracted with EtOAc (3×20 mL). The combined organic layers were washed with brine (10 mL), dried over anhydrous $Na_2SO_4$, filtered and concentrated under reduced pressure to provide 2-(4-chloro-3-fluorophenoxy)-N-(3-(N-(2-oxo-2-(cis-3-(trifluoromethoxy)cyclobutyl)ethyl)formamido)bicyclo[1.1.1]pentan-1-yl)acetamide as a mixture of diastereomers in favor of the cis-configuration. The material was used for the next step without further purification. LC-MS m/z=493.3 [M+H]$^+$.

2-(4-chloro-3-fluoro-phenoxy)-N-[3-[4-[3-cis-(trifluoromethoxy)cyclobutyl]imidazol-1-yl]-1-bicyclo[1.1.1]pentanyl]acetamide and 2-(4-chloro-3-fluorophenoxy)-N-[3-[4-[3-trans-(trifluoromethoxy)cyclobutyl]imidazol-1-yl]-1-bicyclo[1.1.1]pentanyl]acetamide To a solution of 2-(4-chloro-3-fluorophenoxy)-N-(3-(N-(2-oxo-2-(3-cis-(trifluoromethoxy)cyclobutyl)ethyl)formamido)bicyclo[1.1.1]pentan-1-yl)acetamide (0.78 g, 1.58 mmol) in CH$_3$COOH (8 mL) was added CH$_3$COONH$_4$ (476 mg, 6.17 mmol). The mixture was stirred at 110° C. for 12 h. The reaction mixture was diluted with aq. NaHCO$_3$ (50 mL) at 0° C., and extracted with EtOAc (3×30 mL). The combined organic layers were washed with brine (10 mL), dried over anhydrous Na$_2$SO$_4$, filtered and concentrated under reduced pressure. The residue was purified by prep-HPLC (Nano-micro Kromasil C18 100 mm×30 mm, 5 µm; mobile phase: A: 0.1% TFA in water, B: MeCN, gradient: B % in A: 30%-55% over 10 min) to provide a 3:1 mixture of diastereomers. This material was further purified by SFC. SFC conditions: Chiralcel OJ 250 mm×30 mm, 10 µm; mobile phase: A: CO$_2$, B: 0.1% NH$_4$OH in MeOH, gradient: B % in A: 17%-17% over 4 min.

2-(4-chloro-3-fluoro-phenoxy)-N-[3-[4-[3-cis-(trifluoromethoxy)cyclobutyl]imidazol-1-yl]-1-bicyclo[1.1.1]pentanyl]acetamide: $^1$H-NMR (400 MHz, MeOD): δ 7.99 (d, J=0.88 Hz, 1H), 7.39 (t, J=8.71 Hz, 1H), 7.18 (d, J=0.66 Hz, 1H), 6.95 (dd, J=11.03, 2.87 Hz, 1H), 6.84 (ddd, J=8.99, 2.81, 1.21 Hz, 1H), 4.73 (quin, J=7.50 Hz, 1H), 4.52 (s, 2H), 3.10 (tt, J=10.12, 7.63 Hz, 1H), 2.71-2.81 (m, 2H), 2.62 (s, 6H), 2.30-2.46 (m, 2H). LC-MS m/z:=474.1 [M+H]$^+$ 2-(4-chloro-3-fluoro-phenoxy)-N-[3-[4-[3-trans-(trifluoromethoxy)cyclobutyl]imidazol-1-yl]-1-bicyclo[1.1.1]pentanyl]acetamide: $^1$H-NMR (400 MHz, MeOD): δ 7.92 (d, J=0.88 Hz, 1H), 7.39 (t, J=8.71 Hz, 1H), 7.19 (s, 1H), 6.95 (dd, J=10.80, 2.87 Hz, 1H), 6.84 (ddd, J=8.93, 2.87, 1.21 Hz, 1H), 4.98 (quin, J=6.78 Hz, 1H), 4.52 (s, 2H), 3.48-3.58 (m, 1H), 2.63-2.70 (m, 2H), 2.62 (s, 6H), 2.50-2.58 (m, 2H). LC-MS m/z:=474.1 [M+H]$^+$ Example 63

2-[3-cis-(trifluoromethoxy)cyclobutoxy]-N-[3-[4-[3-cis-(trifluoromethoxy)cyclobutyl]imidazol-1-yl]-1-bicyclo[1.1.1]pentanyl]acetamide tert-butyl(3-(2-(3-cis-(trifluoromethoxy)cyclobutoxy)acetamido)bicyclo[1.1.1]pentan-1-yl)carbamate To a solution of 2-[3-cis-(trifluoromethoxy)cyclobutoxy]acetic acid (1.00 g, 4.67 mmol) in DMF (10 mL) was added tert-butyl N-(1-amino-3-bicyclo[1.1.1]pentanyl)carbamate (926 mg, 4.67 mmol), HATU (1.95 g, 5.14 mmol) and DIEA (2.44 mL, 14.0 mmol) at 20° C. Then the mixture was stirred at 20° C. for 2 h. The reaction mixture was poured into ice-water (50 mL) and extracted with EtOAc (3×50 mL), the organic phase was washed with brine (50 mL), dried with anhydrous Na$_2$SO$_4$, filtered and concentrated under reduced pressure to provide a residue, which was purified by silica gel column chromatography. $^1$H-NMR (400 MHz, CDCl$_3$): δ 6.81 (br s, 1H), 4.31 (quin, J=7.2 Hz, 1H), 3.79 (s, 2H), 3.70 (quin, J=6.9 Hz, 1H), 2.90-2.86 (m, 1H), 2.84-2.80 (m, 2H), 2.35 (br s, 6H), 2.30-2.19 (m, 2H), 1.44 (s, 9H).

N-(3-aminobicyclo[1.1.1]pentan-1-yl)-2-(3-cis-(trifluoromethoxy)cyclobutoxy)acetamide HCl Salt To a solution of tert-butyl (3-(2-(3-cis-(trifluoromethoxy)cyclobutoxy)acetamido)bicyclo[1.1.1]pentan-1-yl)carbamate (500 mg, 1.27 mmol) in EtOAc (10 mL) was added EtOAc/HCl (10 mL, 4 M), and the reaction mixture was stirred at 25° C. for 1 h. The reaction mixture was concentrated under reduced pressure to provide a residue, which was used directly. LC-MS: m/z=295.1 [M+H]$^+$.

N-(3-((2-oxo-2-(3-cis-(trifluoromethoxy)cyclobutyl)ethyl)amino)bicyclo[1.1.1]pentan-1-yl)-2-(3-cis-(trifluoromethoxy)cyclobutoxy)acetamide To a mixture of 2-bromo-1-(3-cis-(trifluoromethoxy)cyclobutyl)ethanone (1.04 g, 3.99 mmol; 8:1 to 10:1 ratio of cis- to trans-), N-(3-aminobicyclo[1.1.1]pentan-1-yl)-2-(cis-3-(trifluoromethoxy)cyclobutoxy)acetamide HCl salt (1.2 g, 3.63 mmol) in CH$_3$CN (10 mL) was added Na$_2$CO$_3$ (1.54 g, 14.51 mmol), and the mixture was stirred at 40° C. for 15 h. The reaction mixture was filtered and concentrated under reduced pressure to provide a residue, which was purified by silica gel column chromatography to deliver the desired compound. LC-MS: m/z=475.2 [M+H]$^+$.

N-(3-(N-(2-oxo-2-(3-cis-(trifluoromethoxy)cyclobutyl)ethyl)formamido)bicyclo[1.1.1]pentan-1-yl)-2-(cis-3-(trifluoromethoxy)cyclobutoxy)acetamide Formic acid (3.2 mL, 84 mmol) was added dropwise to Ac$_2$O (630 µL, 6.75 mmol) at 0° C. After addition, N-(3-((2-oxo-2-(3-cis-(trifluoromethoxy)cyclobutyl)ethyl)amino)bicyclo[1.1.1]pentan-1-yl)-2-(3-cis-(trifluoromethoxy)cyclobutoxy)acetamide (800 mg, 1.69 mmol) in DCM (2 mL) was added drop-wise to the reaction mixture at 0° C. The resulting mixture was stirred at 0° C. for 1 h. The reaction mixture was diluted with aq. NaHCO$_3$ (10 mL) at 0° C., adjusted to pH=8-9, and extracted with EtOAc (3×10 mL). The combined organic layers were washed with brine (10 mL), dried over anhydrous Na$_2$SO$_4$, filtered and concentrated under reduced pressure to provide the desired compound. LC-MS: m/z=503.2 [M+H]$^+$.

2-[3-cis-(trifluoromethoxy)cyclobutoxy]-N-[3-[4-[3-cis-(trifluoromethoxy)cyclobutyl]imidazol-1-yl]-1-bicyclo[1.1.1]pentanyl]acetamide To a solution of N-(3-(N-(2-oxo-2-(3-cis-(trifluoromethoxy)cyclobutyl)ethyl)formamido)bicyclo[1.1.1]pentan-1-yl)-2-3-cis-(trifluoromethoxy)cyclobutoxy)acetamide (800 mg, 1.59 mmol) in AcOH mL) was added ammonium acetate (491 mg, 6.37 mmol), and the reaction mixture was stirred at 120° C. for 12 h. The reaction mixture was diluted with aq. NaHCO$_3$ (20 mL) at 0° C., adjusted to pH=8-9, and extracted with EtOAc (3×12 mL). The combined organic layers were washed with brine (20 mL), dried over anhydrous Na$_2$SO$_4$, filtered and concentrated under reduced pressure to provide a residue, which was purified by prep-HPLC. $^1$H-NMR (400 MHz, CDCl$_3$): δ 7.40 (s, 1H), 6.93 (s, 1H), 6.70 (s, 1H), 4.62 (quip, J=7.6 Hz, 1H), 4.34 (quin, J=7.2 Hz, 1H), 3.84 (s, 2H), 3.73 (quin, J=6.9 Hz, 1H), 3.07-2.95 (m, 1H), 2.89-2.81 (m, 2H), 2.77-2.69 (m, 2H), 2.59 (s, 6H), 2.47-2.38 (m, 2H), 2.31-2.24 (m, 2H). LC-MS: m/z=484.4 [M+H]$^+$.

Examples 64 and 65

2-(4-chloro-3-fluoro-phenoxy)-N-[3-[1-[3-trans-(trifluoromethoxy)cyclobutyl]triazol-4-yl]-1-bicyclo[1.1.1]pentanyl]acetamide and 2-(4-chloro-3-fluoro-phenoxy)-N-[3-[1-[3-cis-(trifluoromethoxy)cyclobutyl]triazol-4-yl]-1-bicyclo[1.1.1]pentanyl]acetamide ((3-iodocyclobutoxy)methyl)benzene A mixture of (3-cis-benzyloxycyclobutyl) methanesulfonate (1.0 g, 3.90 mmol) and NaI (1.75 g, 11.7 mmol) in MeCN (10 mL) was stirred at 80° C. for 40 h. The reaction mixture was diluted with H$_2$O (150 mL) and extracted with EtOAc (3×50 mL). The combined organic layers were washed with H$_2$O (50 mL) and brine (50 mL), dried over anhydrous Na$_2$SO$_4$, filtered and concentrated under reduced pressure to provide (3-iodocyclobutoxy)methyl)benzene which was used for the next step directly.

((3-azidocyclobutoxy)methyl)benzene

A mixture of ((3-iodocyclobutoxy)methyl)benzene (1.0 g, 3.47 mmol) and NaN$_3$ (451 mg, 6.94 mmol) in DMF (10 mL) was stirred at 80° C. for 15 h. To the reaction mixture was added H$_2$O (60 mL). The mixture was extracted with EtOAc (3×20 mL). The combined organic layers were washed with H$_2$O (2×20 mL) to provide ((3-azidocyclobutoxy)methyl)benzene. The EtOAc and the solution was used directly.

N-(3-(1-(3-(benzyloxy)cyclobutyl)-1H-1,2,3-triazol-4-yl)bicyclo[1.1.1]pentan-1-yl)-2-(4-chloro-3-fluoro-phenoxy)acetamide A mixture of 2-(4-chloro-3-fluoro-phenoxy)-N-(1-ethynyl-3-bicyclo[1.1.1]pentanyl)acetamide (0.4 g, 1.36 mmol), sodium ascorbate (5.0 mg, 0.027 mmol), CuSO$_4$ (2 mg, 0.013 mmol), benzoic acid (16 mg, 0.136 mmol) and ((3-azidocyclobutoxy)methyl)benzene (414 mg, 2.04 mmol in EtOAc) in t-BuOH (2 mL) and H$_2$O (4 mL) was stirred at 80° C. for 15 h in a sealed tube. The reaction mixture was diluted with H$_2$O (30 mL) and extracted with EtOAc (3×10 mL). The combined organic layers were washed with brine (10 mL), dried over anhydrous Na$_2$SO$_4$, filtered and concentrated under reduced pressure to provide a residue. The residue was purified by silica gel column chromatography (PE:MTBE=1:0 to 0:1) to provide N-(3-(1-(3-(benzyloxy)cyclobutyl)-1H-1,2,3-triazol-4-yl)bicyclo[1.1.1]pentan-1-yl)-2-(4-chloro-3-fluorophenoxy)acetamide. LC-MS: m/z:=497.7 [M+H]$^+$.

2-(4-chloro-3-fluorophenoxy)-N-(3-(1-(3-hydroxycyclobutyl)-1H-1,2,3-triazol-4-yl)bicyclo[1.1.1]pentan-1-yl)acetamide To a solution of N-(3-(1-(3-(benzyloxy)cyclobutyl)-1H-1,2,3-triazol-4-yl)bicyclo[1.1.1]pentan-1-yl)-2-(4-chloro-3-fluorophenoxy)acetamide (0.6 g, 1.21 mmol) in DCM (10 mL) was added BCl$_3$ (4.8 mL, 4.83 mmol, 1 M in DCM) at 0° C. The mixture was stirred at 25° C. for 1 h. The reaction mixture was diluted with H$_2$O (60 mL) and extracted with DCM:i-PrOH (3×60 mL, v:v=3:1). The combined organic layers were washed with brine (30 mL), dried over anhydrous Na$_2$SO$_4$, filtered and concentrated under reduced pressure to provide a residue. The residue was purified by silica gel column chromatography (MTBE:MeOH=1:0 to 3:1) to provide 2-(4-chloro-3-fluorophenoxy)-N-(3-(1-(3-hydroxycyclobutyl)-1H-1,2,3-triazol-4-yl)bicyclo[1.1.1]pentan-1-yl)acetamide. LC-MS: m/z:=407.2 [M+H]$^+$.

O-(3-(4-(3-(2-(4-chloro-3-fluorophenoxy)acetamido)bicyclo[1.1.1]pentan-1-yl)-1H-1,2,3-triazol-1-yl)cyclobutyl) S-methyl carbonodithioate To a solution of 2-(4-chloro-3-fluorophenoxy)-N-(3-(1-(3-hydroxycyclobutyl)-1H-1,2,3-triazol-4-yl)bicyclo[1.1.1]pentan-1-yl)acetamide (180 mg, 0.44 mmol) in DMF (4.0 mL) was added DBU (80 mg, 0.53 mmol) at 0° C. After 0.5 h, CS$_2$ (134 mg, 1.77 mmol) was added to the mixture at 0° C. The mixture was stirred at 0° C. for 0.5 h. To the mixture was added MeI (314 mg, 2.21 mmol) at 0° C. The mixture was stirred at 25° C. for 15 h. The reaction mixture was diluted with H$_2$O (60 mL), and extracted with EtOAc (3×20 mL). The combined organic layers were washed with brine (2×30 mL), dried over anhydrous Na$_2$SO$_4$, filtered and concentrated under reduced pressure to provide a residue which was purified by prep-TLC (PE:EtOAc=1:1) to provide the title compound. LC-MS: m/z:=497.2 [M+H]$^+$.

2-(4-chloro-3-fluoro-phenoxy)-N-[3-[1-[3-trans-(trifluoromethoxy)cyclobutyl]triazol-4-yl]-1-bicyclo[1.1.1]pentanyl]acetamide and 2-(4-chloro-3-fluoro-phenoxy)-N-[3-[1-[3-cis-(trifluoromethoxy)cyclobutyl]triazol-4-yl]-1-bicyclo[1.1.1]pentanyl]acetamide To a solution of 1,3-dibromo-5,5-dimethyl-imidazolidine-2,4-dione (103 mg, 0.362 mmol) in DCM (6 mL) was added pyridine; hydrofluoride (683 mg, 4.83 mmol, 70%) at −78° C. The mixture was stirred at −78° C. for 0.5 h. To the mixture was added O-(3-(4-(3-(2-(4-chloro-3-fluorophenoxy)acetamido)bicyclo[1.1.1]pentan-1-yl)-1H-1,2,3-triazol-1-yl)cyclobutyl) S-methyl carbonodithioate (60 mg, 0.172 mmol) in DCM (2 mL) at −78° C. The mixture was stirred at 0° C. for 1 h. The reaction mixture was quenched by H$_2$O (30 mL), extracted with DCM (3×10 mL). The combined organic layers were washed with sat.NaHCO$_3$ (3×10 mL) and brine (10 mL), dried over anhydrous Na$_2$SO$_4$, filtered and concentrated under reduced pressure to provide a residue which was purified by prep-HPLC (neutral) to provide the desired product as a mixture of diastereomers. The diastereomers were separated by SFC to give:

2-(4-chloro-3-fluoro-phenoxy)-N-[3-[1-[3-trans-(trifluoromethoxy)cyclobutyl]triazol-4-yl]-1-bicyclo[1.1.1]pentanyl]acetamide $^1$H-NMR (400 MHz, CDCl$_3$) δ 7.44-7.29 (m, 2H), 6.93 (s, 1H), 6.82-6.64 (m, 2H), 5.20-5.03 (m, 2H), 4.42 (s, 2H), 3.13-2.99 (m, 2H), 2.96-2.84 (m, 2H), 2.52 (s, 6H). LCMS: m/z:=475.3 [M+H]$^+$.

2-(4-chloro-3-fluoro-phenoxy)-N-[3-[3-cis-(trifluoromethoxy)cyclobutyl]triazol-4-yl]-1-bicyclo[1.1.1]pentanyl]acetamide $^1$H-NMR (400 MHz, CDCl$_3$): δ 7.43 (s, 1H), 7.34 (t, J=8.6 Hz, 1H), 6.92 (s, 1H), 6.78 (dd, J=2.8, 10.2 Hz, 1H), 6.70 (dd, J=1.8, 8.9 Hz, 1H), 4.73 (quin, J=8.3 Hz, 1H), 4.62 (quin, J=7.2 Hz, 1H), 4.42 (s, 2H), 3.17-3.07 (m, 2H), 3.01-2.81 (m, 2H), 2.53 (s, 6H). LC-MS: m/z:=475.3 [M+H]$^+$.

Example 66

2-(4-chloro-3-fluoro-phenoxy)-N-[3-[5-[3-cis-(difluoromethoxy)cyclobutyl]-1,3,4-oxadiazol-2-yl]-1-bicyclo[1.1.1]pentanyl]acetamide methyl 3-cis-(difluoromethoxy)cyclobutanecarboxylate To a solution of methyl 3-cis-hydroxycyclobutanecarboxylate (400 mg, 3.07 mmol) in $CH_3CN$ (5 mL) was added CuI (117 mg, 0.61 mmol), the mixture was heated to 50° C., and a solution of 2,2-difluoro-2-fluorosulfonyl-acetic acid (657 mg, 3.69 mmol) in $CH_3CN$ (5 mL) was added dropwise over a period of 5 min. The reaction mixture stirred at 50° C. for 2 h, was diluted with $H_2O$ (10 mL), and then extracted with EtOAc (3×10 mL). The combined organic layers were washed with brine (10 mL), dried over anhydrous $Na_2SO_4$, filtered and concentrated under reduced pressure to provide methyl 3-(difluoromethoxy)cyclobutanecarboxylate, which was used directly for next step.

3-cis-(difluoromethoxy)cyclobutanecarboxylic acid

To a solution of methyl 3-cis-(difluoromethoxy)cyclobutanecarboxylate (480 mg, 2.66 mmol) in THF (10 mL) was added LiOH·$H_2O$ (447 mg, 10.66 mmol) and $H_2O$ (2 mL), and the mixture was stirred at 25° C. for 16 h. The reaction mixture was diluted with MTBE and the layers were separated. The aqueous phase was extracted with MTBE (3×5 mL) and the aqueous layer pH was adjusted to 3 with HCl (2 N). The acidified mixture was extracted with EtOAc (3×5 mL), the organic phase was washed with brine (5 mL), dried over anhydrous $Na_2SO_4$, filtered and concentrated under reduced pressure to provide 3-cis-(difluoromethoxy)cyclobutanecarboxylic acid, which was used directly for next step.

2-(4-chloro-3-fluorophenoxy)-N-(3-(2-(3-cis-(difluoromethoxy)cyclobutanecarbonyl)hydrazinecarbonyl)bicyclo[1.1.1]pentan-1-yl)acetamide To a solution of 2-(4-chloro-3-fluoro-phenoxy)-N-[1-(hydrazinecarbonyl)-3-cis-bicyclo[1.1.1]pentanyl]acetamide (100 mg, 031 mmol) in THF (10 mL) was added 3-(difluoromethoxy)cyclobutanecarboxylic acid (61 mg, 0.37 mmol), HATU (139 mg, 0.37 mmol) and DIEA (0.16 mL, 0.92 mmol) at 0° C. and the mixture was stirred at 20° C. for 2 h. The reaction mixture was poured into ice-water (10 mL) and was extracted with EtOAc (3×10 mL), the organic phase was washed with brine (10 mL), dried over anhydrous $Na_2SO_4$, filtered and concentrated under reduced pressure to provide the title product, which was used directly. LC-MS m/z:=476.3 $[M+H]^+$.

2-(4-chloro-3-fluoro-phenoxy)-N-[3-[5-[3-cis-(difluoromethoxy)cyclobutyl]-1,3,4-oxadiazol-2-yl]-1-bicyclo[1.1.1]pentanyl]acetamide To 2-(4-chloro-3-fluorophenoxy)-N-(3-(2-(3-cis-(difluoromethoxy)cyclobutanecarbonyl)hydrazinecarbonyl)bicyclo[1.1.1]pentan-1-yl)acetamide (100 mg, 0.21 mmol) in DCM (6 mL) was added TEA (0.12 mL, 0.84 mmol) and p-TsCl (80 mg, 0.42 mmol) at 25° C., and the mixture was stirred at 25° C. for 16 h. The reaction mixture was poured into ice-water (10 mL) and was extracted with DCM (3×10 mL), the organic phase was washed with brine (10 mL), dried with anhydrous $Na_2SO_4$, filtered and concentrated under reduced pressure to provide a residue, which was purified by prep-HPLC (TFA) to provide the desired compound, which was further separated by prep-TLC (DCM:MeOH=10:1) to provide the desired product. $^1$H-NMR (400 MHz, $CDCl_3$): δ 7.35 (t, J=8.60 Hz, 1H), 6.97 (br s, 1H), 6.78 (dd, 10.23, 2.82 Hz, 1H), 6.70 (br d, J=8.78 Hz, 1H), 5.99-6.41 (m, 1H), 4.70 (quin, J=7.53 Hz, 1H), 4.44 (s, 2H), 3.25-3.39 (m, 1H), 2.78-2.88 (m, 2H), 2.66 (s, 6H), 2.57-2.63 (m, 2H). LC-MS m/z:=458.3 $[M+H]^+$.

Example 67

2-(4-chloro-3-fluoro-phenoxy)-N-[3-[4-[1-(2,2,2-trifluoroethyl)azetidin-3-yl]imidazol-1-yl]-1-bicyclo[1.1.1]pentanyl]acetamide O1-benzyl O3-ethyl azetidine-1,3-dicarboxylate To a mixture of ethyl azetidine-3-carboxylate hydrochloride (2.0 g, 12.1 mmol) in THF (20 mL) and $H_2O$ (20 mL) was added aq. NaOH (4 M, 3.0 mL) at 0° C., followed by CbzCl (2.06 g, 12.1 mmol) drop-wise, and then the mixture was stirred at 25° C. for 16 h. The reaction mixture was concentrated under reduced pressure, diluted with EtOAc (30 mL) and water (30 mL), and extracted with EtOAc (3×30 mL). The combined organic layers were washed with brine (20 mL), dried over anhydrous $Na_2SO_4$, filtered and concentrated under reduced pressure to provide a residue, which was purified by silica gel column chromatography (PE:MTBE=100:1 to 1:1) to deliver O1-benzyl O3-ethyl azetidine-1,3-dicarboxylate. LC-MS m/z:=264.1 $[M+H]^+$.

1-benzyloxycarbonylazetidine-3-carboxylic acid

To a mixture of O1-benzyl O3-ethyl azetidine-1,3-dicarboxylate (0.5 g, 1.90 mmol) in THF (2.5 mL) and $H_2O$ (2.5 mL) was added LiOH·$H_2O$ (159 mg, 3.80 mmol) at 0° C., then the mixture was stirred at 25° C. for 1 h. The reaction mixture was concentrated under reduced pressure to provide a residue. The residue was diluted with $H_2O$ (10 mL) and extracted with MTBE (2×10 mL). The water phase was adjusted to pH=2-3 with 2 N HCl at 0° C., and extracted with EtOAc (3×10 mL). The combined organic layers were dried over anhydrous $Na_2SO_4$, filtered and concentrated under reduced pressure to provide 1-benzyloxycarbonylazetidine-3-carboxylic acid.

Benzyl 3-chlorocarbonylazetidine-1-carboxylate

To a mixture of 1-benzyloxycarbonylazetidine-3-carboxylic acid (0.5 g, 2.13 mmol) and DMF (16 mg, 0.21 mmol) in DCM (10 mL) was added $(COCl)_2$ (809 mg, 6.38 mmol) at 0° C., then the mixture was stirred at 25° C. for 2 h. The reaction mixture was concentrated under reduced pressure to provide benzyl 3-chlorocarbonylazetidine-1-carboxylate.

Benzyl 3-(2-diazoacetyl)azetidine-1-carboxylate

To a mixture of benzyl 3-chlorocarbonylazetidine-1-carboxylate (640 mg, 2.52 mmol) in THF (5 mL) and MeCN (5 mL) was added $TMSCHN_2$ (2 M, 3.15 mL) at 0° C., then the mixture was stirred at 25° C. for 1 h. The reaction mixture was concentrated under reduced pressure, then diluted with $H_2O$ (10 mL) and extracted with EtOAc (3×10 mL). The combined organic layers were washed with brine (10 mL), dried over anhydrous $Na_2SO_4$, filtered and concentrated under reduced pressure to provide a residue. The residue was purified by silica gel column chromatography (PE:EtOAc=100:1 to 0:1) to provide benzyl 3-(2-diazoacetyl)azetidine-1-carboxylate. LC-MS m/z:=260.0 [M+H]$^+$.

Benzyl 3-(2-bromoacetyl)azetidine-1-carboxylate

To a mixture of benzyl 3-(2-diazoacetyl)azetidine-1-carboxylate (450 mg, 1.74 mmol) in THF (10 mL) was added HBr (421 mg, 2.08 mmol, 40% in H$_2$O) at 0° C., and the mixture was stirred at 25° C. for 0.5 h. The reaction mixture was diluted with H$_2$O (20 mL) and extracted with EtOAc (3×20 mL). The combined organic layers were washed with brine (20 mL), dried over anhydrous Na$_2$SO$_4$, filtered and concentrated under reduced pressure to provide benzyl 3-(2-bromoacetyl)azetidine-1-carboxylate. LC-MS m/z:=312.0, 314.0 [M+H]$^+$.

Benzyl 3-[2-[[3-[[2-(4-chloro-3-fluoro-phenoxy)acetyl]amino]-1-bicyclo[1.1.1]pentanyl]amino]acetyl]azetidine-1-carboxylate To a mixture of N-(1-amino-3-bicyclo[1.1.1]pentanyl)-2-(4-chloro-3-fluoro-phenoxy)acetamide HCl salt (0.9 g, 2.80 mmol) and benzyl 3-(2-bromoacetyl)azetidine-1-carboxylate (1.05 g, 3.36 mmol) in MeCN (50 mL) was added Na$_2$CO$_3$ (1.19 g, 11.21 mmol), and the mixture was stirred at 40° C. for 2 h. The mixture was filtered and concentrated under reduced pressure and the residue was purified by silica gel column chromatography (PE:EtOAc=100:1 to 0:1) to provide benzyl 3-[2-[[3-[[2-(4-chloro-3-fluoro-phenoxy)acetyl]amino]-1-bicyclo[1.1.1]pentanyl]amino]acetyl]azetidine-1-carboxylate. LC-MS m/z:=516.2, 518.2 [M+H]$^+$.

Benzyl 3-[2-[[1-[[2-(4-chloro-3-fluoro-phenoxy)acetyl]amino]-3-bicyclo[1.1.1]pentanyl]-formyl-amino]acetyl]azetidine-1-carboxylate To a solution of formic acid (102 mg, 2.13 mmol) was added Ac$_2$O (871 mg, 8.53 mmol) at 0° C. To this was added a solution of benzyl 3-[2-[[3-[[2-(4-chloro-3-fluoro-phenoxy)acetyl]amino]-1-bicyclo[1.1.1]pentanyl]amino]acetyl]azetidine-1-carboxylate (1.1 g, 2.13 mmol) dropwise in DCM (3 mL) and the mixture was stirred at 0° C. for 2 h. The reaction mixture was adjusted to pH=7-8 with sat. NaHCO$_3$, the aqueous phase was extracted with EtOAc (3×50 mL), the combined organic layers were washed with brine (50 mL), dried over anhydrous Na$_2$SO$_4$, filtered and concentrated under reduced pressure to provide benzyl 3-[2-[[1-[[2-(4-chloro-3-fluoro-phenoxy)acetyl]amino]-3-bicyclo[1.1.1]pentanyl]-formyl-amino]acetyl]azetidine-1-carboxylate.

Benzyl 3-[1-[1-[[2-(4-chloro-3-fluoro-phenoxy)acetyl]amino]-3-bicyclo[1.1.1]pentanyl]imidazol-4-yl]azetidine-1-carboxylate To a solution of benzyl 3-[2-[[1-[[2-(4-chloro-3-fluoro-phenoxy)acetyl]amino]-3-bicyclo[1.1.1]pentanyl]-formyl-amino]acetyl]azetidine-1-carboxylate (950 mg, 1.75 mmol) in AcOH (10 mL) was added ammonium acetate (673 mg, 8.73 mmol), and the mixture was stirred at 110° C. for 16 h. The reaction mixture was adjusted to pH=7-8 with sat-.NaHCO$_3$, the aqueous phase was extracted with EtOAc (3×50 mL), the combined organic layers were washed with brine (50 mL), dried over anhydrous Na$_2$SO$_4$, filtered and concentrated under reduced pressure. The residue was purified by silica gel column chromatography (DCM:MeOH=100:1 to 10:1) to provide benzyl 3-[1-[1-[[2-(4-chloro-3-fluoro-phenoxy)acetyl]amino]-3-bicyclo[1.1.1]pentanyl]imidazol-4-yl]azetidine-1-carboxylate. LC-MS m/z:=525.2, 527.2 [M+H]$^+$.

N-[3-[4-(azetidin-3-yl)imidazol-1-yl]-1-bicyclo[1.1.1]pentanyl]-2-(4-chloro-3-fluoro-phenoxy)acetamide To a solution of benzyl 3-[1-[1-[[2-(4-chloro-3-fluoro-phenoxy)acetyl]amino]-3-bicyclo[1.1.1]pentanyl]imidazol-4-yl]azetidine-1-carboxylate (100 mg, 0.19 mmol) in EtOH (5 mL) was added Pd(OH)$_2$ (10%). The suspension was degassed under vacuum and purged with H$_2$ three times. The reaction mixture was stirred under H$_2$ (30 psi) at 25° C. for 2.5 h. The reaction mixture was filtered over a pad of celite, and the filtrate was concentrated under reduced pressure to provide N-[3-[4-(azetidin-3-yl)imidazol-1-yl]-1-bicyclo[1.1.1]pentanyl]-2-(4-chloro-3-fluoro-phenoxy)acetamide. LCMS m/z:=391.1, 393.2 [M+H]$^+$.

2-(4-chloro-3-fluoro-phenoxy)-N-[3-[4-[1-(2,2,2-trifluoroethyl)azetidin-3-yl]imidazol-1-yl]-1-bicyclo[1.1.1]pentanyl]acetamide To a solution of N-[3-[4-(azetidin-3-yl)imidazol-1-yl]-1-bicyclo[1.1.1]pentanyl]-2-(4-chloro-3-fluoro-phenoxy)acetamide (80 mg, 0.20 mmol) in THF (2 mL) was added DIEA (106 mg, 0.82 mmol), followed by 2,2,2-trifluoroethyl trifluoromethanesulfonate (71 mg, 0.31 mmol) at 0° C. The reaction mixture was stirred at 50° C. for 4 h and then was diluted with H$_2$O (10 mL). The layers were separated and the aqueous layer was extracted with EtOAc (3×5 mL). The combined organic extracts were washed with brine (10 mL), dried over anhydrous Na$_2$SO$_4$, filtered and concentrated under reduced pressure to provide a residue that was purified by prep-HPLC (neutral) to provide 2-(4-chloro-3-fluoro-phenoxy)-N-[3-[4-[1-(2,2,2-trifluoroethyl)azetidin-3-yl]imidazol-1-yl]-1-bicyclo[1.1.1]pentanyl]acetamide. LCMS m/z:=473.2 [M+H]$^+$. $^1$H-NMR (400 MHz, CDCl$_3$): δ 7.42 (d, J=1.13 Hz, 1H), 7.35 (t, J=8.60 Hz, 1H), 6.96 (s, 1H), 6.75-6.80 (m, 2H), 6.69 (ddd, J=8.88, 2.79, 1.25 Hz, 1H), 4.41-4.49 (m, 2H), 3.81-3.89 (m, 2H), 3.69-3.81 (m, 1H), 3.40-3.50 (m, 2H), 3.08 (q, J=9.49 Hz, 2H), 2.59-2.65 (m, 6H).

Examples 68 and 69

2-(4-chlorophenoxy)-N-[3-[4-[3-cis-(trifluoromethoxy)cyclobutyl]imidazol-1-yl]-1-bicyclo[1.1.1]pentanyl]acetamide and 2-(4-chlorophenoxy)-N-[3-[4-[3-trans-(trifluoromethoxy)cyclobutyl]imidazol-1-yl]-1-bicyclo[1.1.1]pentanyl]acetamide 2-(4-chlorophenoxy)-N-(3-((2-oxo-2-(3-cis-(trifluoromethoxy)cyclobutyl)ethyl)amino)bicyclo[1.1.1]pentan-1-yl)acetamide To a solution of N-(1-amino-3-bicyclo[1.1.1]pentanyl)-2-(4-chlorophenoxy)acetamide HCl salt (0.6 g, 1.98 mmol) and 2-bromo-1-[3-cis-(trifluoromethoxy)cyclobutyl]ethanone (1.03 g, 3.96 mmol; 8:1 to 10:1 ratio of cis- to trans-) in CH$_3$CN (20 mL) was added Na$_2$CO$_3$ (839 mg, 7.92 mmol). The reaction mixture was stirred at 40° C. for 6 h and then was filtered and concentrated under reduced pressure. The residue was diluted with EtOAc (20 mL) and H$_2$O (20 mL) and the layers were separated. The aqueous layer was extracted with EtOAc (3×10 mL), combined organic extracts were washed with brine (10 mL), dried over anhydrous $Na_2SO_4$, filtered and concentrated under reduced pressure. The crude reaction mixture was purified by silica gel column chromatography to provide 2-(4-chlorophenoxy)-N-[1-[[2-oxo-2-[3-cis-(trifluoromethoxy)cyclobutyl]ethyl]amino]-3-bicyclo[1.1.1]pentanyl]acetamide (3:1 ratio of cis- to trans-). LC-MS m/z:=446.9 $[M+H]^+$.

2-(4-chlorophenoxy)-N-(3-(N-(2-oxo-2-(3-cis-(trifluoromethoxy)cyclobutyl)ethyl)formamido)bicyclo[1.1.1]pentan-1-yl)acetamide To a solution of formic acid (3.17 g, 68.9 mmol) was added $Ac_2O$ (457 mg, 4.48 mmol) at 0° C. and a solution of 2-(4-chlorophenoxy)-N-[1-[[2-oxo-2-[3-cis-(trifluoromethoxy)cyclobutyl]ethyl]amino]-3-bicyclo[1.1.1]pentanyl]acetamide (500 mg, 1.12 mmol) in DCM (2.5 mL) was added at 0° C. The mixture was stirred at 0° C. for 2 h and the reaction mixture was diluted with $H_2O$ (10 mL). The pH was adjusted to 8-9 by addition of sat. $NaHCO_3$ (20 mL) at 0° C. and the layers were separated. The aqueous layer extracted with EtOAc (3×20 mL), the combined organic layers were washed with brine (10 mL), dried over anhydrous $Na_2SO_4$, filtered and concentrated under reduced pressure to provide 2-(4-chlorophenoxy)-N-[3-[formyl-[2-oxo-2-[3-cis-(trifluoromethoxy)cyclobutyl]ethyl]amino]-1-bicyclo[1.1.1]pentanyl]acetamide (3:1 ratio of cis- to trans-), which was used without further purification. LC-MS m/z:= 475.3 $[M+H]^+$.

2-(4-chlorophenoxy)-N-[3-[4-[3-cis-(trifluoromethoxy)cyclobutyl]imidazol-1-yl]-1-bicyclo[1.1.1]pentanyl]acetamide and 2-(4-chlorophenoxy)-N-[3-[4-[3-trans-(trifluoromethoxy)cyclobutyl]imidazol-1-yl]-1-bicyclo[1.1.1]pentanyl]acetamide To a solution of 2-(4-chlorophenoxy)-N-[3-[formyl-[2-oxo-2-[3-cis-(trifluoromethoxy)cyclobutyl]ethyl]amino]-1-bicyclo[1.1.1]pentanyl]acetamide (360 mg, 0.76 mmol) in AcOH (4 mL) was added ammonium formate (228 mg, 2.96 mmol) and the reaction mixture was stirred at 110° C. for 12 h. The reaction was diluted with aq. $NaHCO_3$ (30 mL) at 0° C. and adjusted to pH=8-9. The layers were separated and the aqueous layer was extracted with EtOAc (3×10 mL). The combined organic layers were washed with brine (5 mL), dried over anhydrous $Na_2SO_4$, filtered and concentrated under reduced pressure. The crude reaction mixture was purified by prep-HPLC to provide the desired product (3:1 ratio of cis- to trans-). The individual diastereomers were separated by SFC to give:

2-(4-chlorophenoxy)-N-[3-[4-[3-trans-(trifluoromethoxy)cyclobutyl]imidazol-1-yl]-1-bicyclo[1.1.1]pentanyl]acetamide: $^1$H-NMR (400 MHz, MeOD): δ 8.48 (s, 1H), 7.46 (s, 1H), 7.26-7.33 (m, 2H), 6.95-7.02 (m, 2H), 4.93-5.01 (m, 1H), 4.51 (s, 2H), 3.54-3.67 (m, 1H), 2.69-2.77 (m, 2H), 2.67 (s, 6H), 2.55-2.63 (m, 2H). LC-MS=456.3 $[M+H]^+$.

2-(4-chlorophenoxy)-N-[3-[4-[3-cis-(trifluoromethoxy)cyclobutyl]imidazol-1-yl]-1-bicyclo[1.1.1]pentanyl]acetamide: $^1$H-NMR (400 MHz, MeOD): δ 7.96 (d, J=1.13 Hz, 1H), 7.24-7.33 (m, 2H), 7.17 (s, 1H), 6.93-7.02 (m, 2H), 4.66-4.78 (m, 1H), 4.50 (s, 2H), 2.99-3.15 (m, 1H), 2.68-2.81 (m, 2H), 2.62 (s, 6H), 2.29-2.44 (m, 2H). LC-MS m/z:=456.3 $[M+H]^+$.

Example 70

N-[3-[4-(4-chloro-3-fluoro-phenyl)imidazol-1-yl]-1-bicyclo[1.1.1]pentanyl]-2-[3-cis-(trifluoromethoxy)cyclobutoxy]acetamide N-(3-((2-(4-chloro-3-fluorophenyl)-2-oxoethyl)amino)bicyclo[1.1.1]pentan-1-yl)-2-(3-cis-(trifluoromethoxy)cyclobutoxy)acetamide To a mixture of 2-bromo-1-(4-chloro-3-fluoro-phenyl)ethanone (152 mg, 0.60 mmol) and N-(1-amino-3-bicyclo[1.1.1]pentanyl)-2-[3-cis-(trifluoromethoxy)cyclobutoxy]acetamide HCl salt (200 mg, 0.60 mmol) in $CH_3CN$ (20 mL) was added $Na_2CO_3$ (256 mg, 2.42 mmol), and the mixture was stirred at 40° C. for 1 h. The reaction mixture was diluted with water (5 mL) at 0° C., and EtOAc (5 mL). The layers were separated and the aqueous layer was extracted with EtOAc (3×5 mL). The combined organic layers were washed with brine (5 mL), dried over anhydrous $Na_2SO_4$, filtered and concentrated under reduced pressure to provide a residue, which was purified by silica gel column chromatography to provide the desired product, which was used directly. LC-MS m/z:=465.1 $[M+H]^+$.

N-(3-(N-(2-(4-chloro-3-fluorophenyl)-2-oxoethyl)formamido)bicyclo[1.1.1]pentan-1-yl)-2-(3-cis-(trifluoromethoxy)cyclobutoxy)acetamide Formic acid (0.53 mL, 13.98 mmol) was added dropwise to $Ac_2O$ (0.10 mL, 1.12 mmol) at 0° C. after which N-(3-((2-(4-chloro-3-fluorophenyl)-2-oxoethyl)amino)bicyclo[1.1.1]pentan-1-yl)-2-(3-cis-(trifluoromethoxy)cyclobutoxy)acetamide (130 mg, 0.28 mmol) solution in DCM (5 mL) was added dropwise at 0° C. and the mixture was stirred at 0° C. for 2 h. The reaction mixture was diluted with sat. $NaHCO_3$ (10 mL) and EtOAc (10 mL) at 0° C., and the layers were separated. The aqueous layer was extracted with EtOAc (3×5 mL), the combined organic layers were washed with brine (5 mL), dried over anhydrous $Na_2SO_4$, filtered and concentrated under reduced pressure to provide the desired compound, which was used directly. LC-MS m/z:= 492.9 $[M+H]^+$.

N-[3-[4-(4-chloro-3-fluoro-phenyl)imidazol-1-yl]-1-bicyclo[1.1.1]pentanyl]-2-[3-cis-(trifluoromethoxy)cyclobutoxy]acetamide To a solution of N-(3-(N-(2-(4-chloro-3-fluorophenyl)-2-oxoethyl)formamido)bicyclo[1.1.1]pentan-1-yl)-2-(3-cis-(trifluoromethoxy)cyclobutoxy)acetamide (130 mg, 0.26 mmol) in AcOH (1.0 mL) was added ammonium formate (81 mg, 1.06 mmol), and the mixture was stirred at 120° C. for 8 h. The reaction mixture was diluted with sat. $NaHCO_3$ (10 mL) at 0° C. and EtOAc (10 mL). The layers were separated and the aqueous layer was extracted with EtOAc (3×10 mL). The combined organic layers were washed with brine (10 mL), dried over anhydrous $Na_2SO_4$, filtered and concentrated under reduced pressure to provide a residue, which was purified by prep-TLC (EtOAc, 3 times) to deliver N-[3-[4-(4-chloro-3-fluoro-phenyl)imidazol-1-yl]-1-bicyclo[1.1.1]pentanyl]-2-[cis-3-(trifluoromethoxy)cyclobutoxy]acetamide. $^1$H-NMR (400 MHz, $CDCl_3$): δ 7.62-7.43 (m, 3H), 7.41-7.33 (m, 1H), 7.21 (d, J=1.3 Hz, 1H), 6.98 (s, 1H), 4.37-4.30 (m, 1H), 3.85 (s, 2H), 3.74 (quin, J=6.9 Hz, 1H), 2.87-2.81 (m, 2H), 2.69-2.58 (m, 6H), 2.28 (dtd, J=3.5, 6.9, 10.1 Hz, 2H). LC-MS m/z:=474.3.

Examples 71 and 72

2-(4-fluorophenoxy)-N-[3-[5-[3-cis-(trifluoromethoxy)cyclobutyl]-1,3,4-oxadiazol-2-yl]-1-bicyclo[1.1.1]pentanyl]acetamide and 2-(4-fluorophenoxy)-N-[3-[5-[3-trans-(trifluoromethoxy)cyclobutyl]-1,3,4-oxadiazol-2-yl]-1-bicyclo[1.1.1]pentanyl]acetamide To a solution of 2-(4-fluorophenoxy)acetic acid (60 mg, 0.35 mmol) in dry DMF (1 mL) was added HATU (161 mg, 0.42 mmol) at 25° C. After 15 min, 3-(5-(3-cis-(trifluoromethoxy)cyclobutyl]-1,3,4-oxadiazol-2-yl)bicyclo[1.1.1]pentan-1-amine HCl salt (115 mg, 0.35 mmol; 8:1 to 10:1 ratio of cis- to trans-) and DIEA (0.25 mL, 1.41 mmol) were added, and the reaction mixture was stirred at 25° C. for 2 h. The reaction was diluted by addition of ice-water (5 mL), and EtOAc (10 mL). The layers were separated and the aqueous layer was extracted with EtOAc (3×5 mL). The combined organic layers was washed with brine (5 mL), dried over anhydrous $Na_2SO_4$, filtered and concentrated under reduced pressure to provide a residue, which was purified by prep-HPLC to deliver 2-(4-fluorophenoxy)-N-[3-[5-[cis-3-(trifluoromethoxy)cyclobutyl]-1,3,4-oxadiazol-2-yl]-1-bicyclo[1.1.1]pentanyl]acetamide: $^1$H-NMR (400 MHz, $CDCl_3$): δ 7.08-6.99 (m, 3H), 6.93-6.85 (m, 2H), 4.71 (quin, J=7.6 Hz, 1H), 4.42 (s, 2H), 3.33 (tt, J=7.7, 10.2 Hz, 1H), 2.92-2.83 (m, 2H), 2.74-2.67 (m, 2H), 2.66 (s, 6H). LC-MS: m/z=442.2 [M+H]$^+$ 2-(4-fluorophenoxy)-N-[3-[5-[3-trans-(trifluoromethoxy)cyclobutyl]-1,3,4-oxadiazol-2-yl]-1-bicyclo[1.1.1]pentanyl]acetamide: $^1$H-NMR (400 MHz, $CDCl_3$): δ 7.06-7.01 (m, 3H), 6.91-6.87 (m, 2H), 5.00 (quin, J=6.8 Hz, 1H), 4.75-4.68 (m, 1H), 4.42 (s, 2H), 3.77-3.66 (m, 1H), 3.38-3.28 (m, 1H), 2.91-2.74 (m, 4H), 2.65 (s, 5H), 2.67-2.64 (m, 1H). LC-MS: m/z=442.2 [M+H]$^+$.

Example 73

N-[1-[5-(5-fluoro-3-pyridyl)-1,3,4-oxadiazol-2-yl]-3-bicyclo[1.1.1]pentanyl]-2-[3-cis-(trifluoromethoxy)cyclobutoxy]acetamide tert-butyl N-[1-[5-(5-fluoro-3-pyridyl)-1,3,4-oxadiazol-2-yl]-3-bicyclo[1.1.1]pentanyl]carbamate tert-butyl N-[1-(hydrazinecarbonyl)-3-bicyclo[1.1.1]pentanyl]carbamate (80.0 mg, 0.33 mmol), 5-fluoropyridine-3-carboxylic acid (70.2 mg, 0.50 mmol) and NEt3 (0.23 mL, 1.66 mmol) were dissolved in EtOAC (2.5 mL) and T3P solution (300 µL, 0.99 mmol) was added. The resulting reaction mixture was heated to 100° C. overnight. The reaction mixture was diluted with sat. $NaHCO_3$ solution (10 mL) and EtOAc (10 mL) The layers were separated and the aqueous layer was extracted with EtOAc (3×10 mL) The combined organic layers were dried over anhydrous $MgSO_4$, filtered, and concentrated under reduced pressure. The crude reaction mixture was purified employing reverse-phase HPLC.

1-[5-(5-fluoro-3-pyridyl)-1,3,4-oxadiazol-2-yl]bicyclo[1.1.1]pentan-3-amine TFA Salt tert-butyl N-[1-[5-(5-fluoro-3-pyridyl)-1,3,4-oxadiazol-2-yl]-3-bicyclo[1.1.1]pentanyl]carbamate (60.0 mg, 0.17 mmol) was dissolved in DCM (2.0 mL), cooled to 0° C. and TFA (20 mg, 0.17 mmol) was added. The reaction mixture was warmed to rt, stirred 4 h, and concentrated under reduced pressure. The crude reaction mixture was used directly.

N-[1-[5-(5-fluoro-3-pyridyl)-1,3,4-oxadiazol-2-yl]-3-bicyclo[1.1.1]pentanyl]-2-[3-cis-(trifluoromethoxy)cyclobutoxy]acetamide 1-[5-(5-fluoro-3-pyridyl)-1,3,4-oxadiazol-2-yl]bicyclo[1.1.1]pentan-3-amine trifluoroacetic acid salt (60.0 mg, 0.17 mmol), 2-[3-cis-(trifluoromethoxy)cyclobutoxy]acetic acid (42.8 mg, 0.20 mmol), and $NEt_3$ (70 µL, 0.50 mmol) were dissolved in EtOAc (1.0 mL) and T3P solution (63.6 mg, 0.20 mmol) was added. The resulting reaction mixture was heated to 100° C. overnight. The reaction mixture was diluted with sat $NaHCO_3$ solution (10 mL) and EtOAc (10 mL). The layers were separated and the aqueous layer was extracted with EtOAc (3×10 mL). The combined organic layers were dried over anhydrous $MgSO_4$, filtered, and concentrated under reduced pressure. The crude reaction mixture was purified employing reverse-phase HPLC. LC-MS, m/z=443.6 [M+H]$^+$.

Example 74

2-(4-chlorophenoxy)-N-prop-2-ynyl-N-[1-[5-[3-cis-(trifluoromethoxy)cyclobutyl]-1,3,4-oxadiazol-2-yl]-3-bicyclo[1.1.1]pentanyl]acetamide To a solution of 2-(4-chlorophenoxy)-N-[1-[5-[3-cis-(trifluoromethoxy)cyclobutyl]-1,3,4-oxadiazol-2-yl]-3-bicyclo[1.1.1]pentanyl]acetamide (4.2 mg, 0.01 mmol) in THF (0.5 mL) at rt was added NaH (0.2 mg, 0.01 mmol). The reaction was stirred 10 min and propargyl bromide (1.1 mg, 0.01 mmol) was added and the reaction mixture was stirred overnight at rt. The reaction mixture was treated with NH4Cl solution (5 mL) and EtOAc (5 mL). The layers were separated and the aqueous layer was extracted with EtOAc (3×5 mL). The combined organic layers were dried over anhydrous $MgSO_4$, filtered, and concentrated under reduced pressure. The crude reaction mixture was purified employing silica gel column chromatography to provide the desired product. LC-MS, m/z=496.3 [M+H]$^+$.

Example 75

3-[3-cis-(trifluoromethoxy)cyclobutyl]-N-[3-[5-[3-cis-(trifluoromethoxy)cyclobutyl]-1,3,4-oxadiazol-2-yl]-1-bicyclo[1.1.1]pentanyl]propanamide 3-cis-(trifluoromethoxy)cyclobutanecarbaldehyde N-methoxy-N-methyl-3-cis-(trifluoromethoxy)cyclobutanecarboxamide (2.46 g, 10.83 mmol) was dissolved in THF (100 mL) and cooled to −78° C. DIBAL-H (3.08 g, 21.6 mmol) was added and the reaction mixture was stirred for 1 h. The reaction mixture was treated with sat. sodium potassium tartrate solution (100 mL) and EtOAc (100 mL) and the resulting emulsion was stirred at rt for 8 h. The layers were separated and the aqueous layer was extracted with EtOAc (3×50 mL). The combined organic layers were dried over anhydrous MgSO4, filtered, and concentrated under reduced pressure. The crude reaction mixture was used directly.

Ethyl (E)-3-[3-cis-(trifluoromethoxy)cyclobutyl]prop-2-enoate

NaH (534 mg, 13.4 mmol) was suspended in THF (45.0 mL) at 0° C. To this, was added triethyl phosphonoacetate (2.65 mL, 13.4 mmol) in 20 mL of THF. The reaction mixture was stirred until a clear solution formed, and 3-cis-(trifluoromethoxy)cyclobutanecarbaldehyde (1.87 g, 11.1 mmol) was added in 20 mL of THF. The reaction mixture was allowed to warm to rt and TLC (20% EtOAc/hex, KMnO$_4$) showed no starting material and a showed a new, less polar spot. The reaction mixture was treated with NH$_4$Cl solution (25 mL) and EtOAc (25 mL). The layers were separated and the aqueous layer was extracted with EtOAc (3×25 mL). The combined organic layers were dried over anhydrous MgSO4, filtered, and concentrated under reduced pressure. The crude reaction mixture was purified employing silica gel column chromatography (0→15% EtOAc/hex) to provide the desired product.

ethyl 3-[3-cis-(trifluoromethoxy)cyclobutyl]propanoate

Ethyl (E)-3-[3-cis-(trifluoromethoxy)cyclobutyl]prop-2-enoate (63.0 mg, 0.26 mmol) was dissolved in EtOH (2.6 mL) and palladium on carbon (6.3 mg, 10 wt %) was added. H$_2$ gas was bubbled through the reaction mixture for 1 hr. TLC (20% EtOAc/hex, KMnO$_4$) showed no starting material and a new product spot. The reaction mixture was filtered through a pad of celite and was concentrated under reduced pressure. The crude reaction mixture was used directly.

3-[3-cis-(trifluoromethoxy)cyclobutyl]propanoic acid ethyl 3-[3-cis-(trifluoromethoxy)cyclobutyl]propanoate (57.0 mg, 0.24 mmol) was dissolved in MeOH (1.0 mL), 1M NaOH (1.0 mL, 0.24 mmol) was added, and the reaction mixture was stirred overnight at 65° C. The mixture was treated with HCl solution (1M, 10 mL) and EtOAc (10 mL). The layers were separated and the aqueous layer was extracted with EtOAc (3×10 mL). The combined organic layers were dried over anhydrous MgSO$_4$, filtered, and concentrated under reduced pressure. The crude reaction mixture was used directly.

3-[3-cis-(trifluoromethoxy)cyclobutyl]-N-[3-[5-[3-cis-(trifluoromethoxy)cyclobutyl]-1,3,4-oxadiazol-2-yl]-1-bicyclo[1.1.1]pentanyl]propanamide To a solution of 1-[5-[3-cis-(trifluoromethoxy)cyclobutyl]-1,3,4-oxadiazol-2-yl]bicyclo[1.1.1]pentan-3-amine (45.0 mg, 0.16 mmol; 8:1 to 10:1 ratio of cis-to trans-) in EtOAc (1.0 mL), was added N,N-diisopropylethylamine (80 μL, 0.47 mmol) followed by T3P solution (74.2 mg, 0.23 mmol). The resulting reaction mixture was stirred 10 min and cis-3-[3-(trifluoromethoxy)cyclobutyl]propanoic acid (49.5 mg, 0.23 mmol) was added. The reaction mixture was stirred at rt for 4 h. The reaction mixture was diluted with NH$_4$Cl solution (10 mL) and EtOAc (10 mL). The layers were separated and the aqueous layer was extracted with EtOAc (3×25 mL). The combined organic layers are dried over MgSO$_4$, filtered, and concentrated under reduced pressure. The crude reaction mixture was purified using reverse-phase HPLC. LC-MS, m/z=443.58 [M+H]$^+$.

Example 76

5-chloro-N-[3-[5-[3-cis-(trifluoromethoxy)cyclobutyl]-1,3,4-oxadiazol-2-yl]-1-bicyclo[1.1.1]pentanyl]-2,3-dihydrobenzofuran-2-carboxamide 5-chloro-2,3-dihydrobenzofuran-2-carboxylic acid To a mixture of 2,3-dihydrobenzofuran-2-carboxylic acid (1.0 g, 6.09 mmol) in DMF (10 mL) was added NCS (976 mg, 7.31 mmol) at 25° C., and the mixture was heated to 60° C. for 3 h. The reaction mixture was adjusted to pH=5-6 by addition of 1N HCl, and EtOAc was added (10 mL). The layers were separated and the aqueous phase was extracted with EtOAc (3×5 mL). The combined organic phases were washed with brine (5 mL), dried over anhydrous Na$_2$SO$_4$, filtered and concentrated under reduced pressure to provide 5-chloro-2,3-dihydrobenzofuran-2-carboxylic acid.

5-chloro-N-[3-[5-[3-cis-(trifluoromethoxy)cyclobutyl]-1,3,4-oxadiazol-2-yl]-1-bicyclo[1.1.1]pentanyl]-2,3-dihydrobenzofuran-2-carboxamide To a mixture of 1-[5-[3-cis-(trifluoromethoxy)cyclobutyl]-1,3,4-oxadiazol-2-yl]bicyclo[1.1.1]pentan-3-amine HCl salt (120 mg, 0.368 mmol; 8:1 to 10:1 ratio of cis- to trans-) and 5-chloro-2,3-dihydrobenzofuran-2-carboxylic acid (80 mg, 0.405 mmol) in DMF (5.0 mL) was added HATU (154 mg, 0.405 mmol) and DEA (95 mg, 0.736 mmol) at 25° C., and the mixture was stirred at 25° C. for 2 h. The reaction mixture was diluted with water (20 mL) and EtOAc (20 mL) and the layers were separated. The aqueous phase was extracted with EtOAc (3×5 mL), the combined organic phases were washed with brine (2×5 mL), dried over anhydrous Na$_2$SO$_4$, filtered and concentrated under reduced pressure. The residue was purified by prep-HPLC (TFA) to provide the title compound. LC-MS m/z:= 470.1 [M+H]$^+$.
$^1$H-NMR (400 MHz, CDCl$_3$) δ 7.17 (s, 1H), 7.13 (br d, J=8.41 Hz, 1H), 7.06 (br s, 1H), 6.79 (br d, J=8.41 Hz, 1H), 5.12 (br dd, J=10.67, 6.78 Hz, 1H), 4.70 (quin, J=7.50 Hz, 1H), 3.52-3.63 (m, 1H), 3.26-3.47 (m, 2H), 2.81-2.90 (m, 2H), 2.65-2.74 (m, 2H), 2.61 (s, 6H).

Example 77

N-[3-[1-(4-chloro-3-fluoro-phenyl)triazol-4-yl]-1-bicyclo[1.1.1]pentanyl]-2-[3-cis-(trifluoromethoxy)cyclobutoxy]acetamide Tert-butyl(3-(1H-1,2,3-triazol-4-yl)bicyclo[1.1.1]pentan-1-yl)carbamate A mixture of tert-butyl (3-ethynylbicyclo[1.1.1]pentan-1-yl)carbamate (1.0 g, 4.82 mmol), CuI (45 mg, 0.241 mmol) and TMSN$_3$ (833 mg, 7.24 mmol) in DMF (10 mL) and MeOH (2 mL) was stirred at 100° C. for 15 h. The reaction mixture was diluted with H$_2$O (100 mL) and EtOAc (100 mL). The layers were separated and the aqueous layer was extracted with EtOAc (3×30 mL). The combined organic layers were washed with brine (60 mL), dried over anhydrous Na$_2$SO$_4$, filtered and concentrated under reduced pressure to provide a residue which was purified employing silica gel column chromatography (PE:MTBE=1:0 to 0:1) to deliver tert-butyl (3-(1H-1,2,3-triazol-4-yl)bicyclo[1.1.1]

pentan-1-yl)carbamate. $^1$H-NMR (400 MHz, CDCl$_3$): δ 7.51 (s, 1H), 5.15 (br s, 1H), 2.38 (s, 6H), 1.47 (s, 9H).

tert-Butyl(3-(1-(4-chloro-3-fluorophenyl)-1H-1,2,3-triazol-4-yl)bicyclo[1.1.1]pentan-1-yl)carbamate A mixture of tert-butyl (3-(1H-1,2,3-triazol-4-yl)bicyclo[1.1.1]pentan-1-yl)carbamate (0.5 g, 2.0 mmol), (4-chloro-3-fluoro-phenyl)boronic acid (696 mg, 4.0 mmol), Cu(OAc)$_2$ (72 mg, 0.39 mmol) and pyridine (316 mg, 4.0 mmol) in THF (10 mL) was stirred at 60° C. under O$_2$ for 15 h. The reaction mixture was diluted with H$_2$O (60 mL) and EtOAc (60 mL). The layers were separated and the aqueous layer was extracted with EtOAc (3×20 mL). The combined organic layers were washed with brine (30 mL), dried over anhydrous Na$_2$SO$_4$, filtered and concentrated under reduced pressure to provide a residue which was purified using silica gel column chromatography (PE:MTBE=1:0 to 0:1) to provide tert-butyl (3-(2-(4-chloro-3-fluorophenyl)-2H-1,2,3-triazol-4-yl)bicyclo[1.1.1]pentan-1-yl)carbamate and tert-butyl (3-(1-(4-chloro-3-fluorophenyl)-1H-1,2,3-triazol-4-yl)bicyclo[1.1.1]pentan-1-yl)carbamate. LCMS m/z:=379.1, 381.1 [M+H]$^+$.

3-(1-(4-chloro-3-fluorophenyl)-1H-1,2,3-triazol-4-yl)bicyclo[1.1.1]pentan-1-amine A mixture of tert-butyl (3-(1-(4-chloro-3-fluorophenyl)-1H-1,2,3-triazol-4-yl)bicyclo[1.1.1]pentan-1-yl)carbamate (200 mg, 0.527 mmol) in HCl/EtOAc (20 mL) was stirred at 20° C. for 1 h. The mixture was concentrated under reduced pressure to provide 3-(1-(4-chloro-3-fluorophenyl)-1H-1,2,3-triazol-4-yl) bicyclo[1.1.1]pentan-1-amine, HCl salt, which was used directly. LCMS m/z:=279.1, 281.1 [M+H]$^+$.

N-[3-[1-(4-chloro-3-fluoro-phenyl)triazol-4-yl]-1-bicyclo[1.1.1]pentanyl]-2-[3-cis-(trifluoromethoxy)cyclobutoxy]acetamide To a solution of 2-[3-cis-(trifluoromethoxy)cyclobutoxy]acetic acid (119 mg, 0.558 mmol) in DMF (3 mL) was added HATU (212 mg, 0.558 mmol) and DIEA (196 mg, 1.52 mmol). The mixture was stirred at 20° C. for 30 min. To this mixture was added 3-(1-(4-chloro-3-fluorophenyl)-1H-1,2,3-triazol-4-yl)bicyclo[1.1.1]pentan-1-amine, HCl salt (160 mg, 0.507 mmol), and the mixture was stirred at 20° C. for 15 h. The reaction mixture was diluted with H$_2$O (30 mL) and EtOAc (30 mL). The layers were separated, and the aqueous layer was extracted with EtOAc (3×10 mL). The combined organic layers were washed with brine (10 mL), dried over anhydrous Na$_2$SO$_4$, filtered and concentrated under reduced pressure to provide a residue which was purified by prep-HPLC (NH$_4$HCO$_3$) to provide N-[3-[1-(4-chloro-3-fluoro-phenyl)triazol-4-yl]-1-bicyclo[1.1.1]pentanyl]-2-[cis-3-(trifluoromethoxy)cyclobutoxy]acetamide.
$^1$H-NMR (400 MHz, CDCl$_3$): δ 7.75 (s, 1H), 7.63 (dd, J=2.3, 9.3 Hz, 1H), 7.60-7.53 (m, 1H), 7.53-7.44 (m, 1H), 6.92 (s, 1H), 4.34 (quin, J=7.2 Hz, 1H), 3.84 (s, 2H), 3.73 (quin, J=6.9 Hz, 1H), 2.91-2.76 (m, 2H), 2.56 (s, 6H), 2.35-2.21 (m, 2H). LC-MS m/z:=475.3 [M+H]$^+$.

Example 78

N-[3-[2-(4-chloro-3-fluoro-phenyl)triazol-4-yl]-1-bicyclo[1.1.1]pentanyl]-2-[3-cis-(trifluoromethoxy)cyclobutoxy]acetamide 3-(2-(4-chlorophenyl-3-fluorophenyl)-2H-1,2,3-triazol-4-yl)bicyclo[1.1.1]pentan-1-amine HCl Salt A mixture tert-butyl (3-(2-(4-chloro-3-fluorophenyl)-2H-1,2,3-triazol-4-yl)bicyclo[1.1.1]pentan-1-yl)carbamate (350 mg, 0.923 mmol) in HCl/EtOAc (4 M, 20 mL) was stirred at 20° C. for 1 h. The mixture was concentrated under reduced pressure to provide a residue that was used directly.

N-[3-[2-(4-chloro-3-fluoro-phenyl)triazol-4-yl]-1-bicyclo[1.1.1]pentanyl]-2-[3-cis-(trifluoromethoxy)cyclobutoxy]acetamide To a solution of 2-[3-cis-(trifluoromethoxy)cyclobutoxy] acetic acid (74 mg, 0.35 mmol) in DMF (5 mL) was added HATU (132 mg, 0.35 mmol) and DIEA (123 mg, 0.95 mmol). The mixture was stirred at 20° C. for 0.5 h. To this mixture was added 3-(2-(4-chloro-3-fluorophenyl)-2H-1,2,3-triazol-4-yl) bicyclo[1.1.1]pentan-1-amine, HCl salt (100 mg, 0.317 mmol) and the mixture was stirred at 20° C. for 15 h. The reaction mixture was diluted with H$_2$O (30 mL) and EtOAc (30 mL). The layers were separated and the aqueous layer was extracted with EtOAc (3×10 mL). The combined organic layers were washed with brine (10 mL), dried over anhydrous Na$_2$SO$_4$, filtered and concentrated under reduced pressure to provide a residue, which was purified by prep-HPLC (neutral) to provide N-[3-[2-(4-chloro-3-fluoro-phenyl)triazol-4-yl]-1-bicyclo[1.1.1]pentanyl]-2-[cis-3-(trifluoromethoxy)cyclobutoxy]acetamide.
$^1$H-NMR (400 MHz, CDCl$_3$): δ 7.88 (dd, J=2.4, 9.9 Hz, 1H), 7.85-7.78 (m, 1H), 7.62 (s, 1H), 7.48 (t, J=8.2 Hz, 1H), 6.91 (s, 1H), 4.34 (quin, J=7.2 Hz, 1H). 3.84 (s, 2H), 3.74 (quin, J=6.9 Hz, 1H), 2.89-2.79 (m. 2H), 2.53 (s, 6H), 2.36-2.25 (m, 2H). LC-MS m/z:=475.3 [M+H]$^+$.

Example 79

2-(4-chloro-3-fluoro-phenoxy)-N-[3-[2-[3-cis-(trifluoromethoxy)cyclobutyl]triazol-4-yl]-1-bicyclo[1.1.1]pentanyl]acetamide 2-(4-chloro-3-fluoro-phenoxy)-N-[1-(hydroxymethyl)-3-bicyclo[1.1.1]pentanyl]acetamide To a solution of methyl 3-[[2-(4-chloro-3-fluoro-phenoxy)acetyl]amino]bicyclo[1.1.1]pentane-1-carboxylate (4.0 g, 12.2 mmol) in THF (20 mL) was added LiBH$_4$ (2.66 g, 122 mmol) in three portions at 0° C. and the reaction mixture was warmed to 20° C. and stirred at for 16 h. The reaction was poured into ice, and DCM was added. The layers were separated and the aqueous layer was extracted with DCM (3×100 mL). The combined organic layers were washed with brine (3×50 mL), dried over anhydrous Na$_2$SO$_4$, filtered and concentrated under reduced pressure to provide the residue, which was purified by silica gel column chromatography (PE:EtOAc=10:1 to 1:1) to deliver 2-(4-chloro-3-fluoro-phenoxy)-N-[1-(hydroxymethyl)-3-bicyclo[1.1.1]pentanyl]acetamide. LC-MS m/z:=300.1, 302.1 [M+H]$^+$.

2-(4-chloro-3-fluoro-phenoxy)-N-(1-formyl-3-bicyclo[1.1.1]pentanyl)acetamide

A mixture of 2-(4-chloro-3-fluoro-phenoxy)-N-[1-(hydroxymethyl)-3-bicyclo[1.1.1]pentanyl]acetamide (2.0 g, 6.67 mmol) and Dess-Martin (2.27 mL, 7.34 mmol) in DCM (50 mL) was stirred at 20° C. for 16 h. The reaction mixture was diluted with saturated aqueous NaHCO$_3$ (50 mL) and DCM. The layers were separated and the aqueous layer was extracted with DCM (3×50 mL). The combined organic extracts were washed with brine (100 mL), dried over anhydrous Na$_2$SO$_4$, filtered and concentrated under reduced pressure to provide 2-(4-chloro-3-fluoro-phenoxy)-N-(1-formyl-3-bicyclo[1.1.1]pentanyl)acetamide 2-(4-chloro-3-fluoro-phenoxy)-N-(1-ethynyl-3-bicyclo[1.1.1]pentanyl)acetamide To a solution of 2-(4-chloro-3-fluoro-phenoxy)-N-(1-formyl-3-bicyclo[1.1.1]pentanyl)acetamide (1.70 g, 5.71 mmol) in MeOH (20 mL) was added 1-diazo-1-dimethoxyphosphoryl-propan-2-one (1.54 g, 7.99 mmol) and $K_2CO_3$ (2.37 g, 17.13 mmol) and the mixture was stirred at 20° C. for 16 h. The reaction mixture was diluted with saturated aqueous $NaHCO_3$ (50 mL) and EtOAc (30 mL). The layers were separated and the aqueous layer was extracted with EtOAc (3×30 mL). The combined organic layers were washed with brine (30 mL), dried over anhydrous $Na_2SO_4$, filtered and concentrated under reduced pressure to provide 2-(4-chloro-3-fluoro-phenoxy)-N-(1-ethynyl-3-bicyclo[1.1.1]pentanyl)acetamide.

N-(3-(2H-1,2,3-triazol-4-yl)bicyclo[1.1.1]pentan-1-yl)-2-(4-chloro-3-fluorophenoxy)acetamide A mixture of 2-(4-chloro-3-fluorophenoxy)-N-(3-ethynylbicyclo[1.1.1]pentan-1-yl)acetamide (700 mg, 2.38 mmol), $TMSN_3$ (824 mg, 7.15 mmol), sodium ascorbate (9.44 mg, 0.05 mmol), $CuSO_4$ (7.61 mg, 0.05 mmol) and PhCOOH (58 mg, 0.48 mmol) in t-BuOH (3 mL) and $H_2O$ (6 mL) were stirred at 80° C. for 6 h in a sealed tube. The reaction mixture was diluted with $H_2O$ (10 mL), and EtOAc (10 mL). The layers were separated and the aqueous layer was extracted with EtOAc (3×10 mL). The combined organic layers were washed with sat. $NaHCO_3$ (5 mL), brine (10 mL), dried over anhydrous $Na_2SO_4$, filtered and concentrated under reduced pressure to provide N-(3-(2H-1,2,3-triazol-4-yl)bicyclo[1.1.1]pentan-1-yl)-2-(4-chloro-3-fluorophenoxy)acetamide. LC-MS m/z:=337.3, 339.3 $[M+H]^+$.

2-(4-chloro-3-fluorophenoxy)-N-(3-(2-(3-oxocyclobutyl)-2H-1,2,3-triazol-4-yl)bicyclo[1.1.1]pentan-1-yl)acetamide To a solution of N-(3-(2H-1,2,3-triazol-4-yl)bicyclo[1.1.1]pentan-1-yl)-2-(4-chloro-3-fluorophenoxy)acetamide (600 g, 1.78 mmol) in DMF (5 mL) was added $Cs_2CO_3$ (581 mg, 1.78 mmol) and 3-bromocyclobutanone (400 mg, 2.67 mmol) at 0° C., and the mixture was stirred at 0° C. for 2 h. The reaction was poured into ice-water (20 mL), and extracted with EtOAc (3×20 mL), the combined organic phases were washed with brine (20 mL), dried over anhydrous $Na_2SO_4$ and concentrated under reduced pressure to provide 2-(4-chloro-3-fluorophenoxy)-N-(3-(2-(3-oxocyclobutyl)-2H-1,2,3-triazol-4-yl)bicyclo[1.1.1]pentan-1-yl)acetamide. LC-MS m/z:=405.1, 407.1 $[M+H]^+$.

2-(4-chloro-3-fluorophenoxy)-N-(3-(2-(3-cis-hydroxycyclobutyl)-2H-1,2,3-triazol-4-yl)bicyclo[1.1.1]pentan-1-yl)acetamide To a solution of 2-(4-chloro-3-fluorophenoxy)-N-(3-(2-(3-oxocyclobutyl)-2H-1,2,3-triazol-4-yl)bicyclo[1.1.1]pentan-1-yl)acetamide (500 mg, 1.24 mmol) in MeOH (5 mL) was added $NaBH_4$ (42 mg, 1.11 mmol) at −20° C., and the mixture was stirred at −20° C. for 1 h. The reaction mixture was diluted with $NH_4Cl$ (5 mL) and EtOAc (10 mL). The layers were separated and the aqueous layer was and extracted with EtOAc (3×5 mL). The combined organic layers were washed with brine (5 mL), dried over anhydrous $Na_2SO_4$ and concentrated under reduced pressure to provide a residue, which was purified by prep-TLC (100% EtOAc) to provide 2-(4-chloro-3-fluorophenoxy)-N-(3-(2-(3-cis-hydroxycyclobutyl)-2H-1,2,3-triazol-4-yl)bicyclo[1.1.1]pentan-1-yl)acetamide.

O-(3-cis-(4-(3-(2-(4-chloro-3-fluorophenoxy)acetamido)bicyclo[1.1.1]pentan-1-yl)-2H-1,2,3-triazol-2-yl)cyclobutyl) S-methyl carbonodithioate To a solution of 2-(4-chloro-3-fluorophenoxy)-N-(3-(2-(cis-3-hydroxycyclobutyl)-2H-1,2,3-triazol-4-yl)bicyclo[1.1.1]pentan-1-yl)acetamide (180 mg, 0.44 mmol) in dry DMF (2 mL) was added DBU (81 mg, 0.53 mmol) at 0° C. After 30 min $CS_2$ (135 mg, 1.77 mmol) was added 0° C., and the reaction mixture was stirred at 0° C. for another 30 min. At this point, MeI (314 mg, 2.21 mmol) was added at 0° C., and the reaction was stirred at 20° C. for 15 h. The reaction mixture was poured onto sat. $NH_4Cl$ (5 mL), and the aqueous phase was extracted with EtOAc (3×5 mL). The combined organic phases were washed with brine (10 mL), dried with anhydrous $Na_2SO_4$, filtered and concentrated under reduced pressure to provide a residue, which was purified by prep-TLC (PE:EtOAc=2:1) to provide the desired product. LC/MS m/z:=497.1, 499.1 $[M+H]^+$.

2-(4-chloro-3-fluoro-phenoxy)-N-[3-[2-[3-cis-(trifluoromethoxy)cyclobutyl]triazol-4-yl]-1-bicyclo[1.1.1]pentanyl]acetamide To a solution of 1,3-dibromo-5,5-dimethyl-imidazolidine-2,4-dione (86 mg, 0.30 mmol) in DCM (1 mL) was added pyridine·HF (0.52 mL, 4.02 mmol, 70%) at −78° C. After 30 min O-(3-cis-(4-(3-(2-(4-chloro-3-fluorophenoxy)acetamido)bicyclo[1.1.1]pentan-1-yl)-2H-1,2,3-triazol-2-yl)cyclobutyl) S-methyl carbonodithioate (50 mg, 0.1 mmol) was added as a solution in DCM (1 mL), and the resulting reaction mixture was stirred at 0° C. for 1 h. The reaction mixture was poured onto ice-water (4 mL), and was extracted with DCM (3×4 mL). The combined organic phases were washed with brine (4 mL), dried with anhydrous $Na_2SO_4$, filtered and concentrated under reduced pressure to provide a residue, which was purified by prep-HPLC (TFA) to provide the title compound. $^1$H-NMR (400 MHz, $CDCl_3$): δ 7.44 (s, 1H), 7.35 (t. J=8.6 Hz, 1H), 6.91 (s. 1H), 6.79 (dd, J=2.9, 10.3 Hz, 1H), 6.71 (br d, J=9.0 Hz, 1H), 4.74 (quin, J=8.2 Hz, 1H), 4.58 (quin, J=7.3 Hz, 1H), 4.43 (s, 2H), 3.06-2.98 (m, 4H), 2.52-2.48 (m, 1H), 2.50 (s, 5H). LC-MS m/z:=475.2 $[M+H]^+$.

Examples 80, 81 and 82

2-(4-chloro-3-fluoro-phenoxy)-N-[3-[5-[2-trans-(trifluoromethoxymethyl)cyclopropyl]-1,3,4-oxadiazol-2-yl]-1-bicyclo[1.1.1]pentanyl]acetamide Ethyl 2-trans-((trifluoromethoxy)methyl)cyclopropanecarboxylate To a solution of AgOTf (11.23 g, 43.70 mmol) in EtOAc (80 mL) was added 1-(chloromethyl)-4-fluoro-1,4-diazonia-bicyclo[2.2.2]octane;ditetrafluoroborate (7.74 g, 21.85 mmol), KF (3.39 g, 58.27 mmol) and ethyl 2-(hydroxymethyl)cyclopropanecarboxylate (2.1 g, 14.57 mmol) at 25° C. After mixing, 2-fluoropyridine (4.24 g, 43.70 mmol) and trimethyl(trifluoromethyl)silane (6.21 g, 43.70 mmol) were added at 25° C. and the resulting mixture was stirred at 25° C. for 12 h. The reaction mixture was filtered and concentrated under reduced pressure. The residue was purified by silica gel column chromatography (PE:EtOAc=100:1 to 5:1) to provide ethyl 2-(trifluoromethoxymethyl)cyclopropanecarboxylate (1:3 ratio of cis- to trans-).

2-trans-((trifluoromethoxy)methyl)cyclopropanecarboxylic acid

To a solution of ethyl 2-trans-(trifluoromethoxymethyl) cyclopropanecarboxylate (0.86 g, 4.05 mmol) in THF (10 mL) and $H_2O$ (10 mL) was added LiOH·$H_2O$ (510 mg, 12.16 mmol) at 0° C. and the mixture was warmed to rt and stirred for 2 h. The reaction mixture was concentrated under reduced pressure, the residue was diluted with $H_2O$ (20 mL) and was extracted with MTBE (3×10 mL). The aqueous phase was adjusted to pH=1-2 by addition of 2N HCl at 0° C. and was extracted with DCM:MeOH (6×10 mL, v:v=10: 1). The combined organic layers were dried over anhydrous $Na_2SO_4$, filtered and concentrated under reduced pressure to provide trans-2-(trifluoromethoxymethyl)cyclopropanecarboxylic acid (1:5 ratio of cis- to trans-). The crude product was used for the next step without further purification. $^1$H-NMR (400 MHz, $CDCl_3$): δ 3.99 (dd, J=10.80, 6.17 Hz, 1H), 3.81 (dd, J=10.80, 7.28 Hz, 1H), 1.83-1.96 (m, 1H), 1.68 (dt, J=8.54, 4.44 Hz, 1H), 1.34-1.42 (m, 1H), 0.98-1.08 (m, 1H).

2-(4-chloro-3-fluorophenoxy)-N-(3-(2-(2-trans-((trifluoromethoxy)methyl)cyclopropanecarbonyl)hydrazinecarbonyl)bicyclo[1.1.1]pentan-1-yl)acetamide To a solution of 2-trans-(trifluoromethoxymethyl)cyclopropanecarboxylic acid (0.2 g, 1.09 mmol), 2-(4-chloro-3-fluoro-phenoxy)-N-[1-(hydrazinecarbonyl)-3-bicyclo[1.1.1] pentanyl]acetamide (324 mg, 0.99 mmol), and TEA (400 mg, 3.95 mmol) in DMF (2 mL) was added T3P (2.51 g, 3.95 mmol, 50% in EtOAc) in a sealed tube. The mixture was stirred at 80° C. for 12 h. The reaction mixture was diluted with sat. $NaHCO_3$ (5 mL) at 0° C., additional $H_2O$ (5 mL) and EtOAc (10 mL). The layers were separated and the aqueous layer was extracted with EtOAc (3×5 mL). The combined organic layers were washed with brine (3×3 mL), dried over anhydrous $Na_2SO_4$, filtered and concentrated under reduced pressure. The residue was purified by silica gel column chromatography to provide the desired compound. LC-MS m/z:=494.2 [M+H]$^+$.

2-(4-chloro-3-fluoro-phenoxy)-N-[3-[5-[2-trans-(trifluoromethoxymethyl)cyclopropyl]-1,3,4-oxadiazol-2-yl]-1-bicyclo[1.1.1]pentanyl]acetamide To a solution of 2-(4-chloro-3-fluoro-phenoxy)-N-[1-[[[2-trans-(trifluoromethoxymethyl)cyclopropanecarbonyl] amino]carbamoyl]-3-bicyclo[1.1.1]pentanyl]acetamide (300 mg, 0.61 mmol) in 1,4-dioxane (5 mL) was added $POCl_3$ (466 mg, 3.04 mmol) and the mixture was stirred at 100° C. for 1 h. The reaction mixture was poured into ice-water (10 mL) at 0° C., and adjusted to pH=8-9 by addition of sat. $NaHCO_3$ (10 mL). EtOAc (10 mL) was added, the layers were separated, and the aqueous layer was extracted with EtOAc (3×10 mL). The combined organic layers were washed with brine (5 mL), dried over anhydrous $Na_2SO_4$, filtered and concentrated under reduced pressure. The residue was purified by prep-HPLC (Nano-micro Kromasil C18 100 mm×30 mm, 5 µm; mobile phase: A: 0.1% TFA in water, B: MeCN, gradient: B % in A: 45%-65% over 10 min) to provide 2-(4-chloro-3-fluoro-phenoxy)-N-[3-[5-[2-trans-(trifluoromethoxymethyl)cyclopropyl]-1,3,4-oxadiazol-2-yl]-1-bicyclo[1.1.1]pentanyl]acetamide (racemic) (80). $^1$H-NMR (400 MHz, MeOD): δ 7.38 (t, J=8.72 Hz, 1H), 6.94 (dd, J=10.98, 2.82 Hz, 1H), 6.83 (ddd, J=8.91, 2.82, 1.19 Hz, 1H), 4.50 (s, 2H), 4.14 (dd, J=10.92, 6.53 Hz, 1H), 4.00 (dd, J=10.92, 7.53 Hz, 1H), 2.57 (s, 6H), 2.24-2.32 (m, 1H), 1.92 (dq, J=13.46, 6.68 Hz, 1H), 1.42 (dt, J=8.94, 5.25 Hz, 1H), 1.28 (dt, J=8.91, 5.71 Hz, 1H). LC-MS m/z:=476.1 [M+H]$^+$, 478.1 [M+H]$^+$.

Product was separated by chiral SFC (Chiralcel OD-H 250 mm×30 mm, 5 µm, 40° C.; mobile phase: A: $CO_2$, B: 0.1% $NH_4OH$ in EtOH, gradient: B % in A: 30%-30%, Flow: 65 g/min, Pressure 100 bar) to provide:

Enantiomer 1 (Peak 1 in SFC) as the first eluting isomer (81). $^1$H-NMR (400 MHz, MeOD): δ 8.91 (s, 1H), 7.38 (t, J=8.72 Hz, 1H), 6.94 (dd, J=10.92, 2.76 Hz, 1H), 6.83 (ddd, J=8.91, 2.82, 1.19 Hz, 1H), 4.50 (s, 2H), 4.14 (dd, J=10.92, 6.53 Hz, 1H), 4.00 (dd, J=10.92, 7.53 Hz, 1H), 2.57 (s, 6H), 2.24-2.34 (m, 1H), 1.92 (dq, J=13.19, 6.69 Hz, 1H), 1.42 (dt, J=8.91, 5.27 Hz, 1H), 1.28 (dt, J=8.94, 5.69 Hz, 1H). LC-MS m/z:=476.1 [M+H]$^+$. SFC: ee=100%.

Enantiomer 2 (Peak 2 in SFC) as the second eluting isomer (82). $^1$H-NMR (400 MHz, MeOD): δ 7.38 (t, J=8.72 Hz, 1H), 6.94 (dd, J=10.92, 2.89 Hz, 1H), 6.83 (ddd, J=8.97, 2.82, 1.25 Hz, 1H), 4.50 (s, 2H), 4.14 (dd, J=10.92, 6.53 Hz, 1H), 4.00 (dd, J=10.92, 7.53 Hz, 1H), 2.57 (s, 6H), 2.24-2.33 (m, 1H), 1.86-2.01 (m, 1H), 1.42 (dt, J=8.91, 5.27 Hz, 1H), 1.28 (dt, J=8.94, 5.69 Hz, 1H). LC-MS m/z:=476.1 [M+H]$^+$. SFC: ee=100%.

Example 83

2-[(6,6-difluoro-3-bicyclo[3.1.0]hexanyl)oxy]-N-[3-[5-[3-cis-(trifluoromethoxy)cyclobutyl]-1,3,4-oxadiazol-2-yl]-1-bicyclo[1.1.1]pentanyl]acetamide Tert-butyl 2-[(6,6-difluoro-3-bicyclo[3.1.0]hexanyl) oxy]acetate To a mixture of 6,6-difluorobicyclo[3.1.0]hexan-3-ol (100 mg, 0.745 mmol), tert-butyl 2-bromoacetate (218.14 mg, 1.12 mmol), hydrogen sulfate:tetrabutylammonium (12 mg, 0.037 mmol) in toluene (2 mL) and $H_2O$ (0.1 mL) was added drop-wise a solution of NaOH (447 mg, 11.18 mmol) in $H_2O$ (0.5 mL) at 0° C., then the mixture was stirred at 20° C. for 4 h. The reaction mixture was diluted with $H_2O$ (10 mL) and extracted with EtOAc (3×5 mL). The combined organic layers were washed with brine (10 mL), dried over anhydrous $Na_2SO_4$, filtered and concentrated under reduced pressure to provide a residue, The residue was purified by prep-TLC (SiO2, PE:EtOAc=5:1) to provide tert-butyl 2-[(6,6-difluoro-3-bicyclo[3.1.0]hexanyl)oxy]acetate.

2-[(6,6-difluoro-3-bicyclo[3.1.0]hexanyl)oxy]acetic acid

To a mixture of tert-butyl 2-[(6,6-difluoro-3-bicyclo [3.1.0]hexanyl)oxy]acetate (80 mg, 0.322 mmol) in DCM (1 mL) was added TFA (0.2 mL) at 0° C., then the mixture was stirred at 40° C. for 2 h. The reaction mixture was concentrated under reduced pressure to provide 2-[(6,6-difluoro-3-bicyclo[3.1.0]hexanyl)oxy]acetic acid.

2-[(6,6-difluoro-3-bicyclo[3.1.0]hexanyl)oxy]-N-[3-[5-[3-cis-(trifluoromethoxy)cyclobutyl]-1,3,4-oxadiazol-2-yl]-1-bicyclo[1.1.1]pentanyl]acetamide To a mixture of 2-[(6,6-difluoro-3-bicyclo[3.1.0]hexanyl)oxy]acetic acid (49.56 mg, 0.257 mmol) in DMF (1 mL) was added HATU (98 mg, 0.257 mmol), after 20 min, DIEA (103 mg, 0.795 mmol) and 1-[5-[3-cis-(trifluoromethoxy)cyclobutyl]-1,3,4-oxadiazol-2-yl]bicyclo[1.1.1]pentan-3-amine HCl salt (70 mg, 0.214 mmol; 8:1 to 10:1 ratio of cis- to trans-) was added to the mixture, then the mixture was stirred at 25° C. for 12 h. The reaction mixture was diluted with H$_2$O (10 mL) and extracted with EtOAc (3×5 mL). The combined organic layers were washed with brine (10 mL), dried over anhydrous Na$_2$SO$_4$, filtered and concentrated under reduced pressure to provide a residue. The residue was purified by prep-HPLC (neutral) to provide 2-[(6,6-difluoro-3-bicyclo[3.1.0]hexanyl)oxy]-N-[3-[5-[3-cis-(trifluoromethoxy)cyclobutyl]-1,3,4-oxadiazol-2-yl]-1-bicyclo[1.1.1]pentanyl]acetamide. LC-MS m/z:=464.4 [M+H]$^+$. $^1$H-NMR (400 MHz, CDCl$_3$): δ 6.98 (br s, 1H), 6.89 (s, 1H), 4.70 (quin, =7.53 Hz, 1H), 4.23 (quin, J=6.90 Hz, 1H), 3.91-4.06 (m, 1H), 3.91-4.06 (m, 1H), 3.85 (d, J=4.02 Hz, 2H), 3.24-3.40 (m, 1H), 2.80-2.94 (m, 2H), 2.65-2.75 (m, 2H), 2.61 (d, J=2.51 Hz, 6H), 2.26-2.47 (m, 2H), 1.95-2.06 (m, 2H), 1.85 (br dd, J=14.12, 5.84 Hz, 1H).

Examples 84 and 85

2-(4-chloro-3-fluoro-phenoxy)-N-[3-[5-[2-trans-(difluoromethyl)cyclopropyl]-1,3,4-oxadiazol-2-yl]-1-bicyclo[1.1.1]pentanyl]acetamide and 2-(4-chloro-3-fluoro-phenoxy)-N-[3-[5-[2-cis-(difluoromethyl)cyclopropyl]-1,3,4-oxadiazol-2-yl]-1-bicyclo[1.1.1]pentanyl]acetamide

Ethyl 2-(difluoromethyl)cyclopropanecarboxylate

To a solution of ethyl 2-formylcyclopropanecarboxylate (2.0 g, 14.1 mmol) in DCM (6 mL) was added a solution of BAST (5.29 g, 23.92 mmol) in DCM (4 mL) at 0° C. and the mixture was stirred at 25° C. for 12 h. The reaction mixture was diluted with sat. NaHCO$_3$ (30 mL) at 0° C., and then was extracted with EtOAc (3×10 mL). The combined organic layers were washed with brine (5 mL), dried over anhydrous Na$_2$SO$_4$, filtered and concentrated under reduced pressure to provide ethyl 2-(difluoromethyl)cyclopropanecarboxylate (cis:trans=1:2).

2-(difluoromethyl)cyclopropanecarboxylic acid

To a solution of ethyl 2-(difluoromethyl)cyclopropanecarboxylate (1.8 g, 10.97 mmol) in THF (20 mL) and H$_2$O (20 mL) was added LiOH·H$_2$O (1.38 g, 32.90 mmol) at 0° C. and the mixture was stirred at 25° C. for 2 h. The reaction mixture was concentrated under reduced pressure, the residue was diluted with H$_2$O (20 mL) and extracted with MTBE (3×10 mL). The aqueous phase was adjusted to pH=1-2 by addition of 2 N HCl at 0° C. and was extracted with DCM:MeOH (7×10 mL, v:v=10:1). The combined organic layers were dried over anhydrous Na$_2$SO$_4$, filtered and concentrated under reduced pressure to provide 2-(difluoromethyl)cyclopropanecarboxylic acid (crude, cis:trans=1:2).

2-(4-chloro-3-fluorophenoxy)-N-(3-(2-(2-(difluoromethyl)cyclopropanecarbonyl)hydrazinecarbonyl)bicyclo[1.1.1]pentan-1-yl)acetamide To a solution of 2-(difluoromethyl)cyclopropanecarboxylic acid (399 mg, 2.93 mmol) and 2-(4-chloro-3-fluorophenoxy)-N-[1-(hydrazinecarbonyl)-3-bicyclo[1.1.1]pentanyl]acetamide (800 mg, 2.44 mmol) in DMF (10 mL) was added T3P (6.21 g, 9.76 mmol, 50% in EtOAc) and TEA (988 mg, 9.76 mmol) and the resulting mixture was stirred at 80° C. for 12 h in a sealed tube. The reaction mixture was diluted with sat. NaHCO$_3$ (20 mL) at 0° C., additional H$_2$O (20 mL) and EtOAc (20 mL). The layers were separated and the aqueous layer was extracted with EtOAc (3×20 mL). The combined organic layers were washed with H$_2$O (3×10 mL), dried over anhydrous Na$_2$SO$_4$, filtered and concentrated under reduced pressure. The crude reaction mixture was purified by silica gel column chromatography (PE:EtOAc=20:1 to 0:1) to provide 2-(4-chloro-3-fluoro-phenoxy)-N-[1-[[[2-(difluoromethyl)cyclopropanecarbonyl]amino]carbamoyl]-3-bicyclo[1.1.1]pentanyl]acetamide (cis:trans=1:2). LC-MS m/z:=446.0 [M+H]$^+$.

2-(4-chloro-3-fluoro-phenoxy)-N-[3-[5-[2-trans-(difluoromethyl)cyclopropyl]-1,3,4-oxadiazol-2-yl]-1-bicyclo[1.1.1]pentanyl]acetamide and 2-(4-chloro-3-fluoro-phenoxy)-N-[3-[5-[2-cis-(difluoromethyl)cyclopropyl]-1,3,4-oxadiazol-2-yl]4-bicyclo[1.1.1]pentanyl]acetamide To a solution of 2-(4-chloro-3-fluoro-phenoxy)-N-[1-[[[2-(difluoromethyl)cyclopropanecarbonyl]amino]carbamoyl]-3-bicyclo[1.1.1]pentanyl]acetamide (300 mg, 0.67 mmol) in DCM (5 mL) was added TEA (136 mg, 1.35 mmol), followed by TsCl (128 mg, 0.67 mmol) and the resulting mixture was stirred at 25° C. for 3 h. The reaction mixture was diluted with sat. NaHCO$_3$ (10 mL) at 0° C., and was extracted with EtOAc (3×10 mL). The combined organic layers were washed with brine (5 mL), dried over anhydrous Na$_2$SO$_4$, filtered and concentrated under reduced pressure. The residue was purified by prep-HPLC to provide the desired product (cis:trans=1:2 in NMR), which was separated by SFC (mobile phase: A: CO$_2$, B: 0.1% NH$_4$OH in MeOH) to provide:

2-(4-chloro-3-fluoro-phenoxy)-N-[3-[5-[trans-2-(difluoromethyl)cyclopropyl]-1,3,4-oxadiazol-2-yl]-1-bicyclo[1.1.1]pentanyl]acetamide as the first eluting isomer. $^1$H-NMR (400 MHz, MeOD): δ 7.38 (t, J=8.82 Hz, 1H), 6.94 (dd, J=11.03, 2.87 Hz, 1H), 6.83 (ddd, J=8.99, 2.81, 1.21 Hz, 1H), 5.71-6.05 (m, 1H), 4.50 (s, 2H), 2.57 (s, 6H), 2.49 (dt, J=8.71, 5.35 Hz, 1H), 2.01-2.17 (m, 1H), 1.38-1.50 (m, 2H). LC-MS m/z:=428.1 [M+H]$^+$.

2-(4-chloro-3-fluoro-phenoxy)-N-[3-[5-[cis-2-(difluoromethyl)cyclopropyl]-1,3,4-oxadiazol-2-yl]-1-bicyclo[1.1.1]pentanyl]acetamide as the second eluting isomer. $^1$H-NMR (400 MHz, MeOD): δ 7.39 (t, J=8.71 Hz, 1H), 6.95 (dd, J=10.91, 2.76 Hz, 1H), 6.83 (ddd, J=8.93, 2.87, 1.21 Hz, 1H), 5.52-5.87 (m, 1H), 4.50 (s, 2H), 2.58 (s, 6H), 2.49-2.56 (m, 1H), 1.95-2.09 (m, 1H), 1.48-1.60 (m, 2H). LC-MS m/z:=428.1 [M+H]$^+$

Examples 86 and 87

2-(4-chlorophenoxy)-N-[3-[5-[3-cis-(trifluoromethoxymethyl)cyclobutyl]-1,3,4-oxadiazol-2-yl]-1-bicyclo[1.1.1]pentanyl]acetamide and 2-(4-chlorophenoxy)-N-[3-[5-[3-trans-(trifluoromethoxymethyl)cyclobutyl]-1,3,4-oxadiazol-2-yl]-bicyclo[1.1.1]pentanyl]acetamide Methyl 3-(hydroxymethyl)cyclobutanecarboxylate A mixture of 3-(hydroxymethyl)cyclobutanecarbonitrile (1.0 g, 9.00 mmol), concentrated HCl (12 M, 6 mL) and MeOH (6 mL) was stirred at 85° C. for 15 h. The reaction mixture was adjusted to pH=7 by addition of sat. NaHCO$_3$ and was then extracted with EtOAc (3×20 mL). The combined organic layers were washed with brine (30 mL), dried over anhydrous Na$_2$SO$_4$, filtered and concentrated under reduced pressure to provide methyl 3-(hydroxymethyl)cyclobutanecarboxylate.

Methyl 3-((trifluoromethoxy)methyl)cyclobutanecarboxylate

To a mixture of AgOTf (4.28 g, 16.65 mmol), 1-(chloromethyl)-4-fluoro-1,4-diazoniabicyclo[2.2.2]octane;ditetrafluoroborate (2.95 g, 8.32 mmol) and KF (1.29 g, 22.20 mmol) in EtOAc (20 mL) was added methyl 3-(hydroxymethyl)cyclobutanecarboxylate (0.8 g, 5.55 mmol), 2-fluoropyridine (1.62 g, 16.65 mmol) and TMSCF$_3$ (2.37 g, 16.65 mmol). The mixture was stirred at 25° C. for 15 h, and was filtered and concentrated under reduced pressure to provide a residue. The residue was purified by silica gel column chromatography (PE:MTBE=1:0 to 10:1) to provide methyl 3-(trifluoromethoxymethyl)cyclobutanecarboxylate.

3-((trifluoromethoxy)methyl)cyclobutanecarboxylic acid

To a solution of cis-methyl 3-(trifluoromethoxymethyl)cyclobutanecarboxylate (330 mg, 1.56 mmol) in THF (5 mL) and H$_2$O (5 mL) was added LiOH·H$_2$O (195.79 mg, 4.67 mmol). The mixture was stirred at 25° C. for 2 h. The mixture was concentrated under reduced pressure to provide a residue. To the residue was added H$_2$O (60 mL), then extracted with MTBE (3×20 mL). The water layers were adjusted to pH=1 with HCl (2 M), then extracted with DCM:MeOH (3×20 mL, v:v=10:1), washed with brine (20 mL), dried over anhydrous Na$_2$SO$_4$, filtered and concentrated under reduced pressure to provide 3-(trifluoromethoxymethyl)cyclobutanecarboxylic acid.

2-(4-chlorophenoxy)-N-(3-(hydrazinecarbonyl)bicyclo[1.1.1]pentan-1-yl)acetamide

To a mixture of methyl 3-[[2-(4-chlorophenoxy)acetyl]amino]bicyclo[1.1.1]pentane-1-carboxylate (1.0 g, 3.23 mmol) in EtOH (30 mL) was added hydrazine hydrate (1.65 g, 32.3 mmol) at 0° C. and the mixture was stirred at 80° C. for 5 h. The reaction mixture was concentrated under reduced pressure to provide 2-(4-chlorophenoxy)-N-[1-(hydrazinecarbonyl)-3-bicyclo[1.1.1] pentanyl] acetamide. LC-MS m/z:=310.1, 312.1 [M+H]$^+$.

2-(4-chlorophenoxy)-N-(3-(2-(3-((trifluoromethoxy)methyl)cyclobutanecarbonyl)hydrazinecarbonyl)bicyclo[1.1.1]pentan-1-yl)acetamide A mixture of 2-(4-chlorophenoxy)-N-[1-(hydrazinecarbonyl)-3-bicyclo[1.1.1]pentanyl]acetamide (200 mg, 0.645 mmol), 3-(trifluoromethoxymethyl)cyclobutanecarboxylic acid (128 mg, 0.645 mmol), T3P (1.64 g, 2.58 mmol, 50% in EtOAc) and TEA (261.35 mg, 2.58 mmol) in EtOAc (3 mL) was stirred at 25° C. for 15 h. The reaction mixture was diluted with sat. NaHCO$_3$ (30 mL) at 0° C. and EtOAc (10 mL). The layers were separated and the aqueous layer was extracted with EtOAc (3×10 mL). The combined organic layers were washed with brine (2×20 mL), dried over anhydrous Na$_2$SO$_4$, filtered and concentrated under reduced pressure to provide a residue which was purified by silica gel column chromatography (PE:EtOAc=1:0 to 0:1) to provide 2-(4-chlorophenoxy)-N-[1-[[[3-(trifluoromethoxymethyl)cyclobutanecarbonyl]amino]carbamoyl]-3-bicyclo[1.1.1]pentanyl]acetamide. LC/MS m/z=490.1, 492.0 [M+H]$^+$.

2-(4-chlorophenoxy)-N-[3-[5-[3-cis-(trifluoromethoxymethyl)cyclobutyl]-1,3,4-oxadiazol-2-yl]-1-bicyclo[1.1.1]pentanyl]acetamide and 2-(4-chlorophenoxy)-N-[3-[5-[3-trans-(trifluoromethoxymethyl)cyclobutyl]-1,3,4-oxadiazol-2-yl]-1-bicyclo[1.1.1]pentanyl]acetamide A mixture of 2-(4-chlorophenoxy)-N-[1-[[[3-(trifluoromethoxymethyl)cyclobutanecarbonyl]amino]carbamoyl]-3-bicyclo[1.1.1]pentanyl]acetamide (0.2 g, 0.408 mmol) and POCl$_3$ (313.00 mg, 2.04 mmol) in 1,4-dioxane (6 mL) was stirred at 100° C. for 1 h. The reaction mixture was diluted with sat.NH$_4$CO$_3$ (10 mL) and EtOAc (10 mL), the layers were separated and the aqueous layer was extracted with EtOAc (3×10 mL). The combined organic layers were washed with brine (10 mL), dried over anhydrous Na$_2$SO$_4$, filtered and concentrated under reduced pressure to provide a residue which was purified by silica gel chromatography column (PE:MTBE=1:0 to 0:1) followed by SFC to provide:

2-(4-chlorophenoxy)-N-[3-[5-[3-cis-(trifluoromethoxymethyl)cyclobutyl]-1,3,4-oxadiazol-2-yl]-1-bicyclo[1.1.1]pentanyl]acetamide: $^1$H-NMR (400 MHz, CDCl$_3$): δ 7.32-7.27 (m, 2H), 7.03 (s, 1H), 6.90-6.84 (m, 2H), 4.42 (s, 2H), 3.98 (d, J=6.2 Hz, 2H), 3.64 (quin, J=8.9 Hz, 1H). 2.83-2.72 (m, 1H), 2.64 (s, 6H), 2.61-2.51 (m, 2H), 2.33-2.22 (m, 2H). LC-MS m/z:=472.3 [M+H]$^+$.

2-(4-chlorophenoxy)-N-[3-[5-[3-trans-(trifluoromethoxymethyl)cyclobutyl]-1,3,4-oxadiazol-2-yl]-1-bicyclo[1.1.1]pentanyl]acetamide: $^1$H-NMR (400 MHz, CDCl$_3$): δ 7.45-7.27 (m, 2H), 7.02 (s, 1H), 6.90-6.81 (m, 2H), 4.43 (s, 2H), 4.05 (d, J=6.2 Hz, 2H), 3.71 (dtt, J=1.1, 6.5, 9.3 Hz, 1H), 2.96-2.82 (m, 1H), 2.66-2.63 (m, 6H), 2.63-2.55 (m, 2H), 2.42-2.33 (m, 2H). LC-MS m/z:=472.3 [M+H]$^+$.

Example 88

[3-cis-(trifluoromethoxy)cyclobutyl]methyl N-[3-[5-[3-cis-(trifluoromethoxy)cyclobutyl]-1,3,4-oxadiazol-2-yl]-1-bicyclo[1.1.1]pentanyl]carbamate (cis-3-(trifluoromethoxy)cyclobutyl)methanol To a solution of LiAlH$_4$ (96 mg, 2.52 mmol) in THF (5 mL) was added methyl 3-cis-(trifluoromethoxy)cyclobutanecarboxylate (0.5 g, 2.52 mmol) at 0° C., and the mixture was stirred at 0° C. for 1 h. The mixture was diluted with sat. NH$_4$Cl (5 mL) and stirred for 30 min. EtOAc was added and the layers were separated. The aqueous layer was extracted with EtOAc (3×5 mL), the combined organic layers were washed with brine (5 mL), dried over anhydrous Na$_2$SO$_4$, filtered and concentrated under reduced pressure to provide (cis-3-(trifluoromethoxy)cyclobutyl)methanol.

4-nitrophenyl((3-cis-(trifluoromethoxy)cyclobutyl)methyl)carbonate

To a mixture of (3-cis-(trifluoromethoxy)cyclobutyl)methanol (300 mg, 1.76 mmol) in DCM (10 mL) was added 4-nitrophenyl carbonochloridate (462 mg, 2.29 mmol) and DMAP (2.15 mg, 0.02 mmol) at 20° C. After 30 min, DIPEA (0.31 mL, 1.76 mmol) was added, the mixture was stirred at 20° C. for 12 h. The reaction mixture was quenched by water (10 mL) and stirred for 30 min then extracted with DCM (3×10 mL), the combined organic layers were washed with brine (10 mL), dried over anhydrous $Na_2SO_4$ and concentrated under reduced pressure to provide a residue, which was purified by prep-TLC (PE:EtOAc=5:1) to provide 4-nitrophenyl ((3-cis-(trifluoromethoxy)cyclobutyl)methyl) carbonate.

[3-cis-(trifluoromethoxy)cyclobutyl]methyl N-[3-[5-[3-cis-(trifluoromethoxy)cyclobutyl]-1,3,4-oxadiazol-2-yl]-1-bicyclo[1.1.1]pentanyl]carbamate To a solution of 3-(5-(3-cis-(trifluoromethoxy)cyclobutyl)-1,3,4-oxadiazol-2-yl)bicyclo[1.1.1]pentan-1-amine (60 mg, 0.21 mmol; 8:1 to 10:1 ratio of cis- to trans-) in DCM (3 mL) was added 4-nitrophenyl ((cis-3-(trifluoromethoxy)cyclobutyl)methyl) carbonate (70 mg, 0.21 mmol), $Et_3N$ (58 uL, 0.41 mmol) and DMAP (0.25 mg, 0.002 mmol) and the mixture was stirred at 25° C. for 12 h. The reaction mixture was poured into ice-water (5 mL), and was extracted with EtOAc (3×5 mL). The combined organic phases were washed with brine (5 mL), dried over anhydrous $Na_2SO_4$ and concentrated under reduced pressure to provide a residue, which was purified by prep-HPLC (neutral) to provide [3-cis-(trifluoromethoxy)cyclobutyl]methyl N-[3-[5-[3-cis-(trifluoromethoxy)cyclobutyl]-1,3,4-oxadiazol-2-yl]-1-bicyclo[1.1.1]pentanyl]carbamate. $^1$H-NMR (400 MHz, $CDCl_3$): δ 7.01 (br s, 1H), 4.70 (quin, J=7.6 Hz, 1H), 3.85 (s, 2H), 3.32 (tt, J=7.7, 10.2 Hz, 1H), 2.91-2.82 (m, 2H), 2.73-2.64 (m, 2H), 2.62 (s, 6H). LC-MS m/z: =486.2 $[M+H]^+$.

Example 89

N-[3-[5-[3-cis-(trifluoromethoxy)cyclobutyl]-1,3,4-oxadiazol-2-yl]-1-bicyclo[1.1.1]pentanyl]-2-[3-cis-(trifluoromethoxymethyl)cyclobutoxy]acetamide cis-methyl 3-(2-(tert-butoxy)-2-oxoethoxy)cyclobutanecarboxylate To a mixture of cis-methyl 3-hydroxycyclobutanecarboxylate (10.0 g. 76.84 mmol) in THF (120 mL) was added NaH (3.07 g, 76.84 mmol, 60% in mineral oil) at 0° C. After 30 min, tert-butyl 2-bromoacetate (14.99 g, 76.84 mmol) solution in THF (50 mL) was added dropwise at 0° C. The reaction mixture was warmed to rt and was stirred at 25° C. for 1.5 h at which point sat. $NH_4Cl$ (150 mL) was added. EtOAc was added (50 mL), the layers were separated, and the aqueous layer was extracted with EtOAc (3×50 mL). The combined organic layers were washed with brine (40 mL), dried over anhydrous $Na_2SO_4$, filtered and concentrated under reduced pressure. The residue was purified by silica gel column chromatography (PE:MTBE=100:1 to 0:1) to provide cis-methyl 3-(2-(tert-butoxy)-2-oxoethoxy)cyclobutanecarboxylate.

tert-butyl 2-(cis-3-(hydroxymethyl)cyclobutoxy)acetate

To a solution of methyl 3-(2-tert-butoxy-2-oxo-ethoxy)cyclobutanecarboxylate (2.0 g, 8.19 mmol) in THF (50 mL) was added lithium tri-tert-butoxyaluminum hydride (1 M, 20.5 mL) at rt and the mixture was warmed to 84° C. for 6 h. The reaction mixture was diluted with sat. $NH_4Cl$ (40 mL) at 0° C., and extracted with EtOAc (3×20 mL). The combined organic layers were washed with water (5 mL), dried over anhydrous $Na_2SO_4$, filtered and concentrated under reduced pressure. The residue was purified by silica gel column chromatography (PE:MTBE=100:1 to 0:1) to provide tert-butyl 2-(cis-3-(hydroxymethyl)cyclobutoxy)acetate.

tert-butyl 2-(cis-3-((trifluoromethoxy)methyl)cyclobutoxy)acetate

A mixture of AgOTf (2.99 g, 11.65 mmol), 1-(chloromethyl)-4-fluoro-1,4-diazoniabicyclo[2.2.2]octane;ditetrafluoroborate (2.06 g, 5.83 mmol), KF (903 mg, 15.54 mmol) and tert-butyl 2-[3-(hydroxymethyl)cyclobutoxy]acetate (0.84 g, 3.88 mmol) was suspended in EtOAc (40 mL) in the dark and, 2-fluoropyridine (1.13 g, 11.65 mmol) and $TMSCF_3$ (1.66 g, 11.65 mmol) were added. The reaction mixture was stirred at 25° C. for 12 h using a water bath to maintain an inner temperature below 30° C. The reaction mixture was filtered through a plug of silica washing with EtOAc. The filtrate was concentrated under reduced pressure at 20° C. and the residue was purified by silica gel column chromatography (PE:MTBE=1:0 to 0:1) to provide tert-butyl 2-(cis-3-((trifluoromethoxy)methyl)cyclobutoxy)acetate.

2-(cis-3-((trifluoromethoxy)methyl)cyclobutoxy)acetic acid

To a solution of tert-butyl 2-[3-(trifluoromethoxymethyl)cyclobutoxy]acetate (210 mg, 0.74 mmol) in DCM (5 mL) was added TFA (640 mg, 5.61 mmol) at 25° C. The mixture was stirred at 40° C. for 2 h. The reaction mixture was filtered and concentrated under reduced pressure to provide 2-(cis-3-((trifluoromethoxy)methyl)cyclobutoxy)acetic acid.

N-[3-[5-[3-cis-(trifluoromethoxy)cyclobutyl]-1,3,4-oxadiazol-2-yl]-1-bicyclo[1.1.1]pentanyl]-2-[3-cis-(trifluoromethoxymethyl)cyclobutoxy]acetamide To a solution of 2-(cis-3-((trifluoromethoxy)methyl)cyclobutoxy)acetic acid (90 mg, 0.39 mmol) in DMF (3 mL) was added HATU (150 mg, 0.39 mmol) at 0° C. The mixture was stirred for 30 min, and 3-(5-(3-cis-(trifluoromethoxy)cyclobutyl)-1,3,4-oxadiazol-2-yl)bicyclo[1.1.1]pentan-1-amine HCl salt (107 mg, 0.33 mmol; 8:1 to 10:1 ratio of cis- to trans-) and DIEA (157 mg, 1.22 mmol) were added. The reaction mixture was allowed to warm to rt and was stirred for 6 h at which point $H_2O$ (10 mL) was added followed by EtOAc (5 mL). The layers were separated, and the aqueous layer was extracted with EtOAc (3×5 mL). The combined organic layers were washed with $H_2O$ (3×3 mL) and brine (3×3 mL), dried over anhydrous $Na_2SO_4$, filtered and concentrated under reduced pressure. The residue was purified by prep-HPLC (TFA) to provide N-[3-[5-[3-cis-(trifluoromethoxy)cyclobutyl]-1,3,4-oxadiazol-2-yl]-1-bicyclo[1.1.1]pentanyl]-2-[3-cis-(trifluoromethoxymethyl)cyclobutoxy]acetamide $^1$H-NMR (400 MHz, CDCl$_3$): δ 6.95 (s, 1H), 4.71 (quin, J=7.61 Hz, 1H), 4.13 (t, J=6.50 Hz, 1H), 3.90-4.00 (m, 3H), 3.82 (s, 2H), 3.81 (s, 1H), 3.32 (tt, J=10.14, 7.72 Hz, 1H), 2.80-2.92 (m, 2H), 2.64-2.74 (m, 2H), 2.63 (s, 6H), 2.39-2.48 (m, 2H), 2.17-2.29 (m, 1H), 1.78-1.88 (m, 2H). LC-MS m/z:=500.4 [M+H]$^+$.

Examples 90 and 91

2-[cis-3-(trifluoromethoxy)cyclobutoxy]-N-[3-[5-[cis-2-(trifluoromethoxymethyl)cyclopropyl]-1,3,4-oxadiazol-2-yl]-1-bicyclo[1.1.1]pentanyl]acetamide and 2-[3-cis-(trifluoromethoxy)cyclobutoxy]-N-[3-[5-[2-trans-(trifluoromethoxymethyl)cyclopropyl]-1,3,4-oxadiazol-2-yl]-1-bicyclo[1.1.1]pentanyl]acetamide Methyl 3-(2-(cis-3-(trifluoromethoxy)cyclobutoxy)acetamido)bicyclo[1.1.1]pentane-1-carboxylate A mixture of 2-(3-cis-(trifluoromethoxy)cyclobutoxy)acetic acid (1.59 g, 7.43 mmol) and HATU (2.83 g, 7.43 mmol) in DMF (10 mL) was stirred for 30 min at 0° C., at which point methyl 3-aminobicyclo[1.1.1]pentane-1-carboxylate HCl salt (1.1 g, 6.19 mmol) and DIPEA (2.96 g, 22.91 mmol) were added. The reaction mixture was stirred at 25° C. for 12 h and was diluted with H$_2$O (50 mL) and EtOAc (20 mL). The layers were separated, and the aqueous layer was extracted with EtOAc (3×20 mL). The combined organic layers were washed with H$_2$O (3×5 mL), brine (3×5 mL), dried over anhydrous Na$_2$SO$_4$, filtered and concentrated under reduced pressure. The residue was purified by silica gel column chromatography (PE:EtAc=100:1 to 0:1) to provide 3-(2-(cis-3-(trifluoromethoxy)cyclobutoxy)acetamido)bicyclo[1.1.1]pentane-1-carboxylate.

N-(3-(hydrazinecarbonyl)bicyclo[1.1.1]pentan-1-yl)-2-(cis-3-(trifluoromethoxy)cyclobutoxy)acetamide To a solution of 3-(2-(cis-3-(trifluoromethoxy)cyclobutoxy)acetamido)bicyclo[1.1.1]pentane-1-carboxylate (500 mg, 1.48 mmol) in 1,4-dioxane (10 mL) was added hydrazine hydrate (742.10 mg, 14.82 mmol) and the mixture was stirred at 80° C. for 12 h. The reaction mixture was concentrated under reduced pressure, diluted with H$_2$O (5 mL) and extracted with EtOAc (3×5 mL). The combined organic layers were washed with brine (3 mL), dried over anhydrous Na$_2$SO$_4$, filtered and concentrated under reduced pressure to provide N-(3-(hydrazinecarbonyl)bicyclo[1.1.1]pentan-1-yl)-2-(cis-3-(trifluoromethoxy)cyclobutoxy)acetamide.

2-(cis-3-(trifluoromethoxy)cyclobutoxy)-N-(3-(2-(trans-2-((trifluoromethoxy)methyl)cyclopropanecarbonyl)hydrazinecarbonyl)bicyclo[1.1.1]pentan-1-yl)acetamide To a solution of N-(3-(hydrazinecarbonyl)bicyclo[1.1.1]pentan-1-yl)-2-(cis-3-(trifluoromethoxy)cyclobutoxy)acetamide (100 mg, 0.30 mmol) and trans-2-((trifluoromethoxy)methyl)cyclopropanecarboxylic acid (55 mg, 0.30 mmol; 1:5 ratio of cis- to trans-) in EtOAc (3 mL) was added T3P (755 mg, 1.19 mmol, 50% in EtOAc) and TEA (120 mg, 1.19 mmol), and the mixture was stirred at 25° C. for 12 h. The reaction mixture was diluted with sat. NaHCO$_3$ (10 mL) and EtOAc (10 mL). The layers were separated, and the aqueous layer was extracted with EtOAc (3×10 mL). The combined organic layers were washed with brine (5 mL), dried over anhydrous Na$_2$SO$_4$, filtered and concentrated under reduced pressure to provide 2-(cis-3-(trifluoromethoxy)cyclobutoxy)-N-(3-(2-(trans-2-((trifluoromethoxy)methyl)cyclopropanecarbonyl)hydrazinecarbonyl)bicyclo[1.1.1]pentan-1-yl)acetamide as a mixture of diastereomers. The crude reaction mixture was used in the next step without further purification. LC-MS m/z:=504.2 [M+H]$^+$.

2-[3-cis-(trifluoromethoxy)cyclobutoxy]-N-[3-[5-[2-trans-(trifluoromethoxymethyl)cyclopropyl]-1,3,4-oxadiazol-2-yl]-1-bicyclo[1.1.1]pentanyl]acetamide To a solution of 2-(cis-3-(trifluoromethoxy)cyclobutoxy)-N-(3-(2-(trans-2-((trifluoromethoxy)methyl)cyclopropanecarbonyl)hydrazinecarbonyl)bicyclo[1.1.1]pentan-1-yl)acetamide (0.14 g, 0.28 mmol) and DIPEA (180 mg, 1.39 mmol) in CH$_3$CN (5 mL) was added TsCl (106 mg, 0.56 mmol) and the mixture was stirred at 50° C. for 12 h. The reaction mixture was diluted with sat. NaHCO$_3$ (10 mL) at 0° C., and then extracted with EtOAc (3×10 mL). The combined organic layers were washed with brine (5 mL), dried over anhydrous Na$_2$SO$_4$, filtered and concentrated under reduced pressure. The residue was purified by prep-HPLC (Nano-micro Kromasil C18 100 mm×30 mm, 5 μm; mobile phase: A: 0.1% TFA in water, B: MeCN, gradient: B % in A: 45%-65% over 10 min and further separated by SFC (Chiralpak TC 250 mm×30 mm, 5 μm, 40° C.; mobile phase: A: CO$_2$, B: 0.1% NH$_4$OH in i-PrOH, gradient: B % in A: 20%-20% over 5 min, Flow: 65 g/min, Pressure 100 bar):

2-[cis-3-(trifluoromethoxy)cyclobutoxy]-N-[3-[5-[cis-2-(trifluoromethoxymethyl)cyclopropyl]-1,3,4-oxadiazol-2-yl]-1-bicyclo[1.1.1]pentanyl]acetamide as the first eluting isomer from SFC. $^1$H-NMR (400 MHz, MeOD): δ 4.34-4.45 (m, 2H), 3.84 (s, 2H), 3.72-3.82 (m, 2H), 2.81 (dtd, J=9.62, 6.49, 6.49, 3.20 Hz, 2H), 2.55 (s, 6H), 2.49 (td, J=8.32, 6.06 Hz, 1H), 2.19-2.30 (m, 2H), 1.88-1.99 (m, 1H), 1.49 (td, J=8.49, 5.51 Hz, 1H), 1.27-1.35 (m, 2H). LC-MS m/z:=486.2 [M+H]$^+$.

2-[cis-3-(trifluoromethoxy)cyclobutoxy]-N-[3-[5-[trans-2-(trifluoromethoxymethyl)cyclopropyl]-1,3,4-oxadiazol-2-yl]-1-bicyclo[1.1.1]pentanyl]acetamide as the second eluting isomer from SFC. $^1$H-NMR (400 MHz, MeOD): δ 4.42 (quin, J=7.17 Hz, 1H), 4.14 (dd, J=10.91, 6.50 Hz, 1H), 4.00 (dd, J=11.03, 7.50 Hz, 1H), 3.84 (s, 2H), 3.76 (quin, J=6.89 Hz, 1H), 2.80 (dtd, J=9.73, 6.55, 6.55, 3.20 Hz, 2H), 2.55 (s, 6H), 2.19-2.34 (m, 3H), 1.92 (dq, J=13.37, 6.64 Hz, 1H), 1.42 (dt, =8.88, 5.26 Hz, 1H), 1.24-1.33 (m, 2H). LC-MS m/z:=486.2 [M+H]$^+$.

Example 92

2-(3-chlorophenoxy)-N-[3-[5-[3-cis-(trifluoromethoxy)cyclobutyl]-1,3,4-oxadiazol-2-yl]-1-bicyclo[1.1.1]pentanyl]acetamide To a solution of 2-(3-chlorophenoxy)acetic acid (69 mg, 0.37 mmol) in DMF (2 mL) was added HATU (140 mg, 0.37 mmol) at 0° C. under N$_2$. The mixture was stirred for 30 min at 0° C., and then cis-1-[5-[3-cis-(trifluoromethoxy)cyclobutyl]-1,3,4-oxadiazol-2-yl]bicyclo[1.1.1]pentan-3-amine HCl salt (100 mg, 0.31 mmol; 8:1 to 10:1 ratio of cis- to trans-) and DIEA (147 mg, 1.14 mmol) were added to the solution at 0° C. After addition, the mixture was stirred at 16° C. for 14 h. The reaction mixture was quenched by H$_2$O (8 mL) at 0° C. and then extracted with EtOAc (3×5 mL). The combined organic layers were washed with H$_2$O (3×3 mL) and brine (3×3 mL), dried over anhydrous Na$_2$SO$_4$, filtered, and concentrated under reduced pressure. The crude reaction mixture was purified employing reverse-phase HPLC. LC-MS, m/z=458.3 [M+H]$^+$. $^1$H-NMR (400 MHz, CDCl$_3$): δ 7.25 (s, 1H), 7.05 (dt, J=7.99, 0.96 Hz, 1H), 7.01-6.94 (m, 2H), 6.83 (dd, J=8.27, 2.54 Hz, 1H), 4.71 (quin, J=7.61 Hz, 1H), 4.45 (s, 2H), 3.33 (tt, J=10.17, 7.80 Hz, 1H), 2.94-2.81 (m, 2H), 2.74-2.67 (m, 2H), 2.66 (s, 6H).

Example 93

2-(4-chloro-3-fluoro-phenoxy)-N-[3-[5-[3-fluoro-1-(2,2,2-trifluoroethyl)azetidin-3-yl]-1,3,4-oxadiazol-2-yl]-1-bicyclo[1.1.1]pentanyl]acetamide tert-butyl 3-(2-(3-(2-(4-chloro-3-fluorophenoxy) acetamido)bicyclo[1.1.1]pentane-1-carbonyl)hydrazinecarbonyl)-3-fluoroazetidine-1-carboxylate A solution of 2-(4-chloro-3-fluoro-phenoxy)-N-[1-(hydrazinecarbonyl)-3-bicyclo[1.1.1]pentanyl]acetamide (300 mg, 0.92 mmol), 1-tert-butoxycarbonyl-3-fluoro-azetidine-3-carboxylic acid (200 mg, 0.92 mmol), and NEt$_3$ (370 mg, 3.66 mmol) were suspended in EtOAc (10 mL) and T3P (2.33 g, 3.66 mmol) was added. The resulting reaction mixture was stirred at 16° C. for 24 h. The reaction mixture was quenched by sat. NaHCO$_3$ (30 mL) and then extracted with EtOAc (3×10 mL). The combined organic layers were washed with brine (10 mL), dried over anhydrous Na$_2$SO$_4$, filtered, and concentrated under reduced pressure to provide a residue. The residue was purified by silica gel column chromatography. LC-MS: m/z=529.1 [M+H]$^+$.

tert-butyl 3-(5-(3-(2-(4-chloro-3-fluorophenoxy) acetamido)bicyclo[1.1.1]pentan-1-yl)-1,3,4-oxadiazol-2-yl)-3-fluoroazetidine-1-carboxylate To a solution of tert-butyl 3-(2-(3-(2-(4-chloro-3-fluorophenoxy) acetamido) bicyclo [1.1.1] pentane-1-carbonyl) hydrazinecarbonyl)-3-fluoroazetidine-1-carboxylate (100 mg, 0.19 mmol) in MeCN (6 mL) was added DIEA (122 mg, 0.95 mmol) and tosyl chloride (90 mg, 0.472 mmol). The mixture was stirred at 15° C. for 15 h. The reaction mixture was quenched by the addition of sat. NaHCO$_3$ (30 mL). The mixture was extracted with EtOAc (3×10 mL). The combined organic layers were washed with brine (10 mL), dried over anhydrous Na$_2$SO$_4$, filtered and concentrated under reduced pressure to provide a residue. The residue was purified by silica gel column chromatography. LC-MS: m/z=511.2 [M+H]$^+$.

2-(4-chloro-3-fluorophenoxy)-N-(3-(5-(3-fluoroazetidin-3-yl)-1,3,4-oxadiazol-2-yl)bicyclo[1.1.1]pentan-1-yl)acetamide To a solution of tert-butyl 3-(5-(3-(2-(4-chloro-3-fluorophenoxy)acetamido)bicyclo[1.1.1]pentan-1-yl)-1,3,4-oxadiazol-2-yl)-3-fluoroazetidine-1-carboxylate (90 mg, 0.18 mmol) in DCM (2 mL) was added TFA (616 mg, 5.40 mmol) at 0° C. The mixture was stirred at 15° C. for 2 h. The mixture was concentrated under reduced pressure. LC-MS: m/z=411.1 [M+H]$^+$.

2-(4-chloro-3-fluoro-phenoxy)-N-[3-[5-[3-fluoro-1-(2,2,2-trifluoroethyl)azetidin-3-yl]-1,3,4-oxadiazol-2-yl]-1-bicyclo[1.1.1]pentanyl]acetamide To a mixture of 2-(4-chloro-3-fluorophenoxy)-N-(3-(5-(3-fluoroazetidin-3-yl)-1,3,4-oxadiazol-2-yl)bicyclo[1.1.1] pentan-1-yl)acetamide, TFA salt (140 mg, 0.27 mmol) in THF (6 mL) was added 2,2,2-trifluoroethyl trifluoromethanesulfonate (92 mg, 0.40 mmol) and DIEA (137 mg, 1.07 mmol) at 0° C. The mixture was stirred at 50° C. for 15 h. The reaction mixture was quenched by the addition of H$_2$O (30 mL). The mixture was extracted with EtOAc (3×10 mL). The combined organic layers were washed with brine (20 mL), dried over anhydrous Na$_2$SO$_4$, filtered, and concentrated under reduced pressure. The crude reaction mixture was purified employing reverse-phase HPLC. LC-MS, m/z=493.1 [M+H]$^+$. $^1$H-NMR (400 MHz. CDCl$_3$): δ 7.34 (t. 8.6 Hz, 1H), 6.98 (s, 1H), 6.77 (dd, J=2.8, 10.2 Hz, 1H), 6.69 (td, J=1.4, 8.9 Hz, 1H), 4.43 (s, 2H), 4.19 (dd, J=10.1, 15.6 Hz, 2H), 3.98-3.83 (m, 2H), 3.17 (q, J=9.0 Hz, 2H), 2.76-2.64 (m, 6H).

Example 94

N-[3-[5-[3-cis-(trifluoromethoxy)cyclobutyl]-1,3,4-oxadiazol-2-yl]-1-bicyclo[1.1.1]pentanyl]-2-[2-(trifluoromethoxy)ethoxy]acetamide tert-butyl 2-(2-benzyloxyethoxy)acetate A mixture of 2-benzyloxyethanol (10.0 g, 65.7 mmol), tert-butyl 2-bromoacetate (19.2 g, 98.6 mmol), tetrabutylammonium hydrogen sulfate (1.1 g, 3.3 mmol), and water (5 mL) in toluene (200 mL) was added NaOH (39.4 g, 985.6 mmol) in water (60 mL). The mixture was stirred at 20° C. for 2 h. The reaction mixture was quenched by ice-water (90 mL) and then extracted with MTBE (3×90 mL). The combined organic layers were washed with brine (50 mL), dried over anhydrous Na$_2$SO$_4$, filtered, and concentrated under reduced pressure.

tert-butyl 2-(2-hydroxyethoxy)acetate

To a solution of tert-butyl 2-(2-benzyloxyethoxy)acetate (16.3 g, 61.2 mmol) in MeOH (320 mL) was added Pd/C (2 g, 10% on carbon) under N$_2$. The suspension was degassed under vacuum and purged with H$_2$ three times. The mixture was stirred under H$_2$ (50 psi) at 50° C. for 12 h. The reaction mixture was filtered and concentrated under reduced pressure.

tert-butyl 2-[2-(trifluoromethoxy)ethoxy]acetate

To a reaction flask equipped with a stirring bar and covered with tin foil paper in a water bath, AgOTf (21.9 g, 85.1 mmol), Selectfluor (15.1 g, 42.6 mmol), KF (6.6 g, 113.5 mmol), tert-butyl 2-(2-hydroxyethoxy)acetate (5.0 g, 28.4 mmol), and EtOAc (150 mL) were added at 25° C. under N$_2$. And then 2-fluoropyridine (8.3 g, 85.1 mmol) and TMSCF$_3$ (12.1 g, 85.1 mmol) were added dropwise successively while keeping the inner temperature below 30° C. The reaction mixture was stirred at 25° C. for 14 h. The reaction mixture was filtered through a plug of silica and concentrated under reduced pressure at 20° C. The residue was washed with MTBE (100 mL), and filtered, and the filtrate was washed with 1 N CuSO$_4$ (3×30 mL), brine (20 mL), and then dried over anhydrous Na$_2$SO$_4$, filtered, and concentrated under reduced pressure. The residue was purified by silica gel column chromatography.

2-[2-(trifluoromethoxy)ethoxy]acetic acid

To a solution of tert-butyl 2-[2-(trifluoromethoxy)ethoxy] acetate (4.4 g, 17.9 mmol) in DCM (5 mL) was added TFA (10.1 mL, 136.0 mmol). The mixture was stirred at 40° C. for 2 h. The reaction mixture was concentrated under reduced pressure.

N-[3-[5-[3-cis-(trifluoromethoxy)cyclobutyl]-1,3,4-oxadiazol-2-yl]-1-bicyclo[1.1.1]pentanyl]-2-[2-(trifluoromethoxy)ethoxy]acetamide To a solution of 2-[2-(trifluoromethoxy)ethoxy]acetic acid (69.3 mg, 0.37 mmol) in DMF (2 mL) was added HATU (140 mg, 0.37 mmol) at 0° C. under $N_2$. The mixture was stirred for 30 min at 0° C., and then DIEA (147 mg, 1.14 mmol) and cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (100 mg, 0.31 mmol) was added to the solution at 0° C. The reaction mixture was stirred at 16° C. for 14 h. The reaction mixture was quenched by $H_2O$ (10 mL), and then extracted with EtOAc (3×5 mL). The combined organic layers were washed with $H_2O$ (3×3 mL) and brine (3×3 mL), dried over anhydrous $Na_2SO_4$, filtered, and concentrated under reduced pressure. The crude reaction mixture was purified employing reverse-phase HPLC. LC-MS, m/z=460.4 [M+H]$^1$. $^1$H-NMR (400 MHz, CDCl$_3$): δ 7.05 (br s, 1H), 4.70 (quin, J=7.56 Hz, 1H), 4.20-4.10 (m, 2H), 3.98 (s, 2H), 3.82-3.73 (m, 2H), 3.32 (tt, J=10.15, 7.80 Hz, 1H), 2.86 (dtd, J=9.76, 7.29, 2.89 Hz, 2H), 2.73-2.64 (m, 2H), 2.61 (s, 6H).

Example 95

2-[3-trans-(trifluoromethoxy)cyclobutoxy]-N-[3-[5-[3-cis-(trifluoromethoxy)cyclobutyl]-1,3,4-oxadiazol-2-yl]-1-bicyclo[1.1.1]pentanyl]acetamide trans-[3-(2-tert-butoxy-2-oxo-ethoxy)cyclobutyl]4-nitrobenzoate To a mixture of cis-tert-butyl 2-(3-hydroxycyclobutoxy) acetate (2.0 g, 9.9 mmol) and 4-nitrobenzoic acid (1.8 g, 10.9 mmol) in THF (40 mL) was added PPh$_3$ (3.9 g, 14.8 mmol) at 15° C. under $N_2$. Then DIAD (10.0 g, 49.4 mmol) was added at 0° C. under $N_2$. The reaction mixture was stirred at 15° C. for 15 h. The reaction mixture was quenched with water (30 mL) and extracted with EtOAc (3×10 mL). The combined organics were washed with brine (5 mL), dried over anhydrous $Na_2SO_4$, filtered, and concentrated under reduced pressure. The residue was purified by silica gel column chromatography.

trans-tert-butyl 2-(3-hydroxycyclobutoxy)acetate

To a solution of trans-[3-(2-tert-butoxy-2-oxo-ethoxy) cyclobutyl] 4-nitrobenzoate (1.4 g, 4.0 mmol) in THF (10 mL), $H_2O$ (2 mL), and MeOH (20 mL) was added $K_2CO_3$ (559 mg, 4.0 mmol) at 15° C. under $N_2$. The reaction mixture was stirred at 15° C. for 3 h. The reaction mixture was quenched with water (20 mL) and extracted with EtOAc (3×10 mL). The combined organics were washed with brine (5 mL), dried over anhydrous $Na_2SO_4$, filtered and, concentrated under reduced pressure. The residue was purified by silica gel column chromatography.

trans-tert-butyl 2-[3-(trifluoromethoxy)cyclobutoxy] acetate

To a mixture of AgOTf (1.6 g, 6.2 mmol), Selectfluor (1.1 g, 3.1 mmol) and KF (483 mg, 8.3 mmol) in EtOAc (30 mL) was added trans-tert-butyl 2-(3-hydroxycyclobutoxy)acetate (420 mg, 2.1 mmol) at 15° C. under $N_2$ covered with tin foil. Then 2-fluoropyridine (605 mg, 6.2 mmol) was added to the mixture, followed by TMSCF$_3$ (886 mg, 6.2 mmol) at 15° C. The reaction mixture was stirred at 15° C. for 15 h. The reaction mixture was filtered with silica gel and concentrated under reduced pressure. The residue was purified by silica gel column chromatography.

trans-2-[3-(trifluoromethoxy)cyclobutoxy]acetic acid

To a solution of trans-tert-butyl 2-[3-(trifluoromethoxy) cyclobutoxy]acetate (90 mg, 0.33 mmol) in DCM (5 mL) was added TFA (1.5 g, 13.5 mmol) at 15° C. The mixture was heated to 40° C. and stirred for 1 h. The mixture was concentrated under reduced pressure.

2-[3--trans-(trifluoromethoxy)cyclobutoxy]-N-[3-[5-[3-cis-(trifluoromethoxy)cyclobutyl]-1,3,4-oxadiazol-2-yl]-1-bicyclo[1.1.1]pentanyl]acetamide To a mixture of trans-2-[3-(trifluoromethoxy)cyclobutoxy]acetic acid (72 mg, 0.34 mmol) in DMF (5 mL) was added HATU (128 mg, 0.338 mmol) at 15° C. under $N_2$. The mixture was stirred for 30 min, then cis-1-[5-[3-(trifluoromethoxy)cyclobutyl]-1,3,4-oxadiazol-2-yl]bicyclo[1.1.1] pentan-3-amine hydrochloride (8:1 to 10:1 favoring the cis-diastereomer) (100 mg, 0.31 mmol) and DIEA (159 mg, 1.2 mmol) was added. The reaction mixture was stirred for 2 h. The reaction mixture was quenched with water (30 mL) and extracted with EtOAc (3×10 mL). The combined organics were washed with brine (2×5 mL), dried over anhydrous $Na_2SO_4$, filtered, and concentrated under reduced pressure. The crude reaction mixture was purified employing reverse-phase HPLC. LC-MS, m/z=486.4 [M+H]$^+$. $^1$H-NMR (400 MHz, CDCl$_3$): δ 7.00-6.82 (m, 1H), 4.96-4.84 (m, 1H), 4.71 (quin, J=7.55 Hz, 1H), 4.28-4.20 (m, 1H), 3.89-3.79 (m, 2H), 3.32 (tt, J=10.14, 7.72 Hz, 1H), 2.91-2.81 (m, 2H), 2.75-2.64 (m, 2H), 2.63 (s, 6H), 2.57-2.45 (m, 4H).

Example 96

N-[3-[2-methyl-4-[3-(trifluoromethoxy)cyclobutyl] imidazol-1-yl]-bicyclo[1.1.1]pentanyl]-2-[3-cis-(trifluoromethoxy)cyclobutoxy]acetamide cis-tert-butyl(3-(2-3-(trifluoromethoxy)cyclobutoxy) acetamido)bicyclo[1.1.1]pentan-1-yl)carbamate To a solution of cis-2-[3-(trifluoromethoxy)cyclobutoxy] acetic acid (1.0 g, 4.7 mmol) in DMF (10 mL) was added tert-butyl N-(1-amino-3-bicyclo[1.1.1]pentanyl)carbamate (926 mg, 4.7 mmol), HATU (2.0 g, 5.1 mmol) and DIEA (2.4 mL, 14.0 mmol) at 20° C. The reaction mixture was stirred at 20° C. for 2 h. The reaction mixture was poured into ice-water (50 mL) and extracted with EtOAc (3×50 mL). The combined organics were washed with brine (50 mL), dried over anhydrous Na$_2$SO$_4$, filtered, and concentrated under reduced pressure. The residue was purified by silica gel column chromatography.

cis-N-(3-aminobicyclo[1.1.1]pentan-1-yl)-2-(3-(trifluoromethoxy)cyclobutoxy)acetamide

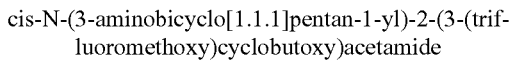

To a solution of cis-tert-butyl N-[1-[[2-[3-(trifluoromethoxy)cyclobutoxy]acetyl]amino]-3-bicyclo[1.1.1]pentanyl]carbamate (500 mg, 1.3 mmol) in EtOAc (10 mL) was added EtOAc/HCl (10 mL). The reaction mixture was stirred at 25° C. for 1 h. The reaction mixture was concentrated under reduced pressure. LC-MS: m/z=295.1 [M+H]$^+$.

cis-N-(3-((2-oxo-2-(3-(trifluoromethoxy)cyclobutyl) ethyl)amino)bicyclo[1.1.1]pentan-1-yl)-2-(3-(trifluoromethoxy)cyclobutoxy)acetamide

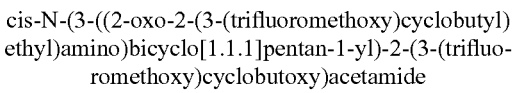

A mixture of 2-bromo-1-(3-(trifluoromethoxy)cyclobutyl)ethanone (1.0 g, 4.0 mmol), cis-N-(3-aminobicyclo[1.1.1]pentan-1-yl)-2-(3-(trifluoromethoxy)cyclobutoxy)acetamide hydrochloride (1.2 g, 3.6 mmol) in CH$_3$CN (10 mL) was added Na$_2$CO$_3$ (1.5 g, 14.5 mmol). The reaction mixture was stirred at 40° C. for 15 h. The reaction mixture was filtered and concentrated under reduced pressure. The residue was purified by silica gel column chromatography. LC-MS: m/z=475.2 [M+H]$^+$.

cis-N-(2-oxo-2-(3-(trifluoromethoxy)cyclobutyl) ethyl)-N-(3-(2-(3-(trifluoromethoxy)cyclobutoxy) acetamido)bicyclo[1.1.1]pentan-1-yl)acetamide

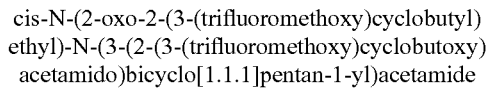

Acetyl chloride (66 mg, 0.83 mmol) was added dropwise to cis-N-(3-((2-oxo-2-(3-(trifluoromethoxy)cyclobutyl) ethyl)amino)bicyclo[1.1.1]pentan-1-yl)-2-(3-(trifluoromethoxy)cyclobutoxy)acetamide (360 mg, 0.76 mmol) and TEA (0.64 mL, 1.9 mmol) in DCM (2 mL) at 0° C. The resulting mixture was stirred at 0° C. for 0.5 h. The reaction mixture was quenched by addition of NaHCO$_3$ (5 mL) at 0° C. and adjusted to pH=8-9 and extracted with EtOAc (3×5 mL). The combined organic layers were washed with brine (5 mL), dried over anhydrous Na$_2$SO$_4$, filtered, and concentrated under reduced pressure. LC-MS: m/z=517.2 [M+H]$^+$.

N-[3-[2-methyl-4-[3-(trifluoromethoxy)cyclobutyl] imidazol-1-yl]-1-bicyclo[1.1.1]pentanyl]-2-[3-cis-(trifluoromethoxy)cyclobutoxy]acetamide

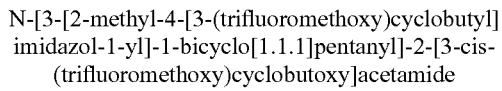

To a solution of cis-N-(2-oxo-2-(3-(trifluoromethoxy)cyclobutyl)ethyl)-N-(3-(2-(3-(trifluoromethoxy)cyclobutoxy) acetamido)bicyclo[1.1.1]pentan-1-yl)acetamide (390 mg, 0.76 mmol) in DMF (0.5 mL) and CH$_3$COOH (4 mL) was added CH$_3$COONH$_4$ (233 mg, 3.0 mmol). The mixture was stirred at 100° C. for 24 h. The reaction mixture was quenched by addition of NaHCO$_3$ at 0° C. to pH=8-9 and extracted with EtOAc (3×10 mL). The combined organic layers were washed with brine (10 mL), dried over anhydrous Na$_2$SO$_4$, filtered, and concentrated under reduced pressure. The crude reaction mixture was purified employing reverse-phase HPLC. LC-MS, m/z=498.4 [M+H]$^+$. $^1$H-NMR (400 MHz, CDCl$_3$): δ 6.91 (s, 1H), 6.58-6.53 (m, 1H), 4.60 (quin, J=7.6 Hz, 1H), 4.34 (quin, J=7.1 Hz, 1H), 3.84 (s, 2H), 3.78-3.70 (m, 1H), 3.00-2.87 (m, 1H), 2.86-2.78 (m, 2H), 2.78-2.66 (m, 2H), 2.66-2.59 (m, 6H), 2.45-2.39 (m, 3H), 2.38-2.19 (m, 4H).

Example 97

2-[(5-chloro-3-pyridyl)methoxy]-N-[3-[5-[3-cis-(trifluoromethoxy)cyclobutyl]-1,3,4-oxadiazol-2-yl]-1-bicyclo[1.1.1]pentanyl]acetamide

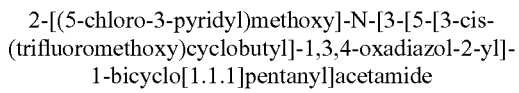

To a mixture of (5-chloro-3-pyridyl)methanol (35 mg, 0.24 mmol) in THF (5.0 mL) was added NaH (13.0 mg, 0.33 mmol, 60% in mineral oil) at 0° C. under N$_2$. The mixture was stirred at 0° C. for 30 min and then 2-bromo-N-[1-[5-[3-cis-(trifluoromethoxy)cyclobutyl]-1,3,4-oxadiazol-2-yl]-3-bicyclo[1.1.1]pentanyl]acetamide (90 mg, 0.22 mmol) was added at 0° C. under N$_2$. The reaction mixture was stirred at 15° C. for 14.5 h. The reaction mixture was quenched by sat. NH$_4$Cl (10 mL) and extracted with EtOAc (3×5 mL). The combined organics were washed with brine (2×3 mL), dried over anhydrous Na$_2$SO$_4$, filtered, and concentrated under reduced pressure. The crude reaction mixture was purified employing reverse-phase HPLC. LC-MS, m/z=473.3 [M+H]$^+$. $^1$H-NMR (400 MHz, CDCl$_3$): δ 8.57 (d, J=2.26 Hz, 1H), 8.48 (d, J=1.38 Hz, 1H), 7.69 (s, 1H), 6.94 (s, 1H), 4.78-4.64 (m, 1H), 4.60 (s, 2H), 3.99 (s, 2H), 3.31 (tt, J=10.12, 7.83 Hz, 1H), 2.86 (dtd, =9.79, 7.31, 7.31, 2.95 Hz, 2H), 2.72-2.65 (m, 2H), 2.61 (s, 6H).

Example 98

5-cyclopropyl-N-[3-[5-[3-cis-(trifluoromethoxy) cyclobutyl]-1,3,4-oxadiazol-2-yl]-1-bicyclo[1.1.1] pentanyl]isoxazole-3-carboxamide

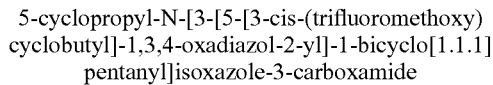

To a mixture of 5-cyclopropylisoxazole-3-carboxylic acid (50 mg, 0.32 mmol) in DMF (1 mL) was added HATU (120 mg, 0.32 mmol) under N$_2$, the mixture was stirred for 30 min, then cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (89 mg, 0.27 mmol) and DIEA (140 mg, 1.1 mmol) were added to the solution at 0° C. The reaction mixture was stirred at 20° C. for 12 h. The reaction mixture was quenched by addition of H$_2$O (10 mL) at 0° C. and extracted with EtOAc (3×10 mL). The combined organic layers were washed with brine (10 mL), dried over anhydrous Na$_2$SO$_4$, filtered, and concentrated under reduced pressure. The crude reaction mixture was purified employing reverse-phase HPLC. LC-MS, m/z=425.3 [M+H]$^+$. $^1$H-NMR (400 MHz, CDCl$_3$): δ 7.25 (s, 1H), 6.32 (s, 1H), 4.71 (quin, J=7.56 Hz, 1H), 3.40-3.26 (m, 1H), 2.94-2.81 (m, 2H), 2.74-2.69 (m, 2H), 2.68 (s, 6H), 2.15-2.03 (m, 1H), 1.19-1.08 (m, 2H), 1.03-0.94 (m, 2H).

Example 99 and 100

(5S)-5-phenyl-N-[3-[5-[3-cis-(trifluoromethoxy) cyclobutyl]-1,3,4-oxadiazol-2-yl]-1-bicyclo[1.1.1] pentanyl]-4,5-dihydroisoxazole-3-carboxamide and (5R)-5-phenyl-N-[3-[5-[3-cis-(trifluoromethoxy) cyclobutyl]-1,3,4-oxadiazol-2-yl]-1-bicyclo[1.1.1] pentanyl]-4,5-dihydroisoxazole-3-carboxamide

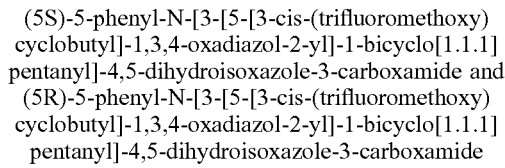

To a mixture of 5-phenyl-4,5-dihydroisoxazole-3-carboxylic acid (71 mg, 0.37 mmol) in DMF (5 mL) was added HATU (141 mg, 0.37 mmol) at 15° C. under N$_2$. The mixture was stirred at 15° C. for 30 min, then cis-1-[5-[3-(trifluoromethoxy)cyclobutyl]-1,3,4-oxadiazol-2-yl]bicyclo[1.1.1] pentan-3-amine hydrochloride (8:1 to 10:1 favoring the cis-diastereomer) (110 mg, 0.34 mmol) and DIEA (87 mg, 0.68 mmol) were added. The reaction mixture was stirred for 2.5 h. The reaction mixture was quenched with water (30 mL) and extracted with EtOAc (3×10 mL). The combined organic phase was washed with brine (3×5 mL), dried over anhydrous $Na_2SO_4$, filtered, and concentrated under reduced pressure. The residue was purified by silica gel column chromatography, which was further separated by SFC to provide:

cis-(R)-5-phenyl-N-(3-(5-(3-(trifluoromethoxy)cyclobutyl)-1,3,4-oxadiazol-2-yl)bicyclo[1.1.1]pentan-1-yl)-4,5-dihydroisoxazole-3-carboxamide (99) (peak 1 in SFC). LC-MS: m/z=463.2 [M+H]$^+$. $^1$H-NMR (400 MHz, $CDCl_3$): δ 7.48-7.29 (m, 5H), 7.18 (br s, 1H), 5.77 (br t, J=9.98 Hz, 1H). 4.81-4.63 (m, 1H), 3.79-3.53 (m, 1H), 3.42-3.19 (m, 2H), 2.86 (br s, 2H), 2.75-2.68 (m, 2H), 2.65 (br s, 6H).

cis-(S)-5-phenyl-N-(3-(5-(3-(trifluoromethoxy)cyclobutyl)-1,3,4-oxadiazol-2-yl)bicyclo[1.1.1]pentan-1-yl)-4,5-dihydroisoxazole-3-carboxamide (100) (peak 2 in SFC). LC-MS: m/z=463.2 [M+H]$^+$. $^1$H-NMR (400 MHz, $CDCl_3$): δ 7.47-7.29 (m, 5H), 7.18 (s, 1H), 5.77 (dd, J=11.29, 8.91 Hz, 1H), 4.71 (quin, J=7.50 Hz, 1H), 3.65 (dd, J=18.01, 11.48 Hz, 1H), 3.42-3.18 (m, 2H), 2.92-2.82 (m, 2H), 2.76-2.68 (m, 2H), 2.66 (s, 6H).

Example 101

N-[3-[5-[3-cis-(trifluoromethoxy)cyclobutyl]-1,3,4-oxadiazol-2-yl]-1-bicyclo[1.1.1]pentanyl]pyrrolo[1,2-c]pyrimidine-3-carboxamide To a mixture of pyrrolo[1,2-c]pyrimidine-3-carboxylic acid (50 mg, 0.31 mmol) in DMF (2 mL) was added HATU (120 mg, 0.31 mmol) under $N_2$, the mixture was stirred for 30 min, then cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (170 mg, 0.59 mmol) and DIEA (130 mg, 1.0 mmol) was added to the solution at 0° C. The reaction mixture was stirred at 20° C. for 12 h. The reaction mixture was quenched by addition of $H_2O$ 10 mL at 0° C. and extracted with EtOAc (3×10 mL). The combined organics were washed with brine (10 mL), dried over anhydrous $Na_2SO_4$, filtered, and concentrated under reduced pressure. The crude reaction mixture was purified employing reverse-phase HPLC. LC-MS: m/z=434.3 [M+H]$^+$. $^1$H-NMR (400 MHz, $CDCl_3$): δ 8.72 (s, 1H), 8.26-8.16 (m, 2H), 7.52 (s, 1H), 7.03-6.95 (m, 1H), 6.76 (d, J=3.89 Hz, 1H), 4.71 (t, J=7.40 Hz, 1H), 3.42-3.29 (m, 1H), 2.86 (br s, 2H), 2.77-2.73 (m, 1H), 2.72 (s, 6H), 2.70-2.64 (m, 1H).

Example 102

(2R,3aR,6aR)-5-(2,2,2-trifluoroethyl)-N-[3-[5-[3-cis-(trifluoromethoxy)cyclobutyl]-1,3,4-oxadiazol-2-yl]-1-bicyclo[1.1.1]pentanyl]-2,3,3a,4,6,6a-hexahydrofuro[2,3-c]pyrrole-2-carboxamide cis-(2R,3aR,6aR)-tert-butyl 2-((3-(5-(3-(trifluoromethoxy)cyclobutyl)-1,3,4-oxadiazol-2-yl)bicyclo[1.1.1]pentan-1-yl)carbamoyl)tetrahydro-2H-furo[2,3-c]pyrrole-5(3H)-carboxylate To a solution of (2R,3aR,6aR)-5-tert-butoxycarbonyl-2,3,3a,4,6,6a-hexahydrofuro[2,3-c]pyrrole-2-carboxylic acid (50 mg, 0.19 mmol) in DMF (2 mL) was added HATU (74 mg, 0.19 mmol) at 0° C. After addition, the mixture was stirred at 0° C. for 30 min, and then cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (63 mg, 0.19 mmol) and DIEA (93 mg, 0.72 mmol) was added at 0° C. The resulting mixture was stirred at 15° C. for 12 h. The reaction mixture was quenched by addition of $H_2O$ (10 mL) at 0° C. and then extracted with EtOAc (3×10 mL). The combined organics were washed with $H_2O$ (3×5 mL) and brine (5 mL), dried over anhydrous $Na_2SO_4$, filtered, and concentrated under reduced pressure. LC-MS: m/z=473.2 [M+H−56]$^+$.

(2R,3aR,6aR)-N-(3-(5-(3-cis-(trifluoromethoxy)cyclobutyl)-1,3,4-oxadiazol-2-yl)bicyclo[1.1.1]pentan-1-yl)hexahydro-2H-furo[2,3-c]pyrrole-2-carboxamide TFA Salt To a solution of (2R,3aR,6aR)-tert-butyl 2-((3-(5-(3-cis-(trifluoromethoxy)cyclobutyl)-1,3,4-oxadiazol-2-yl)bicyclo[1.1.1]pentan-1-yl)carbamoyl)tetrahydro-2H-furo[2,3-c]pyrrole-5(3H)-carboxylate (140 mg, 0.26 mmol) in DCM (2 mL) was added TFA (616 mg, 5.4 mmol). The mixture was stirred at 15° C. for 1 h. The reaction mixture was concentrated under reduced pressure. LC-MS: m/z=429.2 [M+H]$^+$.

(2R,3aR,6aR)-5-(2,2,2-trifluoroethyl)-N-[3-[5-[3-cis-(trifluoromethoxy)cyclobutyl]-1,3,4-oxadiazol-2-yl]-1-bicyclo[1.1.1]pentanyl]-2,3,3a,4,6,6a-hexahydrofuro[2,3-c]pyrrole-2-carboxamide To a solution of (2R,3aR,6aR)-N-(3-(5-(3-cis-(trifluoromethoxy)cyclobutyl)-1,3,4-oxadiazol-2-yl)bicyclo[1.1.1]pentan-1-yl)hexahydro-2H-furo[2,3-c]pyrrole-2-carboxamide TFA salt (150 mg, 0.28 mmol) in THF (3 mL) was added DIEA (179 mg, 1.4 mmol) and 2,2,2-trifluoroethyl trifluoromethanesulfonate (96 mg, 0.41 mmol) at 0° C. The reaction mixture was stirred at 50° C. for 4 h. The reaction mixture was quenched by addition of $H_2O$ (10 mL) at 0° C. and then extracted with EtOAc (3×10 mL). The combined organics were washed with brine (5 mL), dried over anhydrous $Na_2SO_4$, filtered, and concentrated under reduced pressure. The crude reaction mixture was purified employing reverse-phase HPLC. LC-MS: m/z=511.4 [M+H]$^+$. $^1$H-NMR (400 MHz, $CDCl_3$): δ 6.98 (s, 1H), 4.75-4.65 (m, 2H), 4.55 (dd, J=8.82, 6.62 Hz, 1H), 3.32 (tt, J=10.17, 7.80 Hz, 1H), 3.09-2.96 (m, 3H), 2.92-2.82 (m, 4H), 2.74-2.67 (m, 2H), 2.59 (s, 8H), 2.25-2.17 (m, 1H), 2.17-2.06 (m, 1H).

Example 103

6-chloro-N-[3-[5-[3-cis-(trifluoromethoxy)cyclobutyl]-1,3,4-oxadiazol-2-yl]-1-bicyclo[1.1.1]pentanyl]imidazo[1,2-a]pyridine-2-carboxamide To a solution of 6-chloroimidazo[1,2-a]pyridine-2-carboxylic acid (100 mg, 0.51 mmol) in DMF (2 mL) was added HATU (193 mg, 0.51 mmol) at 0° C. under $N_2$. The mixture was stirred for 30 min at 0° C., and then cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (138 mg, 0.42 mmol) and DIEA (203 mg, 1.6 mmol) was added to the solution at 0° C. The reaction mixture was stirred at 16° C. for 14 h. The reaction mixture was quenched by the addition of $H_2O$ (8 mL) at 0° C. and then extracted with EtOAc (3×5 mL). The combined organics were washed with $H_2O$ (3×3 mL) and brine (3×3 mL), dried over anhydrous $Na_2SO_4$, filtered, and concentrated under reduced pressure. The crude reaction mixture was purified employing reverse-phase HPLC. LC- MS: m/z=468.3 [M+H]+. 1H-NMR (400 MHz, CDCl3): δ 8.23 (dd, J=1.87, 0.77 Hz, 1H), 8.11 (s, 1H), 7.81 (s, 1H), 7.52 (d, J=9.70 Hz, 1H), 7.25 (dd, J=9.48, 1.98 Hz, 1H), 4.71 (quin, J=7.55 Hz, 1H), 3.33 (tt, J=10.14, 7.72 Hz, 1H), 2.93-2.82 (m, 2H), 2.74-2.68 (m, 8H).

Example 104

7-chloro-N-[3-[5-[3-cis-(trifluoromethoxy)cyclobutyl]-1,3,4-oxadiazol-2-yl]-1-bicyclo[1.1.1]pentanyl]imidazo[1,2-a]pyridine-2-carboxamide To a solution of 7-chloroimidazo[1,2-a]pyridine-2-carboxylic acid (50 mg, 0.25 mmol) in DMF (2 mL) was added HATU (97 mg, 0.25 mmol). The mixture was stirred for 30 min at 0° C. under N2, then cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (69 mg, 0.21 mmol) and DIEA (101 mg, 0.78 mmol) was added to the solution at 0° C. The reaction mixture was stirred at 16° C. for 14 h. The reaction mixture was quenched by H2O (8 mL) at 0° C., and then extracted with EtOAc (3×5 mL). The combined organics were washed with H2O (3×3 mL) and brine (3×3 mL), dried over anhydrous Na2SO4, filtered, and concentrated under reduced pressure. The crude reaction mixture was purified employing reverse-phase HPLC. LC-MS: m/z=468.3 [M+H]+. 1H-NMR (400 MHz, CDCl3): δ 8.45 (br s, 1H), 8.17-8.16 (m, 1H), 8.24-8.11 (m, 1H), 7.75 (s, 1H), 7.03 (br d, J=6.65 Hz, 1H), 4.72 (br t, J=7.47 Hz, 1H), 3.40-3.28 (m, 1H), 2.88 (br d/=8.66 Hz, 2H), 2.74-2.68 (m, 8H).

Example 105

2-(3-fluorophenoxy)-N-[3-[5-[3-cis-(trifluoromethoxy)cyclobutyl]-1,3,4-oxadiazol-2-yl]-1-bicyclo[1.1.1]pentanyl]acetamide To a mixture of 2-(3-fluorophenoxy)acetic acid (100 mg, 0.59 mmol) in DMF (2 mL) was added HATU (270 mg, 0.71 mmol) under N2. After 20 min, cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (170 g, 0.59 mmol) and DIEA (300 mg, 2.4 mmol) was added to the solution at 0° C. The reaction mixture was stirred at 20° C. for 12 h. The reaction mixture was quenched by the addition of H2O (10 mL) at 0° C. and extracted with EtOAc (3×10 mL). The combined organics were washed with brine (10 mL), dried over anhydrous Na2SO4, filtered, and concentrated under reduced pressure. The crude reaction mixture was purified employing reversephase HPLC. LC-MS: m/z=442.3 [M+H]+. 1H-NMR (400 MHz, CDCl3): δ 7.35-7.28 (m, 1H), 7.02 (s, 1H), 6.81-6.65 (m, 3H), 4.71 (quin. J=7.6 Hz, 1H), 4.45 (s. 2H), 3.39-3.26 (m, 1H), 2.93-2.81 (m, 2H), 2.76-2.68 (m, 2H), 2.66 (s, 6H).

Examples 106 and 107

2-[3-cis-(trifluoromethoxy)cyclobutoxy]-N-[3-[5-[3-cis-(trifluoromethoxymethyl)cyclobutyl]-1,3,4-oxadiazol-2-yl]-1-bicyclo[1.1.1]pentanyl]acetamide and 2-[3-cis-(trifluoromethoxy)cyclobutoxy]-N-[3-[5-[3-trans-(trifluoromethoxymethyl)cyclobutyl]-1,3,4-oxadiazol-2-yl]-1-bicyclo[1.1.1]pentanyl]acetamide methyl 3-aminobicyclo[1.1.1]pentane-1-carboxylate hydrochloride A mixture of methyl 3-(tert-butoxycarbonylamino)bicyclo[1.1.1]pentane-1-carboxylate (500 mg, 2.1 mmol) in EtOAc (15 mL) was added HCl/EtOAc (15 mL, 4 M in EtOAc). The reaction mixture was stirred at 20° C. for 2 h. The reaction mixture was concentrated under reduced pressure.

cis-methyl 3-[[2-[3-(trifluoromethoxy)cyclobutoxy]acetyl]amino]bicyclo[1.1.1]pentane-1-carboxylate To a mixture of cis-2-[3-(trifluoromethoxy)cyclobutoxy] acetic acid (530 mg, 2.5 mmol) in DCM (4 mL) was added HATU (1.1 g, 3.0 mmol) under N2. After 30 min, methyl 3-aminobicyclo[1.1.1]pentane-1-carboxylate hydrochloride (440 mg, 2.5 mmol) and DIEA (1.3 g, 9.9 mmol) were added to the solution at 0° C. The reaction mixture was stirred at 20° C. for 12 h. The reaction mixture was quenched by addition of H2O 15 mL at 0° C., and extracted with EtOAc (3×15 mL). The combined organics were washed with brine (15 mL), dried over anhydrous Na2SO4, filtered, and concentrated under reduced pressure. The residue was purified by silica gel column chromatography.

cis-N-[1-(hydrazinecarbonyl)-3-bicyclo[1.1.1]pentanyl]-2-[3-(trifluoromethoxy)cyclobutoxy]acetamide To a mixture of cis-methyl 3-[[2-[3-(trifluoromethoxy)cyclobutoxy]acetyl]amino]bicyclo[1.1.1]pentane-1-carboxylate (450 mg, 1.3 mmol) in EtOH (10 mL) was added hydrazine hydrate (680 mg, 13.3 mmol) under N2. The reaction mixture was stirred at 80° C. for 2 h. The reaction mixture was concentrated under reduced pressure.

cis-2-[3-(trifluoromethoxy)cyclobutoxy]-N-[1-[[[3-(trifluoromethoxymethyl)cyclobutanecarbonyl]amino]carbamoyl]-3-bicyclo[1.1.1]pentanyl]acetamide To a mixture of cis-N-[1-(hydrazinecarbonyl)-3-bicyclo[1.1.1]pentanyl]-2-[3-(trifluoromethoxy)cyclobutoxy]acetamide (200 mg, 0.59 mmol) in EtOAc (2 mL) was added 3-(trifluoromethoxymethyl)cyclobutanecarboxylic acid (140 mg, 0.71 mmol), T3P (1.5 g, 2.4 mmol, 50% in EtOAc), and Et3N (0.24 g, 2.36 mmol) at 20° C. The reaction mixture was stirred at 20° C. for 12 h. The reaction mixture was quenched by addition of sat. NaHCO3 (5 mL) at 0° C. and extracted with EtOAc (3×15 mL). The combined organics were washed with brine (15 mL), dried over anhydrous Na2SO4, filtered, and concentrated under reduced pressure. The residue was purified by silica gel column chromatography.

2-[3-cis-(trifluoromethoxy)cyclobutoxy]-N-[3-[5-[3-cis-(trifluoromethoxymethyl)cyclobutyl]-1,3,4-oxadiazol-2-yl]-1-bicyclo[1.1.1]pentanyl]acetamide (106) and 2-[3-cis-(trifluoromethoxy)cyclobutoxy]-N-[3-[5-[3-trans-(trifluoromethoxymethyl)cyclobutyl]-1,3,4-oxadiazol-2-yl]-1-bicyclo[1.1.1]pentanyl]acetamide (5:1 Mixture of trans:cis Diastereomers, 107)

To a mixture of cis-2-[3-(trifluoromethoxy)cyclobutoxy]-N-[1-[[[3-(trifluoromethoxymethyl)cyclobutanecarbonyl]amino]carbamoyl]-3-bicyclo[1.1.1]pentanyl]acetamide (20 mg, 0.39 mmol) in CH3CN (2 mL) was added p-TsCl (180 mg, 0.97 mmol) and DIEA (25 mg, 0.19 mmol) under N2. The reaction mixture was stirred at 50° C. for 12 h. The reaction mixture was quenched by addition of sat. NaHCO3 (7 mL) and extracted with EtOAc (3×7 mL). The combined organics were washed with brine (7 mL), dried over anhydrous Na$_2$SO$_4$, filtered, and concentrated under reduced pressure. The crude reaction mixture was purified employing reverse-phase HPLC. The major diastereomer was isolated. LC-MS: m/z=500.4 [M+H]$^+$. $^1$H-NMR (400 MHz, CDCl$_3$): δ 6.92 (s, 1H), 4.34 (quin, J=7.15 Hz, 1H), 3.98 (d, J=6.15 Hz, 2H), 3.83 (s, 2H), 3.73 (quin, J=6.90 Hz, 1H), 3.67-3.58 (m, 1H), 2.83 (dtd, J=9.94, 6.67, 6.67, 3.20 Hz, 2H), 2.80-2.70 (m, 1H), 2.66-2.59 (m, 6H), 2.59-2.52 (m, 2H), 2.34-2.22 (m, 4H).

Examples 108 and 109

1-[3-cis-(trifluoromethoxy)cyclobutyl]-N-[3-[5-[3-cis-(trifluoromethoxy)cyclobutyl]-1,3,4-oxadiazol-2-yl]-1-bicyclo[1.1.1]pentanyl]pyrazole-3-carboxamide and 2-[3-(trifluoromethoxy)cyclobutyl]-N-[3-[5-[3-cis-(trifluoromethoxy)cyclobutyl]-1,3,4-oxadiazol-2-yl]-1-bicyclo[1.1.1]pentanyl]pyrazole-3-carboxamide Ethyl 1-(3-oxocyclobutyl)-1H-pyrazole-3-carboxylate To a solution of ethyl 1H-pyrazole-5-carboxylate (940 mg, 6.7 mmol) in DMF (50 mL) was added Cs$_2$CO$_3$ (2.2 g, 6.71 mmol) and 3-bromocyclobutanone (1.0 g, 6.7 mmol) at −10° C. The reaction mixture was stirred at −10° C. for 1 h. The reaction mixture was quenched by H$_2$O (90 mL) and extracted with EtOAc (3×30 mL). The combined organics were washed with brine (30 mL), dried over anhydrous Na$_2$SO$_4$, filtered, and concentrated under reduced pressure. The residue was purified by silica gel column chromatography. Mixture of regioisomers. LC-MS: m/z=209.1 [M+H]$^+$.

Ethyl 1-(3-hydroxycyclobutyl)-1H-pyrazole-3-carboxylate

A mixture of ethyl 1-(3-oxocyclobutyl)-1H-pyrazole-3-carboxylate (770 mg, 3.7 mmol) in MeOH (10 mL) was added NaBH$_4$ (139 mg, 3.7 mmol) at −30° C. under N$_2$. The reaction mixture was stirred at −30° C. for 0.5 h. The mixture was quenched by the addition of sat. NH$_4$Cl (30 mL) at 0° C. over 30 min. The mixture was concentrated under reduced pressure to remove MeOH and then extracted with EtOAc (3×10 mL). The combined organics were washed with brine (20 mL), dried over anhydrous Na$_2$SO$_4$, filtered, and concentrated. Mixture of regioisomers. LC-MS: m/z=211.1 [M+H]$^+$.

Ethyl 1-(3-(trifluoromethoxy)cyclobutyl)-1H-pyrazole-3-carboxylate

To a mixture of AgOTf (2.4 g, 9.4 mmol), Selectfluor (1.7 g, 4.7 mmol) and KF (729 mg, 12.6 mmol) in EtOAc (20 mL) was added ethyl 1-(3-hydroxycyclobutyl)-1H-pyrazole-3-carboxylate (660 mg, 3.1 mmol) followed by 2-fluoropyridine (914 mg, 9.4 mmol) and TMSCF$_3$ (1.34 g, 9.42 mmol) under N$_2$. The reaction mixture was stirred at 20° C. for 15 h. The reaction mixture was filtered and concentrated under reduced pressure. The residue which was purified by silica gel column chromatography. Mixture of regioisomers. LC-MS: m/z=279.1 [M+H]$^-$.

1-(3-(trifluoromethoxy)cyclobutyl)-1H-pyrazole-3-carboxylic acid

To a solution of ethyl 1-[3-(trifluoromethoxy)cyclobutyl]-1H-pyrazole-3-carboxylate (460 mg, 1.7 mmol) in THF (5 mL) and H$_2$O (5 mL) was added LiOH·H$_2$O (208 mg, 5.0 mmol) at 0° C. The reaction mixture was stirred at 15° C. for 6 h and then 35° C. for 2 h. The reaction mixture was concentrated under reduced pressure. The residue was dissolved in H$_2$O (60 mL) and extracted with MTBE (3×20 mL). The aqueous was then adjusted to pH=1 and extracted with DCM:MeOH (3×20 mL, v:v=10:1). These organics were washed with brine (20 mL), dried over anhydrous Na$_2$SO$_4$, filtered, and concentrated under reduced pressure. Mixture of regioisomers. LC-MS: m/z=251.1 [M+H]$^+$.

1-[3-cis-(trifluoromethoxy)cyclobutyl]-N-[3-[5-[3-cis-(trifluoromethoxy)cyclobutyl]-1,3,4-oxadiazol-2-yl]-1-bicyclo[1.1.1]pentanyl]pyrazole-3-carboxamide and 2-[3-(trifluoromethoxy)cyclobutyl]-N-[3-[5-[3-cis-(trifluoromethoxy)cyclobutyl]-1,3,4-oxadiazol-2-yl]-1-bicyclo[1.1.1]pentanyl]pyrazole-3-carboxamide To a solution of 1-[3-(trifluoromethoxy)cyclobutyl]pyrazole-3-carboxylic acid (60 mg, 0.24 mmol) in DMF (3 mL) was added HATU (91 mg, 0.24 mmol), DIEA (84 mg, 0.65 mmol) and cis-1-[5-[3-(trifluoromethoxy)cyclobutyl]-1,3,4-oxadiazol-2-yl]bicyclo[1.1.1]pentan-3-amine hydrochloride (8:1 to 10:1 favoring the cis-diastereomer) (71 mg, 0.22 mmol) at 0° C. The reaction mixture was stirred at 15° C. for 15 h. The reaction mixture was quenched by H$_2$O (30 mL) and extracted with EtOAc (3×10 mL). The combined organics were washed with brine (10 mL), dried over anhydrous Na$_2$SO$_4$, filtered, and concentrated under reduced pressure. The crude reaction mixture was purified employing reverse-phase HPLC to provide:

1-[cis-3-(trifluoromethoxy)cyclobutyl]-N-[3-[5-[cis-3-(trifluoromethoxy)cyclobutyl]-1,3,4-oxadiazol-2-yl]-1-bicyclo[1.1.1]pentanyl]pyrazole-3-carboxamide (HPLC peak 1, major diastereomer of the major constitutional isomer) LC-MS: m/z=522.4 [M+H]$^+$. $^1$H-NMR (400 MHz, CDCl$_3$): δ 7.43 (d, J=2.3 Hz, 1H), 7.40 (s, 1H), 6.80 (d, J=2.1 Hz, 1H), 4.71 (quin, J=7.5 Hz, 1H), 4.57 (quin, J=7.3 Hz, 1H), 4.48-4.37 (m, 1H), 3.39-3.27 (m, 1H), 3.05-2.83 (m, 6H), 2.70 (s, 8H).

2-[3-(trifluoromethoxy)cyclobutyl]-N-[3-[5-[cis-3-(trifluoromethoxy)cyclobutyl]-1,3,4-oxadiazol-2-yl]-1-bicyclo[1.1.1]pentanyl]pyrazole-3-carboxamide (HPLC peak 2, mixture of diastereomers of the minor constitutional isomer) LC-MS: m/z=522.4 [M+H]$^+$ Examples 110 and 111

(4-chlorophenyl)methyl-N-[3-[5-[3-cis-(trifluoromethoxy)cyclobutyl]-1,3,4-oxadiazol-2-yl]-1-bicyclo[1.1.1]pentanyl]carbamate and (4-chlorophenyl)methyl-N-[3-[5-[3-trans-(trifluoromethoxy)cyclobutyl]-1,3,4-oxadiazol-2-yl]-1-bicyclo[1.1.1]pentanyl]carbamate (4-chlorophenyl)methyl (4-nitrophenyl)carbonate To a solution of (4-chlorophenyl)methanol (3.7 g, 25.6 mmol) in DCM (35 mL) was added (4-nitrophenyl) carbonochloridate (6.7 g, 33.2 mmol) and DMAP (31 mg, 0.26 mmol). After 30 min, DIEA (4.3 g, 33.2 mmol) was added. The reaction mixture was stirred at 25° C. for 12 h. The reaction mixture was quenched by the addition of H$_2$O (35 mL) at 0° C. and extracted with DCM (35 mL) followed by EtOAc (3×35 mL). The combined organics were washed with brine (40 mL), dried over anhydrous Na$_2$SO$_4$, filtered, and concentrated under reduced pressure.

(4-chlorophenyl)methyl-N-[3-[5-[3-cis-(trifluoromethoxy)cyclobutyl]-1,3,4-oxadiazol-2-yl]-1-bicyclo[1.1.1]pentanyl]carbamate and (4-chlorophenyl)methyl-N-[3-[5-[3-trans-(trifluoromethoxy)cyclobutyl]-1,3,4-oxadiazol-2-yl]-1-bicyclo[1.1.1]pentanyl]carbamate To a mixture of (4-chlorophenyl)methyl (4-nitrophenyl) carbonate (213 mg, 0.69 mmol) in DCM (1 mL) was added 1-[5-[3-(trifluoromethoxy)cyclobutyl]-1,3,4-oxadiazol-2-yl]bicyclo[1.1.1]pentan-3-amine (8:1 to 10:1 favoring the cis-diastereomer) (100 mg, 0.35 mmol), Et$_3$N (0.10 mL, 0.69 mmol) and DMAP (4 mg, 0.003 mmol) under N$_2$. The reaction mixture was stirred at 25° C. for 12 h. The reaction mixture was quenched by addition of H$_2$O (5 mL) at 0° C. and extracted with EtOAc (3×5 mL). The combined organics were washed with brine (5 mL), dried over anhydrous Na$_2$SO$_4$, filtered, and concentrated under reduced pressure. The crude reaction mixture was purified employing reverse-phase HPLC to provide:

cis-(3-(5-(3-(trifluoromethoxy)cyclobutyl)-1,3,4-oxadiazol-2-yl)bicyclo[1.1.1]pentan-1-yl)carbamate LC-MS: m/z=458.3 [M+H]$^+$. $^1$H-NMR (400 MHz, CDCl$_3$): δ 7.39-7.32 (m, 2H), 7.32-7.28 (m, 2H), 5.33 (br s, 1H), 5.07 (br s, 2H), 4.70 (quin, J=7.5 Hz, 1H), 3.40-3.25 (m, 1H), 2.92-2.81 (m, 2H), 2.68 (q, J=10.0 Hz, 2H), 2.61-2.45 (m, 6H).

4-chlorobenzyl trans-(3-(5-(3-(trifluoromethoxy)cyclobutyl)-1,3,4-oxadiazol-2-yl)bicyclo[1.1.1]pentan-1-yl)carbamate LC-MS: m/z=458.1 [M+H]$^-$. $^1$H-NMR (400 MHz, CDCl$_3$): δ 7.30-7.25 (m, 2H), 7.24-7.20 (m, 2H), 5.22 (br s, 1H), 5.00 (br s, 2H), 4.91 (quin, J=7.0 Hz, 1H), 3.69-3.56 (m, 1H), 2.85-2.64 (m, 4H), 2.46 (br s, 6H).

Examples 112 and 113

2-(4-chloro-3-fluoro-phenoxy)-N-[3-[5-[2-trans-methylcyclopropyl]-1,3,4-oxadiazol-2-yl]-1-bicyclo[1.1.1]pentanyl]acetamide The racemic mixture of 2-(4-chloro-3-fluoro-phenoxy)-N-[1-[5-(2-methylcyclopropyl)-1,3,4-oxadiazol-2-yl]-3-bicyclo[1.1.1]pentanyl]acetamide was separated by chiral SFC to provide:
2-(4-chloro-3-fluoro-phenoxy)-N-[1-[5-[2-methylcyclopropyl]-1,3,4-oxadiazol-2-yl]-3-bicyclo[1.1.1]pentanyl]acetamide (Peak 1 in SFC, enantiomer 1). LC-MS: m/z=392.3 [M+H]$^+$. $^1$H-NMR (400 MHz, CDCl$_3$): δ 7.34 (t, J=8.6 Hz, 1H), 6.95 (br s, 1H), 6.77 (dd, J=2.9, 10.3 Hz, 1H), 6.72-6.63 (m, 1H), 4.45-4.39 (m, 1H), 4.42 (s, 1H), 2.61 (s, 6H), 1.85-1.79 (m, 1H), 1.53-1.43 (m, 1H), 1.34-1.24 (m, 1H), 1.21 (d, J=6.0 Hz, 3H), 0.93 (ddd, J=4.8, 6.1, 8.5 Hz, 1H).
2-(4-chloro-3-fluoro-phenoxy)-N-[1-[5-[2-methylcyclopropyl]-1,3,4-oxadiazol-2-yl]-3-bicyclo[1.1.1]pentanyl]acetamide (Peak 2 in SFC, enantiomer 2). LC-MS: m/z=392.3 [M+H]$^+$. $^1$H-NMR (400 MHz, CDCl$_3$): δ 7.34 (t, J=8.6 Hz, 1H), 6.95 (s, 1H), 6.77 (dd, J=2.8, 10.2 Hz, 1H), 6.69 (ddd, J=1.3, 2.9, 8.9 Hz, 1H), 4.42 (s, 2H), 2.61 (s, 6H), 1.82 (td, J=4.5, 8.7 Hz, 1H), 1.53-1.43 (m, 1H), 1.33-1.25 (m, 1H), 1.21 (d, J=6.0 Hz, 3H), 0.96-0.88 (m, 1H).

Example 114

N-[3-[5-[3-cis-(trifluoromethoxy)cyclobutyl]-1,3,4-oxadiazol-2-yl]-1-bicyclo[1.1.1]pentanyl]-2-[3-cis-(trifluoromethoxy)cyclopentoxy]acetamide tert-butyl 2-cyclopent-3-en-1-yloxyacetate To a mixture of cyclopent-3-en-1-ol (3.0 g, 35.7 mmol), tert-butyl 2-bromoacetate (10.4 g, 53.5 mmol), tetrabutylammonium hydrogen sulfate (600 mg, 1.8 mmol) and H$_2$O (1.5 mL) in toluene (60 mL) was added NaOH (21.4 g, 535.0 mmol) in H$_2$O (20 mL). The reaction mixture was stirred at 25° C. for 4 h. The reaction mixture was quenched by addition of water (30 mL) at 0° C. and extracted with MTBE (3×30 mL). The combined organics were washed with brine (30 mL), dried over anhydrous Na$_2$SO$_4$, filtered, and concentrated under reduced pressure. The residue was purified by silica gel column chromatography.

tert-butyl 2-(3-hydroxycyclopentoxy)acetate

To a solution of tert-butyl 2-cyclopent-3-en-1-yloxyacetate (1.0 g, 5.0 mmol) in THF (40 mL) was added dropwise 9-BBN (0.5 M in THF, 12.1 mL) at 0° C. over 50 min under N$_2$. The reaction mixture was stirred at 0° C. for 10 min and then warmed to 20° C. and stirred for 4 h. A suspension of sodium perborate monohydrate (1.5 g, 15.1 mmol) in water (56 mL) was then added. The reaction mixture was stirred at 20° C. for 12 h and then filtered and extracted with EtOAc (3×30 mL). The combined organics were washed with brine (30 mL), dried over anhydrous Na$_2$SO$_4$, filtered, and concentrated under reduced pressure. The residue was purified by silica gel column chromatography.

cis-[3-(2-tert-butoxy-2-oxo-ethoxy)cyclopentyl]4-nitrobenzoate

To a mixture tert-butyl 2-[3-hydroxycyclopentoxy]acetate (2.8 g, 13.0 mmol) and 4-nitrobenzoic acid (2.4 g, 14.2 mmol) in THF (40 mL) was added PPh$_3$ (5.1 g, 19.4 mmol) at 20° C. under N$_2$. Then DIAD (13.1 g, 64.7 mmol) was added at 0° C. under N$_2$. The reaction mixture was stirred at 20° C. for 15 h. The reaction mixture was diluted with H$_2$O (30 mL) and extracted with EtOAc (3×30 mL). The combined organics were washed with brine (30 mL), dried over anhydrous Na$_2$SO$_4$, filtered, and concentrated under reduced pressure. The residue was purified by silica gel column chromatography.

cis-tert-butyl 2-(3-hydroxycyclopentoxy)acetate

To a mixture of cis-[3-(2-tert-butoxy-2-oxo-ethoxy)cyclopentyl] 4-nitrobenzoate (3.8 g, 10.4 mmol) in THF (15 mL), H$_2$O (3 mL) and MeOH (30 mL) was added K$_2$CO$_3$ (1.4 g, 10.4 mmol) at 20° C. under N$_2$. The reaction mixture was stirred at 25° C. for 16 h. The reaction mixture was diluted with H$_2$O (50 mL) and extracted with EtOAc (3×50 mL). The combined organics were washed with brine (50 mL), dried over anhydrous Na$_2$SO$_4$, filtered, and concentrated under reduced pressure. The residue was purified by silica gel column chromatography.

cis-tert-butyl 2-[3-(trifluoromethoxy)cyclopentoxy] acetate

To a mixture of AgOTf (2.1 g, 8.3 mmol) in EtOAc (20 mL) was added Selectfluor (1.5 g, 4.2 mmol), KF (0.6 g, 11.1 mmol), and cis-tert-butyl 2-(3-hydroxycyclopentoxy) acetate (0.6 g, 2.8 mmol) under $N_2$ followed by 2-fluoropyridine (0.8 g, 8.3 mmol) and $TMSCF_3$ (1.2 g, 8.3 mmol). The reaction mixture was stirred at 25° C. for 16 h. The reaction mixture was filtered and concentrated under reduced pressure. The residue was purified by silica gel column.

cis-2-[3-(trifluoromethoxy)cyclopentoxy]acetic acid

To a mixture of cis-tert-butyl 2-[3-(trifluoromethoxy) cyclopentoxy]acetate (100 mg, 0.35 mmol) in DCM (3 mL) was added TFA (1.6 g, 14.1 mmol) in one portion under $N_2$. The reaction mixture was stirred at 40° C. for 2 h. The reaction mixture concentrated under reduced pressure.

N-[3-[5-[3-cis-(trifluoromethoxy)cyclobutyl]-1,3,4-oxadiazol-2-yl]-1-bicyclo[1.1.1]pentanyl]-2-[3-cis-(trifluoromethoxy)cyclopentoxy]acetamide To a mixture cis-2-[3-(trifluoromethoxy)cyclopentoxy] acetic acid (60 mg, 0.26 mmol) in DMF (1 mL) was added HATU (120 mg, 0.32 mmol) under $N_2$. The mixture was stirred for 20 min, then 1-[5-[3-cis-(trifluoromethoxy)cyclobutyl]-1,3,4-oxadiazol-2-yl]bicyclo[1.1.1]pentan-3-amine HCl salt (86 mg, 0.26 mmol; 8:1 to 10:1 ratio of cis- to trans-) and DIEA (136 mg, 1.05 mmol) was added to the solution at 0° C. The reaction mixture was stirred at 20° C. for 12 h. The reaction mixture was quenched by the addition of $H_2O$ (5 mL) and extracted with EtOAc (3×5 mL). The combined organics were washed with brine (5 mL), dried over anhydrous $Na_2SO_4$, filtered, and concentrated under reduced pressure. The crude reaction mixture was purified employing reverse-phase HPLC. LC-MS: m/z=500.4 $[M+H]^+$. $^1$H-NMR (400 MHz, $CDCl_3$): δ 7.06 (br s, 1H), 4.80-4.73 (m, 1H), 4.73-4.63 (m, 1H), 4.08-3.99 (m, 1H), 3.95-3.83 (m, 2H), 3.31 (tt, J=10.12, 7.76 Hz, 1H), 2.86 (dtd, J=9.76, 7.26, 7.26, 2.82 Hz, 2H), 2.73-2.63 (m, 2H), 2.60 (s, 6H), 2.14-2.05 (m, 3H), 2.05-1.91 (m, 2H), 1.89-1.79 (m, 1H).

Example 115

2-spiro[2.3]hexan-5-yloxy-N-[3-[5-[3-cis-(trifluoromethoxy)cyclobutyl]-1,3,4-oxadiazol-2-yl]-1-bicyclo[1.1.1]pentanyl]acetamide Prepared using General Procedure A employing 1-[5-[3-cis-(trifluoromethoxy)cyclobutyl]-1,3,4-oxadiazol-2-yl]bicyclo[1.1.1]pentan-3-amine HCl salt (50 mg, 0.15 mmol; 8:1 to 10:1 ratio of cis- to trans-), 2-spiro[2.3]hexan-5-yloxyacetic acid (36 mg, 0.23 mmol), $NEt_3$ (0.07 mL, 0.49 mmol), and T3P (0.27 mL, 0.46 mmol, 50% in EtOAc) in EtOAc (1.5 mL). The crude reaction mixture was purified employing reverse-phase HPLC. LC-MS, m/z=428.2 $[M+H]^+$. $^1$H-NMR (400 MHz; $CDCl_3$): δ 7.05 (s, 1H), 4.72 (t, J=7.5 Hz, 1H), 4.27 (t, J=6.8 Hz, 1H), 3.85 (d, J=4.3 Hz, 2H), 3.33 (d, J=10.2 Hz, 1H), 2.88 (dt, J=7.4, 2.5 Hz, 2H), 2.71-2.69 (m, 2H), 2.64 (s, 6H), 2.32-2.28 (m, 2H), 2.21 (td, J=7.5, 3.8 Hz, 2H), 0.50-0.43 (m, 4H).

Example 116

2-[1-(2,2,2-trifluoroethyl)azetidin-3-yl]oxy-N-[3-[5-[3-cis-(trifluoromethoxy)cyclobutyl]-1,3,4-oxadiazol-2-yl]-1-bicyclo[1.1.1]pentanyl]acetamide Prepared using General Procedure A employing 1-[5-[3-cis-(trifluoromethoxy)cyclobutyl]-1,3,4-oxadiazol-2-yl]bicyclo[1.1.1]pentan-3-amine HCl salt (75 mg, 0.23 mmol; 8:1 to 10:1 ratio of cis- to trans-), 2-[1-(2,2,2-trifluoroethyl) azetidin-3-yl]oxyacetic acid (74 mg, 0.35 mmol), NEt3 (0.16 mL, 1.15 mmol), and T3P (0.41 mL, 0.69 mmol, 50% in EtOAc) in EtOAc (2.3 mL). The crude reaction mixture was purified employing reverse-phase HPLC. LC-MS, m/z=485.4 $[M+H]^+$. $^1$H-NMR (400 MHz; CDCl3): δ 7.01 (s, 1H), 4.71 (q, J=7.5 Hz, 1H), 4.26 (quintet, J=5.4 Hz, 1H), 3.86 (s, 2H), 3.77-3.72 (m, 2H), 3.38-3.28 (m, 3H), 3.07 (q, J=9.3 Hz, 2H), 2.87 (dtt, J=11.2, 6.0, 2.9 Hz, 2H), 2.74-2.66 (m, 2H), 2.66 (d, J=2.0 Hz, 6H).

Example 117

2-[[3-cis-(trifluoromethoxy)cyclobutyl]methoxy]-N-[3-[5-[3-cis-(trifluoromethoxy)cyclobutyl]-1,3,4-oxadiazol-2-yl]-1-bicyclo[1.1.1]pentanyl]acetamide Prepared using General Procedure A employing 1-[5-[3-cis-(trifluoromethoxy)cyclobutyl]-1,3,4-oxadiazol-2-yl]bicyclo[1.1.1]pentan-3-amine HCl salt (50 mg, 0.15 mmol; 8:1 to 10:1 ratio of cis- to trans-), cis-2-[[3-(trifluoromethoxy)cyclobutyl]methoxy]acetic acid (53 mg, 0.23 mmol), $NEt_3$ (0.11 mL, 0.77 mmol), and T3P (0.27 mL, 0.46 mmol, 50% in EtOAc) in EtOAc (1.5 mL). The crude reaction mixture was purified employing reverse-phase HPLC. LC-MS, m/z=500.3 $[M+H]^+$. $^1$H-NMR (400 MHz; $CDCl_3$): δ 6.94 (s, 1H), 4.71 (t, J=7.5 Hz, 1H), 4.60 (t, J=7.4 Hz, 1H), 3.93 (d, J=6.8 Hz, 2H), 3.54 (d, J=5.8 Hz, 2H), 3.36-3.31 (m, 1H), 2.87 (qq, J=6.4, 2.6 Hz, 2H), 2.73-2.65 (m, 2H), 2.65 (d, J=0.5 Hz, 6H), 2.54 (dtd, J=12.9, 7.3, 3.0 Hz, 2H), 2.23 (dd, J=8.6, 6.6 Hz, 1H), 2.07 (td, J=8.8, 2.2 Hz, 2H).

Example 118

N-[3-[5-[1-(2,2,2-trifluoroethyl)pyrazol-4-yl]-1,3,4-oxadiazol-2-yl]-1-bicyclo[1.1.1]pentanyl]-2-[3-cis-(trifluoromethoxy)cyclobutoxy]acetamide cis-N-[1-[5-(1H-pyrazol-4-yl)-1,3,4-oxadiazol-2-yl]-3-bicyclo[1.1.1]pentanyl]-2-[3-(trifluoromethoxy)cyclobutoxy]acetamide (16 mg, 0.04 mmol) was dissolved in DMF (0.8 mL). $Cs_2CO_3$ (25 mg, 0.08 mmol) and 2,2,2-trifluoroethyl trifluoromethanesulfonate (0.01 mL, 0.05 mmol) were then added. The resulting reaction mixture was stirred at ambient temperature overnight. The reaction mixture was diluted with sat $NaHCO_3$ solution (5 mL) and EtOAc (10 mL). The layers were separated and the aqueous layer was extracted with EtOAc (3×10 mL). The combined organic layers were washed with water (2×20 mL) and brine (1×20 mL) and then dried over anhydrous $MgSO_4$, filtered, and concentrated under reduced pressure. The crude reaction mixture was purified employing reverse-phase HPLC. LC-MS, m/z=496.3 $[M+H]^+$. $^1$H-NMR (400 MHz; CDCl3): δ 8.16 (s, 1H), 8.12 (s, 1H), 6.96 (s, 1H), 4.81 (q, J=8.2 Hz, 2H), 4.36 (t, J=7.1 Hz, 1H), 3.86 (s, 2H), 3.75 (t, J=6.9 Hz, 1H), 2.85 (qd, J=6.6, 3.3 Hz, 2H), 2.68 (s, 6H), 2.32-2.29 (m, 2H).

Example 119

N-[3-[5-[1-(2,2,2-trifluoroethyl)pyrazol-3-yl]-1,3,4-oxadiazol-2-yl]-1-bicyclo[1.1.1]pentanyl]-2-[3-cis-(trifluoromethoxy)cyclobutoxy]acetamide cis-N-[1-[5-(1H-pyrazol-3-yl)-1,3,4-oxadiazol-2-yl]-3-bicyclo[1.1.1]pentanyl]-2-[3-cis-(trifluoromethoxy)cyclobutoxy]acetamide (48 mg, 0.12 mmol) was dissolved in DMF (1.2 mL). $Cs_2CO_3$ (76 mg, 0.23 mmol) and 2,2,2-trifluoroethyl trifluoromethanesulfonate (0.02 mL, 0.14 mmol) were then added. The resulting reaction mixture was stirred at ambient temperature overnight. The reaction mixture was diluted with sat $NaHCO_3$ solution (5 mL) and EtOAc (10 mL). The layers were separated and the aqueous layer was extracted with EtOAc (3×10 mL). The combined organic layers were washed with water (2×20 mL) and brine (1×20 mL) and then dried over anhydrous $MgSO_4$, filtered, and concentrated under reduced pressure. The crude reaction mixture was purified employing reverse-phase HPLC. LC-MS, m/z=496.4 $[M+H]^+$. $^1$H-NMR (400 MHz; $CDCl_3$): δ 7.67 (d, J=2.5 Hz, 1H), 7.07 (d, J=2.5 Hz, 1H), 6.95 (s, 1H), 4.86 (q, J=8.2 Hz, 2H), 4.35 (t, J=7.2 Hz, 1H), 3.85 (s, 2H), 3.75 (t, J=6.9 Hz, 1H), 2.85 (dtd, J=9.9, 6.7, 3.2 Hz, 2H), 2.71 (d, J=40.0 Hz, 6H), 2.34-2.27 (m, 2H).

Example 120

2-(4-cyclopropylphenoxy)-N-[3-[5-[3-cis-(trifluoromethoxy)cyclobutyl]-1,3,4-oxadiazol-2-yl]-1-bicyclo[1.1.1]pentanyl]acetamide Prepared using General Procedure A employing 1-[5-[3-cis-(trifluoromethoxy)cyclobutyl]-1,3,4-oxadiazol-2-yl]bicyclo[1.1.1]pentan-3-amine (50 mg, 0.17 mmol; 8:1 to 10:1 ratio of cis- to trans-), 2-(4-cyclopropylphenoxy)acetic acid (50 mg, 0.26 mmol), $NEt_3$ (0.12 mL, 0.86 mmol), and T3P (0.3 mL, 0.52 mmol, 50% in EtOAc) in EtOAc (1.7 mL). The crude reaction mixture was purified employing reverse-phase HPLC. LC-MS, m/z=464.3 $[M+H]^+$. $^1$H-NMR (400 MHz; $CDCl_3$): δ 7.10-7.05 (m, 3H), 6.87-6.83 (m, 2H), 4.72 (t, J=7.5 Hz, 1H), 4.44 (s, 2H), 3.34 (td, J=9.0, 2.4 Hz, 1H), 2.92-2.85 (m, 2H), 2.75-2.67 (m, 2H), 2.67 (s, 6H), 1.89 (dt, J=9.3, 4.2 Hz, 1H), 0.98-0.93 (m, 2H), 0.67-0.63 (m, 2H).

Example 121

2-(4-chloro-3-fluoro-phenoxy)-N-[3-[5-[2-methyl-1-(2,2,2-trifluoroethyl)azetidin-3-yl]-1,3,4-oxadiazol-2-yl]-1-bicyclo[1.1.1]pentanyl]acetamide 2-(4-chloro-3-fluoro-phenoxy)-N-[1-[5-(2-methylazetidin-3-yl)-1,3,4-oxadiazol-2-yl]-3-bicyclo[1.1.1]pentanyl]acetamide; 2,2,2-trifluoroacetic acid (13 mg, 0.03 mmol) was dissolved in EtOAc (0.5 mL). Water (0.5 mL), $NaHCO_3$ (11 mg, 0.13 mmol), and 2,2,2-trifluoroethyl trifluoromethanesulfonate (0.01 mL, 0.05 mmol) were then added. The resulting reaction mixture was stirred at 50° C. overnight. The reaction mixture was cooled to ambient temperature and diluted with sat $NaHCO_3$ solution (5 mL) and EtOAc (10 mL). The layers were separated and the aqueous layer was extracted with EtOAc (3×10 mL). The combined organic layers were dried over anhydrous $MgSO_4$, filtered, and concentrated under reduced pressure. The crude reaction mixture was purified employing reverse-phase HPLC. LC-MS, m/z=489.3 $[M+H]^+$. $^1$H-NMR (400 MHz; $CDCl_3$): δ 7.36 (t, J=8.6 Hz, 1H), 6.97 (s, 1H), 6.79 (dd, J=10.2, 2.8 Hz, 1H), 6.71 (ddd, J=8.9, 2.7, 1.1 Hz, 1H), 4.44 (s, 2H), 3.95 (t, J=7.3 Hz, 1H), 3.68-3.66 (m, 1H), 3.55 (d, J=8.5 Hz, 1H), 3.38 (dd, J=8.8, 7.0 Hz, 1H), 3.14 (d, J=9.7 Hz, 1H), 3.06 (d, J=9.3 Hz, 1H), 2.67 (d, J=5.5 Hz, 6H), 1.37 (d, J=6.0 Hz, 3H).

Example 122 tert-butyl 3-[5-[3-[[2-(4-chloro-3-fluoro-phenoxy)acetyl]amino]-1-bicyclo[1.1.1]pentanyl]-1,3,4-oxadiazol-2-yl]-2-methyl-azetidine-1-carboxylate Prepared using General Procedure C employing 2-(4-chloro-3-fluoro-phenoxy)-N-[1-(hydrazinecarbonyl)-3-bicyclo[1.1.1]pentanyl]acetamide (60 mg. 0.18 mmol), 1-tert-butoxycarbonyl-2-methyl-azetidine-3-carboxylic acid (59 mg, 0.27 mmol), $NEt_3$ (0.13 mL, 0.92 mmol), and T3P (0.65 mL, 0.55 mmol, 50% in EtOAc) in EtOAc (1.8 mL). LC-MS, m/z=451.3 $[M-C_4H_7]^+$. $^1$H-NMR (400 MHz; $CDCl_3$): δ 7.37 (t, J=8.6 Hz, 1H), 6.96 (s, 1H), 6.80 (dd, J=10.2, 2.8 Hz, 1H), 6.72 (ddd, J=8.9, 2.8, 1.2 Hz, 1H), 4.54 (t, J=6.3 Hz, 1H), 4.45 (s, 2H), 4.19 (d, J=8.7 Hz, 1H), 4.15 (d, J=7.2 Hz, 1H), 3.53 (dd, J=6.6, 1.9 Hz, 1H), 2.68 (s, 6H), 1.55 (d, J=6.3 Hz, 3H), 1.49 (s, 9H).

Example 123

2-(4-chloro-3-fluoro-phenoxy)-N-[3-[5-[1-(2,2,2-trifluoro-1-methyl-ethyl)azetidin-3-yl]-1,3,4-oxadiazol-2-yl]-1-bicyclo[1.1.1]pentanyl]acetamide N-[1-[5-(azetidin-3-yl)-1,3,4-oxadiazol-2-yl]-3-bicyclo[1.1.1]pentanyl]-2-(4-chloro-3-fluoro-phenoxy)acetamide; 2,2,2-trifluoroacetic acid (45 mg, 0.09 mmol) was dissolved in $CHCl_3$ (0.9 mL) followed by the addition of 1,1,1-trifluoropropan-2-one (1.6 mL, 17.76 mmol). $NaCNBH_3$ (17 mg, 0.27 mmol) was then added as a solid in one portion followed by MeOH (0.9 mL) at ambient temperature. After 1 h, additional 1,1,1-trifluoropropan-2-one (1.6 mL, 17.76 mmol) was added. After an additional 11 h, another portion of $NaCNBH_3$ (17 mg, 0.27 mmol) was added. After a combined 20 h, the reaction mixture was diluted with sat $NaHCO_3$ solution (15 mL) and EtOAc (40 mL). The layers were separated and the aqueous layer was extracted with EtOAc (3×20 mL). The combined organic layers were dried over anhydrous $MgSO_4$, filtered, and concentrated under reduced pressure. The crude reaction mixture was purified employing reverse-phase HPLC. LC-MS, m/z=489.4 $[M+H]^+$. $^1$H-NMR (400 MHz; $CDCl_3$): δ 7.36 (t, J=8.6 Hz, 1H), 6.99 (s, 1H), 6.79 (dd, J=10.2, 2.8 Hz. 1H), 6.72-6.69 (m, 1H), 4.44 (s, 2H), 3.95 (dd, J=13.1, 6.2 Hz, 2H), 3.81 (ddd, J=8.2, 5.9, 2.3 Hz, 1H), 3.62-3.58 (m, 2H), 2.97 (t, J=6.6 Hz, 1H), 2.67 (s, 6H), 1.18 (d, J=6.6 Hz, 3H).

Example 124

2-(4-chloro-3-fluoro-phenoxy)-N-[3-[5-[5-cis-(trifluoromethoxymethyl)tetrahydrofuran-2-yl]-1,3,4-oxadiazol-2-yl]-1-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), cis-5-(trifluoromethoxymethyl)tetrahydrofuran-2-carboxylic acid (39 mg. 0.18 mmol), $NEt_3$ (0.09 mL, 0.61 mmol), and T3P (0.44 mL, 0.37 mmol, 50% in EtOAc) in EtOAc (1.2 mL). LC-MS, m/z=506.3 $[M+H]^+$. $^1$H-NMR (400 MHz; $CDCl_3$):

δ 7.36 (t, J=8.6 Hz, 1H), 6.95 (s, 1H), 6.80 (dd, J=10.2, 2.8 Hz, 1H), 6.71 (ddd, J=8.9, 2.9, 1.2 Hz, 1H), 5.23 (dd, J=7.5, 5.3 Hz, 1H), 4.44 (s, 2H), 4.41 (d, J=5.0 Hz, 1H), 4.07 (dd, J=10.3, 4.2 Hz, 1H), 4.01 (dd, J=10.3, 5.4 Hz, 1H), 2.67 (s, 6H), 2.52-2.39 (m, 2H), 2.25 (d, J=7.7 Hz, 1H), 2.09 (t, J=6.4 Hz, 1H).

Example 125

2-(4-chloro-3-fluoro-phenoxy)-N-[3-[5-[(3,3-difluoropyrrolidin-1-yl)methyl]-1,3,4-oxadiazol-2-yl]-1-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 2-(3,3-difluoropyrrolidin-1-yl)acetic acid TFA salt (51 mg, 0.18 mmol), NEt$_3$ (0.09 mL, 0.61 mmol), and T3P (0.44 mL, 0.37 mmol, 50% in EtOAc) in EtOAc (1.2 mL). LC-MS, m/z=457.2 [M+H]$^+$. $^1$H-NMR (400 MHz; CDCl$_3$): δ 7.36 (t, J=8.6 Hz, 1H), 6.96 (s, 1H), 6.80 (dd, J=10.2, 2.9 Hz, 1H), 6.71 (ddd, J=8.9, 2.9, 1.3 Hz, 1H), 4.44 (s, 2H), 3.94 (s, 2H), 3.10 (t, J=13.1 Hz, 2H), 2.94 (t, J=7.0 Hz, 2H), 2.68 (s, 6H), 2.35 (dt, J=14.4, 7.3 Hz, 2H).

Example 126

2-(4-chloro-3-fluoro-phenoxy)-N-[3-[5-[[3-(trifluoromethyl)azetidin-1-yl]methyl]-1,3,4-oxadiazol-2-yl]-1-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol), 2,2,2-trifluoroacetic acid; 2-[3-(trifluoromethyl)azetidin-1-yl] acetic acid (54 mg, 0.18 mmol), NEt$_3$ (0.09 mL, 0.61 mmol), and T3P (0.22 mL, 0.37 mmol, 50% in EtOAc) in EtOAc (1.2 mL). LC-MS, m/z=475.3 [M+H]$^+$. $^1$H-NMR (400 MHz; CDCl$_3$): δ 7.39-7.34 (m, 1H), 6.95 (d, J=0.6 Hz, 1H), 6.79 (dd, =10.3, 2.9 Hz, 1H), 6.71 (ddd, J=8.9, 2.9, 1.2 Hz, 1H), 4.44 (d, J=3.0 Hz, 2H), 3.86 (s, 2H), 3.69 (t, J=8.3 Hz, 2H), 3.45 (t, J=7.7 Hz, 2H), 3.28-3.22 (m, 1H), 2.67 (s, 6H).

Example 127

2-(4-chloro-3-fluoro-phenoxy)-N-[3-[5-[4-(2,2,2-trifluoroethyl)morpholin-2-yl]-1,3,4-oxadiazol-2-yl]-1-bicyclo[1.1.1]pentanyl]acetamide 2-(4-chloro-3-fluoro-phenoxy)-N-[1-(5-morpholin-2-yl-1,3,4-oxadiazol-2-yl)-3-bicyclo[1.1.1]pentanyl]acetamide; 2,2,2-trifluoroacetic acid (12 mg, 0.02 mmol) was dissolved in EtOAc (0.5 mL). Water (0.5 mL), NaHCO$_3$ (10 mg, 0.11 mmol), and 2,2,2-trifluoroethyl trifluoromethanesulfonate (0.01 mL, 0.03 mmol) were then added sequentially. The resulting reaction mixture was heated to 50° C. for 6 h followed by the addition of 2,2,2-trifluoroethyl trifluoromethanesulfonate (0.01 mL, 0.03 mmol). The resulting reaction mixture was stirred at 50° C. temperature overnight. The reaction mixture was cooled to ambient temperature and diluted with sat NaHCO$_3$ solution (5 mL) and EtOAc (10 mL). The layers were separated and the aqueous layer was extracted with EtOAc (3×10 mL). The combined organic layers were dried over anhydrous MgSO$_4$, filtered, and concentrated under reduced pressure. The crude reaction mixture was purified employing reverse-phase HPLC. LC-MS, m/z=505.3 [M+H]$^+$. $^1$H-NMR (400 MHz; CDCl$_3$): δ 7.39-7.35 (m, 1H), 6.98-6.92 (m, 1H), 6.83-6.75 (m, 1H), 6.74-6.68 (m, 1H), 4.92-4.82 (m, 1H), 4.53-4.33 (m, 2H), 4.14-3.99 (m, 1H), 3.96-3.80 (m, 1H), 3.31-3.18 (m, 1H), 3.17-3.03 (m, 2H), 3.00-2.86 (m, 2H), 2.78-2.70 (m, 1H), 2.70 (d, J=1.7 Hz, 6H).

Example 128 tert-butyl 2-[5-[3-[[2-(4-chloro-3-fluoro-phenoxy) acetyl]amino]-1-bicyclo[1.1.1]pentanyl]-1,3,4-oxadiazol-2-yl]morpholine-4-carboxylate Prepared using General Procedure C employing 2-(4-chloro-3-fluoro-phenoxy)-N-[1-(hydrazinecarbonyl)-3-bicyclo[1.1.1]pentanyl]acetamide (48 mg, 0.15 mmol), 4-(tert-butoxycarbonyl)morpholine-2-carboxylic acid (51 mg, 0.22 mmol), NEt$_3$ (0.10 mL, 0.73 mmol), and T3P (0.52 mL, 0.44 mmol, 50% in EtOAc) in EtOAc (1.5 mL). LC-MS, m/z=467.2 [M−C$_4$H$_7$]$^+$. $^1$H-NMR (400 MHz; CDCl$_3$): δ 7.36 (t, J=8.6 Hz, 1H), 6.96 (s, 1H), 6.79 (dd, J=10.2, 2.8 Hz, 1H), 6.71 (ddd, J=8.9, 2.9, 1.2 Hz, 1H), 4.74 (dd, J=10.1, 2.9 Hz, 1H), 4.44 (s, 2H), 4.28-4.25 (m, 1H), 4.07-4.03 (m, 1H), 3.97-3.92 (m, 1H), 3.75-3.69 (m, 1H), 3.41-3.33 (m, 1H), 3.19-3.12 (m, 1H), 2.64 (s, 6H), 1.47 (s, 9H).

Example 129

2-(4-chloro-3-fluoro-phenoxy)-N-[3-[5-[(3,3-difluoroazetidin-1-yl)methyl]-1,3,4-oxadiazol-2-yl]-1-bicyclo[1.1.1]pentanyl]acetamide Prepared using General Procedure C employing 2-(4-chloro-3-fluoro-phenoxy)-N-[1-(hydrazinecarbonyl)-3-bicyclo[1.1.1]pentanyl]acetamide (40 mg, 0.12 mmol). 2-(3,3-difluoroazetidin-1-yl)arctic acid; 2,2,2-trifluoroacetic acid (49 mg, 0.18 mmol), NEt$_3$ (0.09 mL, 0.61 mmol), and T3P (0.44 mL, 0.37 mmol, 50% in EtOAc) in EtOAc (1.2 mL). LC-MS, m/z=443.3 [M+H]$^+$. $^1$H-NMR (400 MHz; CDCl$_3$): δ 7.39-7.33 (m, 1H), 6.97-6.95 (m, 1H), 6.81-6.78 (m, 1H), 6.73-6.70 (m, 1H), 4.44-4.43 (m, 2H), 3.98 (dt, J=2.1, 1.0 Hz, 2H), 3.86-3.79 (m, 4H), 2.68 (s, 6H).

Example 130

2-(4-chloro-3-fluoro-phenoxy)-N-[3-[5-[1-(2,2-difluoroethyl)azetidin-3-yl]-1,3,4-oxadiazol-2-yl]-1-bicyclo[1.1.1]pentanyl]acetamide N-[1-[5-(azetidin-3-yl)-1,3,4-oxadiazol-2-yl]-3-bicyclo[1.1.1]pentanyl]-2-(4-chloro-3-fluoro-phenoxy)acetamide (45 mg, 0.11 mmol) was dissolved in EtOAc (1.8 mL). Water (1.0 mL), NaHCO$_3$ (49 mg, 0.57 mmol), and 2,2-difluoroethyl trifluoromethanesulfonate (0.02 mL, 0.14 mmol) were then added sequentially at 0° C. The resulting reaction mixture was stirred at 50° C. temperature overnight. The reaction mixture was cooled to ambient temperature and diluted with sat NaHCO$_3$ solution (5 mL) and EtOAc (10 mL). The layers were separated and the aqueous layer was extracted with EtOAc (3×10 mL). The combined organic layers were dried over anhydrous MgSO$_4$, filtered, and concentrated under reduced pressure. The crude reaction mixture was purified employing reverse-phase HPLC. LC-MS, m/z=457.3 [M+H]$^+$. $^1$H-NMR (400 MHz; CDCl$_3$): δ 7.36 (t, J=8.6 Hz, 1H), 6.96 (s, 1H), 6.80 (dd, J=10.2, 2.9 Hz, 1H), 6.71 (ddd, J=8.9, 2.8, 1.2 Hz, 1H), 5.80 (tt, J=55.8, 4.3

Hz, 1H), 4.44 (s, 2H), 3.98-3.93 (m, 1H), 3.87 (t, J=7.6 Hz, 2H), 3.62-3.59 (m, 2H), 2.95-2.86 (m, 2H), 2.65 (d, J=5.3 Hz, 6H).

Example 131

2-(4-chloro-3-fluoro-phenoxy)-N-[3-[5-(2,2-difluoro-1,1-dimethyl-ethyl)-1,3,4-oxadiazol-2-yl]-1-bicyclo[1.1.1]pentanyl]acetamide Prepared using General Procedure A employing 2-(4-chloro-3-fluoro-phenoxy)-N-[1-(hydrazinecarbonyl)-3-bicyclo[1.1.1]pentanyl]acetamide (40 mg, 0.12 mmol), 3,3-difluoro-2,2-dimethyl-propanoic acid (25 mg, 0.18 mmol), NEt$_3$ (0.09 mL, 0.61 mmol), and T3P (0.22 mL, 0.37 mmol, 50% in EtOAc) in EtOAc (1.2 mL). The crude reaction mixture was purified employing reverse-phase HPLC. LC-MS, m/z=430.2 [M+H]$^+$. $^1$H-NMR (400 MHz; CDCl$_3$): δ 7.36 (t, J=8.6 Hz, 1H), 6.96 (s, 1H), 6.80 (dd, J=10.2, 2.8 Hz, 1H), 6.71 (ddd, J=8.9, 2.9, 1.2 Hz, 1H), 5.95 (t, J=56.0 Hz, 1H), 4.45 (s, 21-1), 2.68 (s, 6H), 1.54 (s, 6H).

Example 132

2-(4-chloro-3-fluoro-phenoxy)-N-[3-[methyl-[2-[3-cis-(trifluoromethoxy)cyclobutoxy]ethyl]amino]-1-bicyclo[1.1.1]pentanyl]acetamide The title compound was made via similar procedures described throughout. LC-MS, m/z=481.4, 483.4 [M+H]$^+$.

Example 133

2-(4-chloro-3-fluoro-phenoxy)-N-[1-[2-[cis-3-(trifluoromethoxy)cyclobutoxy]ethylamino]-3-bicyclo[1.1.1]pentanyl]acetamide N-(1-amino-3-bicyclo[1.1.1]pentanyl)-2-(4-chloro-3-fluoro-phenoxy)acetamide (258.64 mg, 0.91 mmol), 2-[3-cis-(trifluoromethoxy)cyclobutoxy]acetaldehyde (120. mg, 0.61 mmol), and acetic acid (200 mg, 3.33 mmol) were dissolved in in DCE (5 mL). The reaction mixture was stirred at rt overnight. The reaction mixture was diluted with aq. 1N NaOH (50 mL) and DCM (50 mL). The layers were separated and the aqueous layer was extracted with DCM (3×150 mL) The combined organic layers were dried over anhydrous Na$_2$SO$_4$, filtered, and concentrated under reduced pressure. The crude material mixture was purified by preparative HPLC. $^1$H-NMR (400 MHz; CDCl$_3$): δ 7.38-7.33 (m, 1H), 6.89-6.87 (m, 1H), 6.80-6.77 (m, 1H), 6.70 (dtd, J=8.9, 2.6, 1.3 Hz, 1H), 4.35-4.28 (m, 1H), 3.72-3.61 (m, 2H), 3.57-3.46 (m, 2H), 2.91-2.88 (m, 1H), 2.83-2.76 (m, 2H), 2.63-2.44 (m, 5H), 2.33-2.19 (m, 7H). LC-MS m/z=467.36 [M+H]$^+$.

The following Examples as shown in Table 1 were synthesized via procedures similar to those described throughout.

Examples 134-138

| Example | LC-MS (m/z, [M + H]$^+$) | General Procedure |
|---|---|---|
| 134 | 490.3 | Procedure H |
| 135 | 458.3 | Procedure H |
| 136 | 440.4 | Procedure H |
| 137 | 440.3 | Procedure H |
| 138 | 458.3 | Procedure H |

Example 139

N-(3-(4-(4-chlorophenyl)-1H-imidazol-1-yl)bicyclo[1.1.1]pentan-1-yl)-2-(3-cis-(trifluoromethoxy)cyclobutoxy)acetamide N-(3-((2-(4-chlorophenyl)-2-oxoethyl)amino)bicyclo[1.1.1]pentan-1-yl)-2-(3-cis-(trifluoromethoxy)cyclobutoxy)acetamide Prepared using General Procedure F employing 2-bromo-1-[3-(trifluoromethyl)phenyl]ethanone (403 mg, 1.51 mmol) and N-(3-aminobicyclo[1.1.1]pentan-1-yl)-2-(3-cis-(trifluoromethoxy)cyclobutoxy)acetamide HCl salt (500 mg, 1.36 mmol) in MeCN (5 mL). Purified by silica gel column chromatography. LC-MS: m/z: 447.2 [M+H]$^+$.

N-(3-(N-(2-(4-chlorophenyl)-2-oxoethyl)formamido)bicyclo[1.1.1]pentan-1-yl)-2-(3-cis-(trifluoromethoxy)cyclobutoxy)acetamide Prepared using General Procedure G employing N-(3-((2-(4-chlorophenyl)-2-oxoethyl)amino)bicyclo[1.1.1]pentan-1-yl)-2-(3-cis-(trifluoromethoxy)cyclobutoxy)acetamide (235 mg, 0.53 mmol) in DCM (0.9 mL). LC-MS: m/z: 475.2 [M+H]$^+$.

N-(3-(4-(4-chlorophenyl)-1H-imidazol-1-yl)bicyclo[1.1.1]pentan-1-yl)-2-(3-cis-(trifluoromethoxy)cyclobutoxy)acetamide Prepared using General Procedure H employing N-(3-(N-(2-(4-chlorophenyl)-2-oxoethyl)formamido)bicyclo[1.1.1]pentan-1-yl)-2-(3-cis-(trifluoromethoxy)cyclobutoxy)acetamide (100 mg, 0.21 mmol) in AcOH (3 mL). LC-MS: m/z: 456.2 [M+H]$^+$. $^1$H-NMR (400 MHz, CDCl$_3$): δ 7.71-7.68 (m, 2H), 7.51 (s, 1H), 7.35-7.33 (m, 2H), 7.19 (s, 1H), 6.94 (s, 1H), 4.35 (quin, J=7.09 Hz, 1H), 3.86 (s, 2H), 3.75 (quin, J=6.88 Hz. 1H), 2.85 (dtd, J=9.86, 6.56, 3.30 Hz, 2H), 2.67 (s, 6H), 2.24-2.37 (m, 2H).

The following Examples as shown in Table 1 were synthesized via procedures similar to those described throughout.

Examples 140-145

| Example | LC-MS (m/z, [M + H]$^+$) | General Procedure |
|---|---|---|
| 140 | 454.4 | procedure H |
| 141 | 456.2 | Procedure H |
| 142 | 454.4 | Procedure H |
| 143 | 458.0 | Procedure H |
| 144 | 458.0 | Procedure H |
| 145 | 430.1 | Procedure A |

Example 146

N-(3-(4-(4-chloro-2-fluorophenyl)-1H-imidazol-1-yl)bicyclo[1.1.1]pentan-1-yl)-2-(3-cis-(trifluoromethoxy)cyclobutoxy)acetamide

N-(3-((2-(4-chloro-2-fluorophenyl)-2-oxoethyl)amino)bicyclo[1.1.1]pentan-1-yl)-2-(3-cis-(trifluoromethoxy)cyclobutoxy)acetamide N-(3-((2-(4-chloro-2-fluorophenyl)-2-oxoethyl)amino)bicyclo[1.1.1]pentan-1-yl)-2-(3-cis-(trifluoromethoxy)cyclobutoxy)acetamide was prepared using General Procedure F employing N-(3-aminobicyclo[1.1.1]pentan-1-yl)-2-(3-cis-(trifluoromethoxy)cyclobutoxy)acetamide HCl salt (1.0 g, 3.02 mmol) and 2-bromo-1-(4-chloro-2-fluoro-phenyl)ethanone (760 mg, 3.02 mmol) in MeCN (40 mL). Purified by silica gel column chromatography to give the desired product. LC-MS: m/z: 465.2 [M+H]$^+$.

N-(3-(N-(2-(4-chloro-2-fluorophenyl)-2-oxoethyl)amino)bicyclo[1.1.1]pentan-1-yl)-2-(3-cis-(trifluoromethoxy)cyclobutoxy)acetamide N-(3-(N-(2-(4-chloro-2-fluorophenyl)-2-oxoethyl)formamido)bicyclo[1.1.1]pentan-1-yl)-2-(3-cis-(trifluoromethoxy)cyclobutoxy)acetamide was prepared using General Procedure G employing N-(3-((2-(4-chloro-2-fluorophenyl)-2-oxoethyl)amino)bicyclo[1.1.1]pentan-1-yl)-2-(3-cis-(trifluoromethoxy)cyclobutoxy)acetamide (750 mg, 1.61 mmol) in DCM (8.0 mL). LC-MS: m/z: 493.2 [M+H]$^+$.

N-(3-(4-(4-chloro-2-fluorophenyl)-1H-imidazol-1-yl)bicyclo[1.1.1]pentan-1-yl)-2-(3-cis-(trifluoromethoxy)cyclobutoxy)acetamide N-(3-(4-(4-chloro-2-fluorophenyl)-1H-imidazol-1-yl)bicyclo[1.1.1]pentan-1-yl)-2-(3-cis-(trifluoromethoxy)cyclobutoxy)acetamide was prepared using General Procedure H employing N-(3-(N-(2-(4-chloro-2-fluorophenyl)-2-oxoethyl)formamido)bicyclo[1.1.1]pentan-1-yl)-2-(3-cis-(trifluoromethoxy)cyclobutoxy)acetamide (700 mg, 1.42 mmol) in AcOH (10 mL). LC-MS: m/z: 474.1 [M+H]$^+$. $^1$H-NMR (400 MHz, CDCl$_3$): δ 8.08 (t, J=8.4 Hz, 1H), 7.53 (s, 1H), 7.38-7.35 (m, 1H), 7.20 (dd, J=1.8, 8.6 Hz, 1H), 7.14 (dd, J=1.9, 11.1 Hz, 1H), 6.95 (s, 1H), 4.35 (quin, J=7.2 Hz, 1H), 3.86 (s, 2H), 3.75 (quin, J=6.9 Hz, 1H), 2.85 (dtd, J=3.3, 6.6, 9.9 Hz, 2H), 2.66 (s, 6H), 2.39-2.23 (m, 2H).

The following Examples as shown in Table 1 were synthesized via procedures similar to those described throughout.

Examples 147-156

| Example | LC-MS (m/z, [M + H]$^+$) | General Procedure |
|---|---|---|
| 147 | 454.4 | Procedure H |
| 148 | 508.1 | Procedure H |
| 149 | 508.1 | Procedure H |
| 150 | 490.1 | Procedure H |
| 151 | 491.4 | Procedure H |
| 152 | 448.2 | Procedure A |
| 153 | 444.3 | Procedure A |
| 154 | 486.2 | Procedure A |
| 155 | 471.0 | Procedure A |
| 156 | 458.3 | Procedure A |

Examples 157 and 158

6-chloro-N-(3-(5-(3-cis-(trifluoromethoxy)cyclobutyl)-1,3,4-oxadiazol-2-yl)bicyclo[1.1.1]pentan-1-yl)chroman-2-carboxamide Prepared using General Procedure A employing 3-(5-(3-cis-(trifluoromethoxy)cyclobutyl)-1,3,4-oxadiazol-2-yl)bicyclo[1.1.1]pentan-1-amine HCl salt (77 mg, 0.23 mmol; 8:1 to 10:1 ratio of cis- to trans-) and 6-chlorochromane-2-carboxylic acid (50 mg, 0.23 mmol) in EtOAc (2 mL). Purification was accomplished using prep-HPLC (Waters Xbridge 150 mm×25 mm, 5 μm; mobile phase: [A: water (10 mM NH$_4$HCO$_3$) and B: MeCN], B %: 40% to 65% over 10 min) followed by chiral SFC (Chiralpak AD-3, 150 mm×4.6 mm, 3 μm); mobile phase: [A: CO$_2$ and B: MeOH (0.05% IPA), B %: 10% to 40% over 6 minutes Flow rate: 2.5 mL/min, Wavelength: 220 nm, System Back Pressure: 1500 psi) to give:

Example 157, first eluting peak in SFC: $^1$H-NMR (400 MHz, CDCl$_3$): δ 7.12-7.07 (m, 2H), 7.06 (s, 1H), 6.84 (d, J=8.6 Hz, 1H), 4.71 (quin, J=7.5 Hz, 1H), 4.45 (dd, J=2.8, 10.0 Hz, 1H), 3.33 (tt, J=7.7, 10.2 Hz, 1H), 2.90-2.78 (m, 4H), 2.69 (br d, J=10.5 Hz, 2H), 2.65 (s, 6H), 2.47-2.40 (m, 1H), 1.98 (dtd, J=5.4, 10.4, 13.8 Hz, 1H). LC-MS: m/z: 484.2 [M+H]$^+$.

Example 158, second eluting peak in SFC: $^1$H-NMR (400 MHz, CDCl$_3$): δ 7.12-7.07 (m, 2H), 7.06 (s, 1H), 6.84 (d, J=8.6 Hz, 1H), 4.71 (quin, J=7.6 Hz, 1H), 4.45 (dd, J=2.8, 10.1 Hz, 1H), 3.38-3.28 (m, 1H), 2.92-2.76 (m, 4H), 2.73-2.66 (m, 2H), 2.65 (s, 6H), 2.48-2.39 (m, 1H), 1.98 (tdd, J=5.3, 10.3, 19.0 Hz, 1H). LC-MS: m/z: 484.2 [M+H]$^+$.

The following Examples as shown in Table 1 were synthesized via procedures similar to those described throughout.

Examples 159-161

| Example | LC-MS (m/z, [M + H]$^+$) | General Procedure |
|---|---|---|
| 159 | 468.2 | Procedure A |
| 160 | 468.2 | Procedure A |
| 161 | 465.2 | Procedure A |

Example 162

N-[1-[5-[3-cis-(trifluoromethoxy)cyclobutyl]-1,3,4-oxadiazol-2-yl]-3-bicyclo[1.1.1]pentanyl]-2-[4-(trifluoromethyl)phenoxy]acetamide Prepared using General Procedure A employing 1-[5-[3-cis-(trifluoromethoxy)cyclobutyl]-1,3,4-oxadiazol-2-yl]bicyclo[1.1.1]pentan-3-amine HCl salt (8:1 to 10:1 favoring the cis-diastereomer) (100 mg, 0.31 mmol), NEt$_3$ (155 mg, 1.53 mmol), T3P solution (117 mg, 0.37 mmol, 50% in EtOAc), and 2-[4-(trifluoromethyl)phenoxy]acetic acid (81 mg, 0.37 mmol) in EtOAc (1.5 mL) at 20° C. The residue was purified by reverse phase prep-HPLC to give the desired product. LC-MS: m/z:=492.7 [M+H]+.

The following Examples as shown in Table 1 were synthesized via procedures similar to those described throughout.

Examples 163-165

| Example | LC-MS (m/z, [M + H]+) | General Procedure |
|---|---|---|
| 163 | 502.24 | Procedure A |
| 164 | 479.58 | Procedure A |
| 165 | 469.2 | Procedure A |

Example 166

N-[1-[5-[3-cis-(trifluoromethoxy)cyclobutyl]-1,3,4-oxadiazol-2-yl]-3-bicyclo[1.1.1]pentanyl]-6-(trifluoromethyl)quinoline-2-carboxamide Prepared using General Procedure A employing 1-[5-[3-cis-(trifluoromethoxy)cyclobutyl]-1,3,4-oxadiazol-2-yl]bicyclo[1.1.1]pentan-3-amine HCl salt (8:1 to 10:1 favoring the cis-diastereomer) (50 mg, 0.15 mmol), 6-(trifluoromethyl)quinoline-2-carboxylic acid (44 mg, 0.18 mmol), NEt$_3$ (0.11 mL, 0.77 mmol), and T3P (58 mg, 0.18 mmol, 50% in EtOAc) in EtOAc (0.77 mL). Purified by reverse phase prep-HPLC. LC-MS: m/z: 513.8 [M+H]+. $^1$H-NMR (400 MHz, CDCl$_3$): δ 8.73 (s, 1H), 8.47 (d, J=8.4 Hz, 1H), 8.41 (d, J=8.5 Hz, 1H), 8.29-8.25 (m, 2H), 7.98 (dd, J=8.9, 2.1 Hz, 1H), 4.78-4.70 (m, 1H), 3.37 (tt, J=10.2, 7.8 Hz, 1H), 2.94-2.86 (m, 2H), 2.80 (s, 6H), 2.78-2.69 (m, 2H).

Example 167

3-chloro-N-[1-[5-[3-cis-(trifluoromethoxy)cyclobutyl]-1,3,4-oxadiazol-2-yl]-3-bicyclo[1.1.1]pentanyl]quinoline-7-carboxamide Prepared using General Procedure A employing 1-[5-[3-cis-(trifluoromethoxy)cyclobutyl]-1,3,4-oxadiazol-2-yl]bicyclo[1.1.1]pentan-3-amine HCl salt (8:1 to 10:1 favoring the cis-diastereomer) (50 mg, 0.15 mmol) and 3-chloroquinoline-7-carboxylic acid (38 mg, 0.18 mmol), NEt$_3$ (0.11 mL, 0.77 mmol), and T3P solution (58 mg, 0.18 mmol, 50% in EtOAc) in EtOAc (0.77 mL). Purified by reverse phase prep-HPLC. LC-MS: m/z: 479.3 [M+H]+. $^1$H-NMR (400 MHz, CDCl$_3$): δ 8.89 (d, J=2.4 Hz, 1H), 8.45 (t, J=0.8 Hz, 1H), 8.20-8.19 (m, 1H), 8.06 (dd, J=8.5, 1.7 Hz, 1H), 7.85 (d, J=8.5 Hz, 1H), 7.14 (s, 1H), 4.77-4.67 (m, 1H), 3.34 (qt, J=10.2, 7.8 Hz, 1H), 2.93-2.83 (m, 2H), 2.79-2.65 (m, 8H).

The following Examples as shown in Table 1 were synthesized via procedures similar to those described throughout.

Examples 168-188

| Example | LC-MS (m/z, [M + H]+) | General Procedure |
|---|---|---|
| 168 | 479.4 | Procedure A |
| 169 | 479.3 | Procedure A |
| 170 | 452.4 | Procedure A |
| 171 | 468.3 | Procedure A |
| 172 | 469.7 | Procedure A |
| 173 | 508.7 | Procedure A |
| 174 | 493.7 | Procedure A |
| 175 | 485.2 | Procedure A |
| 176 | 469.2 | Procedure A |
| 177 | 469.1 | Procedure A |
| 178 | 453.3 | Procedure A |
| 179 | 512.3 | Procedure A |
| 180 | 452.4 | Procedure A |
| 181 | 468.3 | Procedure A |
| 182 | 479.3 | Procedure A |
| 183 | 480.2, 482.0 | Procedure A |
| 184 | 523.2, 525.1 | Procedure A |
| 185 | 502.3 | Procedure A |
| 186 | 502.4 | Procedure A |
| 187 | 445.6 | Procedure A |
| 188 | 446.6 | Procedure A |

Example 189

6-fluoro-N-[1-[5-[3-cis-(trifluoromethoxy)cyclobutyl]-1,3,4-oxadiazol-2-yl]-3-bicyclo[1.1.1]pentanyl]quinoline-2-carboxamide Prepared according to General Procedure A employing 1-[5-[3-cis-(trifluoromethoxy)cyclobutyl]-1,3,4-oxadiazol-2-yl]bicyclo[1.1.1]pentan-3-amine HCl salt (8:1 to 10:1 favoring the cis-diastereomer) (45 mg, 0.14 mmol) and 6-fluoroquinoline-2-carboxylic acid (40 mg, 0.21 mmol) in EtOAc (1.4 mL). Purified by reverse phase prep-HPLC. LC-MS: m/z: 463.5 [M+H]+. $^1$H-NMR (400 MHz, CDCl$_3$): 8.68 (s, 1H), 8.34-8.29 (m, 2H), 8.15 (dd, J=9.2, 5.3 Hz, 1H), 7.59 (ddd, J=9.2, 8.2, 2.8 Hz, 1H), 7.55-7.52 (m, 1H), 4.77-4.70 (m, 1H), 3.36 (tt, J=10.2, 7.8 Hz, 1H), 2.94-2.86 (m, 2H), 2.80 (s, 6H), 2.77-2.69 (m, 2H).

The following Examples as shown in Table 1 were synthesized via procedures similar to those described throughout.

Examples 190-235

| Example | LC-MS (m/z, [M + H]+) | General Procedure |
|---|---|---|
| 190 | 523.2 | Procedure A |
| 191 | 446.8 | Procedure A |
| 192 | 485.3 | Procedure A |
| 193 | 513.2 | Procedure A |
| 194 | 486.2 | Procedure A |
| 195 | 480.3 | Procedure A |
| 196 | 497.3 | Procedure A |
| 197 | 450.2 | |
| 198 | 473.2 | |
| 199 | 493.3 | |
| 200 | 338.1 | |
| 201 | 476.2 | |
| 202 | 460.2 | Procedure A |
| 203 | 458.3 | |
| 204 | 493.3 | |
| 205 | 458.2 | |
| 206 | 493.3 | |
| 207 | 493.3 | |
| 208 | 493.3, 495.3 | |

| Example | LC-MS (m/z, [M + H]+) | General Procedure |
|---------|------------------------|-------------------|
| 209 | 493.3, 495.3 | |
| 210 | 417.3 | |
| 211 | 476.2 | |
| 212 | 460.3 | |
| 213 | 389.1 | |
| 214 | 387.4 | |
| 215 | 422.4 | |
| 216 | 409.3 | |
| 217 | 434.3 | |
| 218 | 434.3 | |
| 219 | 409.3, 411.4 | |
| 220 | 423.4 | |
| 221 | 451.3 | |
| 222 | 451.3 | |
| 223 | 453.3 | |
| 224 | 492.1 | |
| 225 | 496.3 | |
| 226 | 500.4 | |
| 227 | 475.3 | |
| 228 | 474.2 | |
| 229 | 472.2 | |
| 230 | 457.2 | |
| 231 | 492.0 | |
| 232 | 488.2 | |
| 233 | 431.1 | Procedure A |
| 234 | 431.2 | |
| 235 | 488.4 | |

Example 236

N-(3-(1-(4-chloro-3-fluorophenyl)-1H-pyrazol-4-yl)bicyclo[1.1.1]pentan-1-yl)-2-(3-cis-(trifluoromethoxy)cyclobutoxy)acetamide tert-butyl 2-((4-chloro-3-fluorophenyl)amino)acetate To a solution of 4-chloro-3-fluoro-aniline (5.0 g, 34.4 mmol) and tert-butyl 2-bromoacetate (7.4 g, 37.8 mmol) in DMF (50 mL) were added DIEA (5.33 g, 41.2 mmol) and NaI (1.0 g, 6.87 mmol) in one portion. The mixture was heated to 80° C. and stirred for 16 h. The mixture was poured into water (200 mL) and was extracted with EtOAc (2×100 mL). The combined organic layers were washed with brine (100 mL), dried over anhydrous $Na_2SO_4$, filtered and concentrated under reduced pressure. The residue was purified by silica gel column chromatography LC-MS: m/z: 204.1 [M−t-Bu+H]+. $^1$H-NMR (400 MHz, $CDCl_3$): δ 7.14 (t, J=8.4 Hz, 1H), 6.38-6.28 (m, 2H), 4.41 (br s, 1H), 3.75 (d, J=4.0 Hz, 2H), 1.50 (s, 9H).

2-((4-chloro-3-fluorophenyl)amino)acetic acid

To a solution of tert-butyl 2-((4-chloro-3-fluorophenyl)amino)acetate (4.0 g, 15.4 mmol) in 1,4-dioxane (20 mL) was added TFA (5 mL) and the mixture was heated to 80° C. for 16 h. The mixture was concentrated under reduced pressure. The residue was dispersed in aq. HCl (20 mL, 6 N) and the mixture was concentrated under reduced pressure. The residue was co-evaporated with toluene (50 mL) twice, was triturated in PE:EtOAc (50 mL, v:v 1:1) and then filtered. The filter cake was dried under reduced pressure to give the title compound. LC-MS: m/z: 204.1 [M+H]+.

2-(4-chloro-3-fluoro-N-nitroso-anilino)acetic acid

To a solution of 2-(4-chloro-3-fluoro-anilino)acetic acid (2.4 g, 10.0 mmol) in $H_2O$ (20 mL) and MeCN (10 mL) was added $NaNO_2$ (690 mg, 10.0 mmol) and the mixture was stirred for 16 h at 15° C. The mixture was concentrated under reduced pressure to remove MeCN and the remaining aqueous mixture was filtered. The filter cake was washed with $H_2O$ (2×10 mL) and then was dried under reduced pressure to provide the desired product. $^1$H-NMR (400 MHz, $CDCl_3$): δ 13.23 (br s, 1H), 7.84-7.71 (m, 2H), 7.55 (dd, J=1.6, 8.8 Hz, 1H), 4.78 (s, 2H).

3-(4-chloro-3-fluorophenyl)-1,2,3-oxadiazol-3-ium-5-olate

A solution of 2-(4-chloro-3-fluoro-N-nitroso-anilino)acetic acid (1.5 g, 6.45 mmol) in $Ac_2O$ (15 mL) was heated to 100° C. for 2 h. The mixture was concentrated under reduced pressure, the residue was dispersed in water (20 mL) and then filtered. The filter cake was washed with water (2×10 mL) and then dried under reduced pressure to give the desired compound. LC-MS: m/z: 215.0 [M+H]+.

N-(3-(1-(4-chloro-3-fluorophenyl)-1H-pyrazol-4-yl)bicyclo[1.1.1]pentan-1-yl)-2-(3-cis-(trifluoromethoxy)cyclobutoxy)acetamide To a solution of 3-(4-chloro-3-fluorophenyl)-1,2,3-oxadiazol-3-ium-5-olate (50 mg, 0.23 mmol), N-(3-ethynylbicyclo[1.1.1]pentan-1-yl)-2-(3-cis-(trifluoromethoxy)cyclobutoxy)acetamide (71 mg, 0.23 mmol) and $NEt_3$ (70 mg, 0.70 mmol) in t-BuOH (1 mL) was added disodium 4-[7-(4-sulfonatophenyl)-1,10-phenanthrolin-4-yl]benzenesulfonate (25 mg, 0.046 mmol) followed by a solution of $CuSO_4$ (7.0 mg, 0.046 mmol) in $H_2O$ (0.5 mL) and a solution of sodium ascorbate (92 mg, 0.46 mmol) in $H_2O$ (0.5 mL). The mixture was heated to 60° C. for 3 h. The mixture was cooled to 15° C. and diluted with water (5 mL). The aqueous phase was extracted with EtOAc (2×5 mL), the combined organic layers were washed with brine (5 mL), dried over anhydrous $Na_2SO_4$, filtered and concentrated under reduced pressure. The residue was purified by prep-TLC and further purified by prep-HPLC to give the desired compound. LC-MS: m/z: 474.3 [M+H]+. $^1$H-NMR (400 MHz, $CDCl_3$): δ 7.69 (s, 1H), 7.56 (s, 1H), 7.55-7.51 (m, 1H), 7.47-7.36 (m, 2H), 6.87 (s, 1H), 4.37-4.30 (m, 1H), 3.83 (s, 2H), 3.76-3.69 (m, 1H), 2.86-2.80 (m, 2H), 2.40 (s, 6H), 2.32-2.25 (m, 2H).

The following Examples as shown in Table 1 were synthesized via procedures similar to those described throughout.

Examples 237-247

| Example | LC-MS (m/z, [M + H]+) | General Procedure |
|---------|------------------------|-------------------|
| 237 | 458.4 | |
| 238 | 481.3 | |
| 239 | 475.1 | Procedure A |
| 240 | 434.0 | Procedure A |
| 241 | 475.1 | |
| 242 | 458.1 | |
| 243 | 458.2 | |
| 244 | 459.4 | |
| 245 | 459.3 | |
| 246 | 467.2 | |
| 247 | 475.3 | |

Example 248

N-(3-(3-(4-chloro-3-fluorophenyl)isoxazol-5-yl)
bicyclo[1.1.1]pentan-1-yl)-2-(3-cis-(trifluo-
romethoxy)cyclobutoxy)acetamide (E)-4-chloro-3-fluorobenzaldehyde oxime To a solution of 4-chloro-3-fluorobenzaldehyde (2.0 g, 12.6 mmol) and NH$_2$OH·HCl (1.05 g, 15.1 mmol) in EtOH (20 mL) at 0° C. was added a solution of NaOH (757 mg, 18.9 mmol) in H$_2$O (5 mL) dropwise, and the mixture was warmed to 15° C. and was stirred for 3 h. The mixture was diluted with water (20 mL) and was concentrated under reduced pressure to remove EtOH. The aqueous phase was extracted with EtOAc (2×10 mL), the combined organic layers were washed with brine (20 mL), dried over anhydrous Na$_2$SO$_4$, filtered and concentrated under reduced pressure to give a residue that was used directly. $^1$H-NMR (400 MHz, CDCl$_3$): δ 8.07 (br d, J=8.8 Hz, 1H), 7.83 (br s, 1H), 7.41 (q, J=8.0 Hz, 2H), 7.31-7.22 (m, 1H).

(Z)-4-chloro-3-fluoro-N-hydroxybenzimidoyl chloride

To a solution of (E)-4-chloro-3-fluorobenzaldehyde oxime (500 mg, 2.88 mmol) in DMF (5.0 mL) was added a solution of NCS (423 mg, 3.17 mmol) in DMF (3.0 mL) dropwise at 0° C., and the mixture was warmed to 15° C. and was stirred for 4 h. The mixture was diluted with sat. aq. NH$_4$Cl (20 mL) and was extracted with EtOAc (3×10 mL). The combined organic layers were washed with brine (3×20 mL), dried over anhydrous Na$_2$SO$_4$, filtered and concentrated under reduced pressure to give a residue that was used directly. LC-MS: m/z: 208.0 [M+H]$^+$.

N-(3-(3-(4-chloro-3-fluorophenyl)isoxazol-5-yl)
bicyclo[1.1.1]pentan-1-yl)-2-(3-cis-(trifluo-
romethoxy)cyclobutoxy)acetamide To a solution of N-(3-ethynylbicyclo[1.1.1]pentan-1-yl)-2-(3-cis-(trifluoromethoxy)cyclobutoxy)acetamide (50 mg, 0.16 mmol) and (Z)-4-chloro-3-fluoro-N-hydroxybenzimidoyl chloride (69 mg, 0.33 mmol) in DMF (2 mL) was added NEt$_3$ (25 mg, 0.25 mmol), and the mixture was heated to 60° C. for 2 h. The reaction mixture was filtered and concentrated under reduced pressure. The residue was purified by prep-HPLC. LC-MS: m/z: 475.3 [M+H]$^+$. $^1$H-NMR (400 MHz, CDCl$_3$): δ 7.59 (br d, J=9.6 Hz, 1H), 7.54-7.43 (m, 2H), 6.93 (br s, 1H), 6.33 (s, 1H), 4.38-4.31 (m, 1H), 3.83 (s, 2H), 3.79-3.71 (m, 1H), 2.83 (br dd, J=3.2, 6.4 Hz, 2H). 2.57 (s, 6H), 2.28 (br d, J=7.2 Hz, 2H).

The following Examples as shown in Table 1 were synthesized via procedures similar to those described throughout.

Examples 249-253

| Example | LC-MS (m/z, [M + H]$^+$) |
|---|---|
| 249 | 472.1 |
| 250 | 415.0 |
| 251 | 457.0 |
| 252 | 475.1 |
| 253 | 472.2 |

Example 254

N-(3-(4-(2-hydroxy-4-(trifluoromethyl)phenyl)-1H-
imidazol-1-yl)bicyclo[1.1.1]pentan-1-yl)-2-(3-cis-
(trifluoromethoxy)cyclobutoxy)acetamide tert-butyl N-(3-imidazol-1-yl-1-bicyclo[1.1.1]penta-
nyl)carbamate To a mixture of formaldehyde (4.09 g, 50.4 mmol, 37%) in MeOH (20 mL) was added tert-butyl N-(1-amino-3-bicyclo[1.1.1]pentanyl)carbamate (2.0 g, 10.1 mmol) and ammonium acetate (3.89 g, 50.4 mmol). Oxaldehyde (2.93 g, 50.4 mmol) was added dropwise, and the mixture was stirred at 20° C. for 12 h. The reaction mixture was adjusted to pH=7-8 with sat. aq. NaHCO$_3$ solution, and the aqueous phase was extracted with DCM:MeOH (v:v 3:1, 3×50 mL). The combined organic layers were washed with brine (50 mL), dried over anhydrous Na$_2$SO$_4$, filtered and concentrated under reduced pressure. The residue was purified by silica gel column chromatography to provide the title compound. LC-MS: m/z: 250.2 [M+H]$^+$.

tert-butyl N-[3-(4,5-diiodoimidazol-1-yl)-1-bicyclo
[1.1.1]pentanyl]carbamate

To a mixture of tert-butyl N-(3-imidazol-1-yl-1-bicyclo [1.1.1]pentanyl)carbamate (1.0 g, 4.01 mmol) in DMF (10 mL) was added NIS (2.71 g, 12.03 mmol), and the mixture was heated to 50° C. for 7 h. The reaction mixture was poured onto a mixture of water (30 mL) and sat. aq. Na$_2$S$_2$O$_3$ (20 mL) and then extracted with EtOAc (3×40 mL). The combined organic layers were washed with brine (50 mL), dried over anhydrous Na$_2$SO$_4$, filtered and concentrated under reduced pressure to give a residue, which was purified by silica gel column chromatography. $^1$H-NMR (400 MHz, CDCl$_3$): δ 7.54 (s, 1H), 5.10 (br s, 1H), 2.68 (s, 6H), 1.54-1.42 (m, 9H).

tert-butyl N-[3-(4-iodoimidazol-1-yl)-1-bicyclo
[1.1.1]pentanyl]carbamate

To a mixture of tert-butyl N-[3-(4,5-diiodoimidazol-1-yl)-1-bicyclo[1.1.1]pentanyl]carbamate (300 mg. 0.60 mmol) in THF (5.0 mL) at −78° C. was added i-PrMgCl (2 M, 0.45 mL), and the reaction mixture was stirred at −78° C. for 1 h. The reaction mixture was diluted with sat. aq. NH$_4$Cl (10 mL) and was extracted with EtOAc (3×5 mL). The combined organic layers were washed with brine (10 mL), dried over anhydrous Na$_2$SO$_4$, filtered and concentrated under reduced pressure. The residue was purified by silica gel column chromatography to provide the desired product. LC-MS: m/z: 376.0 [M+H]$^+$.

tert-butyl N-[3-[4-[2-hydroxy-4-(trifluoromethyl)
phenyl]imidazol-1-yl]-1-bicyclo[1.1.1]pentanyl]
carbamate A mixture of tert-butyl N-[3-(4-iodoimidazol-1-yl)-1-bi-cyclo[1.1.1]pentanyl]carbamate (100 mg, 0.27 mmol),

[2-hydroxy-4-(trifluoromethyl)phenyl]boronic acid (110 mg, 0.53 mmol), CsF (121 mg, 0.80 mmol), Pd(dppf)Cl₂ (20 mg, 0.027 mmol) and benzyl(triethyl)ammonium chloride (6 mg, 0.027 mmol) in a microwave tube in toluene (1 mL) and H₂O (1 mL) was sealed and heated at 110° C. for 211 under microwave irradiation. The reaction mixture was filtered, and the filtrate was concentrated under reduced pressure. The residue was purified by prep-TLC to provide the desired product. ¹H-NMR (400 MHz, CDCl₃): δ 7.55 (s, 1H), 7.50 (d, J=7.9 Hz, 1H), 7.28 (s, 1H), 7.22 (s, 1H), 7.07 (d, J=7.5 Hz, 1H), 5.07 (br s, 1H), 2.57 (s, 6H), 1.49 (s, 9H).

2-[1-(1-amino-3-bicyclo[1.1.1]pentanyl)imidazol-4-yl]-5-(trifluoromethyl)phenol HCl Salt tert-butyl N-[3-[4-[2-hydroxy-4-(trifluoromethyl)phenyl]imidazol-1-yl]-1-bicyclo[1.1.1]pentanyl]carbamate (60 mg, 0.15 mmol) in HCl/EtOAc (4 M, 2 mL) was stirred at 25° C. for 10 min. The reaction mixture was concentrated under reduced pressure to give a residue that was used directly.

N-(3-(4-(2-hydroxy-4-(trifluoromethyl)phenyl)-1H-imidazol-1-yl)bicyclo[1.1.1]pentan-1-yl)-2-(3-cis-(trifluoromethoxy)cyclobutoxy)acetamide To a mixture of 2-(3-cis-(trifluoromethoxy)cyclobutoxy)acetic acid (19 mg, 0.086 mmol) in DMF (1.0 mL) at 0° C. were added HATU (36 mg, 0.10 mmol), 2-[1-(1-amino-3-bicyclo[1.1.1]pentanyl)imidazol-4-yl]-5-(trifluoromethyl)phenol HCl salt (30 mg, 0.087 mmol) and N-methyl morpholine (26 mg, 0.26 mmol). The reaction mixture was warmed to rt and was stirred for 40 min. The mixture was diluted with H₂O (10 mL) and was extracted with EtOAc (3×10 mL). The combined organic layers were washed with brine (10 mL), dried over anhydrous Na₂SO₄, filtered and concentrated under reduced pressure to give a residue. The residue was purified by prep-HPLC. LC-MS: m/z: 506.2 [M+H]⁺. ¹H-NMR (400 MHz, CDCl₃): δ 12.32 (br s, 1H), 7.57 (d, J=1.2 Hz, 1H), 7.50 (d, J=8.2 Hz, 1H), 7.30 (d, J=1.1 Hz, 1H), 7.22 (d, J=1.0 Hz, 1H), 7.07 (d, J=8.1 Hz, 1H), 6.97 (s, 1H), 4.36 (quirt, J=7.1 Hz, 1H), 3.87 (s, 2H), 3.75 (quin, J=6.8 Hz, 1H), 2.92-2.80 (m, 2H), 2.69 (s, 6H), 2.38-2.23 (m, 2H).

The following Examples as shown in Table 1 were synthesized via procedures similar to those described throughout.

Examples 255-269

| Example | LC-MS (m/z, [M + H]⁺) |
| --- | --- |
| 255 | 515.1 |
| 256 | 488.2 |
| 257 | 472.2 |
| 258 | 503.0 |
| 259 | 474.1 |
| 260 | 504.2 |
| 261 | 390.2 |
| 262 | 462.1 |
| 263 | 456.1 |
| 264 | 474.1 |
| 265 | 491.1 |
| 266 | 511.1 |
| 267 | 483.1 |
| 268 | 483.1 |
| 269 | 492.1 |

Example 270

N-(3-(4-(4-chloro-2,3-difluorophenyl)-1H-imidazol-1-yl)bicyclo[1.1.1]pentan-1-yl)-2-(3-cis-(trifluoromethoxy)cyclobutoxy)acetamide 4-chloro-2,3-difluorobenzoyl chloride Prepared using General Procedure D employing 4-chloro-2,3-difluorobenzoic acid (1.0 g, 5.19 mmol) (COCl)₂ (725 mg. 5.71 mmol) and DMF (2 mL) in THF (20 mL) at 0° C. under N₂. The mixture was stirred for 1 h. The reaction mixture was used directly.

2-bromo-1-(4-chloro-2,3-difluorophenyl)ethanone

Prepared using General Procedure E employing 4-chloro-2,3-difluorobenzoyl chloride TMSCHN₂ (2 M, 5.19 mL) and HBr (2.10 g, 10.4 mmol, 40%). The mixture was stirred for 1 h. The crude product (0.8 g, 57%) was used directly as light yellow oil. ¹H-NMR (400 MHz, CDCl₃): δ 7.73-7.68 (m, 1H), 8.34-7.32 (m, 1H), 4.47 (s, 2H).

N-(3-((2-(4-chloro-2,3-difluorophenyl)-2-oxoethyl)amino)bicyclo[1.1.1]pentan-1-yl)-2-(-3-cis-(trifluoromethoxy)cyclobutoxy)acetamide Prepared using General Procedure F employing 2-bromo-1-(4-chloro-2,3-difluorophenyl)ethanone (200 mg, 0.74 mmol), N-(3-aminobicyclo[1.1.1]pentan-1-yl)-2-(-3-cis-(trifluoromethoxy)cyclobutoxy)acetamide HCl salt (245 mg, 0.74 mmol) and Na₂CO₃ (315 mg, 2.97 mmol) in MeCN (5 mL) at 40° C. for 1 h. The residue was concentrated under reduced pressure to give the title compound. LC-M: m/z=483.2 [M+H]⁻.

N-(3-(N-(2-(4-chloro-2,3-difluorophenyl)-2-oxoethyl)formamido)bicyclo[1.1.1]pentan-1-yl)-2-(-3-cis-(trifluoromethoxy)cyclobutoxy)acetamide Prepared using General Procedure G employing N-(3-((2-(4-chloro-2,3-difluorophenyl)-2-oxoethyl)amino)bicyclo[1.1.1]pentan-1-yl)-2-(-3-cis-(trifluoromethoxy)cyclobutoxy)acetamide (400 mg, 0.83 mmol), Ac₂O (483 mg, 3.31 mmol) and HCOOH (1.5 mL) in DCM (2 mL) at 1 h at 0° C. The residue was purified by prep-TLC (PE:EtOAc=1:1) to give the desired product. LC-MS: m/z=511.2 [M+H]⁺.

N-(3-(4-(4-chloro-2,3-difluorophenyl)-1H-imidazol-1-yl)bicyclo[1.1.1]pentan-1-yl)-2-(-3-cis-(trifluoromethoxy)cyclobutoxy)acetamide Prepared using General Procedure H employing N-(3-(N-(2-(4-chloro-2,3-difluorophenyl)-2-oxoethyl)formamido)bicyclo[1.1.1]pentan-1-yl)-2-(-3-cis-(trifluoromethoxy)cyclobutoxy)acetamide (150 mg, 0.29 mmol) and NH₄OAc (113 mg, 1.47 mmol) in AcOH (10 mL) at 110° C. for 16 h under N₂. The residue was purified by prep-HPLC (neutral) under the following conditions: column: Waters Xbridge 150×25 mm, 5 µM; mobile phase: [water (10 mM NH₄HCO₃)-ACN]; B %: 45%-75%, 10 min to give the desired product. LC-MS: m/z=492.1 [M+H]⁺. ¹H-NMR (400 MHz, CDCl₃): δ 7.85 (ddd, J=2.0, 7.2, 8.8 Hz, 1H), 7.54 (d, J=0.8 Hz, 1H), 7.40 (dd, J=1.2, 4.0 Hz, 1H), 7.21 (ddd, J=2.0, 6.8, 8.8 Hz, 1H), 6.95 (s, 1H), 4.35 (quin, J=7.2 Hz, 1H), 3.86 (s, 2H), 3.75 (quin, J=6.8 Hz, 1H), 2.85 (dtd, J=3.2, 6.8, 10.0 Hz, 2H), 2.67 (s, 6H), 2.35-2.24 (m, 2H).

The following Examples as shown in Table 1 were synthesized via procedures similar to those described throughout.

Examples 271-277

| Example | LC-MS (m/z, [M + H]$^+$) |
|---|---|
| 271 | 492.1 |
| 272 | 520.1 |
| 273 | 548.2 |
| 274 | 462.1 |
| 275 | 422.4 |
| 276 | 476.3 |
| 277 | 496.4 |

Proton NMR data for select compounds are provided in Table 3.

TABLE 3

| Ex. | Proton NMR data |
|---|---|
| 159 | $^1$H-NMR (400 MHz, CDCl$_3$): δ 7.09 (s, 1 H), 6.84 (dd, J = 6.30, 1.53 Hz, 2 H), 6.80 (br d, J = 8.56 Hz, 1 H), 4.71 (quin, J = 7.55 Hz, 1 H), 4.43 (dd, J = 10.21, 2.75 Hz, 1 H), 3.33 (tt, J = 10.18, 7.73 Hz, 1 H), 2.76-2.93 (m, 4 H), 2.66-2.73 (m, 2 H), 2.65 (s, 6 H), 2.40-2.48 (m, 1 H), 1.92-2.04 (m, 1 H). LC-MS: m/z: 468.2 [M + H]$^+$ |
| 160 | $^1$H-NMR (400 MHz, CDCl$_3$): δ 7.09 (s, 1 H), 6.84 (dd, J = 6.30, 1.53 Hz, 2 H), 6.80 (br d, J = 8.44 Hz, 1 H), 4.71 (quin, J = 7.55 Hz, 1 H), 4.43 (dd, J = 10.21, 2.75 Hz, 1 H), 3.33 (tt, J = 10.18, 7.73 Hz, 1 H), 2.78-2.96 (m, 4 H), 2.68-2.77 (m, 2 H), 2.64 (s, 6 H), 2.39-2.48 (m, 1 H), 1.92-2.03 (m, 1 H) |
| 207 | $^1$H-NMR (400 MHz, CDCl$_3$): δ 7.34 (t, J = 8.60 Hz, 1 H), 6.89 (s, 1 H), 6.77 (dd, J = 10.14, 2.87 Hz, 1 H), 6.69 (ddd, J = 8.99, 2.81, 1.21 Hz, 1 H), 4.53-4.63 (m, 1 H), 4.45-4.52 (m, 1 H), 4.41 (s, 2 H), 3.60 (t, J = 8.49 Hz, 1 H), 3.11 (dd, J = 8.49, 6.95 Hz, 1 H), 2.41-2.58 (m, 8 H), 2.10-2.25 (m, 3 H) |
| 208 | $^1$H-NMR (400 MHz, CDCl$_3$): δ 7.34 (t, J = 8.60 Hz, 1 H), 6.89 (s, 1 H), 6.77 (dd, J = 10.14, 2.87 Hz, 1 H), 6.69 (dt, J = 8.93, 1.38 Hz, 1 H), 4.54-4.63 (m, 1 H), 4.44-4.52 (m, 1 H), 4.41 (s, 2 H), 3.60 (t, J = 8.49 Hz, 1 H), 3.11 (dd, J = 8.49, 6.95 Hz, 1 H), 2.42-2.57 (m, 8 H), 2.10-2.24 (m, 3 H) |
| 209 | $^1$H-NMR (400 MHz, CDCl$_3$): δ 7.34 (t, J = 8.60 Hz, 1 H), 6.88 (s, 1 H), 6.77 (dd, J = 10.14, 2.87 Hz, 1 H), 6.69 (dt, J = 8.93, 1.38 Hz, 1 H), 4.82 (quin, J = 6.67 Hz, 1 H), 4.51-4.62 (m, 1 H), 4.41 (s, 2 H), 3.62 (t, J = 8.49 Hz, 1 H), 3.08 (t, J = 7.94 Hz, 1 H), 2.54-2.63 (m, 1 H), 2.46-2.53 (m, 7 H), 2.33-2.46 (m, 3 H) |
| 210 | $^1$H-NMR (400 MHz, CDCl$_3$): δ 7.34 (t, J = 8.60 Hz, 1 H), 6.88 (s, 1 H), 6.77 (dd, J = 10.14, 2.87 Hz, 1 H), 6.69 (dd, J = 9.26, 2.21 Hz, 1 H), 4.82 (quin, J = 6.78 Hz, 1 H), 4.51-4.60 (m, 1 H), 4.41 (s, 2 H), 3.62 (t, J = 8.60 Hz, 1 H), 3.04-3.14 (m, 1 H), 2.54-2.64 (m, 1 H), 2.46-2.53 (m, 7 H), 2.33-2.45 (m, 3 H) |
| 218 | $^1$H-NMR (400 MHz, CDCl$_3$): δ 7.33 (t, J = 8.6 Hz, 1 H), 6.93 (br s, 1 H), 6.77 (dd, J = 2.8, 10.3 Hz, 1 H), 6.68 (ddd, J = 1.2, 2.8, 8.9 Hz, 1 H), 4.54-4.45 (m, 1 H), 4.40 (s, 2 H), 3.59 (t, J = 8.5 Hz, 1 H), 3.49 (s, 1 H), 3.12-2.97 (m, 2 H), 2.70-2.30 (m, 11 H) |
| 219 | $^1$H-NMR (400 MHz, CDCl$_3$): δ 7.33 (t, J = 8.6 Hz, 1 H), 6.94 (s, 1 H), 6.77 (dd, J = 2.9, 10.3 Hz, 1 H), 6.69 (td, J = 1.4, 8.9 Hz, 1 H), 4.54-4.45 (m, 1 H), 4.40 (s, 2 H), 3.59 (t, J = 8.5 Hz, 1 H), 3.12-2.99 (m, 2 H), 2.72-2.26 (m, 11 H) |

Separation Conditions

Separation conditions for select compounds were as follows.

Compounds 157 and 158 were separated by SFC under the following conditions: column: Chiralpak AD-3 150 mm×4.6 mm, 3 μm; mobile phase: Mobile phase: A for SFC CO$_2$ and B for MeOH (0.05% IPA), Gradient: B in A from 10% to 40% in 6 minutes. Flow rate: 2.5 mL/min Wavelength: 220 nm System Back Pressure: 1500 psi.

Compounds 159 and 160 were separated by SFC under the following conditions: column: DAICEL Chiralpak AD-H (250 mm×30 mm, 5 μm); mobile phase: A: CO$_2$. B: 0.1% NH$_4$OH in MeOH; gradient: B % in A: 25%-25% over 5 min).

Compounds 208 and 209 were separated by SFC under the following conditions: The residue was purified by reverse phase prep-HPLC (Nano-micro Kromasil C18 100 mm×30 mm, 5 μm; mobile phase: A: 0.1% TFA in water, B: MeCN, gradient: B % in A: 45%-65% over 10 min) and then by chiral SFC (Chiralpak IC-H 250 mm×30 mm, 5 μm; mobile phase: A: CO$_2$, B: 0.1% NH$_4$OH in IPA, gradient: B % in A: 45%-45% over 6 min).

Compounds 217 and 218 were separated by SFC under the following conditions: The residue was purified by SFC (Chiralpak AD-H 250 mm×30 mm, 5 μm, 40° C.; mobile phase: A: CO$_2$, B: 0.1% NH$_4$OH in MeOH, gradient: B % in A: 35%-35% over 6 min, Flow: 70 g/min, Pressure 100 bar).

Biochemical Example 1

Biochemical Assay of the Compounds

Cellular stress leads to activation of the integrated stress response pathway through one of four eukaryotic initiation factor 2a kinases and halts global translation, while allowing for the translation of select transcripts like ATF4 (activating transcription factor 4) that are important for the response to cellular stress. During normal conditions, small open reading frames (ORFs) in the 5' UTR of ATF4 occupy the ribosome and prevent translation of the coding sequence of ATF4. During stress conditions however, the ribosome scans past these upstream ORFs and preferentially begins translation at the coding sequence of ATF4. In this way, the translation, and thus protein level of ATF4 is a readout of ISR pathway activation. Thus, a fusion of the uORFs and the beginning of the coding sequence of ATF to a common cellular reporter like nano-luciferase allows for a sensitive and high-throughput readout of ISR pathway activity.

Compounds as provided herein were tested in the following assay. The ATF4 Nano Luciferase reporter was constructed by fusing the human full length 5' untranslated region (5'-UTR) and a small portion of the coding sequence of the ATF4 gene upstream of the Nano Luciferase (NLuc) coding sequence lacking it's start codon. Specifically, nucleotides +1 through +364 (relative to the transcriptional start site) of ATF4 transcript variant 2 (NCBI NM_182810.2) flanked 5' by EcoRI and 3' by BamHI restriction enzyme sites were synthesized and cloned into the EcoRI/BamHI cloning sites of pLVX-EF1a-IRES-Puro lentivirus vector (Clontech). Lentiviral particles were produced with Lenti-X single shots (VSV-G, Clontech) according to the manufacturer's instructions and used to transduce a human H4 neuroglioma cell line (ATCC HTB-148). H4 cells were selected with 1.25 µg/mL Puromycin, and clonal cell lines generated by limiting dilution. We utilized this cell line to generate an integrated stress response (ISR) assay to evaluate the activity of ISR pathway inhibitors via luminescence readout. The H4 ATF4-NLuc (clone 17) cell line is plated at a density of 15,000 or 2,50 cells in 96-well or 384-well respectively in DMEM+10% fetal bovine serum. 24-hours later test compounds diluted in dimethyl sulfoxide (DMSO) are added for 30 minutes at 37 degree Celsius, followed by ISR pathway activation with 50 um sodium arsenite aqueous solution for 6 additional hours. Nano Glo luciferase reagent (N1150, Promega) is added according to manufacturer instructions and the luminescence signal (corresponding to the level of ATF4 translation and thus ISR pathway activation) is read with a standard plate reader with luminescence detection capabilities.

In the table below, activity of the tested compounds is provided in Table 4 as follows: +++=$IC_{50}$<1 µM; ++=$IC_{50}$ 1-10 µM; +=$IC_{50}$>10 µM.

TABLE 4

| Ex. | Activity |
|---|---|
| 1 | ++ |
| 2 | ++ |
| 3 | +++ |
| 4 | ++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | ++ |
| 32 | +++ |
| 33 | +++ |
| 34 | +++ |
| 35 | +++ |
| 36 | +++ |
| 37 | ++ |
| 38 | +++ |
| 39 | +++ |
| 40 | +++ |
| 41 | +++ |
| 42 | ++ |
| 43 | +++ |
| 44 | +++ |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 55 | +++ |
| 56 | ++ |
| 57 | ++ |
| 58 | +++ |
| 59 | ++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | ++ |
| 74 | +++ |
| 75 | ++ |
| 76 | +++ |
| 77 | +++ |
| 78 | +++ |
| 79 | +++ |
| 80 | +++ |
| 81 | +++ |
| 82 | +++ |
| 83 | ++ |
| 84 | +++ |
| 85 | ++ |
| 86 | +++ |
| 87 | +++ |
| 88 | +++ |
| 89 | +++ |
| 90 | + |
| 91 | +++ |
| 92 | +++ |
| 93 | +++ |
| 94 | ++ |
| 95 | +++ |
| 96 | +++ |
| 97 | ++ |
| 98 | ++ |
| 99 | + |
| 100 | +++ |
| 101 | ++ |
| 102 | ++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | +++ |
| 113 | +++ |
| 114 | ++ |
| 115 | ++ |
| 116 | ++ |
| 117 | ++ |
| 118 | ++ |

TABLE 4-continued

| Ex. | Activity |
|---|---|
| 119 | ++ |
| 120 | +++ |
| 121 | +++ |
| 122 | +++ |
| 123 | +++ |
| 124 | +++ |
| 125 | +++ |
| 126 | +++ |
| 127 | +++ |
| 128 | ++ |
| 129 | ++ |
| 130 | +++ |
| 131 | + |
| 132 | +++ |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | +++ |
| 151 | +++ |
| 152 | +++ |
| 153 | +++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | ++ |
| 173 | +++ |
| 174 | +++ |
| 175 | +++ |
| 176 | +++ |
| 177 | +++ |
| 178 | +++ |
| 179 | +++ |
| 180 | ++ |
| 181 | +++ |
| 182 | +++ |
| 183 | +++ |
| 184 | +++ |
| 185 | +++ |
| 186 | +++ |
| 187 | +++ |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |

TABLE 4-continued

| Ex. | Activity |
|---|---|
| 197 | +++ |
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 208 | +++ |
| 209 | +++ |
| 210 | +++ |
| 211 | +++ |
| 212 | +++ |
| 213 | ++ |
| 214 | +++ |
| 215 | ++ |
| 216 | +++ |
| 217 | ++ |
| 218 | +++ |
| 219 | + |
| 220 | +++ |
| 221 | +++ |
| 222 | +++ |
| 223 | ++ |
| 224 | +++ |
| 225 | +++ |
| 226 | +++ |
| 227 | +++ |
| 228 | +++ |
| 229 | +++ |
| 230 | +++ |
| 231 | +++ |
| 232 | +++ |
| 233 | +++ |
| 234 | ++ |
| 235 | +++ |
| 236 | +++ |
| 237 | +++ |
| 238 | +++ |
| 239 | +++ |
| 240 | +++ |
| 241 | +++ |
| 242 | +++ |
| 243 | +++ |
| 244 | +++ |
| 245 | +++ |
| 246 | +++ |
| 247 | +++ |
| 248 | +++ |
| 249 | +++ |
| 250 | +++ |
| 251 | +++ |
| 252 | +++ |
| 253 | +++ |
| 254 | +++ |
| 255 | +++ |
| 256 | +++ |
| 257 | +++ |
| 258 | +++ |
| 259 | +++ |
| 260 | +++ |
| 261 | ++ |
| 262 | +++ |
| 263 | +++ |
| 264 | +++ |
| 265 | +++ |
| 266 | +++ |
| 267 | +++ |
| 268 | +++ |
| 269 | +++ |
| 270 | +++ |
| 271 | +++ |
| 272 | +++ |
| 273 | +++ |
| 274 | +++ |

TABLE 4-continued

| Ex. | Activity |
|---|---|
| 275 | +++ |
| 276 | +++ |
| 277 | +++ |

Specific data for certain compounds is shown below in Table 5.

TABLE 5

| Ex. | IC$_{50}$ |
|---|---|
| 3 | 0.0092 |
| 6 | 0.0025 |
| 15 | 0.0171 |
| 49 | 0.0182 |
| 51 | 0.0137 |
| 61 | 0.0019 |
| 70 | 0.0028 |
| 81 | 0.0118 |
| 133 | 0.0181 |
| 136 | 0.0220 |
| 139 | 0.0043 |
| 146 | 0.0037 |
| 148 | 0.0026 |
| 151 | 0.0355 |
| 152 | 0.0382 |
| 157 | 0.0092 |
| 161 | 0.0134 |
| 162 | 0.0149 |
| 163 | 0.0085 |
| 166 | 0.0081 |
| 167 | 0.0439 |
| 169 | 0.0038 |
| 179 | 0.1025 |
| 189 | 0.0285 |
| 236 | 0.0215 |
| 248 | 0.0282 |
| 254 | 0.0053 |
| 269 | 0.0075 |
| 270 | 0.0011 |

Biological Example 2

MDCKII-MDR1 Permeability

The blood brain barrier (BBB) separates circulating blood from the extracellular fluid of the central nervous system (CNS). The passive membrane permeability (Papp) and the P-gp (P-glycoprotein) substrate efflux potential were determined using the MDCKII-MDR1 cell line as an in vitro model of the effective permeability of a compound through the BBB. A bidirectional assay (Apical to Basolateral (A→B) and Basolateral to Apical (B→A)), in the absence and in the presence of GF120918 (a P-gp inhibitor) was conducted using pre-plated MDCKII-MDR1 cells (Corning HTS Transwell-96) obtained from SOLVO Biotechnology. The assay was run at 3 µM for 90 min (minutes) in triplicate using a HBSS+12.5 mM HEPES pH 7.4 transport buffer. Following incubation of samples from donor and receiver, wells were removed and measured by LC-MS/MS. Samples were extracted by protein precipitation with acetonitrile containing an appropriate internal standard (IS) having a known mass and molecular weight. The precipitate was centrifuged for 10 min at 3000 rpm (revolutions per minute). The supernatants were then collected, diluted if necessary, and injected on to the LC-MS/MS system. Specific parent/daughter ion pairs for the test article and IS were used to selectively measure the test articles. Papp (apparent permeability expressed in nm/sec [nanometer/second]) values were calculated according to the following equation:

$$Papp(\text{nm/sec}) = \left(\frac{dQ}{dt}\right) \times \left(\frac{1}{C0}\right) \times \left(\frac{1}{A}\right)$$

Where dQ/dt is the permeability rate, $C_0$ is the initial concentration in the donor solution (expressed as IS ratio), A and B are the surface areas of the filter (the surface area of the cell monolayer).

Monolayer efflux ratios (ER) were derived using the following equation:

$$EffluxRatio = \left(\frac{B - APapp(\text{nm/sec})}{A - BPapp(\text{nm/sec})}\right)$$

Compounds with a MDCKII-MDR1 efflux ratio of less than or equal to 2.5 are likely to demonstrate ability to cross the blood-brain-barrier.

The following compounds were found to have a MDCKII-MDR1 efflux ratio of less than or equal to 2.5: Example 3, Example 6, Example 49, Example 61, Example 70, Example 81, Example 133, Example 139, Example 146, Example 166, Example 169, Example 189, Example 236, Example 248, Example 254, and Example 270.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A method for treating a disease or condition mediated, at least in part, by eukaryotic initiation factor 2B, the method comprising administering to a subject in need thereof an effective amount of a compound, or a pharmaceutically acceptable salt, isotopically enriched analog, stereoisomer, mixture of stereoisomers, or prodrug thereof, selected from the group consisting of:

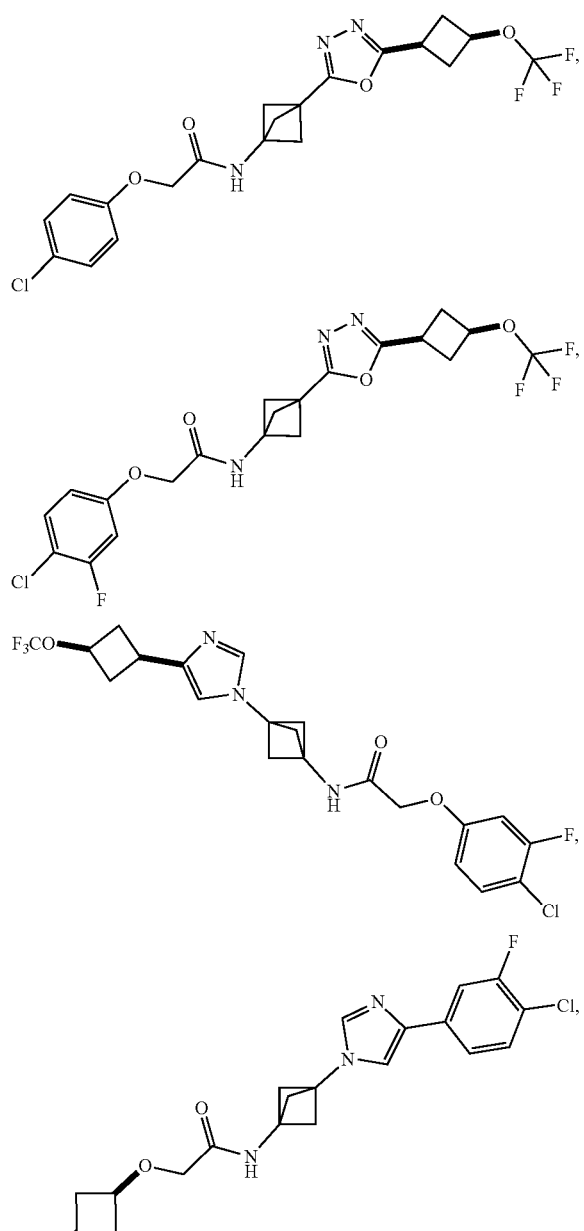

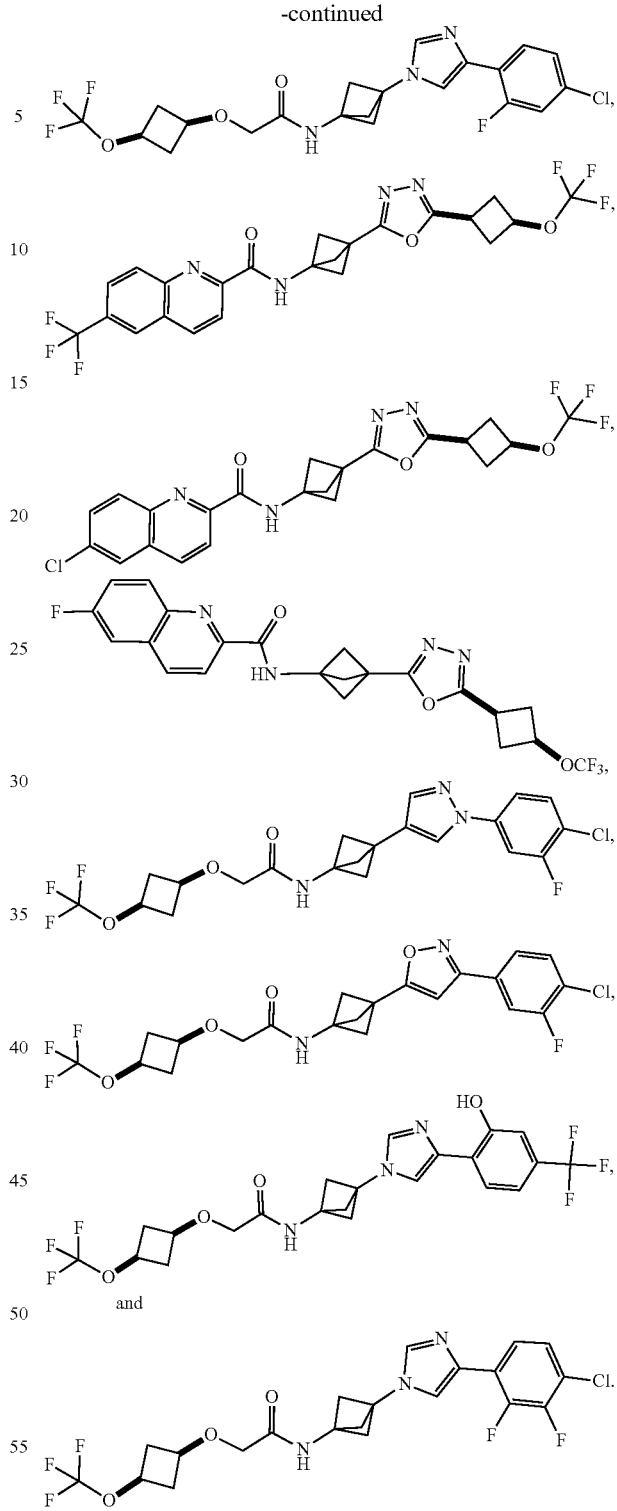

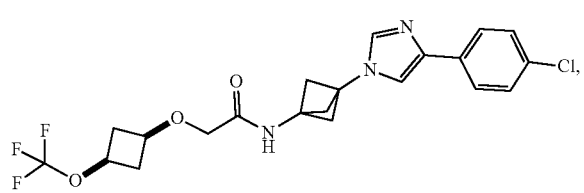

2. The method of claim 1, wherein the disease or condition is a neurodegenerative disease.

3. The method of claim 2, wherein the disease is Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, vanishing white matter (VWM) disease, insulin resistance, or Tabes dorsalis.

4. The method of claim 2, wherein the neurodegenerative disease is vanishing white matter (VWM) disease, Alzheimer's disease, amyotrophic lateral sclerosis (ALS), Parkinson's disease, or dementia.

5. The method of claim 1 comprising administering an effective amount of a compound having the structure:

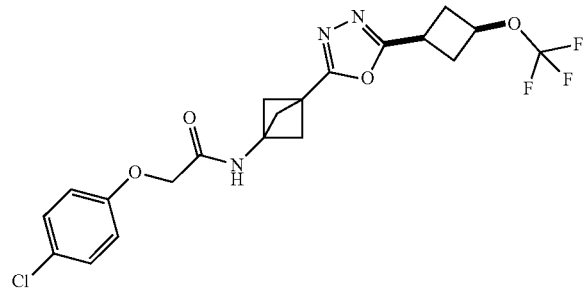

or a pharmaceutically acceptable salt thereof, to a subject in need thereof.

6. The method of claim 1 comprising administering an effective amount of a compound having the structure:

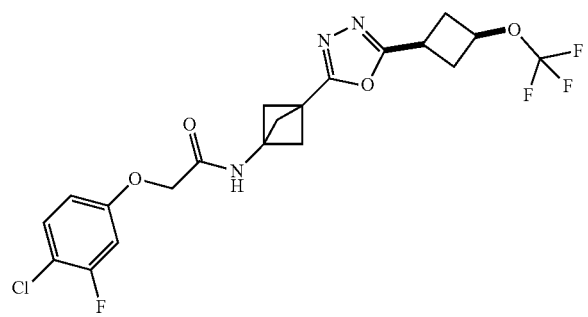

or a pharmaceutically acceptable salt thereof, to a subject in need thereof.

7. The method of claim 1 comprising administering an effective amount of a compound having the structure:

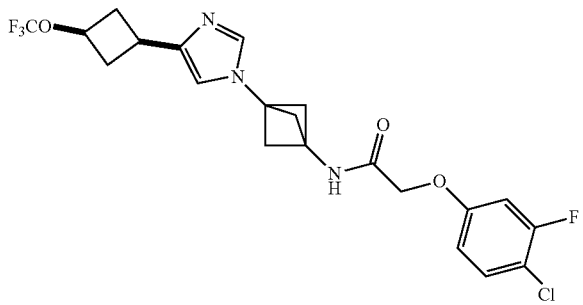

or a pharmaceutically acceptable salt thereof, to a subject in need thereof.

8. The method of claim 1 comprising administering an effective amount of a compound having the structure:

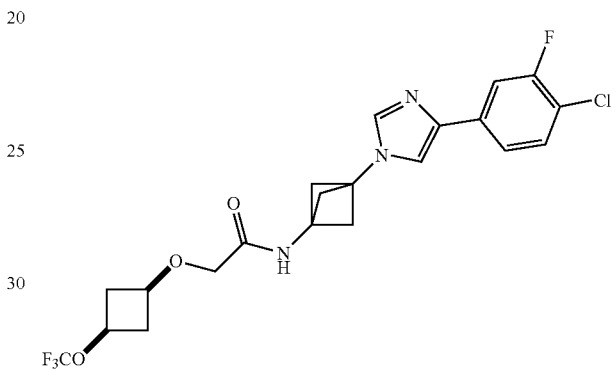

or a pharmaceutically acceptable salt thereof, to a subject in need thereof.

9. The method of claim 1 comprising administering an effective amount of a compound having the structure:

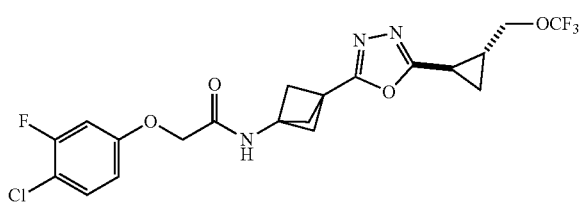

or a pharmaceutically acceptable salt thereof, to a subject in need thereof.

10. The method of claim 1 comprising administering an effective amount of a compound having the structure:

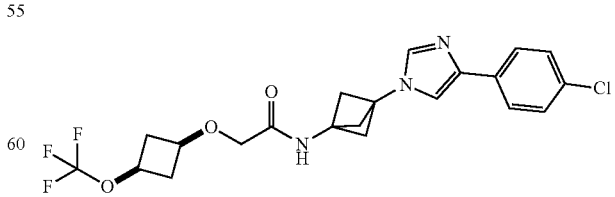

or a pharmaceutically acceptable salt thereof, to a subject in need thereof.

11. The method of claim 1 comprising administering an effective amount of a compound having the structure:

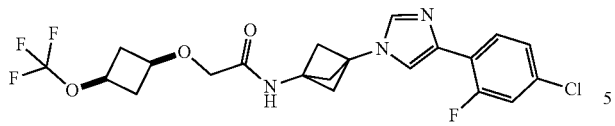

or a pharmaceutically acceptable salt thereof, to a subject in need thereof.

12. The method of claim 1 comprising administering an effective amount of a compound having the structure:

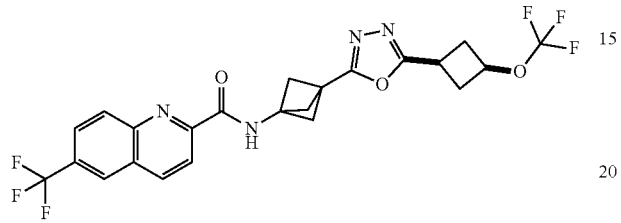

or a pharmaceutically acceptable salt thereof, to a subject in need thereof.

13. The method of claim 1 comprising administering an effective amount of a compound having the structure:

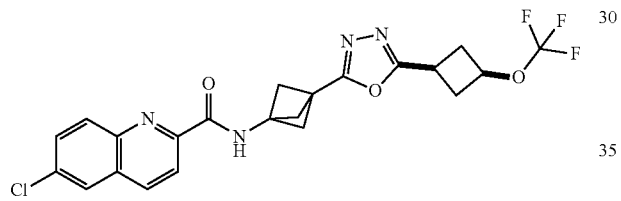

or a pharmaceutically acceptable salt thereof, to a subject in need thereof.

14. The method of claim 1 comprising administering an effective amount of a compound having the structure:

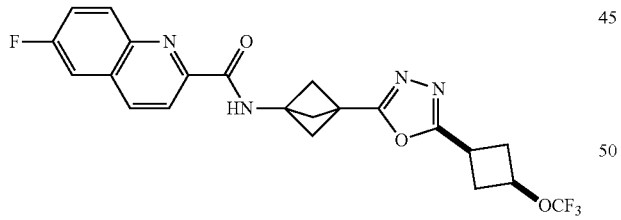

or a pharmaceutically acceptable salt thereof, to a subject in need thereof.

15. The method of claim 1 comprising administering an effective amount of a compound having the structure:

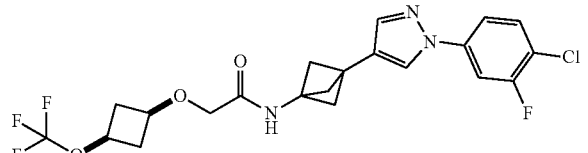

or a pharmaceutically acceptable salt thereof, to a subject in need thereof.

16. The method of claim 1 comprising administering an effective amount of a compound having the structure:

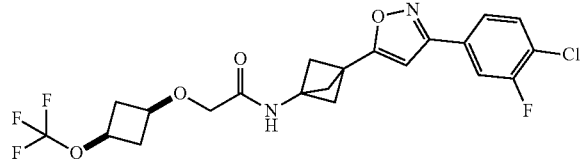

or a pharmaceutically acceptable salt thereof, to a subject in need thereof.

17. The method of claim 1 comprising administering an effective amount of a compound having the structure:

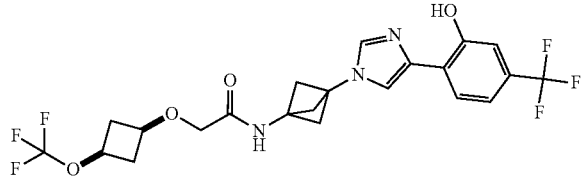

or a pharmaceutically acceptable salt thereof, to a subject in need thereof.

18. The method of claim 1 comprising administering an effective amount of a compound having the structure:

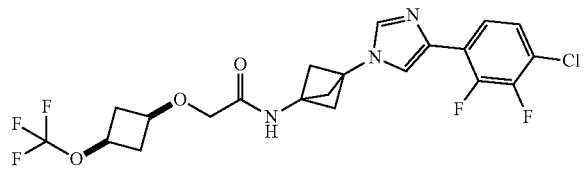

or a pharmaceutically acceptable salt thereof, to a subject in need thereof.

* * * * *